(12) United States Patent
Taylor et al.

(10) Patent No.: US 11,058,698 B2
(45) Date of Patent: Jul. 13, 2021

(54) ACYLATED ACTIVE AGENTS AND METHODS OF THEIR USE FOR THE TREATMENT OF AUTOIMMUNE DISORDERS

(71) Applicant: Flagship Pioneering Innovations V, Inc., Cambridge, MA (US)

(72) Inventors: Steven John Taylor, Winchester, MA (US); Mi-Jeong Kim, Boston, MA (US); Kathleen Nudel, Jamaica Plain, MA (US); Timothy F. Briggs, Waltham, MA (US); Koji Yasuda, Boston, MA (US); Leonard Buckbinder, East Greenwich, RI (US); Bernard Lanter, Somerville, MA (US); Spencer Cory Peck, Watertown, MA (US); Cheri Snedeker, Boston, MA (US); Angela She, Cambridge, MA (US); Jessica Alexander, Waltham, MA (US); Anna Liang, Everett, MA (US); Jenny Liu, Cambridge, MA (US); Dinara Gunasekera, Cambridge, MA (US); David Arthur Berry, Waban, MA (US); John Patrick Casey, Jr., Boston, MA (US); Amir H. Moarefi, Encino, CA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/803,284

(22) Filed: Feb. 27, 2020

(65) Prior Publication Data
US 2020/0188418 A1    Jun. 18, 2020

Related U.S. Application Data

(63) Continuation of application No. PCT/US2019/035677, filed on Jun. 5, 2019.

(60) Provisional application No. 62/776,377, filed on Dec. 6, 2018, provisional application No. 62/680,965, filed on Jun. 5, 2018.

(51) Int. Cl.
| | |
|---|---|
| *A61K 31/7036* | (2006.01) |
| *A61K 31/191* | (2006.01) |
| *A61K 31/196* | (2006.01) |
| *A61K 9/00* | (2006.01) |
| *A61P 37/06* | (2006.01) |
| *A61K 31/353* | (2006.01) |
| *A61K 31/519* | (2006.01) |

(52) U.S. Cl.
CPC ........ *A61K 31/7036* (2013.01); *A61K 9/0053* (2013.01); *A61K 31/191* (2013.01); *A61K 31/196* (2013.01); *A61K 31/353* (2013.01); *A61K 31/519* (2013.01); *A61P 37/06* (2018.01)

(58) Field of Classification Search
CPC .............. A61K 31/7036; A61K 9/0053; A61K 31/196; A61K 31/353; A61K 31/519; A61K 31/191; A61P 37/06
USPC ........................................................ 514/35
See application file for complete search history.

(56) References Cited

U.S. PATENT DOCUMENTS

| | | | |
|---|---|---|---|
| 8,497,256 B2 | 7/2013 | Forbes et al. | |
| 2006/0079492 A1 | 4/2006 | Ahlem et al. | |
| 2007/0173461 A1* | 7/2007 | Nakamura | .............. A61P 43/00 514/25 |
| 2008/0004341 A1 | 1/2008 | Brunet et al. | |
| 2008/0213341 A1* | 9/2008 | Haji Begli | ................ A61P 1/04 424/439 |
| 2010/0204162 A1 | 8/2010 | Platt et al. | |
| 2012/0040916 A1 | 2/2012 | Moon et al. | |
| 2015/0025247 A1 | 1/2015 | Deng et al. | |
| 2016/0271102 A1 | 9/2016 | Epstein | |

FOREIGN PATENT DOCUMENTS

| | | |
|---|---|---|
| WO | WO-2006/038440 A1 | 4/2006 |
| WO | WO-2014/151200 A2 | 9/2014 |
| WO | WO-2017/122495 A1 | 7/2017 |
| WO | WO-2018/226732 A1 | 12/2018 |

OTHER PUBLICATIONS

Wu et al. An optimised sample preparation method for NMR-based faecal metabonomic analysis. Analyst, 2010, 135, 1023-1030. (Year: 2010).*
Ananthakrishnan et al., "Gut Microbiome Function Predicts Response to Anti-integrin Biologic Therapy in Inflammatory Bowel Diseases," Cell Host Microbe. 21(5):603-610 (2017) (26 pages).
Cohen et al., "Functional Metagenomic Discovery of Bacterial Effectors in the Human Microbiome and Isolation of Commendamide, a GPCR G2A/132 agonist," Proc Natl Acad Sci USA. 112(35):E4825-34 (2015).
Dahl et al., "The anti-inflammatory drug mesalamine targets bacterial polyphosphate accumulation," Nat Microbiol. 2:16267 (2017) (5 pages).
Greenblum et al., "Metagenomic Systems Biology of the Human Gut Microbiome Reveals Topological Shifts Associated With Obesity and Inflammatory Bowel Disease," Proc Natl Acad Sci USA. 109(2):594-9 (2012).
International Search Report for International Application No. PCT/US2019/035677, dated Oct. 29, 2019 (7 pages).

(Continued)

*Primary Examiner* — Yih-Horng Shiao
(74) *Attorney, Agent, or Firm* — Clark & Elbing LLP

(57) ABSTRACT

Disclosed herein are acylated active agents and methods of their use, e.g., for modulating an autoimmunity marker or for treating an autoimmune disorder.

2 Claims, 5 Drawing Sheets

(56) References Cited

OTHER PUBLICATIONS

Larsen et al., "Metabolome of Human Gut Microbiome Is Predictive of Host Dysbiosis," Gigascience. 4:42 (2015) (16 pages).
Low et al., "Animal Models of Ulcerative Colitis and Their Application in Drug Research," Drug Des Devel Ther. 7:1341-57 (2013).
Manor et al., "Systematic Characterization and Analysis of the Taxonomic Drivers of Functional Shifts in the Human Microbiome," Cell Host Microbe. 21(2):254-267 (2017) (15 pages).
Moayyedi et al., "Fecal Microbiota Transplantation Induces Remission in Patients With Active Ulcerative Colitis in a Randomized Controlled Trial," Gastroenterology. 149(1):102-109 (2015) (14 pages).
Morgan et al., "Dysfunction of the Intestinal Microbiome in Inflammatory Bowel Disease and Treatment," Genome Biol. 13(9):R79 (2012) (18 pages).
Muthas et al., "Neutrophils in Ulcerative Colitis: A Review of Selected Biomarkers and Their Potential Therapeutic Implications," Scand J Gastroenterol. 52(2):125-135 (2017) (12 pages).
Nikolaus et al., "Increased Tryptophan Metabolism Is Associated With Activity of Inflammatory Bowel Diseases," Gastroenterology. 153(6):1504-1516 (2017) (15 pages).
Palmela et al., "Adherent-invasive *Escherichia coli* in Inflammatory Bowel Disease," Gut. 67(3):574-587 (2017) (15 pages).
Pubchem, Substance Record for SID 33373866, Available Date: Dec. 5, 2007 [retrieved on Oct. 7, 2019]. Retrieved from the Internet: <https://pubchem.ncbi.nlm.nih.gov/substance/33373866>.
Ramos de Mattos et al., "Inflammatory Bowel Disease: An Overview of Immune Mechanisms and Biological Treatments," Mediators Inflamm. 2015:493012 (2015) (12 pages).
Rogler, "Resolution of Inflammation in Inflammatory Bowel Disease," Zurich Open Repository and Archive, University of Zurich (2017) (27 pages).
Saffouri et al., "Small Intestinal Microbial Dysbiosis Underlies Symptoms Associated With Functional Gastrointestinal Disorders," Nat Commun. 10(1):2012 (2019) (11 pages).
Schirmer et al., "Dynamics of Metatranscription in the Inflammatory Bowel Disease Gut Microbiome," Nat Microbiol. 3(3):337-346 (2018) (13 pages).
Simeoli et al., "An Orally Administered Butyrate-Releasing Derivative Reduces Neutrophil Recruitment and Inflammation in Dextran Sulphate Sodium-Induced Murine Colitis," Br J Pharmacol. 174(11):1484-1496 (2016).
Sprouse et al., "Impact of Gut Microbiota on Gut-Distal Autoimmunity: A Focus on T Cells," Immunology. 156(4):305-318 (2018).
Suez et al., "The Path Towards Microbiome-Based Metabolite Treatment," Nat Microbiol. 2:17075 (2017) (5 pages).
Van der Beek et al., "Role of Short-Chain Fatty Acids in Colonic Inflammation, Carcinogenesis, and Mucosal Protection and Healing," Nutr Rev. 75(4):286-305 (2017).
Wong et al., "Potential Benefits of Dietary Fibre Intervention in Inflammatory Bowel Disease," Int J Mol Sci. 17(6):919 (2016) (22 pages).
Written Opinion of the International Searching Authority for International Application No. PCT/US2019/035677, dated Oct. 29, 2019 (8 pages).

* cited by examiner

ACYLATED ACTIVE AGENTS AND METHODS OF THEIR USE FOR THE TREATMENT OF AUTOIMMUNE DISORDERS

FIELD OF THE INVENTION

The invention relates compounds and methods of their medicinal use.

BACKGROUND

Autoimmune disorders are the result of one's own immune system incorrectly attacking one's own tissue. Inflammatory bowel disease is a group of autoimmune disorders (e.g., Crohn's disease and ulcerative colitis). It is believed that inflammatory bowel disease relates to a host immune response toward the resident microbiota. The current standard of care for inflammatory bowel disease includes steroid and immunosuppressant therapies, which often produce undesirable side effects and can carry substantial risks of comorbidity development.

There is a need for new approaches to the treatment of autoimmune disorders.

SUMMARY OF THE INVENTION

In general, the invention provides acylated active agents (e.g., acylated catechin polyphenols, acylated carotenoids, acylated mesalamines, acylated sugars, acylated shikimic acids, acylated ellagic acid, acylated ellagic acid analogue, and acylated hydroxybenzoic acids), active agent combinations (e.g., a first agent that is catechin polyphenol, carotenoid, mesalamine, shikimic acid, or hydroxybenzoic acid and a second agent that is a fatty acid), compositions containing them (e.g., as unit dosage forms), and methods for modulating an autoimmunity marker in a subject or of treating an autoimmunity disorder in a subject.

In one aspect, the invention provides a method of modulating an autoimmunity marker in a subject in need thereof by administering to the subject an effective amount of an active agent. In a related aspect, the invention provides a method of treating an autoimmunity disorder in a subject in need thereof by administering to the subject an effective amount of an active agent.

In some embodiments, the autoimmunity marker is for an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, or granulomatosis with polyangiitis.

In certain embodiments, the autoimmunity marker is for an inflammatory bowel disease (e.g., ulcerative colitis or Crohn's disease). In particular embodiments, the subject suffers from the autoimmune disorder. In some embodiments, the autoimmune disorder is rheumatoid arthritis.

In further embodiments, the autoimmune disorder is an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, or granulomatosis with polyangiitis.

In some embodiments, the autoimmune disorder is rheumatoid arthritis.

In yet further embodiments, the autoimmune disorder is an inflammatory bowel disease (e.g., ulcerative colitis or Crohn's disease). In particular embodiments, the vasculitis is polyarteritis nodosa.

In some embodiments, a CYP1A1 mRNA level, intestinal motility, $CD4^+CD25^+$ Treg cell count, short chain fatty acids level, or mucus secretion is increased following the step of administering. In further embodiments, a CYP1A1 mRNA level is increased following the administration of the acylated active agent to the subject. In certain embodiments, abdominal pain, gastrointestinal inflammation, gastrointestinal permeability, gastrointestinal bleeding, intestinal motility, or frequency of bowel movements is reduced following the step of administering. In particular embodiments, an interleukin-8 (IL-8) level, macrophage inflammatory protein 1α (MIP-1α) level, macrophage inflammatory protein 1β (MIP-1β) level, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, 8-iso-prostaglandin $F_{2\alpha}$ (8-iso-$PGF_{2\alpha}$) level IgA level, calprotectin level, lipocalin-2 level, or indoxyl sulfate level is reduced following the step of administering. In some embodiments, an interleukin-8 (IL-8) level, macrophage inflammatory protein 1α (MIP-1α) level, or macrophage inflammatory protein 10 (MIP-1p) level is reduced following the administration of the acylated active agent to the subject. In further embodiments, the T1 cell count is modulated following the step of administering.

In some embodiments, the active agent is an acylated catechin polyphenol or acylated mesalamine. In particular embodiments, following oral administration to the subject, the active agent is hydrolyzable in the gastrointestinal tract of the subject. In certain embodiments, the active agent releases at least one fatty acid. In further embodiments, the active agent is administered to the subject orally.

In certain embodiments, the active agent is acylated mesalamine. In some embodiments, the active agent is an acylated catechin polyphenol.

In yet further embodiments, the active agent is an acylated hydroxybenzoic acid. In still further embodiments, the acylated hydroxybenzoic acid includes a core selected from the group consisting of salicylic acid and gallic acid.

In certain embodiments, the active agent is an acylated sugar. In some embodiments, the acylated sugar includes a monosaccharide core (e.g., xylose, arabinose, rhamnose, fucose, glucosamine, tagatose, or ribose). In further embodiments, the monosaccharide core is xylose. In yet further embodiments, the monosaccharide core is arabinose. In still further embodiments, the monosaccharide core is rhamnose. In other embodiments, the monosaccharide core is fucose. In yet other embodiments, the monosaccharide core is glucosamine. In still other embodiments, the monosaccharide core is tagatose. In some embodiments, the monosaccharide core is ribose. In certain embodiments, the acylated sugar comprises a sugar acid core. In particular embodiments, the sugar acid core is a uronic acid (e.g., glucuronic acid).

In particular embodiments, the active agent is an acylated shikimic acid. In some embodiments, an acylated shikimic acid is of the following structure:

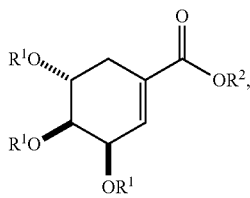

or a salt thereof,
where
each $R^1$ is independently H, acyl, alkyl, a group containing a fatty acid, a group containing a ketone body or pre-ketone body, or a group containing an amino acid metabolite; and $R^2$ is H, alkyl, a group containing a fatty acid, a group containing a ketone body or pre-ketone body, or a group containing an amino acid metabolite;

provided that the compound includes at least one group containing a fatty acid, group containing a ketone body or pre-ketone body, or group containing an amino acid metabolite.

In certain embodiments, at least one $R^1$ is a group containing a fatty acid. In particular embodiments, at least one $R^1$ is a group containing a ketone body or pre-ketone body. In some embodiments, at least one $R^1$ is a group containing an amino acid metabolite. In further embodiments, $R^2$ is H.

In other embodiments, the acylated active agent includes a group containing a fatty acid. In yet other embodiments, the group containing a fatty acid is a monosaccharide (e.g., arabinose, xylose, fructose, galactose, glucose, glucosinolate, ribose, tagatose, fucose, and rhamnose), sugar alcohol, or sugar acid having one or more hydroxyl groups substituted with a fatty acid acyl). In still other embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose).

In further embodiments, the group containing a fatty acid is a fatty acid acyl. In yet further embodiments, the fatty acid is a short chain fatty acid (e.g., acetyl, propionyl, or butyryl). In still further embodiments, the short chain fatty acid is acetyl. In particular embodiments, the short chain fatty acid is butyryl. In certain embodiments, the fatty acid is a medium chain fatty acid (e.g., octanoyl).

In some embodiments, the acylated active agent includes a group containing a ketone body or pre-ketone body. In certain embodiments, the group containing a ketone body or pre-ketone body is a monosaccharide, sugar alcohol, or sugar acid having one or more hydroxyl groups substituted with a ketone body acyl or pre-ketone body acyl. In particular embodiments, the group containing a ketone body or pre-ketone body includes at least one ketone body. In further embodiments, the group containing a ketone body or pre-ketone body includes at least one pre-ketone body. In yet further embodiments, the ketone body is p-hydroxybutyric acid. In still further embodiments, the pre-ketone body is 1,3-butanediol. In still further embodiments, the group containing a ketone body or pre-ketone body is a ketone body acyl or a pre-ketone body acyl.

In certain embodiments, the acylated active agent includes a group containing an amino acid metabolite. In particular embodiments, the group containing an amino acid metabolite is a monosaccharide, sugar alcohol, or sugar acid having one or more hydroxyl groups substituted with an amino acid metabolite acyl. In some embodiments, the group containing an amino acid metabolite is an amino acid metabolite acyl. In further embodiments, the amino acid metabolite is indole-3-acetic acid, indole-3-acrylic acid, or indole-3-pyruvic acid.

In still further embodiments, the acylated catechin polyphenol is a compound of formula (I):

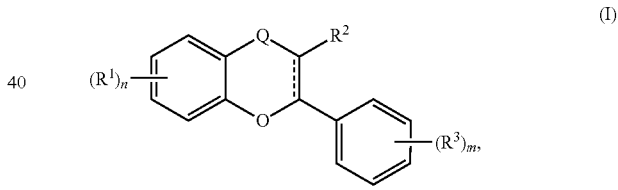

or a pharmaceutically acceptable salt thereof,
wherein
⫼ is a single carbon-carbon bond or double carbon-carbon bond;
Q is —CH$_2$— or —C(O)—;
each $R^1$ and each $R^3$ is independently H, halogen, —OR$^4$, phosphate, or sulfate;
$R^2$ is H or —OR$^4$;
each $R^4$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate;
each of n and m is independently 0, 1, 2, 3, or 4.

In particular embodiments, the compound of formula (I) includes at least one group containing a fatty acid, group containing a ketone body or pre-ketone body, or group containing an amino acid metabolite; and at least one group containing a fatty acid, when present, is a monosaccharide having one, two, three, or four hydroxyls substituted with fatty acid acyls.

In some embodiments, at least one $R^1$ is —$OR^A$, in which $R^A$ is a group containing a fatty acid, group containing a ketone body or pre-ketone body, or group containing an amino acid metabolite.

In certain embodiments, the acylated catechin polyphenol is a compound is of formula (I-a):

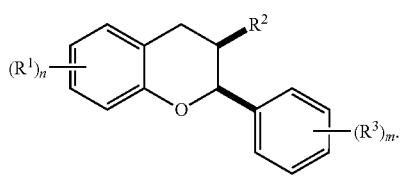

(I-a)

In particular embodiments, the acylated catechin polyphenol is a compound is of formula (I-b):

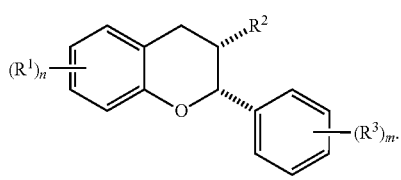

(I-b)

In further embodiments, the acylated catechin polyphenol is a compound is of formula (I-c):

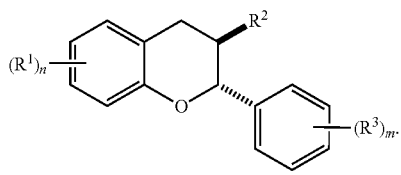

(I-c)

In yet further embodiments, the acylated catechin polyphenol is a compound is of formula (I-d):

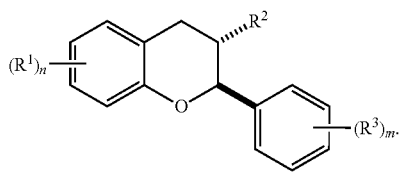

(I-d)

In certain embodiments, the acylated catechin polyphenol is a compound of formula (I-f):

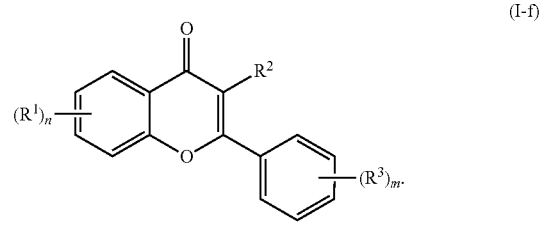

(I-f)

In still further embodiments, n is 2. In certain embodiments, m is 1. In particular embodiments, m is 2. In some embodiments, m is 3. In particular embodiments, each $R^1$ is independently —$OR^A$. In certain embodiments, each $R^3$ is independently H or —$OR^A$. In further embodiments, $R^2$ is H or —$OR^A$. In yet further embodiments, each $R^A$ is independently H, optionally substituted alkyl, a group containing a fatty acid, a group containing a ketone body or pre-ketone body, or a group containing an amino acid metabolite.

In other embodiments, the acylated catechin polyphenol is a compound is of formula (I-e):

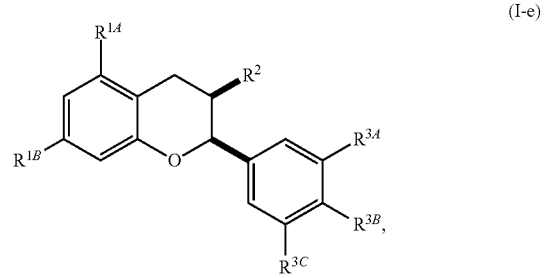

(I-e)

or a pharmaceutically acceptable salt thereof,
wherein each of $R^{1A}$ and $R^{1B}$ is independently as defined for $R^1$; and each of $R^{3A}$, $R^{3B}$, and $R^{3C}$ is independently as defined for $R^3$.

In yet other embodiments, each of $R^{1A}$ and $R^{1B}$ is independently —$OR^A$. In still other embodiments, each of $R^{3A}$, $R^{3B}$, and $R^{3C}$ is independently H, halogen, or —$OR^A$. In some embodiments, $R^2$ is a group of formula:

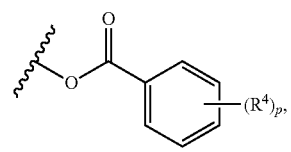

wherein p is 1, 2, 3, or 4, and each $R^4$ is independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate.

In certain embodiments, p is 3. In particular embodiments, each $R^4$ is independently H, hydroxy, halogen, a group containing a fatty acid, a group containing a ketone body or pre-ketone body, a group containing an amino acid metabolite, or an optionally substituted alkoxy. In certain embodiments, $R^2$ is a group of formula:

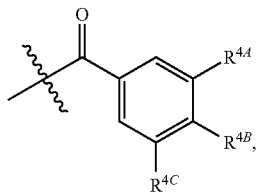

and each of $R^{4A}$, $R^{4B}$, and $R^{4C}$ is as defined for $R^4$.

In further embodiments, each of $R^{4A}$, $R^{4B}$, and $R^{4C}$ is independently H, hydroxy, halogen, a group containing a fatty acid, a group containing a ketone body or pre-ketone body, a group containing an amino acid metabolite, or an optionally substituted alkoxy. In yet further embodiments, each $R^4$ is independently H, optionally substituted alkyl, fatty acid acyl, or optionally acylated monosaccharide.

In still further embodiments, the acylated active agent includes at least one fatty acid acyl (e.g., a short chain fatty acid acyl). In some embodiments, the short chain fatty acid acyl is acetyl, propionyl, or butyryl. In certain embodiments, the short chain fatty acid acyl is acetyl. In particular embodiments, the short chain fatty acid acyl is butyryl.

In another aspect, the invention provides, a composition (e.g., a pharmaceutical composition, nutraceutical composition, food product, food additive, or dietary supplement) including an active agent. In some embodiments, the composition is provided in a unit dosage form. In other embodiments, the active agent is an acylated catechin polyphenol, acylated carotenoid, acylated mesalamine, acylated sugar, acylated shikimic acid, acylated ellagic acid, acylated ellagic acid analogue, and acylated hydroxybenzoic acid.

In still other embodiments, the unit dosage form contains at least 0.5 g (e.g., at least 0.7 g, at least 1 g, or at least 2 g) of the active agent. In certain embodiments, the unit dosage form contains 10 g or less (e.g., 9 g or less, 8 g or less, 7 g or less, 6 g or less, 5 g or less) of the active agent. In particular embodiments, the unit dosage form contains 0.5-10 g (e.g., 0.7-10 g, 1-10 g, 2-10 g, 0.5-9 g, 0.7-9 g, 1-9 g, 2-9 g, 0.5-8 g, 0.7-8 g, 1-8 g, 2-8 g, 0.5-7 g, 0.7-7 g, 1-7 g, 2-7 g, 0.5-6 g, 0.7-6 g, 1-6 g, 2-6 g, 0.5-5 g, 0.7-5 g, 1-10 g, or 2-5 g) of the active agent.

In some embodiments, the unit dosage form is a pharmaceutical unit dosage form. In further embodiments, the unit dosage form is a nutraceutical dosage form. In yet further embodiments, the unit dosage form is a serving of a food product.

In still further embodiments, the active agent is the acylated catechin polyphenol. In certain embodiments, the active agent is an acylated mesalamine. In yet further embodiments, the active agent is an acylated hydroxybenzoic acid. In still further embodiments, the active agent is an acylated sugar. In particular embodiments, the active agent is an acylated shikimic acid. In some embodiments, the active agent is an acylated ellagic acid. In certain embodiments, the active agent is an acylated ellagic acid analogue (e.g., an analogue including urolithin C core). In particular embodiments, the active agent is an acylated carotenoid.

In other embodiments, the acylated active agent includes a group containing a fatty acid. In yet other embodiments, the group containing a fatty acid is a monosaccharide (e.g., arabinose, xylose, fructose, galactose, glucose, glucosinolate, ribose, tagatose, fucose, and rhamnose), sugar alcohol, or sugar acid having one or more hydroxyl groups substituted with a fatty acid acyl). In still other embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). In further embodiments, the group containing a fatty acid is a fatty acid acyl. In yet further embodiments, the fatty acid is a short chain fatty acid (e.g., acetyl, propionyl, or butyryl). In still further embodiments, the short chain fatty acid is acetyl. In particular embodiments, the short chain fatty acid is butyryl. In certain embodiments, the fatty acid is a medium chain fatty acid (e.g., octanoyl).

In other embodiments, the acylated active agent includes a group containing a ketone body or pre-ketone body. In yet other embodiments, the group containing a ketone body or pre-ketone body is a monosaccharide (e.g., arabinose, xylose, fructose, galactose, glucose, glucosinolate, ribose, tagatose, fucose, and rhamnose), sugar alcohol, or sugar acid having one or more hydroxyl groups substituted with a ketone body acyl or pre-ketone body acyl). In still other embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). In further embodiments, the group containing a ketone body or pre-ketone body is a ketone body acyl or pre-ketone body acyl.

In other embodiments, the acylated active agent includes a group containing an amino acid metabolite. In yet other embodiments, the group containing an amino acid metabolite is a monosaccharide (e.g., arabinose, xylose, fructose, galactose, glucose, glucosinolate, ribose, tagatose, fucose, and rhamnose), sugar alcohol, or sugar acid having one or more hydroxyl groups substituted with an amino acid metabolite acyl). In still other embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). In further embodiments, the group containing an amino acid metabolite is an amino acid metabolite acyl.

In still further embodiments, the acylated catechin polyphenol is a compound of formula (I):

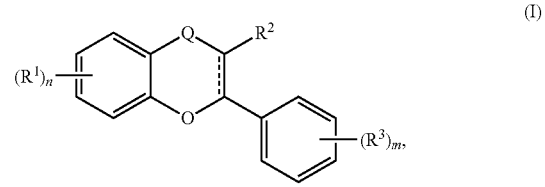

or a pharmaceutically acceptable salt thereof,
wherein
⫫ is a single carbon-carbon bond or double carbon-carbon bond;
Q is —$CH_2$— or —C(O)—;
each $R^1$ and each $R^3$ is independently H, halogen, —$OR^A$, phosphate, or sulfate;
$R^2$ is H or —$OR^A$;
each $R^A$ is independently H, optionally substituted alkyl, a monosaccharide, a sugar acid, a group containing a fatty acid, a group containing a ketone body or pre-ketone body, a group containing an amino acid metabolite acyl, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite acyl, an optionally substituted alkyl, an optionally substituted alkoxy, a monosaccharide, a sugar acid, phosphate, and sulfate;

each of n and m is independently 0, 1, 2, 3, or 4.

In particular embodiments, the compound of formula (I) includes at least one group containing a fatty acid, group containing a ketone body or pre-ketone body, or group containing an amino acid metabolite; and at least one group containing a fatty acid, when present, is a monosaccharide having one, two, three, or four hydroxyls substituted with fatty acid acyls.

In some embodiments, at least one $R^1$ is —$OR^A$, in which $R^A$ is a group containing a fatty acid, group containing a ketone body or pre-ketone body, or group containing an amino acid metabolite acyl.

In certain embodiments, the acylated catechin polyphenol is a compound is of formula (I-a):

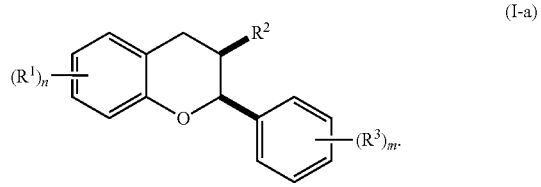

(I-a)

In particular embodiments, the acylated catechin polyphenol is a compound is of formula (I-b):

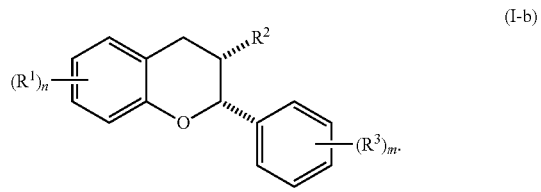

(I-b)

In further embodiments, the acylated catechin polyphenol is a compound is of formula (I-c):

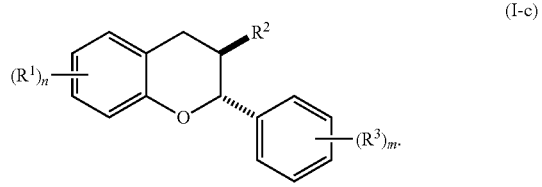

(I-c)

In yet further embodiments, the acylated catechin polyphenol is a compound is of formula (I-d):

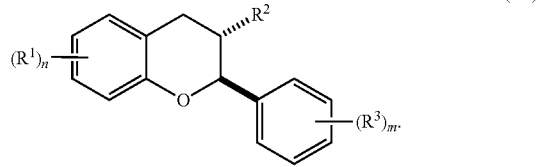

(I-d)

In certain embodiments, the acylated catechin polyphenol is a compound of formula (I-f):

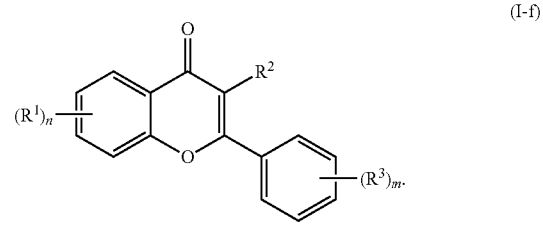

(I-f)

In still further embodiments, n is 2. In certain embodiments, m is 1. In particular embodiments, m is 2. In some embodiments, m is 3. In particular embodiments, each $R^1$ is independently —$OR^A$. In certain embodiments, each $R^3$ is independently H or —$OR^A$. In further embodiments, $R^2$ is H or —$OR^A$. In yet further embodiments, each $R^A$ is independently H, optionally substituted alkyl, a group containing a fatty acid, a group containing a ketone body or pre-ketone body, or a group containing an amino acid metabolite. In some embodiments, at least one $R^A$ is a group containing a fatty acid. In certain embodiments, at least one $R^A$ is a group containing an amino acid metabolite. In particular embodiments, at least one $R^A$ is a group containing a ketone body or pre-ketone body. Preferably, the compound of formula (I-f) includes quercetin core.

In other embodiments, the acylated catechin polyphenol is a compound of formula (I-e):

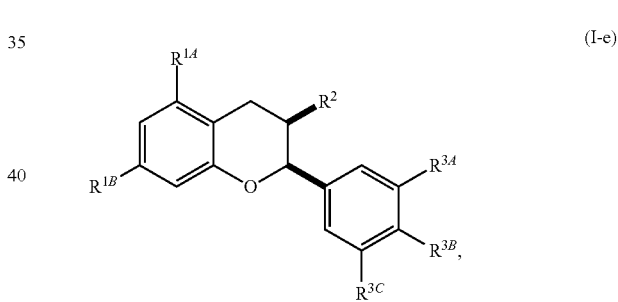

(I-e)

or a pharmaceutically acceptable salt thereof, wherein each of $R^{1A}$ and $R^{1B}$ is independently as defined for $R^1$; and each of $R^{3A}$, $R^{3B}$, and $R^{3C}$ is independently as defined for $R^3$.

In yet other embodiments, each of $R^{1A}$ and $R^{1B}$ is independently —$OR^A$. In still other embodiments, each of $R^{3A}$, $R^{3B}$, and $R^{3C}$ is independently H, halogen, or —$OR^A$. In some embodiments, $R^2$ is a group of formula:

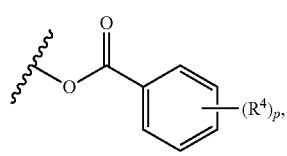

wherein p is 1, 2, 3, or 4, and each $R^4$ is independently selected from the group consisting of H, hydroxy, halogen, a group containing a fatty acid, group containing a ketone body or pre-ketone body, group containing an amino acid metabolite, an optionally substituted alkyl, an optionally substituted alkoxy, a monosaccharide, a sugar acid, phosphate, and sulfate.

In certain embodiments, p is 3. In particular embodiments, each $R^4$ is independently H, hydroxy, halogen, a group containing a fatty acid, group containing a ketone body or pre-ketone body, group containing an amino acid metabolite acyl, or an optionally substituted alkoxy. In certain embodiments, $R^2$ is a group of formula:

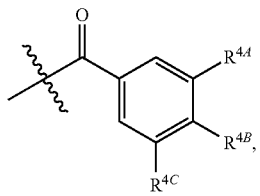

and each of $R^{4A}$, $R^{4B}$, and $R^{4C}$ is as defined for $R^4$.

In further embodiments, each of $R^{4A}$, $R^{4B}$, and $R^{4C}$ is independently H, hydroxy, halogen, a group containing a fatty acid, group containing a ketone body or pre-ketone body, group containing an amino acid metabolite acyl, or an optionally substituted alkoxy. In yet further embodiments, each $R^4$ is independently H, optionally substituted alkyl, fatty acid acyl, or optionally acylated monosaccharide.

In still further embodiments, the acylated catechin polyphenol includes at least one fatty acid acyl (e.g., a short chain fatty acid acyl). In some embodiments, the short chain fatty acid acyl is acetyl, propionyl, or butyryl. In certain embodiments, the short chain fatty acid acyl is acetyl. In particular embodiments, the short chain fatty acid acyl is butyryl.

Definitions

The term "acyl," as used herein, represents a chemical substituent of formula —C(O)—R, where R is alkyl, alkenyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R. Non-limiting examples of acyl include fatty acid acyls (e.g., short chain fatty acid acyls (e.g., acetyl)), amino acid metabolite acyl, ketone body acyl, pre-ketone body acyl, and benzoyl.

The term "acylated active agent," as used herein, represents a compound including two or more agents linked through ester bond(s), amide bond(s), carbonate linker(s), carbamate linker(s), and/or glycosidic bond(s). Non-limiting examples of acylated active agents include an acylated catechin polyphenol and acylated mesalamine.

The term "acylated catechin polyphenol," as used herein, represents a substituted compound having the core of formula (A):

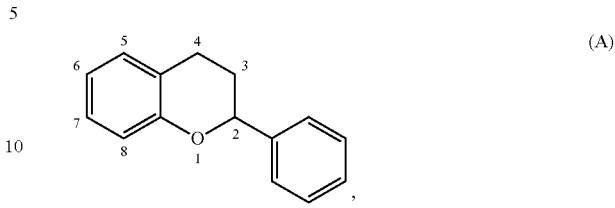

or a multimer thereof, or a salt thereof, where the substituents are independently selected from the group consisting of —$OR^A$, —OCOO—$R^A$, —$NHR^B$, oxo, halogen, optionally substituted $C_{1-20}$ alkyl, optionally substituted $C_{2-20}$ alkenyl, optionally substituted thioalkyl, optionally substituted alkylsulfonyl, optionally substituted alkylsulfenyl, optionally substituted alkylsulfinyl, optionally substituted thioaryl, optionally substituted aryl thioalkyl, optionally substituted thioalkenyl, dialkylamino, sulfate, phosphate, ascorbic acid, optionally substituted heterocyclyl, nitro, amino acids, $C_{1-6}$ esters of amino acids, optionally acylated monosaccharide, and optionally acylated sugar acid, where each $R^A$ is independently H, optionally substituted alkyl, a group containing a fatty acid, a group containing a ketone body or pre-ketone body, or benzoyl optionally substituted with one, two, three, or four substituents independently selected from the group consisting of H, hydroxyl, halogen, a group containing a fatty acid, a group containing a ketone body or pre-ketone body, optionally substituted alkoxy, and optionally substituted alkyl, and where $R^B$ is independently H or optionally substituted alkyl;

where the carbon-carbon bond connecting carbon 2 and carbon 3 in formula (A) is a single bond or a double bond;

where the multimer includes a total of 2 or 3 cores of formula (A), each core substituted independently as described above; and where two vicinal centers in core (A) may be further substituted with a group —$(O)_q$-L-$L^2$-, where q is 0 or 1, $L^1$ is optionally substituted alkylene, optionally substituted alkenylene, or optionally substituted heterocyclylene; and $L^2$ is a covalent bond, optionally substituted heterocyclylene, or optionally substituted cycloalkylene;

provided that at least one of positions 5, 6, 7, and 8 is —$OR^A$, where $R^A$ is a group containing a fatty acid, a group containing a ketone body or pre-ketone body, or a benzoyl optionally substituted with one, two, three, or four substituents independently selected from the group consisting of H, hydroxyl, a halogen, a group containing a fatty acid, a group containing a ketone body or pre-ketone body, an optionally substituted alkoxy, and an optionally substituted alkyl; and provided that the substituted compound includes at least one group containing a fatty acid, group containing a ketone body or pre-ketone body, or group containing an amino acid metabolite acyl. Preferably, the acylated catechin polyphenol includes quercetin core.

The term "acylated carotenoid," as used herein, represents a carotenoid, in which at least one hydroxyl group is replaced with a substituent —OR, where each R is independently selected from the group consisting of an acyl, alkyl, a group containing a fatty acid, a group containing a ketone body or pre-ketone body, and a group containing an amino acid metabolite, provided that at least one R is a group containing a fatty acid, a group containing a ketone body or pre-ketone body, or a group containing an amino acid metabolite. Non-limiting examples of an acylated carotenoid include astaxanthin having one or both hydroxyl groups independently substituted with an acyl, alkyl, group containing a fatty acid, or group containing a ketone body or pre-ketone body, provided that at least one hydroxyl is substituted with a group containing a fatty acid, a group containing a ketone body or pre-ketone body, or a group containing an amino acid metabolite.

The term "acylated catechin polyphenol" also refers to a compound of formula (I):

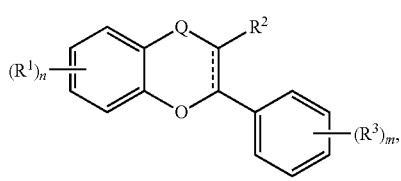

or a pharmaceutically acceptable salt thereof,
where
⫶ is a single carbon-carbon bond or double carbon-carbon bond;
Q is —CH$_2$— or —C(O)—;
each R$^1$ and each R$^3$ is independently H, halogen, —OR$^A$, phosphate, or sulfate;
R$^2$ is H or —OR$^A$;
each R$^A$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, or a group containing an amino acid metabolite an optionally substituted alkyl, an optionally substituted alkoxy, a monosaccharide, a sugar acid, phosphate, and sulfate; and
each of n and m is independently 0, 1, 2, 3, or 4.

The term "acylated hydroxybenzoic acid," as used herein, represents a compound of formula:

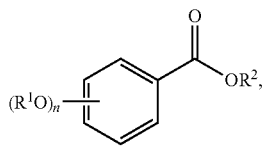

or a salt thereof,
where
n is 1, 2, or 3;
each R$^1$ is independently H, acyl, alkyl, a group containing a fatty acid, a group containing a ketone body or pre-ketone body, or a group containing an amino acid metabolite; and
R$^2$ is H, alkyl, a group containing a fatty acid, a group containing a ketone body or pre-ketone body, or a group containing an amino acid metabolite;
provided that the compound includes at least one group containing a fatty acid, group containing a ketone body or pre-ketone body, or group containing an amino acid metabolite.

Non-limiting examples of acylated hydroxybenzoic acids include salicylic acid, in which the phenolic hydroxyl is substituted with a group containing a fatty acid, group containing a ketone body or pre-ketone body, or group containing an amino acid metabolite; and gallic acid, in which one, two, or three phenolic hydroxyls are independently substituted with groups containing a fatty acid, group containing a ketone body or pre-ketone body, or group containing an amino acid metabolite.

The term "acylated mesalamine," as used herein, represents a mesalamine, in which, one H in one or more of —NH$_2$, —OH, or —COOH is replaced with an acyl or a group containing a fatty acid, group containing a ketone body or pre-ketone body, or group containing an amino acid metabolite; provided that acylated mesalamine contains at least one group containing a fatty acid, group containing a ketone body or pre-ketone body, or group containing an amino acid metabolite. In some embodiments, acylated mesalamine is a compound of formula (II):

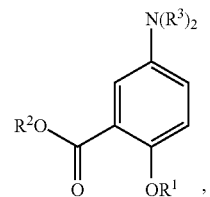

where
R$^1$ is H, alkyl, acyl, a group containing a fatty acid, a group containing a ketone body or pre-ketone body, or a group containing an amino acid metabolite;
R$^2$ is H, alkyl, a group containing a fatty acid, a group containing a ketone body or pre-ketone body, or a group containing an amino acid metabolite; and
each R$^3$ is independently H, alkyl, acyl, a group containing a fatty acid, a group containing a ketone body or pre-ketone body, or a group containing an amino acid metabolite; or both R$^2$ groups combine to form:

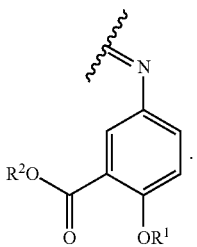

The acylated mesalamine includes at least one group containing a fatty acid, group containing a ketone body or pre-ketone body, or group containing an amino acid metabolite.

The term "acylated shikimic acid," as used herein, represents a compound of formula:

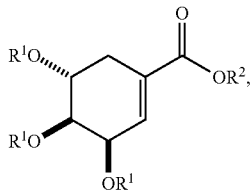

or a salt thereof, where each $R^1$ is independently H, acyl, alkyl, a group containing a fatty acid, a group containing a ketone body or pre-ketone body, or a group containing an amino acid metabolite; and $R^2$ is H, alkyl, a group containing a fatty acid, a group containing a ketone body or pre-ketone body, or a group containing an amino acid metabolite;

provided that the compound includes at least one group containing a fatty acid, group containing a ketone body or pre-ketone body, or group containing an amino acid metabolite.

The term "acylated sugar," as used herein, represents a monosaccharide having one or more hydroxyls substituted with alkyl, acyl, a group containing a fatty acid, a group containing a ketone body or pre-ketone body, or a group containing an amino acid metabolite. The monosaccharide is present in the pyranose or furanose form. Preferably, the monosaccharide is present in the pyranose form. The monosaccharide may be an aldose or ketose. Non-limiting examples of monosaccharides are arabinose, xylose, fructose, galactose, glucose, ribose, tagatose, fucose, and rhamnose. In some embodiments, the monosaccharide is L-arabinose, D-xylose, fructose, galactose, D-glucose, D-ribose, D-tagatose, L-fucose, or L-rhamnose. Preferably, the monosaccharide is xylose, arabinose, rhamnose, fucose, glucosamine, or tagatose. The monosaccharide may include an anomeric carbon bonded to —OR, where R is H, alkyl, acyl, a group containing a fatty acid, a group containing a ketone body or pre-ketone body, or a group containing an amino acid metabolite. Preferably, R is alkyl or a group containing a fatty acid.

The term "acylated ellagic acid," as used herein, represents compounds of the following structures:

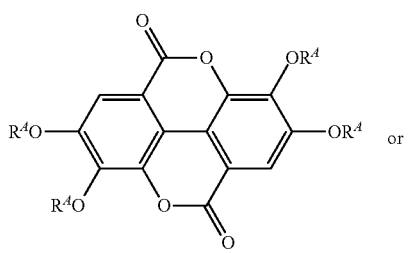

or

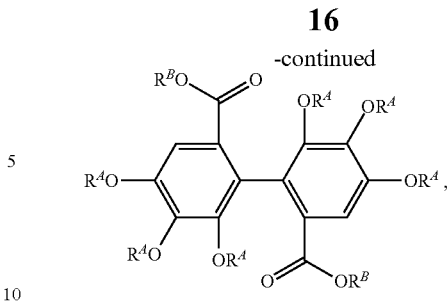

or a salt thereof, where each $R^A$ is independently H, alkyl, acyl, a group containing a fatty acid, a group containing a ketone body or pre-ketone body, or a group containing an amino acid metabolite; and each $R^B$ is independently H, alkyl, a group containing a fatty acid, a group containing a ketone body or pre-ketone body, or a group containing an amino acid metabolite; provided that at least one $R^A$ and/or at least one $R^B$, when present, is a group containing a fatty acid, a group containing a ketone body or pre-ketone body, or a group containing an amino acid metabolite.

The term "acylated ellagic acid analogue," as used herein, represents compounds of the following structure:

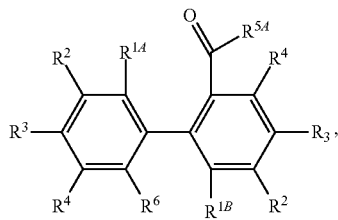

or a salt thereof,
where
each of $R^2$, $R^3$, and $R^4$ is independently H or —$OR^A$;
$R^6$ is H or —(CO)—$R^{5B}$;
$R^{1A}$ is H or —$OR^A$, and $R^{5A}$ is —OH or —$OR^B$; or $R^{1A}$ and $R^{5A}$ combine to form —O—;
$R^{1B}$ is H or —$OR^A$, and $R^{5B}$ is absent, —OH, or —$OR^B$; or $R^{1B}$ and $R^{5B}$ combine to form —O—;
each $R^A$ is independently H, O-protecting group, alkyl, acyl, a group containing a fatty acid, a group containing a ketone body or pre-ketone body, or a group containing an amino acid metabolite;
each $R^B$ is independently H, O-protecting group, alkyl, a group containing a fatty acid, a group containing a ketone body or pre-ketone body, or a group containing an amino acid metabolite;
provided that at least one $R^A$ and/or at least one $R^B$ is a group containing a fatty acid, a group containing a ketone body or pre-ketone body, or a group containing an amino acid metabolite.

The term "acyloxy," as used herein, represents a chemical substituent of formula —OR, where R is acyl. An optionally substituted acyloxy is an acyloxy that is optionally substituted as described herein for acyl.

The term "alcohol oxygen atom," as used herein, refers to a divalent oxygen atom bonded to an $sp^3$-hybridized carbon atom and to another $sp^3$-hybridized carbon atom or an $sp^2$-hybridized carbon atom of a carbonyl group.

The term "aldonyl," as used herein, refers to a monovalent substituent that is aldonic acid in which a carboxylate hydroxyl is replaced with a valency.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkenyl," as used herein, represents acyclic monovalent straight or branched chain hydrocarbon groups containing one, two, or three carbon-carbon double bonds. Alkenyl, when unsubstituted, has from 2 to 22 carbons, unless otherwise specified. In certain preferred embodiments, alkenyl, when unsubstituted, has from 2 to 12 carbon atoms (e.g., 1 to 8 carbons). Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkyl," as used herein, refers to an acyclic straight or branched chain saturated hydrocarbon group, which, when unsubstituted, has from 1 to 22 carbons (e.g., 1 to 20 carbons), unless otherwise specified. In certain preferred embodiments, alkyl, when unsubstituted, has from 1 to 12 carbons (e.g., 1 to 8 carbons). Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; =O; =S; and =NR', where R' is H, alkyl, aryl, or heterocyclyl. Each of the substituents may itself be unsubstituted or, valency permitting, substituted with unsubstituted substituent(s) defined herein for each respective group.

The term "alkenylene," as used herein, refers to a straight or branched chain alkenyl group with one hydrogen removed, thereby rendering this group divalent. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. An optionally substituted alkenylene is an alkenylene that is optionally substituted as described herein for alkyl.

The term "alkylene," as used herein, refers to a saturated divalent hydrocarbon group that is a straight or branched chain saturated hydrocarbon, in which two valencies replace two hydrogen atoms. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. An optionally substituted alkylene is an alkylene that is optionally substituted as described herein for alkyl.

The term "alkylsulfenyl," as used herein, represents a group of formula —S-(alkyl). An optionally substituted alkylsulfenyl is an alkylsulfenyl that is optionally substituted as described herein for alkyl.

The term "alkylsulfinyl," as used herein, represents a group of formula —S(O)-(alkyl). An optionally substituted alkylsulfinyl is an alkylsulfinyl that is optionally substituted as described herein for alkyl.

The term "alkylsulfonyl," as used herein, represents a group of formula —S(O)$_2$-(alkyl). An optionally substituted alkylsulfonyl is an alkylsulfonyl that is optionally substituted as described herein for alkyl.

The term "amino acid," as used herein, represents proline, taurine, or a compound having an amino group and a carboxylate or sulfonate group separated by an optionally substituted alkylene or optionally substituted aryene. Amino acids are small molecules and have a molecular weight of <900 g/mol (preferably, <500 g/mol). Preferably, when the linker is alkylene, the linker may be optionally substituted as described herein for alkyl. In some embodiments, optionally substituted alkylene is an alkylene substituted with 1 or 2 groups that are independently hydroxyl, thiol, amino, guanidine, carbamoylamino, imidazolyl, indolyl, —SeH, oxo, 4-hydroxyphenyl, phenyl, or —SMe. Non-limiting examples of amino acids include alanine, arginine, asparagine, aspartic acid, cysteine, glutamic acid, glutamine, glycine, histidine, isoleucine, leucine, lysine, methionine, phenylalanine, proline, selenocysteine, serine, threonine, tyrosine, tryptophan, ornithine, citrulline, aminobenzoic acid, and taurine.

The term "amino acid metabolite," as used herein, represents proteinogenic amino acids, in which the α-amino group is replaced with —OH or —H, in which the 1-carboxyl group is replaced with H, in which the α-(CHNH$_2$) group is replaced with a carbonyl, in which the α-amino group and β-hydrogen atom are replaced with a double bond, or in which the 1-carboxyl group is replaced with hydroxyl and the α-(CHNH$_2$) group is replaced with a carbonyl. Non-limiting examples of amino acid metabolites include indole-3-acetic acid, indole-3-propionic acid, 3-(indole-3-yl)-acrylic acid, indole-3-pyruvic acid, and 3-(indol-3-yl)-2-hydroxypropionic acid.

The term "amino acid metabolite acyl," as used herein, represents an amino acid metabolite, in which carboxylate —OH is replaced with a valency.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. An optionally substituted aryl alkyl is an aryl alkyl, in which aryl and alky portions may be optionally substituted as the individual groups as described herein.

The term "aryloxy," as used herein, represents a group —OR, where R is aryl. Aryloxy may be an optionally substituted aryloxy. An optionally substituted aryloxy is aryloxy that is optionally substituted as described herein for aryl.

The term "autoimmune disorder," as used herein, refers to a group of diseases resulting from one's own immune system incorrectly attacking one's own tissue. Non-limiting examples of autoimmune disorders include an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, and granulomatosis with polyangiitis. Preferably, the autoimmune disorder is an inflammatory bowel disease (e.g., Crohn's disease or ulcerative colitis).

The term "autoimmunity marker," as used herein, is an observable indication of the presence, absence, or risk of an autoimmune disorder (e.g., an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, and granulomatosis with polyangiitis).

The level of an autoimmune marker may directly or inversely correlate with an autoimmune disorder state. Non-limiting examples of the autoimmunity markers are a CYP1A1 mRNA level, intestinal motility, $CD4^+CD25^+$ Treg cell (e.g., $CD4^+CD25^+Foxp3^+$ Treg cell) count, mucus secretion, T1 cell count, interleukin-8 (IL-8) level, macrophage inflammatory protein $1\alpha$ (MIP-$1\alpha$) level, macrophage inflammatory protein 1p (MIP-1) level, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, 8-iso-prostaglandin $F_{2\alpha}$ (8-iso-PGF$_{2\alpha}$) level, IgA level, calprotectin level, lipocalin-2 level, short chain fatty acids level, and indoxyl sulfate level.

Autoimmunity markers may be measured using methods known in the art. For example, blood sample analyses may be used to measure a $CD4^+CD25^+$ Treg cell (e.g., $CD4^+CD25+Foxp3^+$ Treg cell) count, $T_h1$ cell count, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, and 8-iso-prostaglandin $F_{2\alpha}$ (8-iso-PGF$_{2\alpha}$) level. Stool sample analyses may be performed to measure an IgA level, calprotectin level, lipocalin-2 level, and short chain fatty acids level. Urine sample analysis may be performed to measure an indoxyl sulfate level.

The term "carboxylate," as used herein, represents group —COOH or a salt thereof.

The term "carotenoid," as used herein, represents a compound of formula:

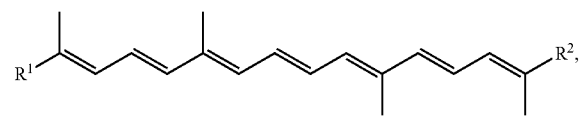

where
R$^1$ is

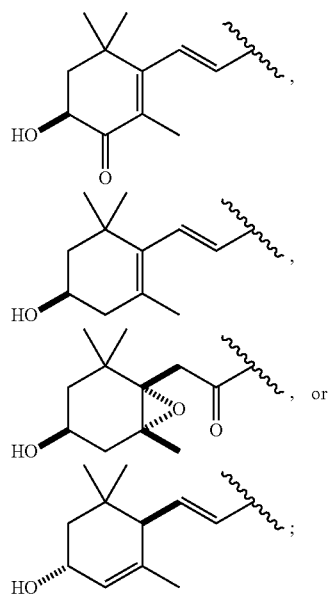

and

R² is

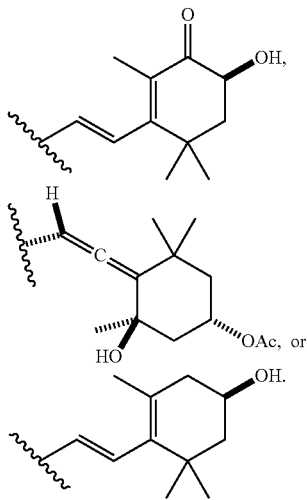

Non-limiting examples of the carotenoid include:

When the carotenoid is acylated, one or both of the hydroxyl groups in the carotenoid is independently substituted with a group containing a fatty acid acyl or a group containing a ketone body or pre-ketone body.

The term "catechin polyphenol," as used herein, refers to a compound of formula:

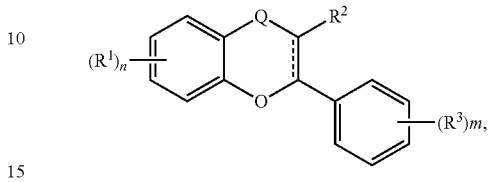

where

⫴ is a single carbon-carbon bond or double carbon-carbon bond;

Q is —CH$_2$— or —C(O)—;

each R$^1$ and each R$^3$ is independently H, halogen, —OR$^A$, phosphate, or sulfate;

R$^2$ is H or —OR$^A$;

each R$^A$ is independently H, optionally substituted alkyl, a monosaccharide, a sugar acid, or benzoyl optionally sub-

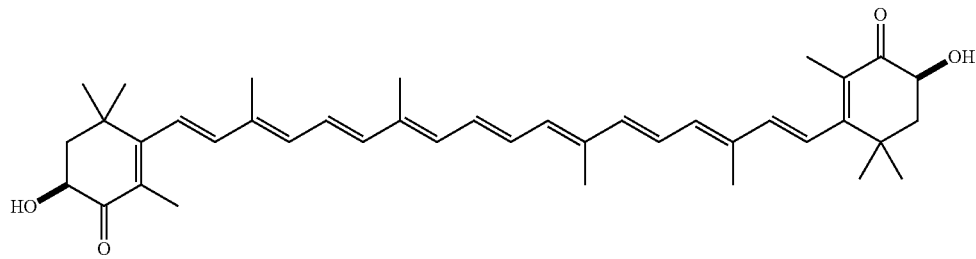

astaxanthin

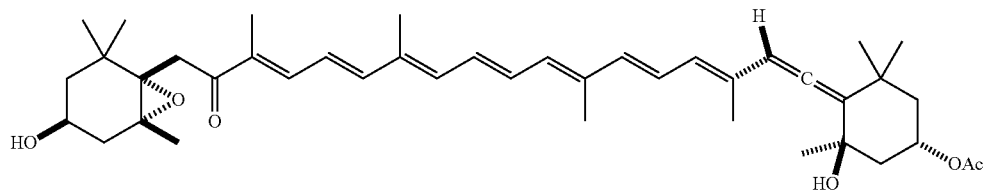

fucoxanthin

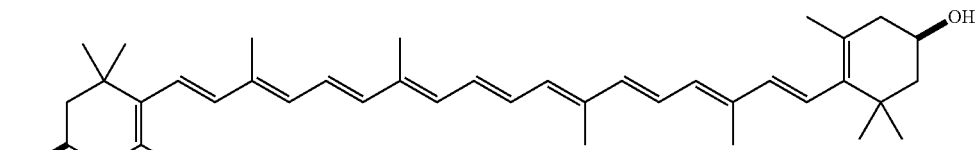

zeaxanthin

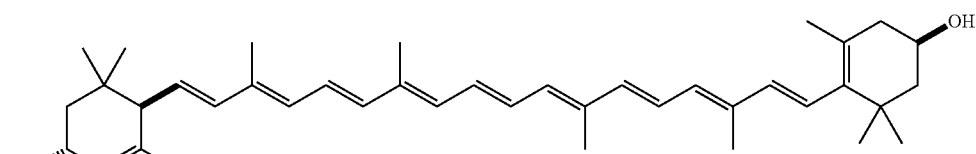

lutein stituted with 1, 2, 3, or 4 substituents independently selected from the group consisting of H, hydroxy, halogen, optionally substituted alkyl, optionally substituted alkoxy, monosaccharide, sugar acid, phosphate, and sulfate; and each of n and m is independently 1, 2, 3, or 4.

Non-limiting examples of catechin polyphenols include epigallocatechin gallate, quercetin, or myricetin. Preferably, the catechin polyphenol is quercetin. When a catechin polyphenol is acylated, one or more of the hydroxyl groups in the catechin polyphenol are independently substituted with a group containing a fatty acid, a group containing a ketone body or pre-ketone body, or a group containing an amino acid metabolite.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "cycloalkylene," as used herein, represents a divalent group that is a cycloalkyl group, in which one hydrogen atom is replaced with a valency. An optionally substituted cycloalkylene is a cycloalkylene that is optionally substituted as described herein for cycloalkyl.

The term "cycloalkoxy," as used herein, represents a group —OR, where R is cycloalkyl. An optionally substituted cycloalkoxy is cycloalkoxy that is optionally substituted as described herein for cycloalkyl.

The term "dialkylamino," as used herein, refers to a group —$NR_2$, where each R is independently alkyl.

The terms "ellagic acid" and "ellagic acid analogue," as used herein, collectively refer to a compound of the structure:

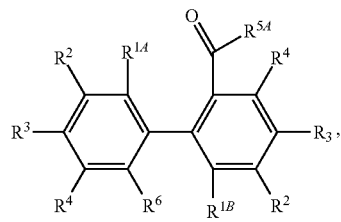

where
each of $R^2$, $R^3$, and $R^4$ is independently H or —$OR^A$;
$R^6$ is H or —(CO)—$R^{5B}$;
$R^{1A}$ is H or —$OR^A$, and $R^{5A}$ is —OH or —$OR^A$; or $R^{1A}$ and $R^{5A}$ combine to form —O—;
$R^{1B}$ is H or —$OR^A$, and $R^{5B}$ is absent, —OH, or —$OR^A$; or $R^{1B}$ and $R^{5B}$ combine to form —O—;
each $R^A$ is independently H or O-protecting group.

When the ellagic acid or its analogue is present in an acylated ellagic acid or an acylated ellagic acid analogue, from one to all hydroxyls in the ellagic acid or its analogue are substituted with a group containing a fatty acid, a group containing a ketone body or pre-ketone body, or a group containing an amino acid metabolite. The term "ellagic acid analogue," refers to the compounds and groups of the above structure that are not ellagic acid. The term "ellagic acid" refers to the following two compounds:

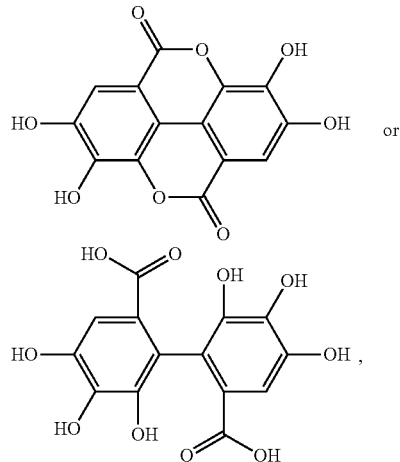

or these compounds within the structure of an acylated ellagic acid.

Non-limiting examples of ellagic acid analogues include urolithin A, urolithin B, urolithin C, urolithin D, urolithin E, and urolithin M5.

The term "ester bond," as used herein, refers to a covalent bond between an alcohol or phenolic oxygen atom and a carbonyl group that is further bonded to a carbon atom.

The term "fatty acid," as used herein, refers to a short-chain fatty acid, a medium chain fatty acid, a long chain fatty acid, a very long chain fatty acid, or an unsaturated analogue thereof, or a phenyl-substituted analogue thereof. Short chain fatty acids contain from 1 to 6 carbon atoms, medium chain fatty acids contain from 7 to 13 carbon atoms, and a long-chain fatty acids contain from 14 to 22 carbon atoms.

A fatty acid may be saturated or unsaturated. An unsaturated fatty acid includes 1, 2, 3, 4, 5, or 6 carbon-carbon double bonds. Preferably, the carbon-carbon double bonds in unsaturated fatty acids have Z stereochemistry.

The term "fatty acid acyl," as used herein, refers to a fatty acid, in which the hydroxyl group is replaced with a valency.

The term "fatty acid acyloxy," as used herein, refers to group —OR, where R is a fatty acid acyl.

The term "a group containing an amino acid metabolite," as used herein, represents a monovalent substituent including at least one amino acid metabolite within its structure and having the valency on a carbon atom of a carbonyl group or on an anomeric carbon atom. A group containing an amino acid metabolite bonds to a core through a carbonate linker, carbamate linker, ester bond, glycosidic bond, or amide bond. A group containing an amino acid metabolite may be a group selected from the group consisting of monosaccharide, ketone body, pre-ketone body, aldonyl, uronyl, ulosonyl, and amino acid metabolite acyl, and where each hydroxyl in the monosaccharide, ketone body, pre-ketone body, aldonyl, uronyl, and ulosonyl is optionally and independently substituted with an amino acid metabolite acyl.

The term "group containing a fatty acid," as used herein, represents a monovalent substituent including at least one fatty acid within its structure and having the valency on a carbon atom of a carbonyl group or on an anomeric carbon atom. A group containing a fatty acid bonds to a core through a carbonate linker, carbamate linker, ester bond, glycosidic bond, or amide bond. A group containing a fatty acid may be a group selected from the group consisting of monosaccharide, ketone body, pre-ketone body, aldonyl, uronyl, ulosonyl, and fatty acid acyl, and where each hydroxyl in the monosaccharide, ketone body, pre-ketone body, aldonyl, uronyl, and ulosonyl is optionally and independently substituted with a fatty acid acyl.

The term "group containing a ketone body or pre-ketone body," as used herein, represents a monovalent substituent including at least one ketone body and/or at least one pre-ketone body within its structure and having the valency on a carbon atom of a carbonyl group or on an anomeric carbon atom. A group containing a ketone body or pre-ketone body bonds to a core through a carbonate linker, ester bond, or glycosidic bond. A group containing a ketone body or pre-ketone body may be a group selected from the group consisting of monosaccharide, ketone body, aldonyl, uronyl, ulosonyl, and —C(O)—R, where R is a pre-ketone body or ketone body, and where each hydroxyl in the monosaccharide, ketone body, pre-ketone body, aldonyl, uronyl, and ulosonyl is optionally and independently substituted with an acyl or ketone body, a hydroxyl group in which, if present, is optionally substituted with an acyl.

The term "halogen," as used herein, represents a halogen selected from bromine, chlorine, iodine, and fluorine.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, or four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkenyl; alkoxy; acyloxy; aryloxy; alkylsulfenyl; alkylsulfinyl; alkylsulfonyl; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl. Each of the substituents may itself be unsubstituted or substituted with unsubstituted substituent(s) defined herein for each respective group.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl;

alkenyl; alkoxy; acyloxy; alkylsulfenyl; alkylsulfinyl; alkylsulfonyl; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; =S; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as the described for heterocyclyl and alkyl, respectively.

The term "heterocyclylene," as used herein, represents a heterocyclyl, in which one hydrogen atom is replaced with a valency. An optionally substituted heterocyclylene is a heterocyclylene that is optionally substituted as described herein for heterocyclyl.

The term "heterocyclyloxy," as used herein, refers to a structure —OR, in which R is heterocyclyl. Heterocyclyloxy can be optionally substituted as described for heterocyclyl.

The term "hydroxybenzoic acid," as used herein, represents a compound of the following structure:

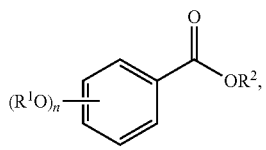

or a salt thereof,
where
n is 1, 2, or 3;
each R$^1$ is independently H or alkyl; and
R$^2$ is H or alkyl.

Non-limiting examples of hydroxybenzoic acids include salicylic acid and gallic acid.

The terms "hydroxyl" and "hydroxy," as used interchangeably herein, represent —OH.

The term "ketone body," as used herein, refers to (i) p-hydroxybutyric acid, or (ii) a group that is p-hydroxybutyric acid, where at least one hydroxyl hydrogen atom is replaced with a valency or a carboxylate —OH is replaced with a valency.

The term "ketone body acyl," as used herein, refers to a p-hydroxybutyric acid, in which the carboxylate —OH group is replaced with a valency.

The term "4-methyl-1,3-dioxan-2-yl," as used herein, refers to the monovalent group of formula:

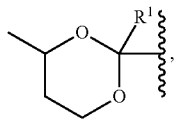

where R$^1$ is optionally substituted C-s alkyl (e.g., methyl).

The term "modulating," as used herein, refers to an observable change in the level of a marker in a subject, as measured using techniques and methods known in the art for the measurement of the marker. Modulating the marker level in a subject may result in a change of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In some embodiments, modulating is increasing the level of a marker in a subject. Increasing the marker level in a subject may result in an increase of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In other embodiments, modulating is decreasing the level of a marker in a subject. Decreasing the marker level in a subject may result in a decrease of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In embodiments in which a parameter is increased or decreased (or reduced) in a subject following a step of administering a composition described herein, the increase or decrease may take place and/or be detectable within a range of time following the administration (e.g., within six hours, 24 hours, 3 days, a week or longer), and may take place and/or be detectable after one or more administrations (e.g., after 2, 3, 4, 5, 6, 7, 8, 9, 10 or more administrations, e.g., as part of a dosing regimen for the subject).

The term "oxo," as used herein, represents a divalent oxygen atom (e.g., the structure of oxo may be shown as =O).

The term "phenolic oxygen atom," as used herein, refers to a divalent oxygen atom within the structure of a compound, where one valency of the phenolic oxygen atom is bonded to a first carbon atom, and another valency is bonded to a second carbon atom, where the first carbon atom is an sp$^2$-hybridized carbon atom within a benzene ring, and the second carbon atom is an sp$^3$-hybridized carbon atom or an sp$^2$-hybridized carbon atom.

The term "phosphate, as used herein, represents group —OPO(OH)$_2$ or a salt thereof.

The term "pre-ketone body," as used herein, represents (i) a ketone body having hydroxymethyl instead of a carboxylate, or (ii) a group that is a ketone body having hydroxymethyl instead of a carboxylate, where at least one hydroxyl is replaced with —OR, where R is a valency. A non-limiting example of a pre-ketone body is butane-1,3-diol or 4-hydroxybutan-2-one. The term "pre-ketone body," as used herein, also represents (4-methyl-1,3-dioxan-2-yl)-(alkylene)$_n$-CO—R$^A$, where n is 0 or 1, and R$^A$ is —OH, if the pre-ketone body is not part of an acylated active agent, or a valency if the pre-ketone body is part of a group including a pre-ketone body (e.g., a pre-ketone body acyl). A non-limiting example of a pre-ketone body is butane-1,3-diol or 4-hydroxybutan-2-one.

The term "pre-ketone body acyl," as used herein, refers to a pre-ketone body, in which the carboxylate —OH group is replaced with a valency.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3$^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifuoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "subject," as used herein, represents a human or non-human animal (e.g., a mammal) that is suffering from, or is at risk of, disease, disorder, or condition, as determined by a qualified professional (e.g., a doctor or a nurse practitioner) with or without known in the art laboratory test(s) of sample(s) from the subject. Non-limiting examples of diseases, disorders, and conditions include autoimmune disorders, as described herein.

The term "sugar acid," as used herein, refers to a monosaccharide, in the linear form of which, one or both terminal positions are oxidized to a carboxylic acid. There are four classes of sugar acids: aldonic acid, ulosonic acid, uronic acid, and aldaric acid. Any of the four sugar acid classes may be used in acylated active agent disclosed herein. Non-limiting examples of sugar acids include gluconic acid.

The term "sulfate," as used herein, represents group —OSO$_3$H or a salt thereof.

The term "thioalkenyl," as used herein, represents a group —SR, where R is alkenyl. An optionally substituted thioalkenyl is thioalkenyl that is optionally substituted as described herein for alkenyl.

The term "thioalkyl," as used herein, represents a group —SR, where R is alkyl. An optionally substituted thioalkyl is thioalkyl that is optionally substituted as described herein for alkyl.

The term "thioaryl," as used herein, represents a group —SR, where R is aryl. An optionally substituted thioaryl is thioaryl that is optionally substituted as described herein for aryl.

"Treatment" and "treating," as used herein, refer to the medical management of a subject with the intent to improve, ameliorate, stabilize, prevent or cure a disease, disorder, or condition. This term includes active treatment (treatment directed to improve the disease, disorder, or condition); causal treatment (treatment directed to the cause of the associated disease, disorder, or condition); palliative treatment (treatment designed for the relief of symptoms of the disease, disorder, or condition); preventative treatment (treatment directed to minimizing or partially or completely inhibiting the development of the associated disease, disorder, or condition); and supportive treatment (treatment employed to supplement another therapy).

The term "ulosonyl," as used herein, refers to a monovalent substituent that is a ulosonic acid in which a carboxylate hydroxyl is replaced with a valency.

The term "uronyl," as used herein, refers to a monovalent substituent that is a uronic acid in which a carboxylate hydroxyl is replaced with a valency.

The compounds described herein, unless otherwise noted, encompass isotopically enriched compounds (e.g., deuterated compounds), tautomers, and all stereoisomers and conformers (e.g. enantiomers, diastereomers, E/Z isomers, atropisomers, etc.), as well as racemates thereof and mixtures of different proportions of enantiomers or diastereomers, or mixtures of any of the foregoing forms as well as salts (e.g., pharmaceutically acceptable salts).

DETAILED DESCRIPTION

Figure 1:
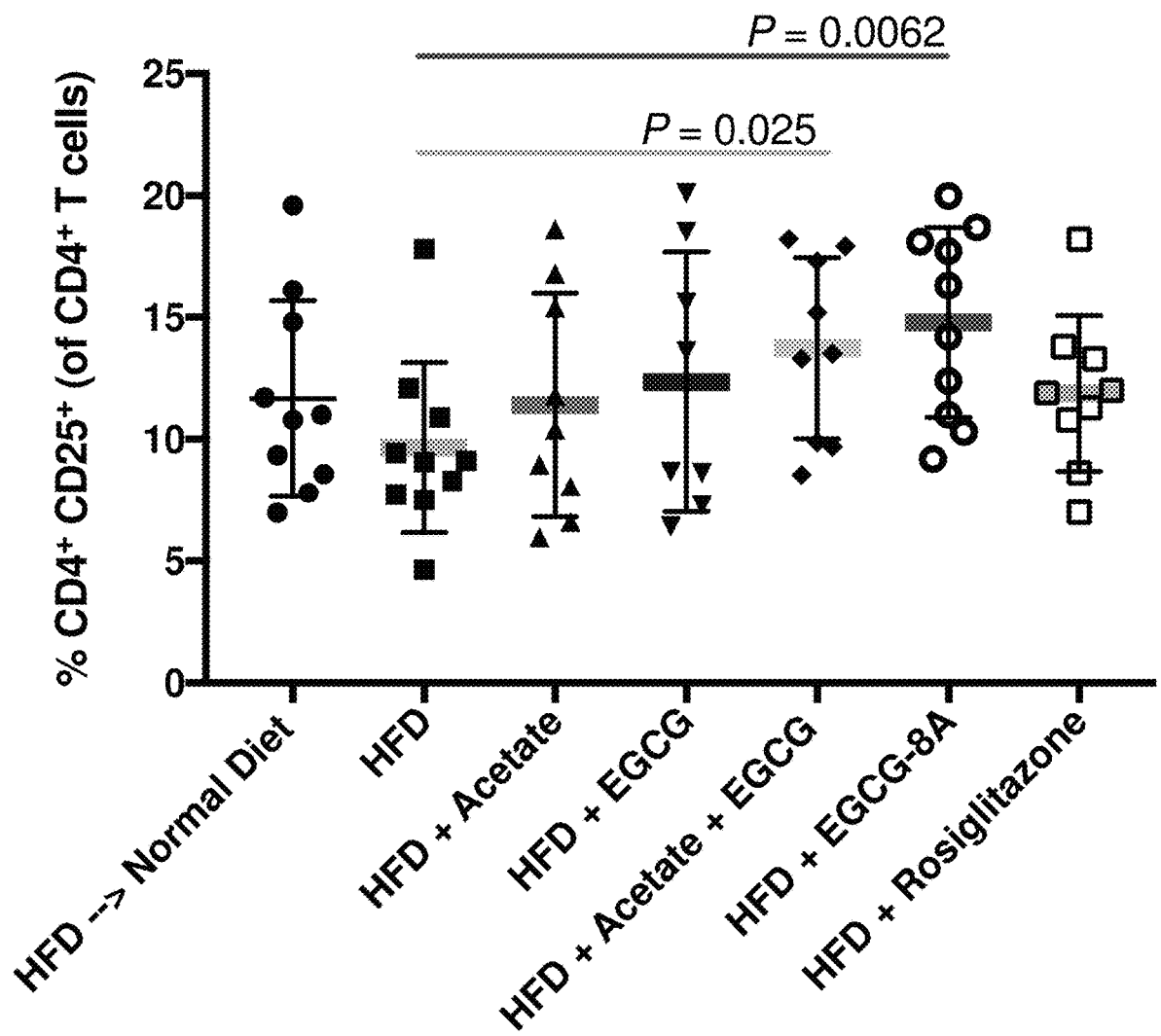
FIG. 1 is a chart showing the CD4$^+$CD25+ cell counts as a percentage of all CD4$^+$ T cells in seven animal cohorts: (1) untreated animals receiving a normal diet, (2) untreated animals receiving a high-fat diet, (3) animals receiving acetate along with a high-fat diet, (4) animals receiving epigallocatechin gallate (EGCG) along with a high-fat diet, (5) animals receiving epigallocatechin gallate (EGCG) and acetate as different compounds along with a high-fat diet, (6) animals receiving epigallocatechin gallate octaacetate (EGCG-8A) along with a high-fat diet, and (7) animals receiving rosiglitazone along with a high-fat diet.

The invention provides acylated active agents (e.g., acylated catechin polyphenols, acylated carotenoids, acylated mesalamines, acylated sugars, acylated hydroxybenzoic acids, acylated ellagic acid, acylated ellagic acid analogues, and acylated shikimic acids) and methods for modulating an autoimmunity marker in a subject. Without wishing to be bound by theory, the disclosed acylated active agents are believed to act in concert with, or in lieu of, the microbiota of a subject to modulate, for example, the host's immune system.

It has been surprisingly found that administration of an acylated active agent (e.g., acylated catechin polyphenol (e.g., epigallocatechin-3-gallate octaacetate)) to a subject can induce Treg differentiation (e.g., CD4$^+$CD25$^+$ Treg differentiation) and thus can produce beneficial effects in subjects having an autoimmune disorder.

The components of the acylated active agent (e.g., acylated catechin polyphenol (e.g., short chain fatty acid acyls (e.g., acetyl) and epigallocatechin gallate)) may act synergistically to modulate an autoimmunity marker, e.g., upon hydrolysis in the GI tract of the subject receiving the acylated catechin polyphenol. The components of the acylated catechin polyphenol (e.g., short chain fatty acid acyls (e.g., acetyl) and epigallocatechin gallate) may act synergistically to treat an autoimmune disorder, e.g., upon hydrolysis in the GI tract of the subject receiving the acylated catechin polyphenol.

Advantageously, acylated active agents (e.g., acylated catechin polyphenols) disclosed herein may have superior organoleptic properties (e.g., palatability). This provides an important advantage as the individual components (e.g., acetic acid or epigallocatechin gallate) may exhibit less desirable organoleptic properties (e.g., palatability). Improved organoleptic properties facilitate oral administration, and are particularly advantageous for delivery of high unit dosages (e.g., unit dosages of 0.5 g or higher).

Acylated Active Agents

An acylated active agent disclosed herein may be an acylated catechin polyphenol, acylated carotenoid, acylated mesalamine, acylated shikimic acid, acylated sugar, acylated ellagic acid, acylated ellagic acid analogue, or acylated hydroxybenzoic acid.

Typically, an acylated active agent includes a core of formula (A) (e.g., a catechin polyphenol core) linked to at least one group (e.g., a group containing a fatty acid, a group containing a ketone body or pre-ketone body, or a group containing an amino acid metabolite) through ester bond(s), amide bond(s), carbonate linker(s), carbamate linker(s), and/or glycosidic bond(s). For example, an acylated active agent may include a catechin polyphenol substituted with one or more substituents independently selected from the group consisting of an alkyl, acyl, group containing a fatty acid (e.g., a short chain fatty acid or a medium chain fatty acid), group containing a ketone body or pre-ketone body, and group containing an amino acid metabolite. The fatty acid may be, e.g., a short chain fatty acid (e.g., acetyl, propionyl, or butyryl). In some embodiments, the short chain fatty acid is acetyl. In particular embodiments, the short chain fatty acid is butyryl.

An acylated active agent disclosed herein may include, e.g., at least one group containing a fatty acid, group containing a ketone body or pre-ketone body, or group containing an amino acid metabolite.

A group containing a fatty acid may be, e.g., a fatty acid acyl (e.g., short chain fatty acid or medium chain fatty acid), a monosaccharide having one or more hydroxyl groups substituted with fatty acid acyls (e.g., short chain fatty acid acyls or medium chain fatty acid acyls), or a sugar acid (e.g., aldonic acid) having one or more alcohol hydroxyl groups substituted with fatty acid acyls (e.g., short chain fatty acid acyls or medium chain fatty acid acyls). A monosaccharides may be, e.g., arabinose, xylose, fructose, galactose, glucose, glucosinolate, ribose, tagatose, fucose, or rhamnose. In some embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). The group containing a fatty acid may be, e.g., a fatty acid acyl.

A group containing an amino acid metabolite may be, e.g., an amino acid metabolite acyl (e.g., indole-3-acetyl, indole-3-acryloyl, or indole-3-pyruvyl), a monosaccharide having one or more hydroxyl groups substituted with amino acid metabolite acyls (e.g., indole-3-acetyl, indole-3-acryloyl, or indole-3-pyruvyl), or a sugar acid (e.g., aldonic acid) having one or more alcohol hydroxyl groups substituted with amino acid metabolite acyls (e.g., indole-3-acetyl, indole-3-acryloyl, or indole-3-pyruvyl). A monosaccharide may be, e.g., arabinose, xylose, fructose, galactose, glucose, glucosinolate, ribose, tagatose, fucose, or rhamnose. In some embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). The group containing an amino acid metabolite may be, e.g., an amino acid metabolite acyl.

A group containing a ketone body or pre-ketone body may be, e.g., a ketone body acyl (e.g., β-hydroxybutyrate acyl), a pre-ketone body acyl, a monosaccharide having one or more hydroxyl groups substituted with ketone body acyls (e.g., β-hydroxybutyrate acyl) and/or pre-ketone body acyls, or a sugar acid (e.g., aldonic acid) having one or more alcohol hydroxyl groups substituted with ketone body acyls (e.g., β-hydroxybutyrate acyl) and/or pre-ketone body acyls. A monosaccharide may be, e.g., arabinose, xylose, fructose, galactose, glucose, glucosinolate, ribose, tagatose, fucose, or rhamnose. In some embodiments, the monosaccharide is L-arabinose, D-xylose, fructose, galactose, D-glucose, glucosinolate, D-ribose, D-tagatose, L-fucose, or L-rhamnose (e.g., the monosaccharide is D-xylose). The group containing a ketone body or pre-ketone body may be, e.g., a ketone body acyl or a pre-ketone body acyl. Preferably, the group containing a ketone body or pre-ketone body is a group containing a ketone body (e.g., a group containing β-hydroxybutyrate).

In certain embodiments, the group may be a monovalent group of the following formula:

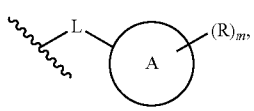

(B)

where

L is absent, carbamate linker, or carbonate linker;

group A is a fatty acid acyl, ketone body, pre-ketone body, amino acid metabolite acyl, monosaccharide, or sugar acid;

each R is independently ketone body optionally having a hydroxyl group that is optionally substituted with an acyl (e.g., a fatty acid acyl), pre-ketone body optionally having a hydroxyl group that is optionally substituted with an acyl (e.g., a fatty acid acyl), or acyl (e.g., a fatty acid acyl, a ketone body acyl, a pre-ketone body acyl, or an amino acid metabolite acyl); and m is an integer from 0 to the total number of available hydroxyl groups in group A (e.g., 1, 2, 3, 4, or 5);

provided that

L is a carbonate linker or carbamate linker, if group A has a valency on a non-glycosidic alcohol oxygen atom; and L is absent, if group A has a valency on a carbonyl carbon atom.

In certain embodiments, the group of formula (B) includes at least one fatty acid acyl and/or at least one ketone body and/or at least one pre-ketone body and/or at least one amino acid metabolite.

In some embodiments, the fatty acid(s) are short chain fatty acid acyls (e.g., butyryls). In particular embodiments, the fatty acid(s) in the group containing a fatty acid are medium chain fatty acid acyls (e.g., octanoyl).

Non-limiting examples of the groups are:

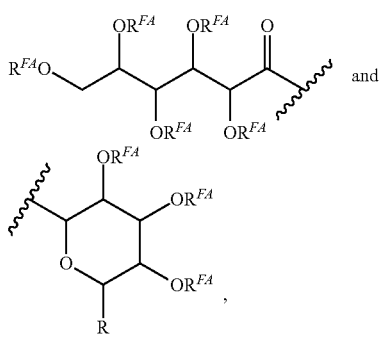

where

R is H, —CH$_3$, or —CH$_2$OR$^{FA}$; and each R$^{FA}$ is independently H, a fatty acid acyl (e.g., a short chain fatty acid acyl or medium chain fatty acid acyl), a ketone body acyl (e.g., p-hydroxybutyrate acyl), a pre-ketone body acyl, or an amino acid metabolite acyl (e.g., indole-3-acetyl, indole-3-acyloyl, or indole-3-pyruvyl).

Acylated Catechin Polyphenols

An acylated catechin polyphenol of the invention may be a substituted compound having the core of formula (A):

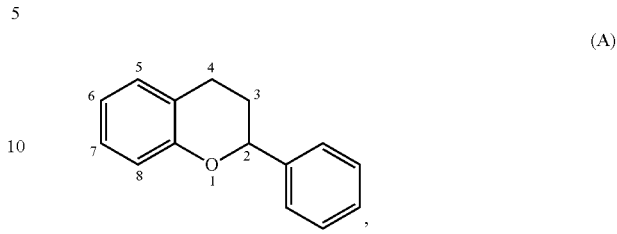

(A)

or a multimer thereof, or a salt thereof, where the substituents are independently selected from the group consisting of —OR$^A$, —OCOO—R$^A$, —NHR$^B$, oxo, halogen, optionally substituted C$_{1-20}$ alkyl, optionally substituted C$_{2-20}$ alkenyl, optionally substituted thioalkyl, optionally substituted alkylsulfonyl, optionally substituted alkylsulfenyl, optionally substituted alkylsulfinyl, optionally substituted thioaryl, optionally substituted aryl thioalkyl, optionally substituted thioalkenyl, dialkylamino, sulfate, phosphate, ascorbic acid, optionally substituted heterocyclyl, nitro, amino acids, C$_{1-6}$ esters of amino acids, optionally acylated monosaccharide, and optionally acylated sugar acid, where each R$^A$ is independently H, optionally substituted alkyl, a group containing a fatty acid, a group containing a ketone body or pre-ketone body, a group containing an amino acid metabolite, or benzoyl optionally substituted with one, two, three, or four substituents independently selected from the group consisting of H, hydroxyl, halogen, a group containing a fatty acid, a group containing a ketone body or pre-ketone body, a group containing an amino acid metabolite, optionally substituted alkoxy, and optionally substituted alkyl, and where R$^B$ is independently H or optionally substituted alkyl;

where the carbon-carbon bond connecting carbon 2 and carbon 3 in formula (A) is a single bond or a double bond;

where the multimer includes a total of 2 or 3 cores of formula (A), each core substituted independently as described above; and where two vicinal centers in core (A) may be further substituted with a group —(O)$_q$-L-L$^2$-, where q is 0 or 1, L$^1$ is optionally substituted alkylene, optionally substituted alkenylene, or optionally substituted heterocyclylene; and L$^2$ is a covalent bond, optionally substituted heterocyclylene, or optionally substituted cycloalkylene.

In some embodiments, at least one of positions 5, 6, 7, and 8 is —OR$^A$, where R$^A$ is a group containing a fatty acid, group containing a ketone body or pre-ketone body, group containing an amino acid metabolite, or benzoyl optionally substituted with one, two, three, or four substituents independently selected from the group consisting of H, hydroxyl, halogen, a group containing a fatty acid, group containing a ketone body or pre-ketone body, group containing an amino acid metabolite, optionally substituted alkoxy, and optionally substituted alkyl. In some embodiments, the compound of formula (A) includes at least one group containing a fatty acid. In some embodiments, the compound of formula (A) includes at least one group containing a ketone body or pre-ketone body. In some embodiments, the compound of formula (A) includes at least one group containing an amino acid metabolite.

An acylated catechin polyphenol of the invention may be a catechin polyphenol, in which one or more hydroxyl groups are independently replaced with —OR, where each R is independently selected from the group consisting of an acyl, alkyl, group containing a fatty acid, group containing a ketone body or pre-ketone body, and group containing an amino acid metabolite. In some embodiments, at least one R is a group containing a fatty acid. In some embodiments, at least one R is a group containing a ketone body or pre-ketone body. In some embodiments, at least one R is a group containing an amino acid metabolite.

An acylated catechin polyphenol may be a compound of formula (I):

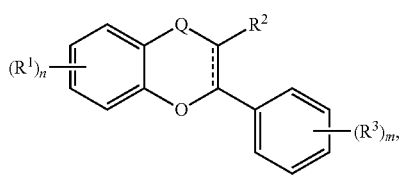

(I)

or a pharmaceutically acceptable salt thereof,
where

┤ is a single carbon-carbon bond or double carbon-carbon bond;

Q is —CH$_2$— or —C(O)—;

each R$^1$ and each R$^3$ is independently H, halogen, —OR$^4$, phosphate, or sulfate;

R$^2$ is H or —OR$^4$;

each R$^4$ is independently H, optionally substituted alkyl, a monosaccharide, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate; and each of n and m is independently 0, 1, 2, 3, or 4.

In some embodiments, the compound includes at least one group containing a fatty acid. In particular embodiments, at least one R$^1$ is —OR$^4$, in which R$^4$ is a group containing a fatty acid, a group containing a ketone body or pre-ketone body, or a group containing an amino acid metabolite.

In particular embodiments, ┤ is a single carbon-carbon bond. In certain embodiments, Q is —CH$_2$—.

In some embodiments, the acylated catechin polyphenol is of formula (I-a):

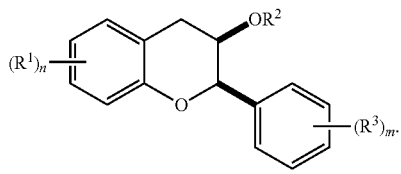

(I-a)

In certain embodiments, the acylated catechin polyphenol is of formula (I-b):

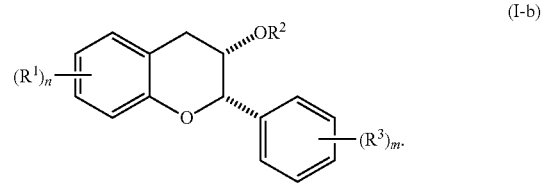

(I-b)

In particular embodiments, the acylated catechin polyphenol is of formula (I-c):

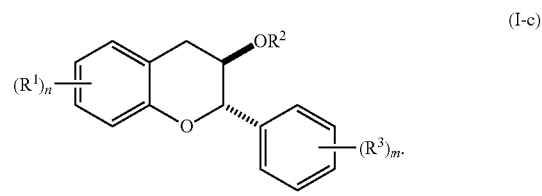

(I-c)

In further embodiments, the acylated catechin polyphenol is of formula (I-d):

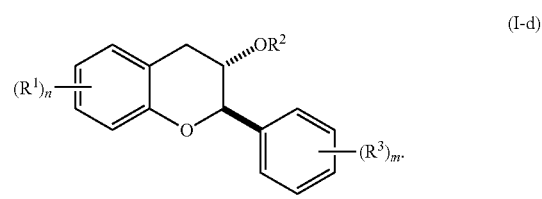

(I-d)

In certain embodiments, the acylated catechin polyphenol is a compound of formula (I-f):

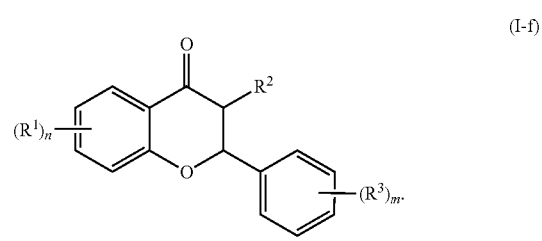

(I-f)

In still further embodiments, n is 2. In certain embodiments, m is 1. In particular embodiments, m is 2. In some embodiments, m is 3. In particular embodiments, each R$^1$ is independently —OR$^4$. In certain embodiments, each R$^3$ is independently H or —OR$^4$. In further embodiments, R$^2$ is H or —OR$^4$. In yet further embodiments, each R$^4$ is independently H, optionally substituted alkyl, a group containing a fatty acid, a group containing a ketone body or pre-ketone body, or a group containing an amino acid metabolite.

In some embodiments, $R^2$ is a group of formula:

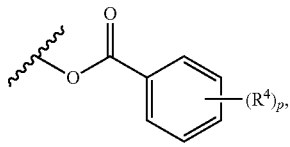

where p is 1, 2, 3, or 4, and each $R^4$ is independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate.

In certain embodiments, p is 3. In particular embodiments, $R^4$ is independently H, hydroxy, halogen, a group containing a fatty acid, a group containing a ketone body or pre-ketone body, a group containing an amino acid metabolite, or an optionally substituted alkoxy.

In some embodiments, the acylated catechin polyphenol is of formula (I-e):

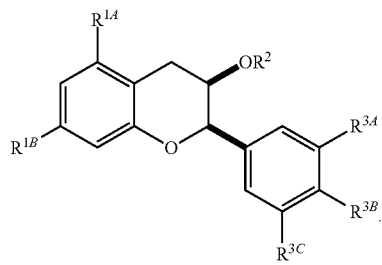

In certain embodiments, each of $R^{1A}$ and $R^{1B}$ is independently —$OR^4$. In particular embodiments, each of $R^{3A}$, $R^{3B}$, and $R^{3C}$ is independently H, halogen, or —$OR^4$.

In further embodiments, $R^2$ is a group of formula:

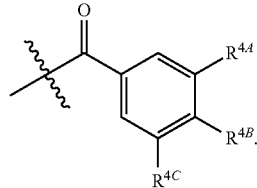

In yet further embodiments, $R^4$, $R^{4B}$, and $R^{4C}$ is independently H, hydroxy, halogen, a group containing a fatty acid, a group containing a ketone body or pre-ketone body, a group containing an amino acid metabolite, or an optionally substituted alkoxy.

In some embodiments, each $R^4$ is independently H, optionally substituted alkyl, fatty acid acyl, or optionally acylated monosaccharide.

In certain embodiments, the acylated catechin polyphenol includes at least one fatty acid acyl (e.g., a short chain fatty acid acyl (e.g., the short chain fatty acid acyl is acetyl, propionyl, or butyryl)).

In some embodiments, the acylated catechin polyphenol is compound 5.

Acylated Mesalamines

An acylated mesalamine of the invention may be a mesalamine, in which one or more of —$NH_2$, —OH, or —COOH is replaced with an acyl, a group containing a fatty acid, a group containing a ketone body or pre-ketone body, or a group containing an amino acid metabolite. An acylated mesalamine contains at least one group containing a fatty acid, group containing a ketone body or pre-ketone body, or group containing an amino acid metabolite. A group containing a fatty acid, ketone body or pre-ketone body, or an amino acid metabolite is bonded to mesalamine through a glycosidic bond, ester bond, amide bond, carbonate linker, or carbamate linker. In some embodiments, a group containing a fatty acid is bonded to mesalamine through a glycosidic bond. In some embodiments, acylated mesalamine is a compound of formula (II):

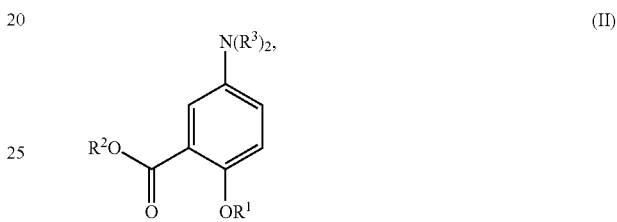

where $R^1$ is H, alkyl, acyl, a group containing a fatty acid, a group containing a ketone body or pre-ketone body, or a group containing an amino acid metabolite;

$R^2$ is H, alkyl, a group containing a fatty acid, a group containing a ketone body or pre-ketone body, or a group containing an amino acid metabolite; and each $R^3$ is independently H, alkyl, acyl, a group containing a fatty acid, a group containing a ketone body or pre-ketone body, or a group containing an amino acid metabolite; or both $R^2$ groups combine to form:

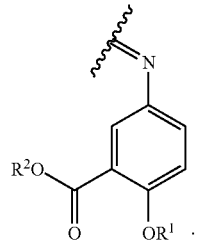

The acylated mesalamine includes at least one group containing a fatty acid, at least one group containing a ketone body or pre-ketone body, or at least one group containing an amino acid metabolite.

In some embodiments, the acylated mesalamine is compound 44.

Acylated Shikimic Acid

An acylated active agent may be, e.g., an acylated shikimic acid of the following structure:

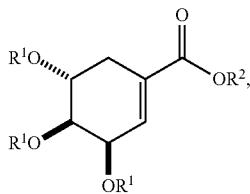

or a salt thereof,
where
each $R^1$ is independently H, acyl, alkyl, a group containing a fatty acid, a group containing a ketone body or pre-ketone body, or a group containing an amino acid metabolite; and $R^2$ is H, alkyl, a group containing a fatty acid, a group containing a ketone body or pre-ketone body, or a group containing an amino acid metabolite;

provided that the compound includes at least one group containing a fatty acid, group containing a ketone body or pre-ketone body, or group containing an amino acid metabolite.

Acylated Carotenoids

An acylated active agent may be, e.g., an acylated carotenoid. Acylated carotenoids are carotenoids, in which at least one hydroxyl group is replaced with a substituent —OR, where each R is independently selected from the group consisting of an acyl, alkyl, a group containing a fatty acid, a group containing a ketone body or pre-ketone body, and a group containing an amino acid metabolite, provided that at least one R is a group containing a fatty acid, a group containing a ketone body or pre-ketone body, or a group containing an amino acid metabolite. Non-limiting examples of an acylated carotenoid include astaxanthin having one or both hydroxyl groups independently substituted with an acyl, alkyl, group containing a fatty acid, or group containing a ketone body or pre-ketone body, provided that at least one hydroxyl is substituted with a group containing a fatty acid, a group containing a ketone body or pre-ketone body, or a group containing an amino acid metabolite Acylated Ellagic Acid and Acylated Ellagic Acid Analogues An acylated ellagic acid includes an ellagic acid core having one or more hydroxyls substituted with an acyl (e.g., a fatty acid acyl). An acylated ellagic acid analogue includes an ellagic acid analogue core having one or more hydroxyls substituted with an acyl (e.g., a fatty acid acyl).

An acylated ellagic acid is a compound of the following structures:

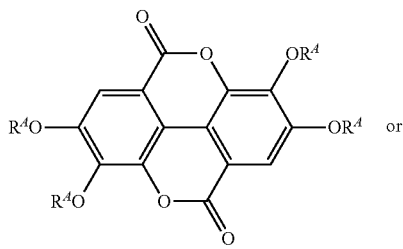

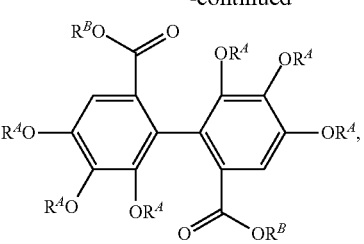

or a salt thereof,
where each $R^A$ is independently H, alkyl, acyl, a group containing a fatty acid, a group containing a ketone body or pre-ketone body, or a group containing an amino acid metabolite; and each $R^B$ is independently H, alkyl, a group containing a fatty acid, a group containing a ketone body or pre-ketone body, or a group containing an amino acid metabolite; provided that at least one $R^A$ and/or at least one $R^B$, when present, is a group containing a fatty acid, a group containing a ketone body or pre-ketone body, or a group containing an amino acid metabolite.

An acylated ellagic acid analogue is a compound of the following structure:

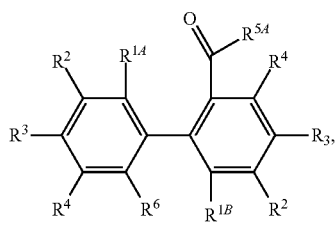

or a salt thereof,
where
each of $R^2$, $R^3$, and $R^4$ is independently H or —$OR^A$;
$R^6$ is H or —(CO)—$R^{58}$;
$R^{1A}$ is H or —$OR^A$, and $R^{5A}$ is —OH or —$OR^B$; or $R^{1A}$ and $R^{5A}$ combine to form —O—;
$R^{1B}$ is H or —$OR^A$, and $R^{5B}$ is absent, —OH, or —$OR^B$; or $R^{1B}$ and $R^{5B}$ combine to form —O— each $R^A$ is independently H, O-protecting group, alkyl, acyl, a group containing a fatty acid, a group containing a ketone body or pre-ketone body, or a group containing an amino acid metabolite;
each $R^B$ is independently H, O-protecting group, alkyl, a group containing a fatty acid, a group containing a ketone body or pre-ketone body, or a group containing an amino acid metabolite;
provided that at least one $R^A$ and/or at least one $R^B$ is a group containing a fatty acid, a group containing a ketone body or pre-ketone body, or a group containing an amino acid metabolite.

Non-limiting examples of ellagic acid analogues include urolithin A, urolithin B, urolithin C, urolithin D, urolithin E, and urolithin M5.

Acylated Hydroxybenzoic Acid

An acylated active agent may be, e.g., an acylated hydroxybenzoic acid of the following structure:

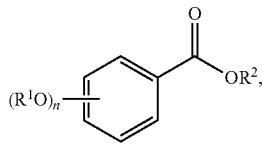

or a salt thereof,
where
n is 1, 2, or 3;
each R¹ is independently H, acyl, alkyl, a group containing a fatty acid, a group containing a ketone body or pre-ketone body, or a group containing an amino acid metabolite; and
R² is H, alkyl, a group containing a fatty acid, a group containing a ketone body or pre-ketone body, or a group containing an amino acid metabolite;
provided that the compound includes at least one group containing a fatty acid, group containing a ketone body or pre-ketone body, or group containing an amino acid metabolite.

Non-limiting examples of acylated hydroxybenzoic acids include salicylic acid, in which the phenolic hydroxyl is substituted with a group containing a fatty acid, group containing a ketone body or pre-ketone body, or group containing an amino acid metabolite; and gallic acid, in which one, two, or three phenolic hydroxyls are independently substituted with groups containing a fatty acid, group containing a ketone body or pre-ketone body, or group containing an amino acid metabolite.

Acylated Sugar

An acylated active agent may be, e.g., an acylated sugar. An acylated sugar is a monosaccharide having one or more hydroxyls substituted with alkyl, acyl, a group containing a fatty acid, a group containing a ketone body or pre-ketone body, or a group containing an amino acid metabolite. The monosaccharide is present in the pyranose or furanose form. Preferably, the monosaccharide is present in the pyranose form. The monosaccharide may be an aldose or ketose. Non-limiting examples of monosaccharides are arabinose, xylose, fructose, galactose, glucose, ribose, tagatose, fucose, and rhamnose. In some embodiments, the monosaccharide is L-arabinose, D-xylose, fructose, galactose, D-glucose, D-ribose, D-tagatose, L-fucose, or L-rhamnose. Preferably, the monosaccharide is xylose, arabinose, rhamnose, fucose, glucosamine, or tagatose. The monosaccharide may include an anomeric carbon bonded to —OR, where R is H, alkyl, acyl, a group containing a fatty acid, a group containing a ketone body or pre-ketone body, or a group containing an amino acid metabolite. Preferably, R is alkyl or a group containing a fatty acid.

Methods

Acylated active agents described herein may be used to treat an autoimmune disorder in a subject in need thereof.

Without wishing to be bound by theory, metabolic products of the microbiome can interact with the host immune system in several ways. The metabolites can have effects remote to the gastrointestinal tract, for example, through bidirectional interactions with the central nervous system. Examples include SCFA interacting with free fatty acid receptors. Short-chain fatty acids may impact autoimmunity by expanding regulatory T cells and by suppressing the JNK1/P38 pathway. An acylated active agent described herein can biodegrade, for example, in the distal small intestine or colon, thereby providing high levels of the active agent and fatty acids (e.g., short chain fatty acids) in the distal gut, where these compounds can interact with the immune system.

A method of treating an autoimmune disorder in a subject in need thereof may include administering an acylated active agent (e.g., a pharmaceutical or nutraceutical composition containing an acylated active agent) to the subject in need thereof.

In some embodiments, the components of the acylated active agent (e.g., short chain fatty acid acyls (e.g., acetyl) and epigallocatechin gallate) may act synergistically to treat an autoimmune disorder, e.g., upon hydrolysis in the GI tract of the subject receiving the acylated active agent.

Non-limiting examples of autoimmune disorders include an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, and granulomatosis with polyangiitis. In some embodiments, the autoimmune disorder is an inflammatory bowel disease (e.g., Crohn's disease or ulcerative colitis).

Additionally or alternatively, acylated active agents described herein may be used for modulating an autoimmunity marker in a subject in need thereof.

A method of modulating an autoimmunity marker in a subject in need thereof may include administering an acylated active agent (e.g., a pharmaceutical or nutraceutical composition containing an acylated active agent) to the subject in need thereof.

In some embodiments, the components of the acylated active agent (e.g., short chain fatty acid acyls (e.g., acetyl) and epigallocatechin gallate) may act synergistically to modulate an autoimmunity marker, e.g., upon hydrolysis in the GI tract of the subject receiving the acylated active agent.

Non-limiting examples of autoimmunity markers include markers for an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barré syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Ménière's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjögren's syndrome, stiff-man syndrome, Takayasu arteritis, giant cell arteritis, ulcerative colitis, uveitis, vasculitis, and granulomatosis with polyangiitis. In some embodiments, the autoimmune marker is a marker for an inflammatory bowel disease (e.g., Crohn's disease or ulcerative colitis).

The autoimmunity markers include, for example, a CYP1A1 mRNA level, intestinal motility, mucus secretion, $CD4^+CD25^+$ Treg cell (e.g., $CD4^+CD25+Foxp3^+$ Treg) count, T1 cell count, interleukin-8 (IL-8) level, macrophage inflammatory protein 1α (MIP-1α) level, macrophage inflammatory protein 1β (MIP-1p) level, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, 8-iso-prostaglandin $F_2a$ (8-iso-$PGF_{2\alpha}$) level, IgA level, calprotectin level, lipocalin-2 level, short chain fatty acids level, and indoxyl sulfate level.

The autoimmunity markers can be measured in a sample from a subject using methods known in the art. For example, $CD4^+CD25^+$ Treg cell (e.g., $CD4^+CD25+Foxp3^+$ Treg) count and T1 cell count are measured via routine blood test, followed by flow cytometry analysis of cell markers and/or cytokines (e.g., CD4, CD25, Foxp3, IFNγ, IL2, and/or IL4). NFκB and iNOS levels can be measured using routine blood tests. Stool sample analyses may be performed to measure an IgA level, calprotectin level, lipocalin-2 level, and short chain fatty acids level. Urine sample analysis may be performed to measure an indoxyl sulfate level. Mucus secretion can be assessed through biopsy or by analysis of fecal matter content. Mucus secretion can be measured using HT-29 cell counts or by measuring mucin gene expression in biopsy samples, e.g., by PCR (Recio, The impact of Food Bioactive on Health: In vitro and ex vivo models, Chapter 11, HT29 Cell line, (2015)). Intestinal motility can be assessed using gastrointestinal scintigrapghy (e.g., wireless pH and motility capsules) or by examining effect of a test article on its ability to improve transepithelial electrical resistance (TEER) in either a cell line (e.g., CACO-2) or on a co-culture complex system (e.g., MATEK epi-intestinal) (Kickman, J. Lab. Autom., 20:107-126, 2015). Gastrointestinal permeability can be measured using a dual sugar absorption test known in the art. For example, dual sugar absorption test involves administering a predetermined amount of a drink containing lactulose and mannitol, and measuring absorption of these two sugars over six hours. Abdominal pain is typically assessed by a survey. Gastrointestinal bleeding may be assessed by the presence or absence of blood in a stool sample from a subject. Gastrointestinal inflammation can be assessed by biopsy.

In some embodiments, upon administration to a subject in need thereof, an acylated active agent described herein increases an autoimmune marker, e.g., intestinal motility, $CD4^+CD25^+$ Treg cell count, short chain fatty acids level, or mucus secretion in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In some embodiments, upon administration to a subject in need thereof, an acylated active agent described herein increases an autoimmune marker, e.g., a CYP1A1 mRNA level in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In certain embodiments, upon administration to a subject in need thereof, an acylated active agent described herein decreases an autoimmune marker, e.g., iNOS, MMP9, IFNγ, IL17, ICAM, CXCL13, 8-iso-$PGF_{2\alpha}$ in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In certain embodiments, upon administration to a subject in need thereof, an acylated active agent described herein decreases an interleukin-8 (IL-8) level in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In certain embodiments, upon administration to a subject in need thereof, an acylated active agent described herein decreases a macrophage inflammatory protein 1α (MIP-1α) level in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In certain embodiments, upon administration to a subject in need thereof, an acylated active agent described herein decreases macrophage inflammatory protein 10 (MIP-10) level in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In further embodiments, upon administration to a subject in need thereof, an acylated active agent described herein modulates (increases or decreases) an autoimmune marker, e.g., T1 cell count in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). The $T_h1$ cell count increase or decrease may be desirable depending on the particular condition and its state. An attendant doctor or nurse practitioner can determine whether an increase or a decrease in the T1 cell count is desired.

In some embodiments, an acylated active agent described herein decreases gastrointestinal inflammation (upper intestine, cecum, ileum, colon, rectum) in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration)). In certain embodiments, an acylated active agent described herein decreases abdominal pain (e.g., incidence and/or intensity) in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In particular embodiments, an acylated active agent described herein decreases gastrointestinal permeability in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In further embodiments, an acylated active agent described herein increases intestinal motility or frequency of bowel movements in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In yet further embodiments, an acylated active agent described herein decreases intestinal motility or frequency of bowel movements in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In still further embodiments, an acylated active agent described herein decreases gastrointestinal bleeding in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration). In other embodiments, am acylated active agent described herein decreases or increases mucus secretion or improves mucosal health in a gastrointestinal cell, tissue or in a subject (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration).

Pharmaceutical and Nutraceutical Compositions

The acylated active agents disclosed herein may be formulated into pharmaceutical or nutraceutical compositions for administration to human subjects in a biologically compatible form suitable for administration in vivo. Pharmaceutical and nutraceutical compositions typically include an acylated active agent as described herein and a physiologically acceptable excipient (e.g., a pharmaceutically acceptable excipient).

The acylated active agents described herein can also be used in the form of the free acid/base, in the form of salts, zwitterions, or as solvates. All forms are within the scope of the invention. The acylated active agents, salts, zwitterions, solvates, or pharmaceutical or nutraceutical compositions thereof, may be administered to a subject in a variety of forms depending on the selected route of administration, as will be understood by those skilled in the art. The acylated active agents described herein may be administered, for example, by oral, parenteral, buccal, sublingual, nasal, rectal, patch, pump, or transdermal administration, and the pharmaceutical or nutraceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, an acylated active agent disclosed herein can be administered alone or in admixture with a pharmaceutical or nutraceutical carrier selected regarding the intended route of administration and standard pharmaceutical practice. Pharmaceutical and nutraceutical compositions for use in accordance with the present invention thus can be formulated in a conventional manner using one or more physiologically acceptable carriers comprising excipients and auxiliaries that facilitate processing of acylated active agents disclosed herein into preparations which can be used pharmaceutically.

This disclosure also includes pharmaceutical and nutraceutical compositions which can contain one or more physiologically acceptable carriers. In making the pharmaceutical or nutraceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives. Nutraceutical compositions may be administered enterally (e.g., orally). A nutraceutical composition may be a nutraceutical oral formulation (e.g., a tablet, powder, lozenge, sachet, cachet, elixir, suspension, emulsion, solution, syrup, or soft or hard gelatin capsule), food additive (e.g., a food additive as defined in 21 C.F.R. § 170.3), food product (e.g., food for special dietary use as defined in 21 C.F.R. § 105.3), or dietary supplement (e.g., where the active agent is a dietary ingredient (e.g., as defined in 21 U.S.C. § 321(ff))). Active agents can be used in nutraceutical applications and as food additive or food products. Non-limiting examples of compositions including an active agent of the invention are a bar, drink, shake, powder, additive, gel, or chew.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $21^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, $6^{th}$ Edition, Rowe et al., Eds., Pharmaceutical Press (2009).

These pharmaceutical and nutraceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, $21^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical and nutraceutical formulation. In preparing a formulation, the acylated active agents can be milled to provide the appropriate particle size prior to combining with the other ingredients. If the acylated active agent is substantially insoluble, it can be milled to a particle size of less than 200 mesh. If the acylated active agent is substantially water soluble, the particle size can be adjusted by milling to provide a substantially uniform distribution in the formulation, e.g., about 40 mesh.

Dosages

The dosage of the acylated active agent used in the methods described herein, or pharmaceutically acceptable salts or prodrugs thereof, or pharmaceutical or nutraceutical compositions thereof, can vary depending on many factors, e.g., the pharmacodynamic properties of the acylated active agent; the mode of administration; the age, health, and weight of the recipient; the nature and extent of the symptoms; the frequency of the treatment, and the type of concurrent treatment, if any; and the clearance rate of the acylated active agent in the subject to be treated. One of skill in the art can determine the appropriate dosage based on the above factors. The acylated active agents used in the methods described herein may be administered initially in a suitable dosage that may be adjusted as required, depending on the clinical response. In general, a suitable daily dose of an acylated active agent disclosed herein will be that amount of the acylated active agent that is the lowest dose effective to produce a therapeutic effect. Such an effective dose will generally depend upon the factors described above.

An acylated active agent disclosed herein may be administered to the subject in a single dose or in multiple doses. When multiple doses are administered, the doses may be separated from one another by, for example, 1-24 hours, 1-7 days, or 1-4 weeks. The acylated active agent may be administered according to a schedule, or the acylated active agent may be administered without a predetermined schedule. It is to be understood that, for any particular subject, specific dosage regimes should be adjusted over time according to the individual need and the professional judgment of the person administering or supervising the administration of the compositions.

The acylated active agents may be provided in a dosage form. In some embodiments, the unit dosage form may be an oral unit dosage form (e.g., a tablet, capsule, suspension, liquid solution, powder, crystals, lozenge, sachet, cachet, elixir, syrup, and the like) or a food product serving (e.g., the active agents may be included as food additives or dietary ingredients). In certain embodiments, the dosage form is designed for administration of at least one acylated active agent disclosed herein, where the total amount of an administered acylated active agent is from 0.1 g to 10 g (e.g., 0.5 g to 9 g, 0.5 g to 8 g, 0.5 g to 7 g, 0.5 g to 6 g, 0.5 g to 5 g, 0.5 g to 1 g, 0.5 g to 1.5 g, 0.5 g to 2 g, 0.5 g to 2.5 g, 1 g to 1.5 g, 1 g to 2 g, 1 g to 2.5 g, 1.5 g to 2 g, 1.5 g to 2.5 g, or 2 g to 2.5 g). In other embodiments, the acylated active agent is consumed at a rate of 0.1 g to 10 g per day (e.g., 0.5 g to 9 g, 0.5 g to 8 g, 0.5 g to 7 g, 0.5 g to 6 g, 0.5 g to 5 g, 0.5 g to 1 g per day, 0.5 g to 1.5 g per day, 0.5 g to 2 g per day, 0.5 g to 2.5 g per day, 1 g to 1.5 g per day, 1 g to 2 g per day, 1 g to 2.5 g per day, 1.5 g to 2 g per day, 1.5 g to 2.5 g per day, or 2 g to 2.5 g per day) or more. The attending physician ultimately will decide the appropriate amount and dosage regimen, an effective amount of the acylated active agent disclosed herein may be, for example, a total daily dosage of, e.g., between 0.5 g and 5 g (e.g., 0.5 to 2.5 g) of any of the acylated active agent described herein. Alternatively, the dosage amount can be calculated using the body weight of the subject. Preferably, when daily dosages exceed 5 g/day, the dosage of the acylated active agent may be divided across two or three daily administration events.

In the methods of the invention, the time period during which multiple doses of an acylated active agent disclosed herein are administered to a subject can vary. For example, in some embodiments doses of the acylated active agents are administered to a subject over a time period that is 1-7 days; 1-12 weeks; or 1-3 months. In other embodiments, the acylated active agents are administered to the subject over a time period that is, for example, 4-11 months or 1-30 years. In yet other embodiments, the acylated active agents disclosed herein are administered to a subject at the onset of symptoms. In any of these embodiments, the amount of the acylated active agent that is administered may vary during the time period of administration. When an acylated active agent is administered daily, administration may occur, for example, 1, 2, 3, or 4 times per day.

Formulations

An acylated active agent described herein may be administered to a subject with a pharmaceutically acceptable diluent, carrier, or excipient, in unit dosage form. Conventional pharmaceutical practice may be employed to provide suitable formulations or compositions to administer the acylated active agent to subjects suffering from a disorder. Administration may begin before the subject is symptomatic.

Exemplary routes of administration of the acylated active agents disclosed herein or pharmaceutical or nutraceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The acylated active agents desirably are administered with a physiologically acceptable carrier (e.g., a pharmaceutically acceptable carrier). Pharmaceutical formulations of the acylated active agents described herein formulated for treatment of the disorders described herein are also part of the present invention. In some preferred embodiments, the acylated active agents disclosed herein are administered to a subject orally. In other preferred embodiments, the acylated active agents disclosed herein are administered to a subject topically.

Formulations for Oral Administration

The pharmaceutical and nutraceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with physiologically acceptable excipients (e.g., pharmaceutically acceptable excipients). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other physiologically acceptable excipients (e.g., pharmaceutically acceptable excipients) can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of acylated active agents, or by incorporating the acylated active agent into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the acylated active agents and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical and nutraceutical vehicles.

Formulations for Buccal Administration

Dosages for buccal or sublingual administration typically are 0.1 to 500 mg per single dose as required. In practice, the physician determines the actual dosing regimen which is most suitable for an individual subject, and the dosage varies with the age, weight, and response of the particular subject. The above dosages are exemplary of the average case, but individual instances exist where higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a acylated active agent disclosed herein with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of acylated active agents disclosed herein. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. Nos. 5,112,598 and 5,556,611, each of which is herein incorporated by reference).

Formulations for Nasal or Inhalation Administration

The acylated active agents may also be formulated for nasal administration. Compositions for nasal administration also may conveniently be formulated as aerosols, drops, gels, and powders. The formulations may be provided in a single or multidose form. In the case of a dropper or pipette, dosing may be achieved by the subject administering an appropriate, predetermined volume of the solution or suspension. In the case of a spray, this may be achieved, for example, by means of a metering atomizing spray pump.

The acylated active agents may further be formulated for aerosol administration, particularly to the respiratory tract by inhalation and including intranasal administration. The acylated active agents for nasal or inhalation administration will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the acylated active agent in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The acylated active agents described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. For example, to prepare such a composition, the acylated active agents disclosed herein may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., an acylated active agent disclosed herein or a solution thereof);

(2) "Drug for Injection:" the drug substance (e.g., an acylated active agent disclosed herein) as a dry solid that will be combined with the appropriate sterile vehicle for parenteral administration as a drug injection;

(3) "Drug Injectable Emulsion:" a liquid preparation of the drug substance (e.g., an acylated active agent disclosed herein) that is dissolved or dispersed in a suitable emulsion medium;

(4) "Drug Injectable Suspension:" a liquid preparation of the drug substance (e.g., an acylated active agent disclosed herein) suspended in a suitable liquid medium; and (5) "Drug for Injectable Suspension:" the drug substance (e.g., an acylated active agent disclosed herein) as a dry solid that will be combined with the appropriate sterile vehicle for parenteral administration as a drug injectable suspension.

Exemplary formulations for parenteral administration include solutions of the acylated active agents prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 21$^{st}$ Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the acylated active agents or biologically active agents within acylated active agents. Other potentially useful parenteral delivery systems for acylated active agents include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the acylated active agent. Exemplary formulations for parenteral release of the acylated active agent include: aqueous solutions, powders for reconstitution, cosolvent solutions, oil/water emulsions, suspensions, oil-based solutions, liposomes, microspheres, and polymeric gels.

Preparation of Acylated Active Agents

Acylated active agents may be prepared using synthetic methods and reaction conditions known in the art. Optimum reaction conditions and reaction times may vary depending on the reactants used. Unless otherwise specified, solvents, temperatures, pressures, and other reaction conditions may be selected by one of ordinary skill in the art.

Ester Preparation Strategy #1 (Acylation)

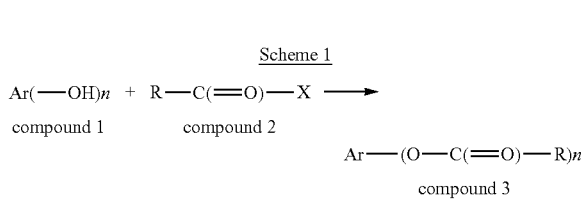

In Scheme 1, a polyphenolic compound, compound 1 where n represents an integer from 1 to 15, is treated with an acylating agent, compound 2, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents relative to compound 1.

The product, compound 3, can be purified by methods known to those of skill in the art.

Ester Preparation Strategy #2 (Acylation)

In some cases, the polyphenolic compound 1 may contain a functional group, Y, required to remain unreacted in the course of ester formation. In this case, it is appropriate to protect the functional group, Y, in the polyphenolic compound from acylation. This functional group may be an amino group or a hydroxyl group or other functionality with a labile hydrogen attached to a heteroatom. Such polyphenol esters can be prepared according to Scheme 2.

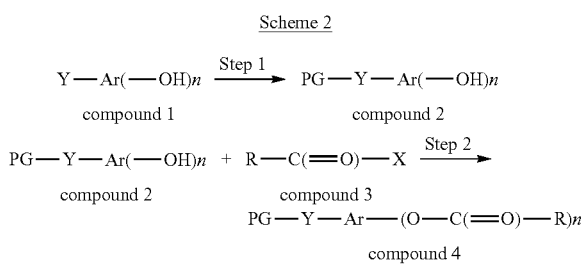

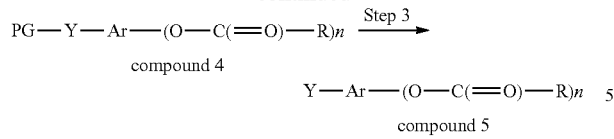

compound 4 compound 5

In Scheme 2 Step 1, compound 1, a polyphenolic compound containing a functional group Y with a labile hydrogen in need of protection, is treated with a protecting reagent such as BOC anhydride, benzyoxycarbonyl chloride, FMOC chloride, benzyl bromide and the like in an appropriate solvent, optionally in the presence of a catalyst to provide compound 2 scheme 2. Compound 2 can be purified by methods known to those of skill in the art.

In Scheme 2 Step 2, compound 2 is treated with an acylating agent, compound 3, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents, relative to compound 3. Compound 4 can be purified by methods known to those of skill in the art.

In Scheme 2 Step 3, compound 4 is subjected to conditions that cleave the protecting group, PG.

In the case of a BOC protecting group, the protecting group of compound 4 is removed under acidic conditions to give compound 5 of the invention. Suitable acids include trifluoroacetic acid, hydrochloric acid, p-toluenesulfonic acid and the like.

In the case of an FMOC protecting group, the protecting group of compound 4 is removed under basic conditions to give compound 5 of the invention. Suitable bases include piperidine, triethylamine and the like. Suitable solvents include DMF, NMP dichoromethane and the like. The FMOC group is also removed under non-basic conditions such as by treatment with tetrabutylammonium fluoride trihydrate in a suitable solvent such as DMF. The FMOC group is also removed by catalytic hydrogenation. Suitable catalysts for hydrogenation include 10% palladium-on-charcoal and palladium (II) acetate and the like. Suitable solvents for hydrogenation include DMF, ethanol, and the like In the case of a benzyoxycarbonyl or benzyl protecting group the protecting group of compound 4 is removed by hydrogenation to give compound 5. Suitable catalysts for hydrogenation include 10% Palladium-on-charcoal and Palladium acetate and the like. Suitable solvents for hydrogenation include DMF, ethanol, methanol, ethyl acetate, and the like. The product, compound 5, can be purified by methods known to those of skill in the art.

Ester Preparation Strategy #3 (Acylation)

Scheme 3

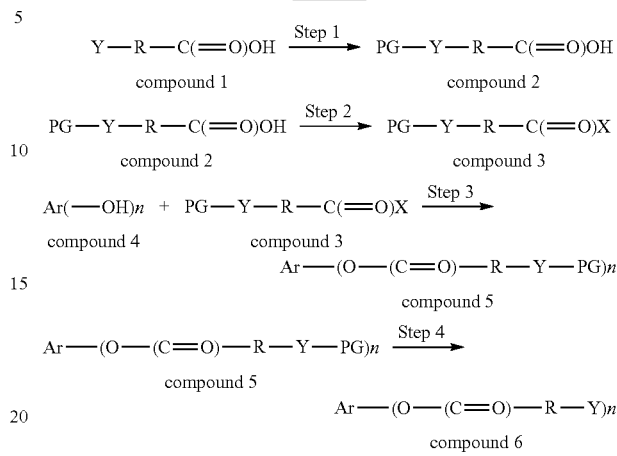

In Scheme 3 Step 1, compound 1, an acyl compound containing a functional group Y with a labile hydrogen in need on protection, is treated with a protecting reagent such as BOC anhydride, benzyoxycarbonyl chloride, FMOC chloride, benzyl bromide and the like in an appropriate solvent, optionally in the presence of a catalyst to provide compound 2 scheme 3. Compound 2 can be purified by methods known to those of skill in the art.

In Scheme 3 Step 2, compound 2 is treated with an activating reagent such as thionyl chloride, phosphorus oxychloride, EDC or EEDQ or the like to generate the activated acyl compound 3.

In Scheme 3 Step 3, the polyphenol compound 4 is treated with the activated acyl compound 3, in an appropriate solvent, optionally in the presence of a catalyst. Suitable catalysts include pyridine, dimethylaminopyridine, trimethylamine and the like to generate compound 5. The catalyst can be used in quantities ranging from 0.01 to 1.1 equivalents, relative to compound 3. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. The activated acyl compound 3 can be used in quantities ranging from 0.5 to 15 equivalents relative to compound 4.

In Scheme 3 Step 4, compound 5 is subjected to conditions designed to cleave the protecting group, PG, illustrated in Scheme 2 above. The product, compound 6, can be purified by methods known to those of skill in the art.

Ester Preparation Strategy #4 (Acylation)

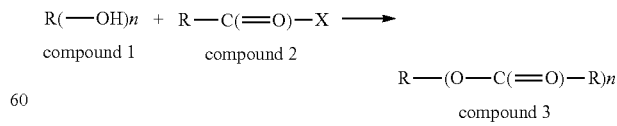

In Scheme 4 Step 1 a poly-ol compound, compound 1, where R represents a non-aromatic cyclic or acyclic moiety and n represents an integer from 1 to 15, is treated with an acylating agent, compound 2, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents, relative to compound 1. The product, compound 3, can be purified by methods known to those of skill in the art.

Ester Preparation Strategy #5 (Baeyer-Villiger Oxidation)

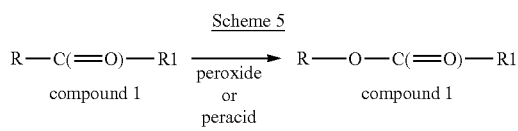

In Scheme 5 Step 1, a ketone compound, compound 1, where R and R1 represent non-aromatic cyclic or acyclic moieties, is treated with a peroxide or peroxyacid agent, such as meta-chloroperbenzoic acid, performic acid, peracetic acid, hydrogen peroxide, tert-butyl hydroperoxide and the like in an appropriate solvent, optionally in the presence of a catalyst. Suitable solvents include methylene chloride, diethyl ether, combinations thereof and the like. Suitable catalysts include $BF_3$, carboxylic acids and the like. Reaction temperatures range from −10° C. to the boiling point of the solvent used; reaction completion times range from 1 to 96 h. The product, compound 2, can be purified by methods known to those of skill in the art.

The R and R1 groups of compound 1 in Scheme 5 may optionally include additional ketone functionality that can undergo reaction. In addition the R and R1 groups of compound 1 may form a ring.

Ester Preparation Strategy #6 (Mitsunobu Reaction)

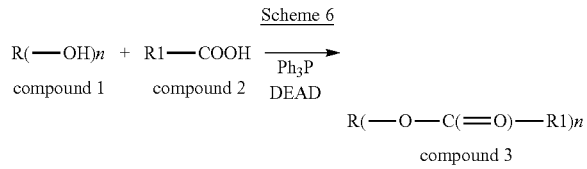

In Scheme 6 Step 1, a mixture of an alcohol compound, compound 1, where R represents a non-aromatic cyclic or acyclic moiety, and a carboxylic acid, compound 2 where R1 represents an alkanoyl group optionally substituted with one or more protected hydroxyl groups or oxo is treated with triphenylphosphine and a diazo compound such as diethylazodicarboxylate (DEAD) and the like in an appropriate solvent. Suitable solvents include methylene chloride, THF, acetonitrile, toluene, diethyl ether, combinations thereof and the like. Reaction temperatures range from −10° C. to the boiling point of the solvent used; reaction completion times range from 1 to 96 h. The product, compound 3 can be purified by methods known to those of skill in the art.

Where compound 3 is optionally substituted by one or more protected alcohol groups deprotection is accomplished by the methods illustrated in Scheme 2 above.

Ester preparation strategy #7 (Nucleophilic Alkylation)

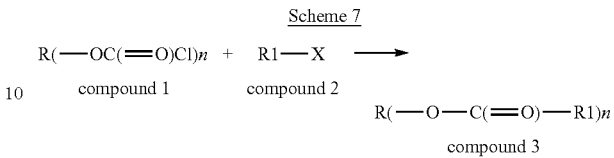

In Scheme 7 Step 1, a chloroformate compound, compound 1, where R represents an aromatic moiety or a non-aromatic cyclic or acyclic moiety, is treated, in an appropriate solvent, with an organometallic compound, compound 2 where R1 represents an alkyl group optionally substituted with one or more protected hydroxyl groups and X represents a metal such as Cu, Zn, Mg which is optionally coordinated by one or more counterions, such as chloride. Suitable solvents include methylene chloride, THF, acetonitrile, toluene, diethyl ether, combinations thereof, and the like. Reaction temperatures range from −10° C. to the boiling point of the solvent used; reaction completion times range from 1 to 96 h. The product, compound 3, can be purified by methods known to those of skill in the art.

Compound 1 can be prepared from the corresponding alcohol or polyol compounds by standard methods familiar to one skilled in the art.

Where compound 2 is optionally substituted by one or more protected alcohol groups deprotection is accomplished by the methods illustrated in Scheme 2 above.

Further modification of the initial product by methods known in the art and illustrated in the examples below, may be used to prepare additional compounds of this invention.

Ester Preparation Strategy #8 (Acylation)

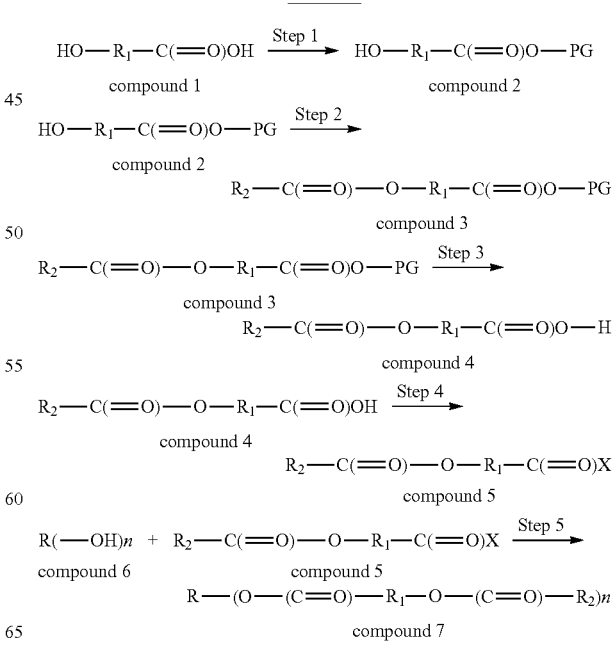

In Scheme 8 Step 1, compound 1, an acyl compound containing a hydroxyl group to be acylated, is treated with a protecting reagent such as benzyl bromide and the like in an appropriate solvent, optionally in the presence of a catalyst to provide compound 2 scheme 8. Compound 2 can be purified by methods known to those of skill in the art.

In scheme 8 Step 2, compound 2 is treated with an acylating agent, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by a reaction of a carboxylic acid with an activating reagent such as EDC or EEDQ or the like. The acylating agents can be used in quantities ranging from 0.5 to 15 equivalents relative to compound 1.

In Scheme 8 Step 3, compound 3 is subjected to conditions that cleave the protecting group, PG. In the case of a benzyl protecting group, the protecting group of compound 3 is removed by hydrogenation to give compound 4. Suitable catalysts for hydrogenation include 10% palladium-on-charcoal and palladium acetate and the like. Suitable solvents for hydrogenation include, DMF, ethanol, methanol, ethyl acetate and the like. The product, compound 4, can be purified by methods known to those of skill in the art.

In Scheme 8 Step 4, compound 4 is treated with an activating reagent such as thionyl chloride, phosphorus oxychloride, EDC or EEDQ or the like to generate the activated acyl compound 5.

In Scheme 8 Step 5, the poly-hydroxyl compound, compound 6, where R represents an aromatic or an aliphatic cyclic or acyclic core, is treated with the activated acyl compound 5, in an appropriate solvent, optionally in the presence of a catalyst. Suitable catalysts include pyridine, dimethylaminopyridine, trimethylamine and the like to generate compound 5. The catalyst can be used in quantities ranging from 0.01 to 1.1 equivalents, relative to compound 3. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. The activated acyl compound 5 can be used in quantities ranging from 0.5 to 15 equivalents relative to compound 6.

The product, compound 7, can be purified by methods known in the art.

The following examples are meant to illustrate the invention. They are not meant to limit the invention in any way.

EXAMPLES

Example 1. Preparation of Exemplary Acylated Active Agents

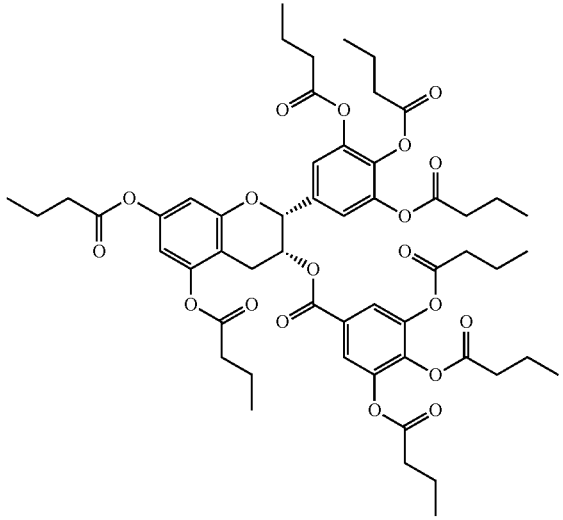 [SMILES: CCCC(=O)Oc1cc(OC(=O)CCC)c2c(c1)O[C@H](c1cc(OC(=O)CCC)c(OC(=O)CCC)c(OC(=O)CCC)c1)[C@H](OC(=O)c1cc(OC(=O)CCC)c(OC(=O)CCC)c(OC(=O)CCC)c1)C2]

Compound 1: [(2R,3R)-5,7-di(butanoyloxy)-2-[3,4,5-tri(butanoyloxy)phenyl]chroman-3-yl] 3,4,5-tri(butanoyloxy)benzoate Butyryl chloride (6.03 mL) was added to a stirring solution of epigallo catechin gallate (2.0 g) and pyridine (6.28 mL) in dichloromethane (20 mL) over 2 h between −5° C. to 5° C. The resulting mixture was stirred overnight at room temperature. The reaction mixture was then diluted with dichloromethane (100 mL), washed sequentially with water (50 mL), 2N HCl (50 mL), saturated sodium bicarbonate (50 mL), and brine. The organic layer was evaporated in vacuo, and the resulting crude material was purified by flash chromatography by 30% ethyl acetate/heptane to give compound 1 (800 mg, 18%). $^1$H NMR (CDCl$_3$): 7.6 (s, 2H), 7.22 (s, 2H), 6.78 (s, 1H), 6.6 (s, 1H), 5.62 (t, 1H), 5.18 (s, 1H), 2.98-3.02 (m, 2H), 2.4-2.6 (m, 16H), 1.6-1.8 (m, 16H), 0.92-1.02 (m, 24H).

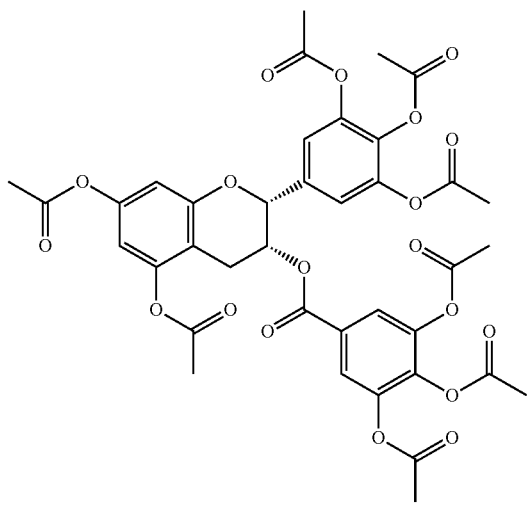 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

Compound 2: [(2R,3R)-5,7-diacetoxy-2-(3,4,5-triacetoxyphenyl)chroman-3-yl] 3,4,5-triacetoxybenzoate Acetic anhydride (6.1 mL) was added dropwise to epigallo catechin gallate (2.0 g) in pyridine (20 mL) at 0° C., and the resulting mixture was stirred overnight at room temperature. Water was added to the reaction mixture, and the solid was filtered and washed with aq. 1N HCl (10 mL) and heptane (20 mL). The solid was then dissolved in dichloromethane and passed through a silica gel filter column with dichloromethane as a mobile phase to furnish compound 2 (1.0 g, 28%) upon evaporation of volatiles. $^1$H NMR (CDCl$_3$): 7.6 (s, 2H), 7.2 (s, 2H), 6.75 (s, 1H), 6.6 (s, 1H), 5.6 (t, 1H), 5.19 (s, 1H), 2.98-3.02 (m, 2H), 2.18-2.28 (m, 24H).

Step 2:

To a solution of [(2R,3R)-5,7-dihydroxy-2-(3,4,5-trihydroxyphenyl)chroman-3-yl] 3,4,5-trihydroxybenzoate (1 g, 2.18 mmol, 1 equiv.) and K$_2$CO$_3$ (4.52 g, 32.72 mmol, 15 equiv.) in acetonitrile (100 mL) was added a solution of 4-phenylbutanoyl chloride (7.97 g, 43.63 mmol, 20 equiv.) in acetonitrile (10 mL), then the mixture was stirred at 20° C. for 10 h. The mixture was filtered, and the filtrate was concentrated in vacuum. The crude product was purified by silica gel chromatography (petroleum ether/ethyl acetate=20:1-1:1) to afford compound 3 (2.2 g, 1.28 mmol, 58.73% yield, 94.8% purity) as a white solid. LC/MS (M+H$_3$O$^+$): 1645.1

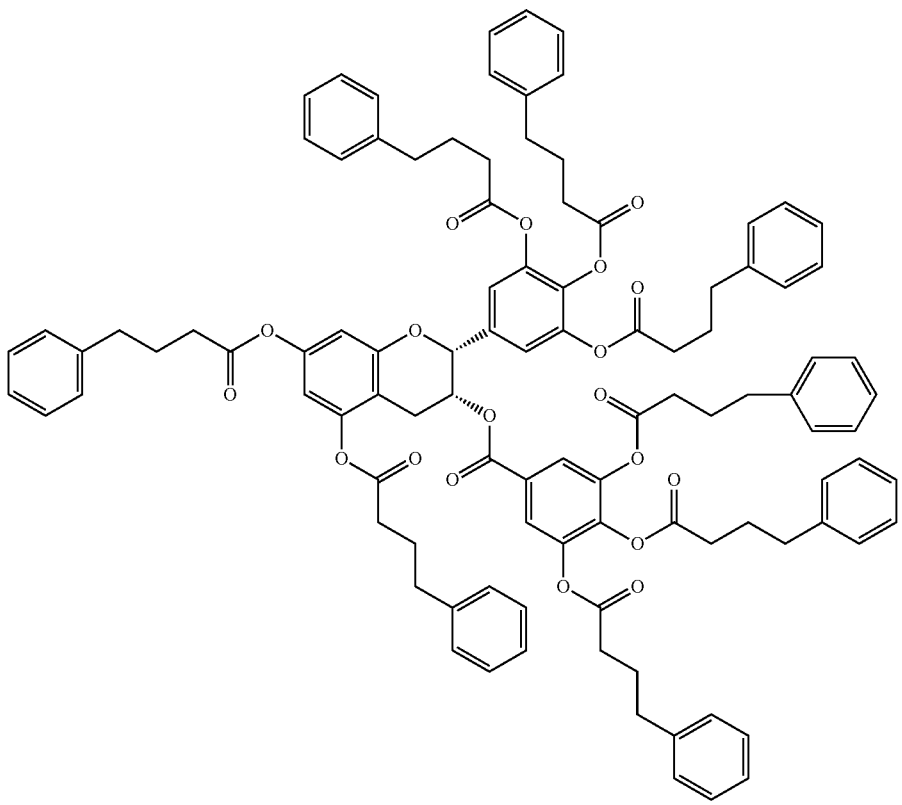 [SMILES: O=C(CCCc1ccccc1)Oc1cc(OC(=O)CCCc2ccccc2)c2c(c1)O[C@H](c1cc(OC(=O)CCCc3ccccc3)c(OC(=O)CCCc3ccccc3)c(OC(=O)CCCc3ccccc3)c1)[C@H](OC(=O)c1cc(OC(=O)CCCc3ccccc3)c(OC(=O)CCCc3ccccc3)c(OC(=O)CCCc3ccccc3)c1)C2]

Compound 3: [(2R,3R)-5,7-bis(4-phenylbutanoyloxy)-2-[3,4,5-tris(4-phenylbutanoyloxy)phenyl]chroman-3-yl] 3,4,5-tris(4-phenylbutanoyloxy)benzoate Step 1:

To a solution of 4-phenylbutanoic acid (3 g, 18.27 mmol, 1 equiv.) and SOCl$_2$ (10.87 g, 91.35 mmol, 6.63 mL, 5 equiv.) in dichloromethane (50 mL) is added one drop of DMF, then the mixture stirred at 20° C. for 5 h. The solvent is removed in vacuum and toluene (20 mL) added to the mixture. The mixture is concentrated in vacuo to afford 4-phenylbutanoyl chloride (3.5 g, crude).

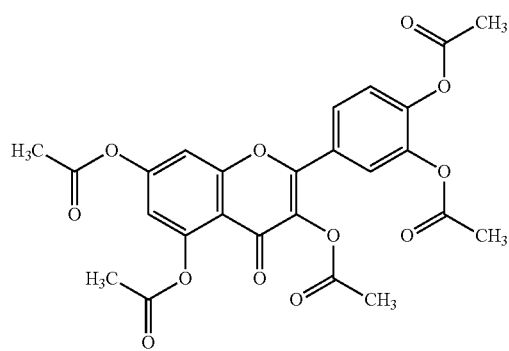 [SMILES: CC(=O)Oc1cc(OC(C)=O)c2c(=O)c(OC(C)=O)c(-c3ccc(OC(C)=O)c(OC(C)=O)c3)oc2c1]

Compound 4: [2-acetoxy-4-(3,5,7-triacetoxy-4-oxo-chromen-2-yl)phenyl] acetate To a mixture of 2-(3,4-dihydroxyphenyl)-3,5,7-trihydroxy-chromen-4-one (1 g) and acetic anhydride (2.36 g) in THF (40 mL) was added $K_2CO_3$ (3.2 g) at 25° C., then the mixture was stirred at 55° C. for 12 h. Additional acetic anhydride was added (3 equiv.) and the mixture and stirred for another 3 h. The reaction mixture was concentrated in vacuum and purified by reverse phase prep-HPLC (C18; water (0.05% HCl)-ACN gradient) to give compound 4 (0.837 g, 49%) as a white solid. LCMS: 513.2 (M+H$^+$)$^1$H NMR (400 MHz, CDCl$_3$). 7.742-7.703 (m, 2H), 7.373-7.346 (m, 2H), 6.888 (s, 1H), 2.443, (s, 3H), 2.356 (s, 6H), 2.350 (s, 6H).

Compound 5: [2-butanoyloxy-4-[3,5,7-tri(butanoyloxy)-4-oxo-chromen-2-yl]phenyl]butanoate To a mixture of 2-(3,4-dihydroxyphenyl)-3,5,7-trihydroxy-chromen-4-one (1 g) and butanoyl chloride (3.53 g) in THF (40 mL) was added TEA (3.35 g) at 25° C., then the mixture was stirred at 55° C. for 12 h. The reaction mixture was concentrated in vacuum and purified by reverse phase prep-HPLC (C18, water (0.05% HCl)-ACN gradient) to give compound 5 (1.13 g, 52% yield) as a colorless solid. LCMS: 653.3 (M+H$^+$)$^1$H NMR (400 MHz, CDCl$_3$). 7.666-7.608 (m, 2H), 7.292-7.210 (m, 2H), 6.880 (s, 1H), 2.542 (t, 2H), 2.535-2.484 (m, 8H), 1.753 (m, 10H), 1.020-0.997 (m, 12H), 0.949 (t, 3H).

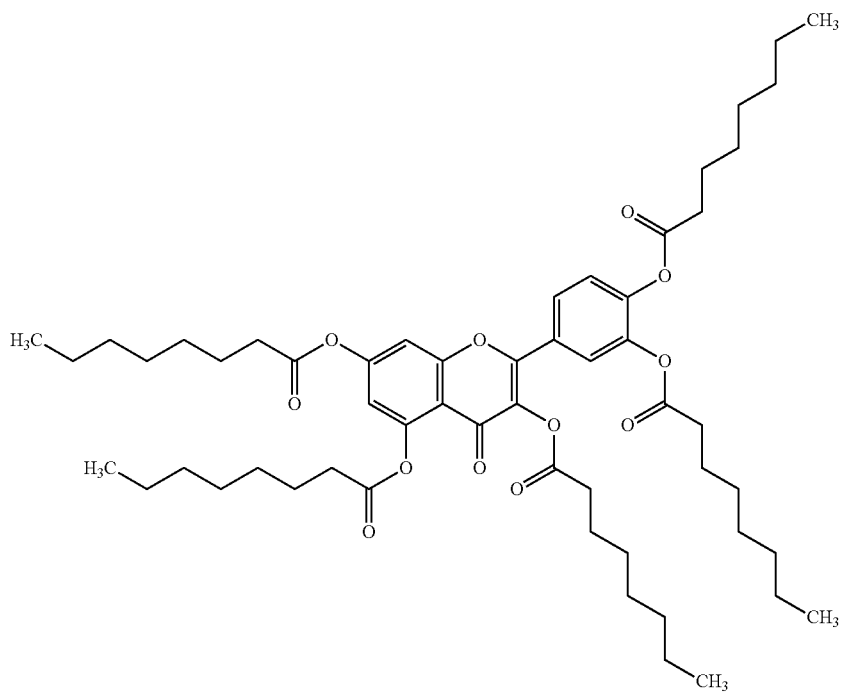

Compound 6: [2-octanoyloxy-4-[3,5,7-tri(octanoyloxy)-4-oxo-chromen-2-yl] phenyl] octanoate

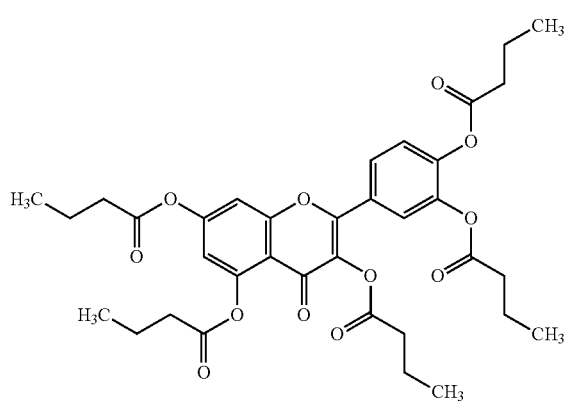 [SMILES: CCCC(=O)Oc1cc(OC(=O)CCC)c2c(=O)c(OC(=O)CCC)c(-c3ccc(OC(=O)CCC)c(OC(=O)CCC)c3)oc2c1]

To a mixture of 2-(3,4-dihydroxyphenyl)-3,5,7-trihydroxy-chromen-4-one (0.32 g) and octanoyl chloride (1.72 g) in THF (20 mL) was added TEA (1.07 g) at 25° C. Then the mixture was stirred at 55° C. for 12 h. A portion of the solvent was removed in vacuum and the precipitate was collected by filtration to give compound 6 (0.20 g, 20%) as a white solid. $^1$H NMR (400 MHz, CDCl$_3$). 7.709-7.655 (m, 2H), 7.329-7.301 (m, 2H), 6.837 (s, 1H), 2.723 (t, 2H), 2.612-2.539 (m, 8H), 1.751 (m, 10H), 1.412-1.309 (m, 40H), 0.896 (m, 15H).

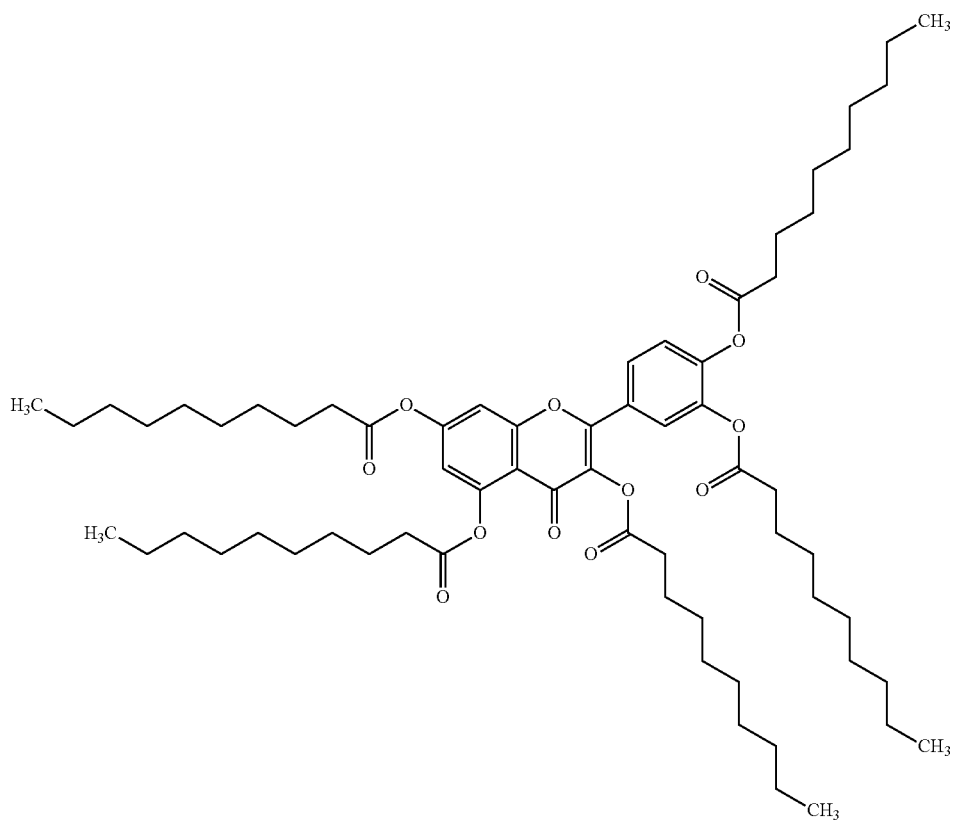 [SMILES: CCCCCCCCCC(=O)Oc1cc(OC(=O)CCCCCCCCC)c2c(=O)c(OC(=O)CCCCCCCCC)c(-c3ccc(OC(=O)CCCCCCCCC)c(OC(=O)CCCCCCCCC)c3)oc2c1]

Compound 7: [2-decanoyloxy-4-[3,5,7-tris(decanoyloxy)-4-oxo-chromen-2-yl] phenyl] decanoate To a mixture of 2-(3,4-dihydroxyphenyl)-3,5,7-trihydroxy-chromen-4-one (1 g) and decanoyl chloride (6.31 g) in THF (50 mL) was added TEA (3.35 g) at 25° C., then the mixture was stirred at 55° C. for 12 h. A portion of the solvent was removed in vacuum and the precipitate was collected by filtration to give compound 7 (2.47 g, 69%) as a white solid. $^1$H NMR (400 MHz, CDCl$_3$). 7.772-7.669 (m, 2H), 7.343-7.321 (m, 2H), 6.685 (s, 1H), 2.736 (t, 2H), 2.610-2.551 (m, 8H), 1.762 (m, 10H), 1.557-1.295 (m, 50H), 0.899 (m, 15H).

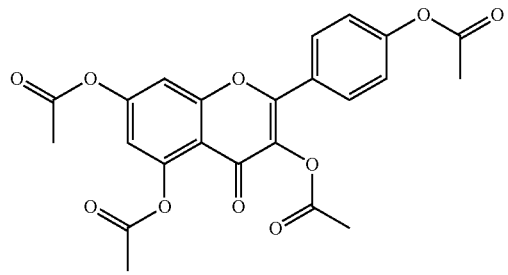 [SMILES: CC(=O)Oc1ccc(-c2oc3cc(OC(C)=O)cc(OC(C)=O)c3c(=O)c2OC(C)=O)cc1]

Compound 8: [4-(3,5,7-triacetoxy-4-oxo-chromen-2-yl)phenyl] acetate

To a mixture of 3,5,7-trihydroxy-2-(4-hydroxyphenyl)chromen-4-one (2 g) in pyridine (15 mL) was added acetyl acetate (30 g), and then the mixture was stirred at 15° C. for 12 hr under N$_2$ atmosphere. The solvent was removed under reduced pressure and the residue was poured into crushed ice with vigorous stirring. The solid precipitate was collected by filtration and washed with cold water and then with methanol. Compound 8 (2.1 g, 65% yield) was obtained as a white solid. LCMS: 455.0 (M+H$^+$) $^1$H NMR (400 MHz, CDCl$_3$) 7.858 (d, 2H), 7.339 (d, 1H), 7.278-7.257 (m, 2H), 6.883 (d, 1H), 2.447 (s, 3H), 2.357 (s, 6H), 2.333 (s, 3H)

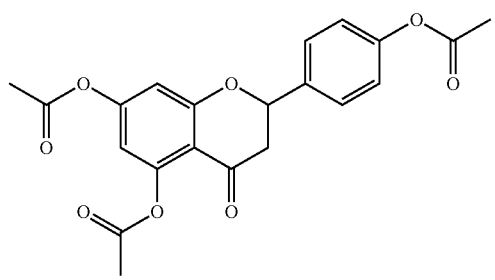 [SMILES: CC(=O)Oc1ccc(C2CC(=O)c3c(OC(C)=O)cc(OC(C)=O)cc3O2)cc1]

Compound 9: [4-(5,7-diacetoxy-4-oxo-chroman-2-yl)phenyl] acetate 5,7-dihydroxy-2-(4-hydroxyphenyl)chroman-4-one (0.500 g) was dissolved with pyridine (10 mL), and then acetyl acetate (0.844 g) was added to the mixture reaction. The reaction mixture was stirred at 15° C. for 12 h. The mixture reaction was concentrated under reduced pressure. The residue was purified by column chromatography (SiO$_2$, petroleum ether/ethyl acetate gradient) to give compound 9 (0.300 g, 39% yield) as a white solid. LCMS: 416.1 (M+H$_3$O$^+$)$^1$H NMR (400 MHz, CDCl$_3$) 7.468 (d, 2H), 7.166 (d, 2H), 6.793 (d, 1H), 6.551 (d, 1H), 5.497 (dd, 1H), 3.039 (dd, 1H), 2.783 (dd, 1H), 2.393 (s, 3H), 2.326 (s, 3H), 2.308 (s, 3H).

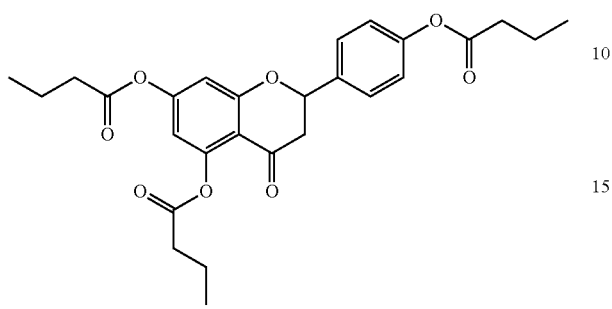

Compound 10: [4-[5,7-di(butanoyloxy)-4-oxo-chroman-2-yl]phenyl]butanoate

To a solution of 5,7-dihydroxy-2-(4-hydroxyphenyl)chroman-4-one (0.500 g) in pyridine (10 mL), was added butanoyl butanoate (1.02 g). The reaction mixture was stirred at 15° C. for 12 h. The mixture was concentrated. The residue was purified by column chromatography (SiO$_2$, petroleum ether/ethyl acetate gradient) to give compound 10 (0.325 g, 34% yield) as a white solid. LCMS: 500.2 (M+H$_3$O$^+$)$^1$H NMR (400 MHz, CDCl$_3$) 7.463 (d, 2H), 7.158 (d, 2H), 6.786 (d, 1H), 6.536 (d, 1H), 5.483 (m, 1H), 3.031 (m, 1H), 2.662 (m, 1H), 2.586-2.524 (m, 6H), 1.837-1.785 (m, 6H), 1.089-1.021 (m, 9H)

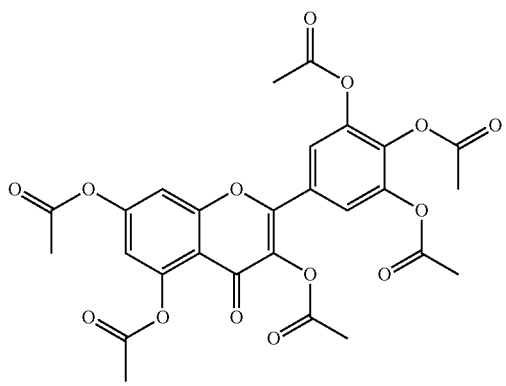 [SMILES: CC(=O)Oc1cc(OC(C)=O)c2c(=O)c(OC(C)=O)c(-c3cc(OC(C)=O)c(OC(C)=O)c(OC(C)=O)c3)oc2c1]

Compound 11: [3,5-diacetoxy-4-oxo-2-(3,4,5-triacetoxyphenyl)chromen-7-yl] acetate To a solution of 3,5,7-trihydroxy-2-(3,4,5-trihydroxyphenyl)chromen-4-one (1 g) in pyridine (10 mL) was added acetyl acetate (15.26 g), then the mixture was stirred at 15° C. for 16 h. The solvent was removed and the mixture was poured into ice water under stirring. The solid was filtered, washed with water and dried in vacuum to give compound 11 (1.1 g, 61% yield) as a gray solid. LCMS 571.1 (M+H$^+$) $^1$H NMR (400 MHz, CDCl$_3$) 7.260 (s, 2H), 7.349 (d, 1H), 6.886 (d, 1H), 2.441 (s, 3H), 2.372 (s, 3H), 2.353 (s, 3H), 2.341 (s, 3H), 2.333 (s, 6H)

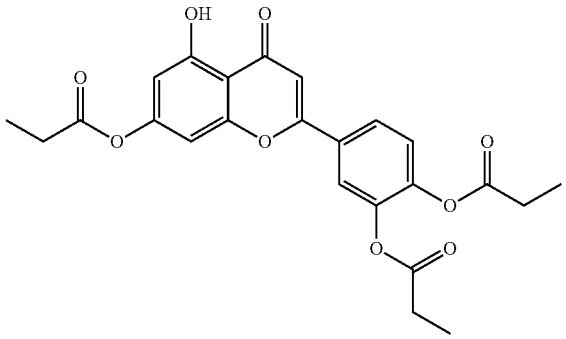 [SMILES: CCC(=O)Oc1cc(O)c2c(=O)cc(-c3ccc(OC(=O)CC)c(OC(=O)CC)c3)oc2c1]

Compound 12: [4-[4-oxo-5,7-di(propanoyloxy) chromen-2-yl]-2-propanoyloxy-phenyl]propanoate Propionic anhydride (1.33 mL, 10.4 mmol) was added dropwise to a stirred solution of luteolin (0.3 g, 1.04 mmol) in anhydrous pyridine (2.5 mL, 31.2 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HCl (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield compound 12 (0.073 g, 15% yield) as an off-white solid. 1H-NMR (DMSO-d6, 400 MHz): δ 12.75 (s, 1H), 8.07 (m, 2H), 7.5 (m, 1H), 7.15 (s, 1H), 7.12 (d, 1H), 6.66 (d, 1H), 2.59-2.66 (m, 6H), 1.11-1.17 (m, 9H)

Compound 13: [4-oxo-3,5-di(propanoyloxy)-2-[3,4,5-tri(propanoyloxy)phenyl]chromen-7-yl]propanoate Propionic anhydride (2 mL, 15.6 mmol) was added dropwise to a stirred solution of myricetin (0.5 g, 1.56 mmol) in anhydrous pyridine (2.78 mL, 47.1 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HC (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 13 (0.31 g, 30% yield) as a white solid. $^1$H-NMR (DMSO-d6, 400 MHz): δ 7.77 (s, 2H), 7.64 (d, 1H), 7.16 (d, 1H), 2.60-2.70 (m, 12H), 1.07-1.17 (m, 18H)

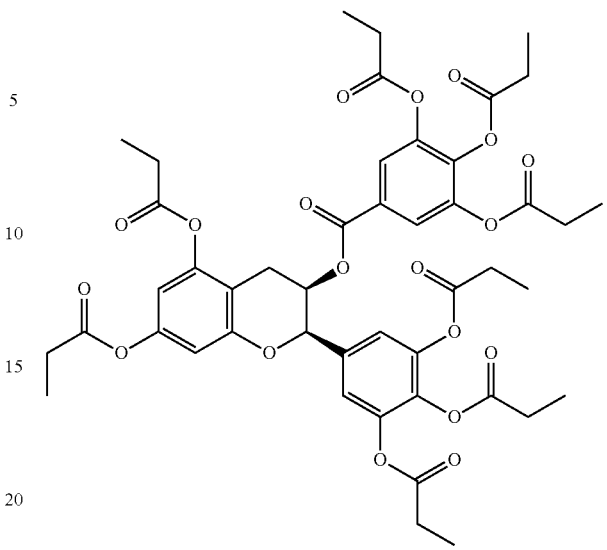

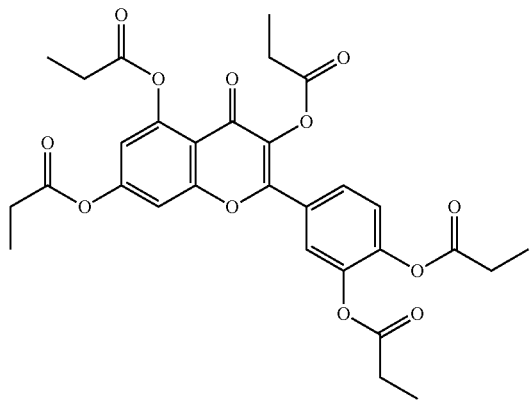 [SMILES: CCC(=O)Oc1cc(OC(=O)CC)c2c(=O)c(OC(=O)CC)c(-c3ccc(OC(=O)CC)c(OC(=O)CC)c3)oc2c1]

Compound 15: [(2R,3R)-5,7-di(propanoyloxy)-2-[3,4,5-tri(propanoyloxy)phenyl]chroman-3-yl]3,4,5-tri(propanoyloxy)benzoate Propionic anhydride (2.78 mL, 21.8 mmol) was added dropwise to a stirred solution of epigallocatechin gallate (0.5 g, 1.09 mmol) in anhydrous pyridine (2.61 mL, 32.6 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HCl (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 15 (0.695 g, 70% yield) as a white solid. 1H-NMR (DMSO-d6, 400 MHz): δ 7.54 (s, 2H), 7.38 (s, 2H), 6.79 (m, 1H), 6.66 (m, 1H), 5.66 (m, 1H), 5.54 (s, 1H), 3.13-3.17 (m, 1H), 2.96 (d, 1H), 2.5-2.65 (m, 16H), 1.0-1.2 (m, 24H)

Compound 14: [4-[4-oxo-3,5,7-tri(propanoyloxy)chromen-2-yl]-2-propanoyloxy-phenyl]propanoate Propionic anhydride (2.1 mL, 16.5 mmol) was added dropwise to a stirred solution of quercetin (0.5 g, 1.65 mmol) in anhydrous pyridine (3.98 mL, 49.5 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HCl (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 14 (0.1 g, 10% yield) as a white solid. 1H-NMR (DMSO-d6, 400 MHz): δ 7.85 (m, 2H), 7.66 (d, 1H), 7.54 (d, 1H), 7.18 (d, 1H), 2.62-2.89 (m, 10H), 1.09-1.19 (m, 20H)

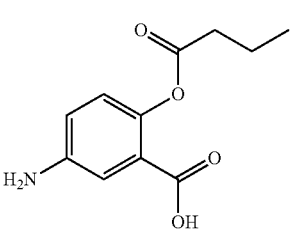 [SMILES: CCCC(=O)Oc1ccc(N)cc1C(=O)O]

Compound 16: 5-amino-2-butanoyloxy-benzoic acid

Step 1:
To a mixture of 5-amino-2-hydroxy-benzoic acid (3 g, 19.59 mmol, 1 equiv.) in methanol (50 mL) was added Boc$_2$O (4.28 g, 19.59 mmol, 4.50 mL, 1 equiv.) in one portion at 15° C. under N$_2$. The mixture was stirred at 15° C. for 5 h. The residue was poured into water (100 mL). The aqueous phase was extracted with EtOAc (100 mL), and the organic phase was dried with anhydrous Na₂SO₄, filtered, and concentrated in vacuo. The residue was used in next step without further purification. 5-(tert-butoxycarbonylamino)-2-hydroxy-benzoic acid (4 g, crude) as crude was obtained.

Step 2:

To a solution of 5-(tert-butoxycarbonylamino)-2-hydroxy-benzoic acid (4 g, 15.79 mmol, 1 equiv.) and triethylamine (119.87 mg, 1.18 mmol, 164.88 μL, 1 equiv.) in THF (30 mL) was added butanoyl chloride (126.22 mg, 1.18 mmol, 123.74 μL, 1 equiv.) drop-wise at 0° C., while the temperature was maintained below 0° C. The reaction mixture was warmed to 15° C. and stirred for 2 h. The reaction was quenched by slow addition of ice, and then the mixture was extracted with EtOAc (100 mL). The organic phase was dried over anhydrous Na₂SO₄, filtered, and concentrated in vacuo. The residue was purified by recrystallization with EtOAc (20 mL) to give the pure 2-butanoyloxy-5-(tert-butoxycarbonylamino)benzoic acid (1.5 g, 4.64 mmol, 29.37% yield) as white solid.

Step 3:

A solution of 2-butanoyloxy-5-(tert-butoxycarbonylamino)benzoic acid (1.5 g, 4.64 mmol, 1 equiv.) in HCl-EtOAc (20 mL, 4 M) was stirred at 15° C. for 1 h. The mixture was filtered to obtain the product 5-amino-2-butanoyloxy-benzoic acid as off-white solid (0.74 g, 2.76 mmol, 59.58% yield, 96.993% purity, HCl salt). LC/MS: (M+H⁴) 224.1

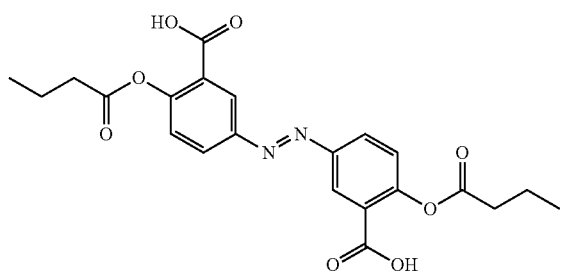 [SMILES: CCCC(=O)Oc1ccc(/N=N/c2ccc(OC(=O)CCC)c(C(=O)O)c2)cc1C(=O)O]

Compound 17: 2-butanoyloxy-5-[(E)-(4-butanoyloxy-3-carboxy-phenyl)azo]benzoic acid A solution of [2-carboxy-4-[(E)-(3-carboxy-4-sodiooxyphenyl)azo]phenoxy] sodium (2 g, 5.78 mmol, 1 equiv.), butanoyl chloride (2.46 g, 23.11 mmol, 2.41 mL, 4 equiv.), and NaOH (462.12 mg, 11.55 mmol, 2 equiv.) in DMF (100 mL) was stirred at 50° C. for 0.5 h. The solid was filtered, water (150 mL) was added to the filtrate, and the mixture was filtered again. The resulting solids filter cake was dried in vacuo. 2-butanoyloxy-5-[(E)-(4-butanoyloxy-3-carboxy-phenyl)azo]benzoic acid (0.8 g) was obtained as brown solid. LC/MS: (M+H⁺): 443.1

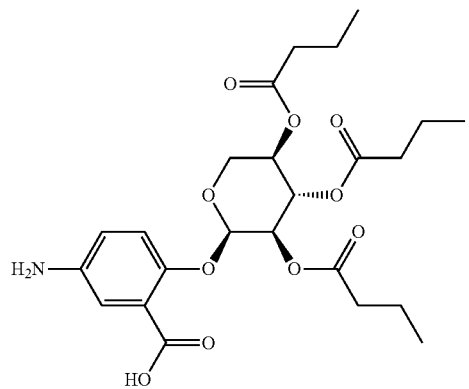 [SMILES: CCCC(=O)O[C@@H]1[C@@H](OC(=O)CCC)[C@@H](Oc2ccc(N)cc2C(=O)O)OC[C@H]1OC(=O)CCC]

Compound 18: 5-amino-2-[(2R,3R,4S,5R)-3,4,5-tri(butanoyloxy)tetrahydropyran-2-yl]oxy-benzoic acid Xylose tributyrate (1.87 g, 5.18 mmol, 1 eq), tert-butyl 5-((tert-butoxycarbonyl)amino)-2-hydroxybenzoate (2.4 g, 7.8 mmol, 1.5 eq) and triphenylphosphine (2.05 g, 7.8 mmol, 1.5 eq) were dissolved in anhydrous THF (37.5 mL) under N₂ and cooled to 0° C. Di-tert-butyl azodicarboxylate (1.8 g, 7.8 mmol, 1.5 eq) was added and the reaction was stirred at 0° C. for 1 hour under N₂. The ice bath was removed and the reaction was stirred at room temperature overnight. The reaction mixture was loaded directly onto silica and dried by rotary evaporation. The solid loaded sample was purified by multiple rounds of column chromatography (gradient: 0-50% ethyl acetate in hexanes) to separate the anomers and yield (2S,3R,4S,5R)-2-(2-(tert-butoxycarbonyl)-4-((tert-butoxycarbonyl)amino)phenoxy)tetrahydro-2H-pyran-3,4,5-triyl tributyrate (45 mg). The purified compound was dissolved in chloroform (1 mL), followed by addition of 4 M HCl in dioxane (1.2 mL). After deprotection was complete as confirmed by LCMS, the solution was concentrated by rotary evaporation and dried under high vacuum overnight to yield the title compound (11 mg, 0.021 mmol, 0.4% yield). LCMS [M−H]⁻: 494.5. ¹H NMR (400 MHz, DMSO-d6) δ 6.83-6.75 (m, 2H), 6.64-6.53 (m, 1H), 5.58 (d, J=3.6 Hz, 1H), 5.53 (t, J=9.9 Hz, 1H), 5.03-4.90 (m, 2H), 3.89 (t, J=10.9 Hz, 1H), 3.73 (dd, J=10.9, 5.9 Hz, 1H), 2.38-2.12 (m, 6H), 1.58-1.39 (m, 6H), 0.92-0.76 (m, 9H).

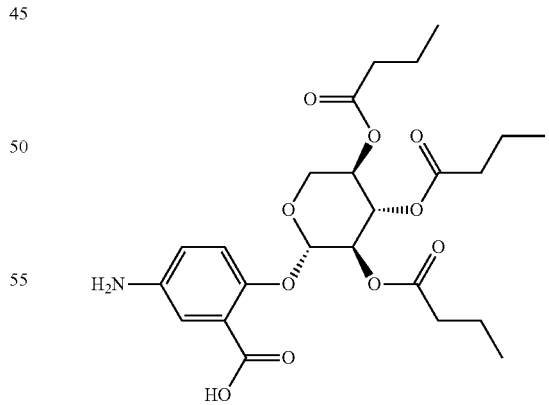

Compound 19: 5-amino-2-[(2S,3R,4S,5R)-3,4,5-tri(butanoyloxy)tetrahydropyran-2-yl]oxy-benzoic acid Step 1

5-Amino salicylic acid (10.0 g) was dissolved in a mixture of dioxane (100 mL), water (100 mL), and NaOH (2.60 g), and the resulting solution was cooled in an ice-bath. Di-tert-butyl dicarbonate (Boc anhydride) (15.60 g) was added, and the mixture was warmed to room temperature and stirred for 1.0 h. The solution was concentrated to 60 mL, diluted with ethyl acetate (100 mL), and the resulting mixture was cooled in an ice-bath. The mixture was acidified with aq. KHSO$_4$ to pH 2-3. The aqueous layer was extracted with EtOAc. The organic phase was washed with water, brine, dried over Na$_2$SO$_4$, filtered, and concentrated to afford 5-(tert-butoxycarbonylamino)-2-hydroxy-benzoic acid (7.0 g, 42%).

Step 2

5-(tert-butoxycarbonylamino)-2-hydroxy-benzoic acid (3 g) was dissolved in DMF, and the resulting solution was cooled to 0° C. 1,1'-Carbonyldiimidazole (CDI) was added, and the mixture was stirred at room temperature for 2 h. Then, tert-butylalcohol (1.7 g) and DBU (2.1 g) were added. The reaction was stirred at room temperature overnight. The reaction mixture was poured onto ice-water, and the solid product, tert-butyl 5-(tert-butoxycarbonylamino)-2-hydroxy-benzoate, was collected by filtration (3.0 g, 81.9%).

Step 3

To a mixture of tert-butyl 5-(tert-butoxycarbonylamino)-2-hydroxy-benzoate, [(3R,4S,5R)-4,5-di(butanoyloxy)-6-hydroxy-tetrahydropyran-3-yl] butanoate (1.2 g) and triphenylphosphene (1.2 g) in THF (50 mL) was added di-t-butyl azodicarboxylate (DTAD) (1.1 g) DTAD, and the mixture was stirred overnight at room temperature. The product was purified by reverse phase chromatography using acetonitrile-water to afford tert-butyl 5-(tert-butoxycarbonylamino)-2-[(3R,4S,5R)-3,4,5-tri(butanoyloxy)tetrahydropyran-2-yl]oxy-benzoate as sticky solid (0.6 g, 30.0%).

Step 4

Tert-butyl 5-(tert-butoxycarbonylamino)-2-[(3R,4S,5R)-3,4,5-tri(butanoyloxy)tetrahydropyran-2-yl]oxy-benzoate (600 mg) was added to 4M HCl in dioxane (15 mL) and stirred at room temperature overnight. After the consumption of the starting material, the organic phase was evaporated, and the residue was co-evaporated with heptane and dichloromethane twice more. The solid obtained was dried under high vacuum to afford compound the title product as dark brown solid (200 mg, 43.8%). Fractionation of the product afforded two anomeric isomers (Compounds 21 and 22). $^1$H NMR (DMSO d6): Isomer 1: δ 7.62 (d, 1H), 7.45 (dd, 1H), 7.38 (d, 1H), 6 (d, 1H), 5.6 (t, 1H), 5.0-5.1 (m, 1H), 4.7-4.75 (m, 1H), 3.6-3.8 (m, 1H), 3.45-3.6 (1H), 2.1-2.3 (m, 6H), 1.4-1.6 (m, 6H), 0.75-0.85 (m, 9H). Isomer 2: δ 7.82 (d, 1H), 7.5 (dd, 1H), 7.05 (d, 1H), 5.5 (d, 1H), 5.3 (t, 1H), 5.1-5.15 (m, 1H), 4.9-5.0 (m, 1H), 4.0-4.08 (m, 1H), 3.7-3.8 (1H), 2.1-2.3 (m, 6H), 1.4-1.6 (m, 6H), 0.75-0.85 (m, 9H) ppm

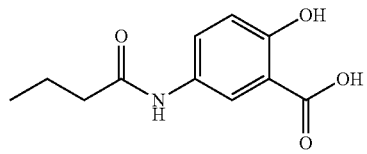 [SMILES: CCCC(=O)Nc1ccc(O)c(C(=O)O)c1]

Compound 20:
5-(butanoylamino)-2-hydroxy-benzoic acid

To the solution of 5-amino-2-hydroxy-benzoic acid (1 g) and triethylamine (0.991 g) in dioxane (20 mL) and H$_2$O (10 mL) was added butyric anhydride (1.24 g), and the mixture was stirred at 20° C. for 16 h. The dioxane was removed under reduced pressure and the pH was adjusted to 5-6 by adding aqueous 3N HCl at 0° C. The solid was filtered, washed three times with water (20 mL) and concentrated in vacuum. The crude product was purified by reverse phase prep-HPLC (C18, water (0.05% HCl)-acetonitrile gradient) to give 5-(butanoylamino)-2-hydroxy-benzoic acid (0.3 g, 20%) as a light pink solid. LCMS: 224.1 (M+H$^+$)$^1$H NMR (400 MHz, DMSO-d6): δ 11.015 (br, 1H), 9.807 (s, 1H), 8.106 (d, 1H), 7.652 (dd, 1H), 6.893 (d, 1H), 2.239 (m, 2H), 1.604 (m, 2H), 0.902 (t, 3H) ppm

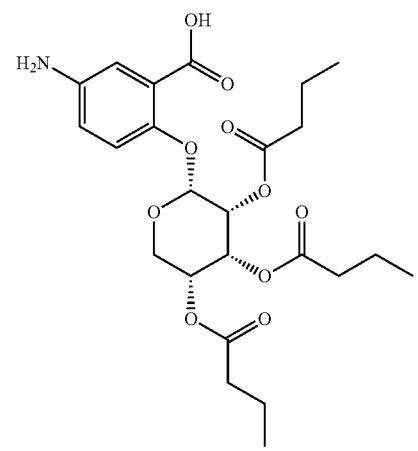 [SMILES: CCCC(=O)O[C@H]1[C@@H](Oc2ccc(N)cc2C(=O)O)OC[C@@H](OC(=O)CCC)[C@H]1OC(=O)CCC]

Compound 21:5-amino-2-(((2R,3R,4R,5R)-3,4,5-tris(butyryloxy)tetrahydro-2H-pyran-2-yl)oxy)benzoic acid Step 1. Ribose tetrabutyrate To a stirred solution of D-(+)-ribose 1 (5 g) in anhydrous pyridine (24.2 mL) was added solution of butyryl chloride (23.70 g) in dichloromethane (50 mL) at 0-5° C. The reaction mixture was brought to room temperature and stirred for 16 h. The mixture was diluted with dichloromethane (100 ml) and washed successively with water (100 mL), 2N aqueous HCl (300 mL), saturated sodium bicarbonate solution (300 mL) and brine (100 mL). The organic layer was dried over sodium sulphate and concentrated under reduced pressure. The residue was purified by column chromatography over silica gel (5-10% EtOAc-hexane gradient) to afford ribose tetrabutyrate as a colorless oil (7.5 g, 52%, mixture of α/β anomers).

Step 2. Ribose tributyrate

Ammonium hydroxide (11 mL) was added slowly to a mixture of ribose tetrabutyrate 2 (7.5 g) in acetonitrile (60 mL) at room temperature and the resulting reaction mixture was stirred for 5 h. The mixture was diluted with MTBE (75 mL) and stirred for 15 minutes. The organic layer was separated and concentrated under reduced pressure and the residue was partitioned between MTBE (100 mL) and water (75 mL). The MTBE layer was separated, dried over sodium sulphate and concentrated under reduced pressure. The residue was purified by column chromatography [using silica gel 100-200 mesh and 10-20% EtOAc-Hexane as eluting solvent] to afford ribose tributyrate as a colorless oil (1.1 g, 17%).

Step 3. 5-tert-butoxycarbonylamino-2-hydroxy-benzoic acid

To the stirred solution of 5-amino salicylic acid 4 (5 g) in 1,4-dioxane and water (1:1; 100 mL) was added NaOH (1.3 g) and Boc-anhydride (7.83 g) at 0° C. and the resulting reaction mixture was stirred at room temperature for 1 h. The reaction mixture was concentrated under reduced pressure, the residue was diluted with EtOAc (50 mL) and the pH was adjusted to ~3-4 by dropwise addition of 0.5N aqueous HCl at 0° C. The organic layer was separated and aqueous layer was extracted with EtOAc (50 mL). The combined organic layer was dried over sodium sulphate and concentrated under reduced pressure to provide 5-tert-butoxycarbonylamino-2-hydroxy-benzoic acid as off white solid (5.3 g, 64%).

Step 4. 5-tert-butoxycarbonylmethyl-2-hydroxy-benzoic acid tert-butyl ester

To a stirred solution of 5-tert-butoxycarbonylamino-2-hydroxy-benzoic acid 5 (5.3 g) in DMF (50 mL) was added CDI (3.39 g) at 0-5° C. and stirred for 2 h. tert-Butanol (4.025 mL) and DBU (2.54 mL) were then added and the mixture was stirred at room temperature for 16 h. The mixture was diluted with water (100 mL) and extracted with EtOAc (200 mL). The organic layer was separated, dried over sodium sulphate and concentrated under reduced pressure. The residue was purified by column chromatography using silica gel [100-200 mesh; under gradient elution of 5-10% EtOAc-Hexane] to afford 5-tert-butoxycarbonylmethyl-2-hydroxy-benzoic acid tert-butyl ester as off white solid (2 g, 31%).

Step 5. 5-tert-butoxycarbonylamino-2-(3,4,5-tris-butyryloxy-tetrahydro-pyran-2-yloxy)-benzoic acid tert-butyl ester To a stirred solution of 5-tert-butoxycarbonylmethyl-2-hydroxy-benzoic acid tert-butyl ester 6 (0.850 g) and ribose tributyrate (1.04 g) in THF (5 mL) was sequentially added triphenylphosphine (1.03 g) and di-tert-butyl azodicarboxylate (0.948 g) at room temperature and the mixture was stirred for 16 h. The mixture was concentrated under reduced pressure and the residue was purified by column chromatography over silica gel (5 to 18% EtOAc-Hexane gradient) to afford of crude 5-tert-butoxycarbonylamino-2-(3,4,5-tris-butyryloxy-tetrahydro-pyran-2-yloxy)-benzoic acid tert-butyl ester (1.3 g) which was used directly in the next step.

Step 6. 5-amino-2-[(3R,4R,5R)-3,4,5-tri(butanoyloxy)tetrahydropyran-2-yl]oxy-benzoic acid To a stirred solution of crude 5-tert-butoxycarbonylamino-2-(3,4,5-tris-butyryloxy-tetrahydro-pyran-2-yloxy)-benzoic acid tert-butyl ester 7 (1.3 g, crude from above experiment) in 1,4-dioxane (7 mL) was added 4N HCl in 1,4-dioxane (10 mL) at 0° C. and the resulting reaction mixture was stirred at room temperature for 16 h. Then reaction mixture was concentrated under reduced pressure and the residue was purified by reverse phase prep-HPLC to provide 5-amino-2-(((2R,3R,4R,5R)-3,4,5-tris(butyryloxy)tetrahydro-2H-pyran-2-yl)oxy)benzoic acid (0.05 g). LCMS: 496.5 (M+H$^+$) 1H NMR (400 MHz, DMSO-d6): δ 6.919-6.898 (m, 2H), 6.658 (m, 1H), 5.431 (m, 1H), 5.350 (m, 1H), 5.234 (m, 1H), 5.161 (m, 1H), 4.213 (m 1H), 3.749 (m, 1H), 2.497-2.268 (m, 4H), 2.197 (m, 1H), 1.620-1.487 (m, 6H), 0.926-0.888 (m, 9H) ppm

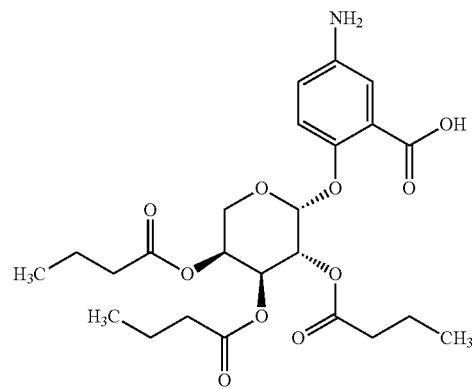 [SMILES: CCCC(=O)O[C@@H]1[C@@H](OC(=O)CCC)[C@@H](Oc2ccc(N)cc2C(=O)O)OC[C@@H]1OC(=O)CCC]

Compound 22: 5-amino-2-[(2R,3R,4S,5S)-3,4,5-tri(butanoyloxy)tetrahydropyran-2-yl]oxy-benzoic acid Step 1: 2-Hydroxy-4-nitro-benzoate (20 g) and KHCO$_3$ (13.1 g) were suspended in DMF (100 mL). To the suspension was added benzyl bromide (22.4 g) and the reaction mixture was stirred at room temperature overnight. Water (150 mL) was added and the resulting mixture was extracted with ethyl acetate (250 mL). The organic phase was separated and washed twice with water, brine, and dried over Na$_2$SO$_4$. The solvent was removed under reduced pressure and the residue was purified by column chromatography (hexanes/ethyl acetate gradient). Recrystallization from 15% ethyl acetate in hexanes provided benzyl 2-hydroxy-4-nitro-benzoate (10.5 g).

Step 2: Benzyl 2-hydroxy-4-nitro-benzoate (8.5 g), arabinose tributyrate (7.5 g) and triphenylphosphine (8.2 g) were dissolved in THF (150 mL) and stirred at 0° C. To this mixture was added di-t-butyl azodicarboxylate (7.2 g) and stirring was continued at 0° C. for 1 h, then at room temperature overnight. The reaction mixture was concentrated and purification by column chromatography (hexanes/ethyl acetate gradient) provided benzyl 5-nitro-2-[(2R,3R,4S,5S)-3,4,5-tri(butanoyloxy)tetrahydropyran-2-yl]oxy-benzoate (1.78 g, 14%).

Step 3: 5-nitro-2-[(2R,3R,4S,5S)-3,4,5-tri(butanoyloxy)tetrahydropyran-2-yl]oxy-benzoate (0.095 g) was dissolved in methanol (15 mL) and stirred at room temperature. To this mixture was added 10% Pd/C (0.05 g). The suspension was stirred under a hydrogen atmosphere at room temperature overnight. The reaction mixture was filtered through Celite and washed with methanol. The combined filtrate and washing were concentrated. The residue was purified by reverse phase chromatography (C-18, 0.1% trifluoroacetic acid in acetonitrile and 0.1% trifluoroacetic acid in water) to give 5-amino-2-[(2R,3R,4S,5S)-3,4,5-tri(butanoyloxy)tetrahydropyran-2-yl]oxy-benzoic acid (0.045 g, 59%). MS 494.2 (M−H) NMR (DMSO d6): δ 7.223 (m, 1H), 7.139 (m, 1H), 6.997 (s, 1H), 7.851 (d, 1H), 5.469 (m, 1H), 5.350 (m, 1H), 5.239 (m, 1H) 4.127 (d, 1H), 3.672 (d, 1H), 2.490-2.369 (M, 6H), 1.596-1.485 (m, 6H), 0.924-0.818 (m, 9H) ppm

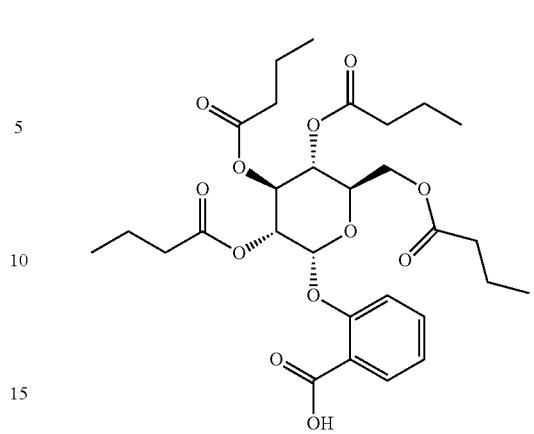

Compound 24: 2-(((2R,3R,4S,5R,6R)-3,4,5-tris(butyryloxy)-6-((butyryloxy)methyl)tetrahydro-2H-pyran-2-yl)oxy)benzoic acid

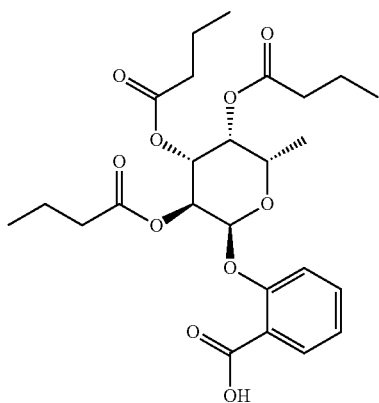 [SMILES: CCCC(=O)O[C@H]1[C@H](OC(=O)CCC)[C@H](Oc2ccccc2C(=O)O)O[C@@H](C)[C@H]1OC(=O)CCC]

Compound 23: 2-(((2S,3S,4R,5R,6S)-3,4,5-tris(butyryloxy)-6-methyltetrahydro-2H-pyran-2-yl)oxy) benzoic acid Step 1:

To a mixture of [(2S,3R,4R,5S)-4,5-di(butanoyloxy)-6-hydroxy-2-methyl-tetrahydropyran-3-yl]butanoate (0.95 g, 2.54 mmol) and tert-butyl 2-hydroxybenzoate (0.468 g, 2.41 mmol) in THF (10 mL) was added tert-butyl (NE)-N-tert-butoxycarbonyliminocarbamate (0.876 g, 3.81 mmol) and PPh₃ (0.952 g, 3.63 mmol) in one portion at 15° C. under N₂. The mixture was stirred at 15° C. for 12 h. The reaction mixture was filtered and concentrated under reduced pressure to give a residue which was purified by prep-HPLC [water (10 mM NH₄HCO₃)-ACN] to give tert-butyl 2-[(3S, 4R,5R,6S)-3,4,5-tri(butanoyloxy)-6-methyl-tetrahydropyran-2-yl]oxybenzoate (0.3 g, 0.544 mmol, 21% yield) as a white solid.

Step 2:

To a solution of tert-butyl 2-[(3S,4R,5R,6S)-3,4,5-tri(butanoyloxy)-6-methyl-tetrahydropyran-2-yl]oxybenzoate (0.15 g, 0.272 mmol) in DCM (5 mL) was added TFA (0.031 g, 0.27 mmol). The mixture was stirred at 15° C. for 12 hr. The reaction mixture was filtered and concentrated under reduced pressure to give a residue. The residue was purified by prep-HPLC [water (0.1% TFA)-ACN] to give compound 23 and compound 29.

Compound 23 was prepared as a colorless oil (0.003 g, 1.9% yield). LCMS: 517.2 (M+Na⁺); ¹H NMR CDCl₃ 8.192 (m, 1H), 7.565 (m, 1H0, 7.441 (m, 1H), 7.255 (m, 1H), 5.813 (m, 1H), 5.525-5.444 (m, 3H), 4.413 (m, 1H), 2.460 (t, 2H), 2.356 (t, 2H), 2.233 (t, 2H), 1.627 (m, 6H), 1.225 (d, 3H), 1.028 (t, 3H), 0.938 (t, 3H), 0.919 (t, 3H)

Compound 24 was synthesized in a similar manner to compound 22.

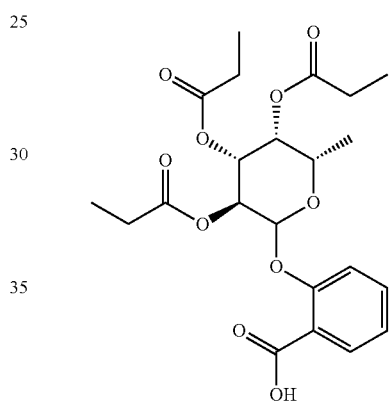

Compound 25: 2-(((3S,4R,5R,6S)-6-methyl-3,4,5-tris(propionyloxy)tetrahydro-2H-pyran-2-yl)oxy) benzoic acid Step 1

To a mixture of [(2S,3R,4R,5S)-6-hydroxy-2-methyl-4,5-di(propanoyloxy)tetrahydropyran-3-yl]propanoate (1 g, 3.01 mmol) and tert-butyl 2-hydroxybenzoate (1.17 g, 6.02 mmol) in THF (10 mL) was added di-tert-butyl azodicarboxylate (1.04 g, 4.51 mmol) and triphenylphosphine (2.77 g, 4.51 mmol) in one portion at 15° C. under N₂. The mixture was stirred at 15° C. for 12 h. The reaction mixture was filtered and concentrated under reduced pressure and the residue was purified by prep-HPLC. [water (10 mM NH₄HCO₃)-ACN] to give tert-butyl 2-[(3S,4R,5R,6S)-6-methyl-3,4,5-tri(propanoyloxy)tetrahydropyran-2-yl]oxybenzoate (0.6 g, 39% yield) as a yellow solid.

Step 2

To a mixture of tert-butyl 2-[(3S,4R,5R,6S)-6-methyl-3, 4,5-tri(propanoyloxy)tetrahydropyran-2-yl]oxybenzoate (0.44 g, 0.865 mmol) in DCM (5 mL) was added TFA (0.099 g, 0.865 mmol) in one portion at 15° C. under N₂. The mixture was stirred 12 h. The reaction mixture was filtered and concentrated under reduced pressure to give a residue. The residue was purified by prep-HPLC [water (0.1% TFA)-

ACN]0.2-[(3S,4R,5R,6S)-6-methyl-3,4,5-tri(propanoyloxy)tetrahydropyran-2-yl]oxybenzoic acid (0.067 g, 15% yield) as a white solid. MS 475.1 (M+Na) NMR (DMSO d6): δ 8.1 (m, 1H), 7.5 (m, 1H), 7.1 (m, 2H), 5.6 (m, 1H), 5.4 (m, 1H), 5.3 (m, 1H), 5.1 (m, 1H) 4.0 (m, 1H), 2.2 (m, 6H), 1.2 (m, 12H).

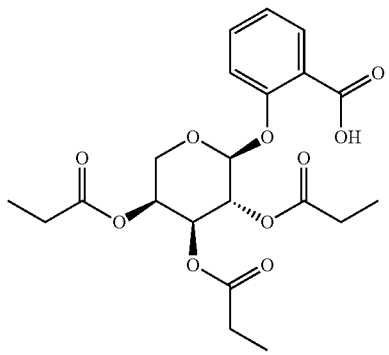 [SMILES: CCC(=O)O[C@@H]1[C@@H](OC(=O)CC)[C@H](Oc2ccccc2C(=O)O)OC[C@@H]1OC(=O)CC]

Compound 26: 2-(((2S,3R,4S,5S)-3,4,5-tris(propionyloxy)tetrahydro-2H-pyran-2-yl)oxy)benzoic acid Step 1

To a solution of (3R,4S,5S)-2-hydroxytetrahydro-2H-pyran-3,4,5-triyl tripropionate (188.47 mg, 592.09 umol, 1 eq), tert-butyl 2-hydroxybenzoate (230 mg, 1.18 mmol, 2 eq) and triphenylphosphine (545.97 mg, 888.14 umol, 1.5 eq) in THF (10 mL) was added di-tertbutyazodicarboxylate (204.50 mg, 888.14 umol, 1.5 eq) at 0° C. The mixture was stirred at 15° C. for 16 hr. TLC indicated new spot formed. The reaction mixture was concentrated under reduced pressure to give a residue. The residue was purified by column chromatography (SiO₂, Petroleum ether/Ethyl acetate=10:1 to 1:1). Compound tert-butyl tert-butyl 2-[(3R,4S,5S)-3,4,5-tri(propanoyloxy)tetrahydropyran-2-yl]oxybenzoate (200 mg, 404.42 umol, 68.30% yield) was obtained as a white solid.

Step 2

To a solution of tert-butyl 2-[(3R,4S,5S)-3,4,5-tri(propanoyloxy)tetrahydropyran-2-yl] oxybenzoate (100 mg, 202.21 umol, 1 eq) in CH₂Cl₂ (1 mL) was added TFA (138.34 mg, 1.21 mmol, 89.83 uL, 6 eq) at 15° C. The mixture was stirred at 15° C. for 2 hr. LCMS showed desired MS was detected. The reaction mixture was concentrated under reduced pressure to give a residue. The residue was purified by prep-TLC (SiO₂, Petroleum ether/Ethyl acetate=1:1). Compound 2-[(3R,4S,5S)-3,4,5-tri(propanoyloxy)tetrahydropyran-2-yl]oxybenzoic acid (30 mg, 32.84 μmol, 16.24% yield, 46.66% purity) was obtained as a colorless oil. LCMS: (M−1) 437.1 NMR (CDCl₃): δ8.2 (m, 1H), 7.4 (m, 1H), 7.2 (m, 2H), 5.3 (m, 4H), 4.0 (dd, 2H), 2.47-1.1 (m, 9H) ppm.

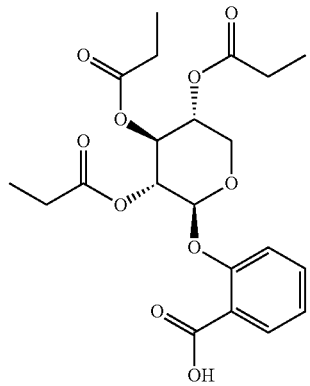 [SMILES: CCC(=O)O[C@@H]1[C@@H](OC(=O)CC)[C@H](Oc2ccccc2C(=O)O)OC[C@H]1OC(=O)CC]

Compound 27: 2-(((2S,3R,4S,5R)-3,4,5-tris(propionyloxy)tetrahydro-2H-pyran-2-yl)oxy)benzoic acid Step 1:

To a solution of [(3R,4S,5R)-6-hydroxy-4,5-di(propanoyloxy)tetrahydropyran-3-yl] propanoate (0.500 g, 1.57 mmol), tert-butyl 2-hydroxybenzoate (0.610 g, 3.14 mmol) and PPh₃ (0.824 g, 3.14 mmol) in THF (10 mL) was added di-tert-butyl azodicarboxylate (0.723 g, 3.14 mmol) at 0° C. The reaction was stirred for 12 h at 15° C. The mixture reaction was concentrated under reduced pressure. The residue was purified by column chromatography (SiO₂, petroleum ether/ethyl acetate=30/1 to 5:1) to give tert-butyl 2-[(3R, 4S, 5R)-3,4,5-tri(propanoyloxy)tetrahydropyran-2-yl]oxybenzoate (0.320 g, 37% yield) as a brown solid.

Step 2:

To a solution of TFA (10 mL) in CH₂Cl₂ (30 mL) was added tert-butyl 2-[(3R,4S,5R)-3,4,5-tri(propanoyloxy)tetrahydropyran-2-yl]oxybenzoate (0.300 g, 606 mmol) and the mixture was stirred at 15° C. for 2 h. The mixture reaction was concentrated under reduced pressure. The residue was purified by prep-HPLC (column: Waters Xbridge Prep OBD C18 150*40 10 u; mobile phase: [water (10 mM NH₄HCO₃)-ACN]; B %: 1%-50%, 11 min) to give 2-[(3R,4S,5R)-3,4,5-tri(propanoyloxy)tetrahydropyran-2-yl]oxybenzoic acid (0.010 g, 3.4% yield) as a yellow oil. MS 437.1 (M−H) NMR (DMSO d6): δ 7.5 (m, 1H), 7.3 (m, 1H), 7.1 (m, 1H), 7.0 (m, 1H), 5.9 (m, 1H), 5.6 (1H) 5.0 (m, 2H), 4.0 (m, 1H), 3.7 (m, 1H), 2.2 (m, 6H), 0.97 (m, 9H).

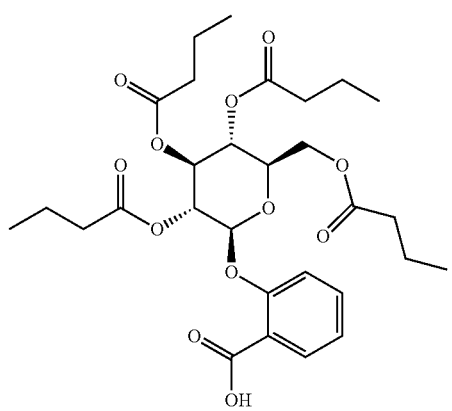 [SMILES: CCCC(=O)OC[C@H]1O[C@@H](Oc2ccccc2C(=O)O)[C@H](OC(=O)CCC)[C@@H](OC(=O)CCC)[C@@H]1OC(=O)CCC]

Compound 28: 2-(((2S,3R,4S,5R,6R)-3,4,5-tris(butyryloxy)-6-((butyryloxy)methyl)tetrahydro-2H-pyran-2-yl)oxy)benzoic acid To the solution of 2-hydroxybenzoic acid (6 g, 43.44 mmol, 7.50 mL, 1 eq) and CDI (8.45 g, 52.13 mmol, 1.2 eq) in DMF (50 mL) was added DBU (7.94 g, 52.13 mmol, 7.86 mL, 1.2 eq) and t-BuOH (6.47 g, 87.32 mmol, 8.35 mL, 2.01 eq). The mixture was stirred at 15° C. for 16 h. LCMS (ET14826-364-P1A) showed the reaction was completed. The solvent was removed under reduced pressure. The crude product was purified by silica gel chromatography eluted with Petroleum ether/Ethyl acetate=1:0-2:1 to give tert-butyl 2-hydroxybenzoate (5 g, 25.74 mmol, 59.26% yield)

To the solution of (2R,3S,4R,5R)-2,3,4,5,6-pentahydroxyhexanal (20 g, 111.02 mmol, 1 eq) in DCM (500 mL) was added butyryl chloride (94.63 g, 888.12 mmol, 92.77 mL, 8 eq) and the mixture was stirred at 15° C. for 0.5 h. Then pyridine (70.25 g, 888.12 mmol, 71.68 mL, 8 eq) was added to the solution dropwise slowly. After the addition, the mixture was stirred at 15° C. for another 16 h. LCMS (ET14826-367-P1A) showed the reaction was completed. The solvent was removed under reduced pressure. The crude product was purified by silica gel chromatography eluted with Petroleum ether/Ethyl acetate=1:0-5:1 to give (3R,4S,5R,6R)-6-((butyryloxy)methyl) tetrahydro-2H-pyran-2,3,4,5-tetrayl tetrabutyrate (58 g, 109.31 mmol, 98.46% yield) as yellow oil To the solution of (3R,4S,5R,6R)-6-((butyryloxy)methyl) tetrahydro-2H-pyran-2,3,4,5-tetrayl tetrabutyrate (10 g, 18.85 mmol, 1 eq) in THF (85 mL) and H₂O (5 mL) was added methanamine/THF (2 M, 12.25 mL, 1.3 eq). Then the mixture was stirred at 15° C. for 16 h. LCMS (ET14826-370-P1A2) showed most of the starting material was consumed and the desired MS was detected. The solvent was removed under reduced pressure. The crude product was purified by silica gel chromatography eluted with Petroleum ether/Ethyl acetate=10:1-1:1 to give (2R,3R,4S,5R)-2-((butyryloxy)methyl)-6-hydroxytetrahydro-2H-pyran-3,4,5-triyl tributyrate (10 g, 21.50 mmol, 57.03% yield, 99% purity) as yellow oil.

To the solution of (2R,3R,4S,5R)-2-((butyryloxy)methyl)-6-hydroxytetrahydro-2H-pyran-3,4,5-triyl tributyrate (0.85 g, 1.85 mmol, 1 eq) and tert-butyl 2-hydroxybenzoate (340.57 mg, 1.75 mmol, 0.95 eq) in THF (20 mL) was added PPh₃ (692.29 mg, 2.64 mmol, 1.43 eq) and di-tert-butyl azodicarboxylate (637.51 mg, 2.77 mmol, 1.5 eq). Then the mixture was stirred at 15° C. for 16 h. LCMS showed the reaction was completed and the desired MS was detected. The solvent was removed under reduced pressure. The crude product was purified by p-HPLC (column: Phenomenex Luna C18 200*40 mm*10 um; mobile phase: [water (0.1% TFA)-ACN]; B %: 75%-95%, 10 min) to give (3R,4S,5R,6R)-2-(2-(tert-butoxycarbonyl)phenoxy)-6-((butyryloxy)methyl)tetrahydro-2H-pyran-3,4,5-triyl tributyrate (0.2 g, 314.11 umol, 17.02% yield) as brown oil.

To the solution of (3R,4S,5R,6R)-2-(2-(tert-butoxycarbonyl)phenoxy)-6-((butyryloxy)methyl) tetrahydro-2H-pyran-3,4,5-triyl tributyrate (0.2 g, 314.11 umol, 1 eq) in DCM (10 mL) was added TFA (1.54 g, 13.51 mmol, 1 mL, 43.00 eq). Then the solution was stirred at 15° C. for 16 h. LCMS showed the reaction was completed and the desired MS was detected. The solvent was removed under reduced pressure. The crude product was purified by p-HPLC (column: Nano-micro Kromasil C18 100*30 mm 5um; mobile phase: [water (0.1% TFA)-ACN]; B %: 60%-78%, 10 min) to afford the title compound (24 mg, 40.10 umol, 12.76% yield, 97% purity, temporary assigned) as yellow oil. LCMS: (M+18): 598.2 NMR (DMSO d6): δ 8.1 (d, 1H), 7.5 (dd, 1H), 7.4 (d, 1H), 7.2 (m, 1H), 5.8 (m, 1H), 5.6 (t, 1H), 5.2 (m, 2H), 4.1 (m, 3H), 2.3 (m, 8H), 1.6 (m, 8H), 0.87 (m, 12H) ppm.

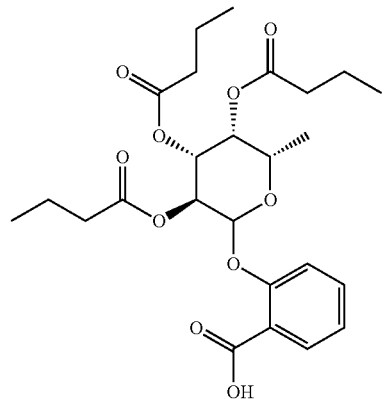 [SMILES: CCCC(=O)O[C@@H]1[C@H](OC(=O)CCC)[C@H](C)OC(Oc2ccccc2C(=O)O)[C@H]1OC(=O)CCC]

Compound 29: 2-(((3S,4R,5R,6S)-3,4,5-tris(butyryloxy)-6-methyltetrahydro-2H-pyran-2-yl)oxy)benzoic acid Compound 29 was prepared as a colorless oil (0.03 g, 22% yield). LCMS: 517.2 (M+Na⁺); ¹H NMR CDCl₃ 8.080 (m, 1H), 7.491 (m, 1H), 7.164 (m, 1H), 7.086 (m, 1H), 5.494 (m, 1H), 5.292 (m, 1H), 5.197 (m, 1H), 5.133 (m, 1H), 3.946 (m, 1H), 2.413-2.153 (m, 6H), 1.653-1.546 (m, 6H), 1.204 (d, 3H), 0.946 (t, 3H), 0.869 (t, 3H), 0.850 (t, 3H).

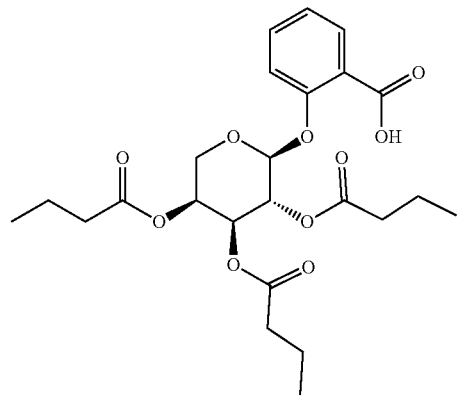 [SMILES: CCCC(=O)O[C@@H]1[C@@H](OC(=O)CCC)[C@H](Oc2ccccc2C(=O)O)OC[C@@H]1OC(=O)CCC]

Compound 30: 2-(((2S,3R,4S,5S)-3,4,5-tris(butyryloxy)tetrahydro-2H-pyran-2-yl)oxy)benzoic acid Compound 30 was prepared in an analogous matter to compound 29. Compound 30 was prepared in 27% yield (15 mg). LCMS: 503 (M+Na⁺); ¹H NMR CDCl3 8,095 (m, 1H), 7.484 (m, 1H), 7.326 (m, 1H), 7.154 (m, 1H), 5.775 (d, 1H), 5.482-5.404 (m, 3H), 4.084 (d, 1H), 3.840 (d, 1H), 2.372-2.276 (m, 6H), 1.658-1.497 (m, 6H), 0.937 (t, 3H), 0.863 (t, 3H), 0.823 (t, 3H).

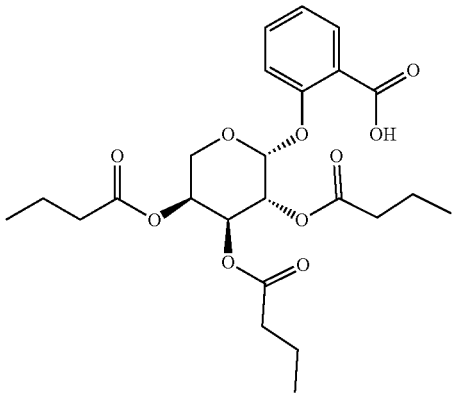 [SMILES: CCCC(=O)O[C@@H]1[C@@H](OC(=O)CCC)[C@@H](Oc2ccccc2C(=O)O)OC[C@@H]1OC(=O)CCC]

Compound 31: 2-(((2R,3R,4S,5S)-3,4,5-tris(butyryloxy)tetrahydro-2H-pyran-2-yl)oxy)benzoic acid Step 1:

A solution of DCC (8 g, 38.8 mmol) in THF (50 mL) was added dropwise to a solution of 2-hydroxybenzoic acid (5 g, 36.2 mmol) and DMAP (0.17 g, 1.39 mmol) in t-BuOH (100 mL) and the mixture was stirred at 15° C. for 16 h. The crude product was purified by silica gel chromatography (petroleum ether/ethyl acetate=1:0) to give tert-butyl 2-hydroxybenzoate (3 g, 42.7%) as colorless oil.

Step 2:

To a solution of (3R,4S,5S)-2-hydroxytetrahydro-2H-pyran-3,4,5-triyl tributyrate (0.7 g, 1.94 mmol) and tert-butyl 2-hydroxybenzoate (0.358 g, 1.85 mmol) in THF (30 mL) was added PPh₃ (0.728 g, 2.78 mmol) and DBAD (0.671 g, 2.91 mmol) in portions. Then the mixture was stirred at 15° C. for 16 h. The solvent was removed under reduced pressure. The crude product was purified by prep-HPLC (column: Agela innoval ods-2 250*80 mm; mobile phase: [water (0.1% TFA)-ACN]; B %: 37%-67%, 20 min) to give (3R,4S,5S)-2-(2-(tert-butoxycarbonyl)phenoxy)tetrahydro-2H-pyran-3,4,5-triyl tributyrate (0.4 g, 0.745 mmol, 38.4%) as a yellow oil.

Step 3:

To a solution of (3R,4S,5S)-2-(2-(tert-butoxycarbonyl) phenoxy)tetrahydro-2H-pyran-3,4,5-triyl tributyrate (0.2 g, 0.37 mmol) in DCM (10 mL) was added TFA (3.08 g, 27 mmol). Then the mixture was stirred at 15° C. for 16 h under N₂. The solvent was removed under reduced pressure. The crude product was purified by prep-HPLC (column: Waters Xbridge 150*25 5 u; mobile phase: [water (0.1% TFA)-ACN]; B %: 47%-67%, 12 min) to give the title compound. LCMS: 503 (M+Na⁺); ¹H NMR CDCl3 8.202 (m, 1H), 7.567 (m, 1H), 7.264-7.213 (m, 2H), 5.480-5.351 (m, 4H), 4.061 (m, 1H), 3.8 (m, 1H), 2.425-2.297 (m, 6H), 1.688-1.650 (m, 6H), 0.959 (m, 9H)

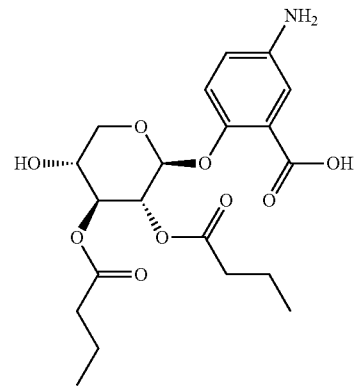 [SMILES: CCCC(=O)O[C@@H]1[C@@H](OC(=O)CCC)[C@H](Oc2ccc(N)cc2C(=O)O)OC[C@H]1O]

Compound 32: 5-amino-2-(((2S,3R,4S,5R)-3,4-bis(butyryloxy)-5-hydroxytetrahydro-2H-pyran-2-yl)oxy)benzoic acid Pancreatin from porcine pancreas (200 mg) and FaSSIF/FeSSIF/FaSSGF powder (44.8 mg, sourced from biorelevant.com) were suspended in 20 mL of SIF buffer (10.5 mM sodium hydroxide, 28.6 mM monobasic sodium phosphate monohydrate, 106 mM sodium chloride, pH 6.5) and incubated at 37° C. on a laboratory rocker for 30 minutes. Compound 19 (200 mg, 0.404 mmol, 1 eq) was then added to 20 mL of the SIF suspension and rocked at 37° C. overnight. The suspension was added to a separatory funnel and diluted with additional water (20 mL). Product was extracted with dichloromethane (40 mL) three times, then the organic layer was dried over magnesium sulfate. After filtering out the salts, the solution was concentrated by rotary evaporation and re-dissolved in DMSO before injection and purification by reverse phase C18 column chromatography (gradient: 10% acetonitrile in deionized water to 100% acetonitrile). Fractions containing product were lyophilized to yield the title compound as a white powder (95 mg, 0.223 mmol, 55% yield). LCMS [M−H]⁻: 424.2. ¹H NMR (400 MHz, DMSO-d6) δ 6.84 (d, J=8.7 Hz, 1H), 6.76 (d, J=2.8 Hz, 1H), 6.60 (dd, J=8.7, 2.9 Hz, 1H), 5.41 (d, J=5.3 Hz, 1H), 5.02-4.93 (m, 2H), 4.84 (dd, J=9.7, 7.8 Hz, 1H), 3.83 (dd, J=11.3, 5.5 Hz, 1H), 3.71-3.59 (m, 1H), 3.38 (t, J=10.8 Hz, 1H), 2.33-2.08 (m, 4H), 1.56-1.40 (m, 4H), 0.89-0.77 (m, 6H).

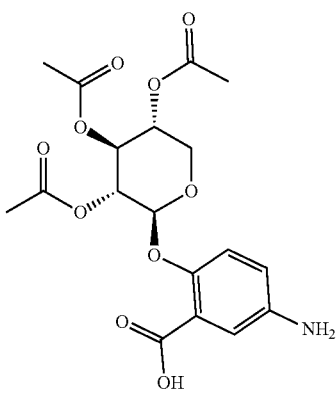 [SMILES: CC(=O)O[C@@H]1[C@@H](OC(C)=O)[C@H](Oc2ccc(N)cc2C(=O)O)OC[C@H]1OC(C)=O]

Compound 33: 5-amino-2-(((2S,3R,4S,5R)-3,4,5-triacetoxytetrahydro-2H-pyran-2-yl)oxy)benzoic acid (3R,4S,5R)-tetrahydro-2H-pyran-2,3,4,5-tetrayl tetraacetate (3.90 g, 12.3 mmol) was dissolved in tetrahydrofuran (80.0 mL). The solution was stirred at room temperature when methylamine (40% wt. in water, 1.59 mL, 18.4 mmol) was added dropwise. The mixture was stirred overnight and concentrated to give crude (3R,4S,5R)-2-hydroxytetrahydro-2H-pyran-3,4,5-triyl triacetate as a brown oil.

Crude (3R,4S,5R)-2-hydroxytetrahydro-2H-pyran-3,4,5-triyl triacetate (500 mg, 1.81 mmol) was dissolved in N N-dimethylformamide (4.00 mL) at room temperature. The solution was stirred when benzyl 2-fluoro-5-nitrobenzoate (752 mg, 2.73 mmol) and then 1,4-diazabicyclo[2.2.2]octane (1.06 g, 9.36 mmol) were added. Stirring was continued for 90 h. Water (50 mL) was added and the mixture was extracted with ethyl acetate (5×20 mL). The combined organic layers were washed with water (20 mL), brine (2×20 mL), dried over anhydrous $Na_2SO_4$, filtered and concentrated to give a brown oil. The crude material was adsorbed on celite and purified by automated chromatography (40 g, $SiO_2$, 0 to 60% ethyl acetate in hexanes) to afford (2S,3R,4S,5R)-2-(2-((benzyloxy)carbonyl)-4-nitrophenoxy)tetrahydro-2H-pyran-3,4,5-triyl triacetate (413 mg, 43%) as a pale yellow foam. LCMS calcd for $C_{25}H_{25}O_{12}$ 531.14, found 554.4 [M+Na] at 1.86 min.

(2S,3R,4S,5R)-2-(2-((benzyloxy)carbonyl)-4-nitrophenoxy)tetrahydro-2H-pyran-3,4,5-triyl triacetate (413 mg, 0.777 mmol) was dissolved in methanol (3.00 mL) at room temperature. The solution was stirred under nitrogen when palladium on carbon (10% wt., 50.0 mg, 0.0470 mmol) was added. The mixture was degassed with hydrogen and then stirred under hydrogen overnight. The mixture was filtered on celite and concentrated to give a brown oil. The crude material was purified by automated reverse phase chromatography (24 g, C18, 5 to 40% acetonitrile in 10 mM aqueous ammonium formate) as a solution in N N-dimethylformamide (10% water). After lyophilization, 5-amino-2-(((2S,3R,4S,5R)-3,4,5-triacetoxytetrahydro-2H-pyran-2-yl)oxy)benzoic acid (59.8 mg, 19%) was obtained as a white solid. $^1$H NMR (400 MHz, DMSO-$d_6$) δ 6.87 (d, J=8.8 Hz, 1H), 6.79 (d, J=2.9 Hz, 1H), 6.62 (dd, J=8.7, 2.9 Hz, 1H), 5.21 (t, J=8.8 Hz, 1H), 5.11 (d, J=7.0 Hz, 1H), 4.96 (dd, J=9.0, 7.0 Hz, 1H), 4.89 (td, J=8.9, 5.2 Hz, 1H), 4.04 (dd, J=11.6, 5.2 Hz, 1H), 3.62 (dd, J=11.6, 9.1 Hz, 1H), 2.02-1.97 (m, 9H). LCMS calcd for $C_{18}H_{21}O_{10}$ 411.12, found 410.3 [M–H] at 1.10 min.

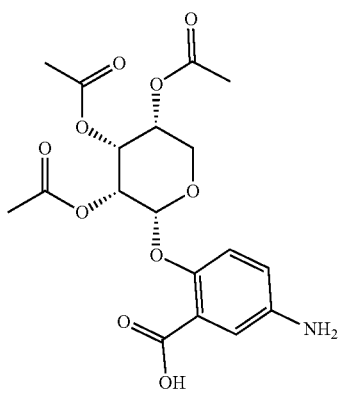 [SMILES: CC(=O)O[C@H]1[C@@H](Oc2ccc(N)cc2C(=O)O)OC[C@@H](OC(C)=O)[C@H]1OC(C)=O]

Compound 34: 5-amino-2-(((2R,3R,4R,5R)-3,4,5-triacetoxytetrahydro-2H-pyran-2-yl)oxy)benzoic acid D-(−)-ribose (1.99 g, 13.1 mmol) was dissolved in pyridine (40 mL) under nitrogen. The solution was stirred when acetic acid (10.0 mL, 106 mmol) and then 4-dimethylaminopyridine (126 mg, 1.01 mmol) were added. Stirring was continued overnight Water (150 mL) was added and after 1 h of additional stirring, the mixture was extracted with ethyl acetate (3×40 mL). The combined organic layers were washed with saturated aqueous $NaHCO_3$ (3×50 mL), water (50 mL), brine (2×50 mL), dried over anhydrous $Na_2SO_4$, filtered and concentrated to give a pale yellow oil. The crude material was adsorbed on celite and purified by automated chromatography (80 g, $SiO_2$, 0 to 80% ethyl acetate in heptanes) to afford (3R,4R,5R)-tetrahydro-2H-pyran-2,3,4,5-tetrayl tetraacetate (3.90 g, 93%) as a colorless oil. (3R,4R,5R)-tetrahydro-2H-pyran-2,3,4,5-tetrayl tetraacetate (3.6 g, 11.3 mmol) was dissolved in acetonitrile (14.0 mL) at room temperature. Aqueous perchloric acid (70% wt., 974 μL, 11.3 mmol) was added in one portion and the mixture was stirred for 1 h. The mixture was washed with aqueous saturated $NaHCO_3$, water and brine, dried over anhydrous $Na_2SO_4$, filtered and concentrated to give crude (3R,4R,5R)-2-hydroxytetrahydro-2H-pyran-3,4,5-triyl triacetate (1.11 g, 36%). $^1$H NMR (400 MHz, DMSO-d6) δ 7.02 (s, 1H, OH), 5.93-5.82 (m, 1H), 5.51-5.04 (m, 1H), 4.99-4.44 (m, 2H), 3.98-3.38 (m, 2H), 2.12-1.91 (m, 9H).

(3R,4R,5R)-2-hydroxytetrahydro-2H-pyran-3,4,5-triyl triacetate (1.11 g, 4.02 mmol) was dissolved in N N-dimethylformamide (7.0 mL). The solution was stirred at room temperature when benzyl 2-fluoro-5-nitrobenzoate (1.11 g, 4.02 mmol) and then 1,4-diazabicyclo[2.2.2]octane (2.28 g, 20.1 mmol) were added. Stirring was continued for 2 d. Then, water was added. The aqueous layer was extracted with ethyl acetate. The combined organic layers were washed with brine, dried over anhydrous $Na_2SO_4$, filtered and concentrated to give a brown oil. The crude material was adsorbed on celite and purified by automated chromatography ($SiO_2$, ethyl acetate gradient in hexanes) to give (3R,4R,5R)-2-(2-((benzyloxy)carbonyl)-4-nitrophenoxy)tetrahydro-2H-pyran-3,4,5-triyl triacetate (295 mg, 14%) as a yellow oil. $^1$H NMR (400 MHz, CDCl$_3$) δ 8.70 (d, J=2.9 Hz, 1H), 8.31 (dd, J=9.2, 2.9 Hz, 1H), 7.44-7.27 (m, 6H), 6.00 (d, J=4.8 Hz, 0.5 Ha), 5.73 (d, J=2.7 Hz, 1Ha'), 5.46 (t, J=3.6 Hz, 1H), 5.38 (app q, J=12.1 Hz, 2H), 5.29-5.26 (m, 1H), 5.15-4.99 (m, 2H), 4.02-3.94 (m, 2H), 3.80 (dd, J=12.9, 3.1 Hz, 1H), 2.20-1.97 (m, 9H). LCMS calcd for $C_{25}H_{25}NO_{12}$ 531.14, found 554.3 [M+Na] at 1.79 min.

(3R,4R,5R)-2-(2-((benzyloxy)carbonyl)-4-nitrophenoxy)tetrahydro-2H-pyran-3,4,5-triyl triacetate (280 mg, 527 μmol) was dissolved in methanol (5.0 mL). Palladium on carbon (10% wt., 22.4 mg, 21.1 μmol) was added to the stirring solution under nitrogen. The mixture was degassed with hydrogen and allowed to stir under hydrogen for 2 h. The mixture was filtered through a pad of celite and washed with methanol and dichloromethane. The filtrate was concentrated and purified by automated reverse phase chromatography (C18, 15 to 25% acetonitrile in 10 mM aqueous ammonium formate). After lyophilisation, 5-amino-2-(((2R,3R,4R,5R)-3,4,5-triacetoxytetrahydro-2H-pyran-2-yl)oxy)benzoic acid (26.7 mg, 12%) as a white solid. $^1$H NMR (400 MHz, DMSO-d6) δ 6.85 (dd, J=5.6, 2.7 Hz, 2H), 6.60 (dd, J=8.6, 2.5 Hz, 1H), 5.36 (t, J=3.6 Hz, 1H), 5.31 (d, J=3.0 Hz, 1H), 5.15 (t, J=3.3 Hz, 1H), 5.09 (d, J=3.2 Hz, 1H), 4.18 (dd, J=12.8, 1.9 Hz, 1H), 3.73 (dd, J=12.7, 3.7 Hz, 1H), 2.04 (d, J=4.3 Hz, 7H), 1.93 (s, 3H). LCMS calcd for $C_{18}H_{21}NO_{10}$ 411.12, found 412.1 [M+H] at 1.02 min

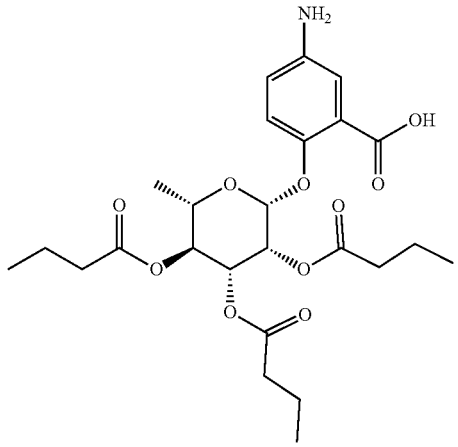 [SMILES: CCCC(=O)O[C@@H]1[C@@H](OC(=O)CCC)[C@H](C)O[C@H](Oc2ccc(N)cc2C(=O)O)[C@@H]1OC(=O)CCC]

Compound 35: 5-amino-2-(((2R,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (316 mg, 0.844 mmol), benzyl 2-hydroxy-5-nitrobenzoate (355 mg, 1.30 mmol) and triphenylphosphine (374 mg, 1.43 mmol) were dissolved in dry tetrahydrofuran (2.50 mL) under nitrogen at room temperature. The solution was stirred at 0° C. when di-tert-butyl azodicarboxylate (299 mg, 1.27 mmol) was added in one portion. After 30 min of additional stirring, the flask was removed from the cooling bath, the mixture was allowed to warm up till room temperature and stir overnight. The mixture was adsorbed on celite and purified by automated chromatography (40 g, $SiO_2$, 0 to 30% ethyl acetate in hexanes) to afford (2R,3R,4R,5S,6S)-2-(2-((benzyloxy)carbonyl)-4-nitrophenoxy)-6-methyltetrahydro-2H-pyran-3,4,5-triyl tributyrate (197 mg, 37%). LCMS calcd for $C_{32}H_{39}NO_{12}$ 629.25, found 647.0 [M+$NH_4$] at 2.20 min.

(2R,3R,4R,5S,6S)-2-(2-((benzyloxy)carbonyl)-4-nitrophenoxy)-6-methyltetrahydro-2H-pyran-3,4,5-triyl tributyrate (197 mg, 0.313 mmol) was dissolved in methanol (2.50 mL) at room temperature. The solution was stirred under nitrogen when palladium on carbon (10% wt., 2.30 mg, 0.0216 mmol) was added in one portion. The suspension was stirred, degassed with hydrogen and allowed to stir under hydrogen overnight. The mixture was diluted with dichloromethane and filtered on celite. The crude material was concentrated and purified by automated reverse phase chromatography (12 g, C18, 10 to 60% acetonitrile in 10 mM aqueous ammonium formate) as a solution in N N-dimethylformamide (10% water). After lyophilisation, 5-amino-2-(((2R,3R,4R,5S,6S)-3,4,5-tris(butyryloxy)-6-methyltetrahydro-2H-pyran-2-yl)oxy)benzoic acid (78.4 mg, 49%) was obtained as a white solid. $^1$H NMR (400 MHz, DMSO-d6) δ 6.89 (d, J=2.9 Hz, 1H), 6.87 (d, J=8.7 Hz, 1H), 6.65 (dd, J=8.7, 2.9 Hz, 1H), 5.58 (dd, J=3.3, 0.9 Hz, 1H), 5.30 (d, J=1.0 Hz, 1H), 5.18 (dd, J=10.2, 3.4 Hz, 1H), 5.05 (br s, 2H), 4.90 (t, J=9.9 Hz, 1H), 3.80-3.70 (m, J=6.2 Hz, 1H), 2.41-2.34 (m, 2H), 2.33-2.22 (m, 2H), 2.14 (td, J=7.2, 3.2 Hz, 2H), 1.66-1.56 (m, 2H), 1.56-1.42 (m, 4H), 1.12 (d, J=6.2 Hz, 3H), 0.94 (t, J=7.4 Hz, 3H), 0.89-0.80 (m, 6H). LCMS calcd for $C_{25}H_{35}NO_{10}$ 509.23, found 508.3 [M−H] at 1.74 min.

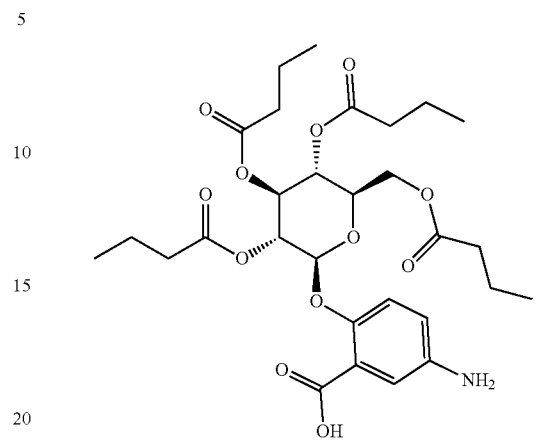

Compound 36: 5-amino-2-(((2S,3R,4S,5R,6R)-3,4,5-tris(butyryloxy)-6-((butyryloxy)methyl)tetrahydro-2H-pyran-2-yl)oxy)benzoic acid 2R,3R,4S,5R)-2-((butyryloxy)methyl)-6-hydroxytetrahydro-2H-pyran-3,4,5-triyl tributyrate (239 mg, 519 μmol) was dissolved in N N-dimethylformamide (1 mL). The solution was stirred at room temperature when benzyl 2-fluoro-5-nitrobenzoate (186 mg, 675 μmol) and then 1,4-diazabicyclo[2.2.2]octane (294 mg, 2.59 mmol) were added. Stirring was continued for 2 d and water was added. The aqueous layer was extracted with ethyl acetate. The combined organic layers were washed with brine, dried over anhydrous $Na_2SO_4$, filtered and concentrated to give a brown oil. The crude material was adsorbed on celite to be purified by automated chromatography ($SiO_2$, ethyl acetate gradient in hexanes) to afford (3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 45%). LCMS calcd for $C_{36}H_{45}NO_{14}$ 715.28, found 733.6 [M+$NH_4$] at 2.26 min.

(3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 236 μmol) was dissolved in methanol (5.0 mL) at room temperature. The solution was stirred under nitrogen when palladium on carbon (10% wt., 25.1 mg, 23.6 μmol) was added in one portion. Then, the solvent was degassed with hydrogen and the reaction was allowed to stir under hydrogen for 2 h. The mixture was diluted with dichloromethane and filtered on celite. The crude material was purified by automated reverse phase chromatography (C18, 25% to 65% acetonitrile in 10 mM aqueous ammonium formate). After lyophilisation, 5-amino-2-(((2S,3R,4S,5R,6R)-3,4,5-tris(butyryloxy)-6-((butyryloxy)methyl)tetrahydro-2H-pyran-2-yl)oxy)benzoic acid (32.3 mg, 23%) was obtained as a white solid $^1$H NMR (400 MHz, DMSO-d6) δ 6.88 (d, J=8.8 Hz, 1H), 6.76 (d, J=2.8 Hz, 1H), 6.60 (dd, J=8.8, 2.8 Hz, 1H), 5.36 (t, J=9.6 Hz, 1H), 5.21 (d, J=8.0 Hz, 1H), 5.03-4.93 (m, 3H), 4.18-4.05 (m, 2H, H), 2.30-2.09 (m, 8H), 1.58-1.39 (m, 8H), 0.90-0.77 (m, 12H). LCMS calcd for $C_{29}H_{41}NO_{12}$ 595.26, found 613.3 [M+$NH_4$].

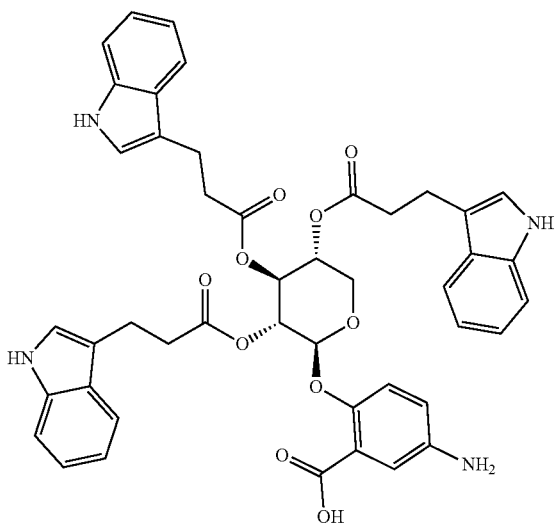 [SMILES: Nc1ccc(O[C@@H]2OC[C@@H](OC(=O)CCc3c[nH]c4ccccc34)[C@H](OC(=O)CCc3c[nH]c4ccccc34)[C@H]2OC(=O)CCc2c[nH]c3ccccc23)c(C(=O)O)c1]

Compound 37:5-amino-2-(((2S,3R,4S,5R)-3,4,5-tris((3-(1H-indol-3-yl)propanoyl)oxy)tetrahydro-2H-pyran-2-yl)oxy)benzoic acid 3-Indolepropionic acid (20.0 g, 104 mmol) and dicyclohexylcarbodiimide (10.3 g, 49.3 mmol) were dissolved in tetrahydrofuran (345 mL). The reaction was stirred under nitrogen for 2 d. The solution was filtered, washed with tetrahydrofuran and the filtrate was concentrated to give crude 3-(1H-indol-3-yl)propanoic anhydride (26 g, 69%).

Crude 3-(1H-indol-3-yl)propanoic anhydride (26.0 g, 72.1 mmol) was dissolved in pyridine (150 mL) under nitrogen. 4-dimethylaminopyridine (450 mg, 3.61 mmol) and d-(+)-xylose (1.11 g, 7.43 mmol) were added. The mixture was stirred for 24 h. 1 N aqueous hydrochloric acid was added and the aqueous layer was extracted with ethyl acetate. The combined organic layers were concentrated. The crude material was purified by automated reverse phase chromatography (C18, 60 to 65% acetonitrile in 10 mM aqueous ammonium formate) to afford (3R,4S,5R)-tetrahydro-2H-pyran-2,3,4,5-tetrayl tetrakis(3-(1H-indol-3-yl)propanoate (3.49 g, 58%) as a yellow suspension. LCMS calcd for $C_{49}H_{46}N_4O_9$ 834.33, found 833.6 [M−H] at 2.05 min.

(3R,4S,5R)-tetrahydro-2H-pyran-2,3,4,5-tetrayl tetrakis(3-(1H-indol-3-yl)propanoate) (1.06 g, 1.27 mmol) was dissolved in acetonitrile (13.0 mL) at room temperature. Aqueous perchloric acid (70% wt., 110 µL, 1.27 mmol) was added and the mixture was stirred for 3 h. The mixture was washed with saturated aqueous $NaHCO_3$, water and brine and dried over anhydrous $Na_2SO_4$, filtered and concentrated. The crude material was purified by automated reverse phase chromatography (C18, acetonitrile in 10 mM aqueous ammonium formate). After lyophilisation, (3R,4S,5R)-2-hydroxytetrahydro-2H-pyran-3,4,5-triyl tris(3-(1H-indol-3-yl)propanoate (121 mg, 14%) was obtained as a yellow solid. $^1$H NMR (400 MHz, DMSO-$d_6$) δ 10.75 (s, 3H), 7.46-7.34 (m, 3H), 7.25 (d, J=10.6 Hz, 3H), 7.02 (m, 8H), 6.94-6.82 (m, 4H), 5.41 (t, J=9.8 Hz, 0.5H), 5.26 (s, 0.3H), 5.16 (s, 1H), 4.92-4.69 (m, 2H), 3.64 (m, 2H), 2.84 (dd, J=15.8, 7.8 Hz, 6H), 2.53-2.49 (m, 6H). LCMS calcd for $C_{38}H_{37}N_3O_8$ 663.26, found 681.2 [M+NH$_4$] at 1.80 min.

(3R,4S,5R)-2-hydroxytetrahydro-2H-pyran-3,4,5-triyl tris(3-(1H-indol-3-yl)propanoate) (121 mg, 182 µmol) was dissolved in N N-dimethylformamide (600 µL). The solution was stirred at room temperature when benzyl 2-fluoro-5-nitrobenzoate (65.2 mg, 237 µmol) and then 1,4-diazabicyclo[2.2.2]octane (102 mg, 912 µmol) were added. Stirring was continued for 2 d. Then, water was added. The aqueous layer was extracted with ethyl acetate. The combined organic layers were washed with brine, dried over anhydrous $Na_2SO_4$, filtered and concentrated to give a brown oil. The crude material was adsorbed on celite and purified by automated chromatography ($SiO_2$, ethyl acetate gradient in hexanes) to afford (3R,4S,5R)-2-(2-((benzyloxy)carbonyl)-4-nitrophenoxy)tetrahydro-2H-pyran-3,4,5-triyl tris(3-(1H-indol-3-yl)propanoate) (36.0 mg, 21%) as a yellow oil. LCMS calcd for $C_{52}H_{46}N_4O_{12}$ 918.31, found 936 [M+NH$_4$] at 2.10 min.

(3R,4S,5R)-2-(2-((benzyloxy)carbonyl)-4-nitrophenoxy)tetrahydro-2H-pyran-3,4,5-triyl tris(3-(1H-indol-3-yl)propanoate) (36.0 mg, 39.2 µmol) was dissolved in methanol (800 µL) and stirred at room temperature under nitrogen. To this stirring solution, palladium on carbon (10% wt. 4.17 mg, 3.92 µmol) was added. The suspension was degassed with hydrogen and allowed to stir under hydrogen for 2 h. The mixture was filtered through celite and washed with methanol. The filtrate was concentrated under vacuo. The crude material was purified by preparative HPLC-MS (CSH column, acetonitrile in 10 mM aqueous ammonium formate). After lyophilisation, 3-carboxy-4-(((2S,3R,4S,5R)-3,4,5-tris((3-(1H-indol-3-yl)propanoyl)oxy)tetrahydro-2H-pyran-2-yl)oxy)benzenaminium formate (4.20 mg, 13%) was obtained as a white solid. $^1$H NMR (400 MHz, DMSO-$d_6$) δ 10.77 (t, J=12.5 Hz, 3H), 8.40 (s, 3H), 7.53-7.38 (m, 3H), 7.28 (dd, J=8.0, 4.8 Hz, 3H), 7.03 (dd, J=13.2, 4.9 Hz, 6H), 6.96-6.85 (m, 3H), 6.82-6.67 (m, 2H), 6.53 (d, J=7.0 Hz, 1H), 5.29 (t, J=8.5 Hz, 1H), 5.18 (d, J=6.7 Hz, 1H), 5.06-5.01 (m, 1H), 4.91 (dd, J=13.5, 8.3 Hz, 1H), 3.98 (dd, J=11.6, 4.9 Hz, 1H), 3.60-3.51 (m, 1H), 2.91-2.79 (m, 7H), 2.74-2.67 (m, 1H), 2.63-2.54 (m, 4H). LCMS calcd for $C_{45}H_{42}N_4O_{10}$ 798.29, found 816 [M+NH$_4$] at 1.80 min.

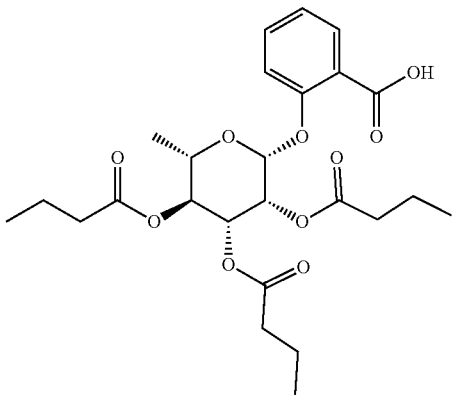 [SMILES: CCCC(=O)O[C@@H]1[C@@H](OC(=O)CCC)[C@H](C)O[C@H](Oc2ccccc2C(=O)O)[C@@H]1OC(=O)CCC]

Compound 38: 2-(((2R,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (1.20 g, 3.20 mmol), benzyl 2-hy droxybenzoate (1.10 g, 4.81 mmol) and triphenylphosphine (1.27 g, 4.81 mmol) were dissolved in tetrahydrofuran (54.0 mL) and stirred at 0° C. Di-tert-butyl azodicarboxylate (1.11 g, 4.81 mmol) was added portion wise and the reaction mixture was stirred at 0° C. for 1 h and allowed to warm up till room temperature to stir overnight. The mixture was adsorbed on silica to be purified by automated chromatography (100 g, SiO$_2$, 0 to 35% ethyl acetate in hexanes). (2S,3R,4R,5S,6S)-2-(2-((benzyloxy)carbonyl)phenoxy)-6-methyltetrahydro-2H-pyran-3,4,5-triyl tributyrate (165 mg, 8.1%) and (2R,3R,4R,5S,6S)-2-(2-((benzyloxy)carbonyl)phenoxy)-6-methyltetrahydro-2H-pyran-3,4,5-triyl tributyrate (427 mg, 21%) were separated but containing other impurities.

(2S,3R,4R,5S,6S)-2-(2-((benzyloxy)carbonyl)phenoxy)-6-methyltetrahydro-2H-pyran-3,4,5-triyl tributyrate (166 mg, 284 µmol) was dissolved in methanol (9.00 mL) and stirred at room temperature under nitrogen. To this mixture was added palladium on carbon (10% wt., 11.0 mg, 73.0 µmol). The suspension was degassed with hydrogen and stir under hydrogen overnight. The mixture was filtered through celite and washed with methanol. The filtrate was concentrated under vacuo. The crude material was purified by automated chromatography (25 g, SiO$_2$, 0 to 100% ethyl acetate in hexanes) as a solution in dichloromethane to afford 2-(((2S,3R,4R,5S,6S)-3,4,5-tris(butyryloxy)-6-methyltetrahydro-2H-pyran-2-yl)oxy)benzoic acid (9 mg, 6%) as a white solid. $^1$H NMR (400 MHz, DMSO-d6) δ 7.71 (d, J=8.2 Hz, 1H), 7.51 (t, J=8.1 Hz, 1H), 7.29 (d, J=8.0 Hz, 1H), 7.14 (t, J=7.9 Hz, 1H), 5.76 (d, J=3.1 Hz, 2H), 5.43 (d, J=8.3 Hz, 2H), 5.02 (t, J=9.8 Hz, 1H), 1.54 (ddt, J=22.7, 14.8, 7.4 Hz, 6H), 1.05 (d, J=6.3 Hz, 3H), 0.95 (t, J=7.4 Hz, 3H), 0.85 (q, J=7.4 Hz, 6H). LCMS calcd for C$_{25}$H$_{34}$O$_{10}$ 494.22, found 512.3 [M+NH$_4$] at 1.94 min.

(2R,3R,4R,5S,6S)-2-(2-((benzyloxy)carbonyl)phenoxy)-6-methyltetrahydro-2H-pyran-3,4,5-triyl tributyrate (427 mg, 711 µmol) was dissolved methanol (9.00 mL) and stirred at room temperature under nitrogen. To this mixture was added palladium on carbon (10% wt., 11.0 mg, 73.0 µmol). The suspension was degassed with hydrogen and stir under hydrogen overnight. The mixture was filtered through celite and washed with methanol. The filtrate was concentrated under vacuo. The crude material was purified by automated chromatography (50 g, SiO$_2$, 0 to 100% ethyl acetate in hexanes) as a solution in dichloromethane to afford 2-(((2R,3R,4R,5S,6S)-3,4,5-tris(butyryloxy)-6-methyltetrahydro-2H-pyran-2-yl)oxy)benzoic acid (18 mg, 5%) as a white solid. $^1$H NMR (400 MHz, DMSO-d6) δ 7.62 (dd, J=7.5, 1.6 Hz, 1H), 7.46 (t, J=7.9 Hz, 1H), 7.14 (d, J=7.8 Hz, 1H), 7.08 (td, J=7.6, 0.8 Hz, 1H), 5.68 (d, J=0.8 Hz, 1H), 5.55 (dd, J=3.5, 1.0 Hz, 1H), 5.22 (dd, J=10.2, 3.4 Hz, 1H), 4.90 (t, J=9.9 Hz, 1H), 3.90-3.82 (m, 1H), 2.38 (t, J=7.1 Hz, 2H), 2.27 (m, 2H), 2.13 (td, J=7.2, 2.7 Hz, 2H), 1.60 (m, 2H), 1.48 (m, 4H), 1.12 (d, J=6.2 Hz, 3H), 0.93 (t, J=7.4 Hz, 3H), 0.85 (t, J=8.5 Hz, 3H), 0.83 (t, J=8.1 Hz, 3H). LCMS calcd for C$_{21}$H$_{34}$O$_{10}$ 494.22, found 493.3 [M−H] at 1.87 min.

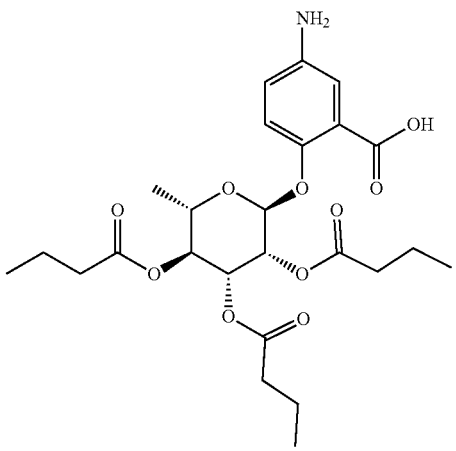 [SMILES: CCCC(=O)O[C@@H]1[C@@H](OC(=O)CCC)[C@H](C)O[C@@H](Oc2ccc(N)cc2C(=O)O)[C@@H]1OC(=O)CCC]

Compound 39:5-amino-2-(((2S,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (197 mg, 0.526 mmol) and benzyl 2-fluoro-5-nitrobenzoate (194 mg, 0.705 mmol) were dissolved in N N-dimethylformamide (1.0 mL) at room temperature. The solution was stirred when 1,4-diazabicyclo[2.2.2]octane (282 mg, 2.51 mmol) was added in one portion and stirring was continued for 88 h. Water (60 mL) was added and the aqueous layer was extracted with ethyl acetate (3×20 mL). The combined organic layers were washed with brine (3×20 mL), dried over anhydrous Na$_2$SO$_4$, filtered and concentrated. The crude material was adsorbed on celite and purified by automated chromatography (12 g, SiO$_2$, 0 to 20% ethyl acetate in hexanes) to afford (2S,3R,4R,5S,6S)-2-(2-((benzyloxy)carbonyl)-4-nitrophenoxy)-6-methyltetrahydro-2H-pyran-3,4,5-triyl tributyrate (136 mg, 41%) as a colorless gum. $^1$H NMR (400 MHz, CDCl$_3$) 8.75 (d, J=2.9 Hz, 1H), 8.33 (dd, J=9.2, 2.9 Hz, 1H), 7.51-7.46 (m, 2H), 7.41-7.30 (m, 4H), 5.66 (d, J=1.9 Hz, 1H), 5.61 (dd, J=10.2, 3.5 Hz, 1H), 5.58-5.44 (m, 3H), 5.23 (t, J=10.0 Hz, 1H), 3.99-3.91 (m, 1H), 2.51-2.38 (m, 2H), 2.31-2.20 (m, 4H), 1.77-1.67 (m, 2H), 1.67-1.57 (m, 4H), 1.18 (d, J=6.3 Hz, 3H), 1.01 (t, J=7.4 Hz, 3H), 0.97-0.90 (m, 6H). LCMS calcd for C$_{32}$H$_{39}$NO$_{12}$ 629.25, found 647.1 [M+NH$_4$] at 2.25 min.

(2S,3R,4R,5S,6S)-2-(2-((benzyloxy)carbonyl)-4-nitrophenoxy)-6-methyltetrahydro-2H-pyran-3,4,5-triyl tributyrate (136 mg, 0.216 mmol) was dissolved in methanol (2.00 mL) at room temperature under nitrogen. Palladium on carbon (10% wt., 2.30 mg, 0.0216 mmol) was added in one portion. The suspension was stirred, degassed with hydrogen and allowed to stir under hydrogen overnight. The mixture was diluted with dichloromethane and filtered on celite. The filtrate was concentrated and this material was purified by preparative HPLC-MS (CSH column, 40 to 60% acetonitrile in 10 mM aqueous ammonium formate) as a solution in N N-dimethylformamide (10% water). After lyophilization, 5-amino-2-(((2S,3R,4R,5S,6S)-3,4,5-tris(butyryloxy)-6-methyltetrahydro-2H-pyran-2-yl)oxy)benzoic acid (70.9 mg, 64%) was obtained as a white solid. 1H NMR (400 MHz, DMSO-d6) δ 6.93 (d, J=2.9 Hz, 1H), 6.90 (d, J=8.7 Hz, 1H), 6.66 (dd, J=8.7, 2.9 Hz, 1H), 5.45 (dd, J=3.4, 1.8 Hz, 1H), 5.32 (dd, J=10.2, 3.4 Hz, 1H), 5.30 (d, J=1.4 Hz, 1H), 5.21-5.03 (m, 2H), 5.00 (t, J=10.1 Hz, 1H), 4.20-4.12 (m, 1H), 2.40-2.22 (m, 4H), 2.15 (td, J=7.2, 1.3 Hz, 2H), 1.64-1.43 (m, 6H), 1.08 (d, J=6.3 Hz, 3H), 0.93 (t, J=7.4 Hz, 3H), 0.89-0.81 (m, 6H). LCMS calcd for $C_{25}H_{35}NO_{10}$ 509.23, found 508.3 [M−H] at 1.78 min.

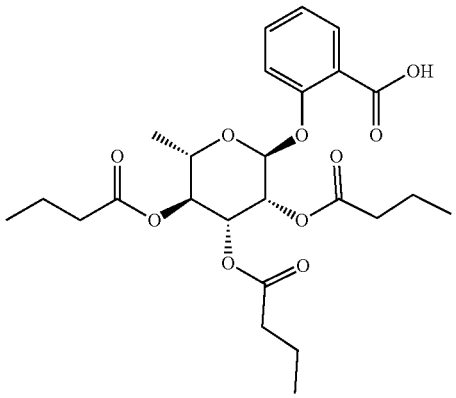 [SMILES: CCCC(=O)O[C@@H]1[C@@H](OC(=O)CCC)[C@H](C)O[C@@H](Oc2ccccc2C(=O)O)[C@@H]1OC(=O)CCC]

Compound 40: 2-(((2S,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (1.20 g, 3.20 mmol), benzyl 2-hydroxybenzoate (1.10 g, 4.81 mmol) and triphenylphosphine (1.27 g, 4.81 mmol) were dissolved in tetrahydrofuran (54.0 mL) and stirred at 0° C. Di-tert-butyl azodicarboxylate (1.11 g, 4.81 mmol) was added portion wise and the reaction mixture was stirred at 0° C. for 1 h and allowed to warm up till room temperature to stir overnight. The mixture was adsorbed on silica to be purified by automated chromatography (100 g, SiO2, 0 to 35% ethyl acetate in hexanes). (2S,3R,4R,5S,6S)-2-(2-((benzyloxy)carbonyl)phenoxy)-6-methyltetrahydro-2H-pyran-3,4,5-triyl tributyrate (165 mg, 8.1%) and (2R,3R,4R,5S,6S)-2-(2-((benzyloxy)carbonyl)phenoxy)-6-methyltetrahydro-2H-pyran-3,4,5-triyl tributyrate (427 mg, 21%) were separated but containing other impurities.

(2S,3R,4R,5S,6S)-2-(2-((benzyloxy)carbonyl)phenoxy)-6-methyltetrahydro-2H-pyran-3,4,5-triyl tributyrate (166 mg, 284 μmol) was dissolved in methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (25 g, SiO2, 0 to 100% ethyl acetate in hexanes) as a solution in dichloromethane to afford 2-(((2S,3R,4R,5S,6S)-3,4,5-tris(butyryloxy)-6-methyltetrahydro-2H-pyran-2-yl)oxy)benzoic acid (9 mg, 6%) as a white solid. 1H NMR (400 MHz, DMSO-d6) δ 7.71 (d, J=8.2 Hz, 1H), 7.51 (t, J=8.1 Hz, 1H), 7.29 (d, J=8.0 Hz, 1H), 7.14 (t, J=7.9 Hz, 1H), 5.76 (d, J=3.1 Hz, 2H), 5.43 (d, J=8.3 Hz, 2H), 5.02 (t, J=9.8 Hz, 1H), 1.54 (ddt, J=22.7, 14.8, 7.4 Hz, 6H), 1.05 (d, J=6.3 Hz, 3H), 0.95 (t, J=7.4 Hz, 3H), 0.85 (q, J=7.4 Hz, 6H). LCMS calcd for $C_{25}H_{34}O_{10}$ 494.22, found 512.3 [M+NH4] at 1.94 min.

(2R,3R,4R,5S,6S)-2-(2-((benzyloxy)carbonyl)phenoxy)-6-methyltetrahydro-2H-pyran-3,4,5-triyl tributyrate (427 mg, 711 μmol) was dissolved methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (50 g, SiO2, 0 to 100% ethyl acetate in hexanes) as a solution in dichloromethane to afford 2-(((2R,3R,4R,5S,6S)-3,4,5-tris(butyryloxy)-6-methyltetrahydro-2H-pyran-2-yl)oxy)benzoic acid (18 mg, 5%) as a white solid. 1H NMR (400 MHz, DMSO-d6) δ 7.62 (dd, J=7.5, 1.6 Hz, 1H), 7.46 (t, J=7.9 Hz, 1H), 7.14 (d, J=7.8 Hz, 1H), 7.08 (td, J=7.6, 0.8 Hz, 1H), 5.68 (d, J=0.8 Hz, 1H), 5.55 (dd, J=3.5, 1.0 Hz, 1H), 5.22 (dd, J=10.2, 3.4 Hz, 1H), 4.90 (t, J=9.9 Hz, 1H), 3.90-3.82 (m, 1H), 2.38 (t, J=7.1 Hz, 2H), 2.27 (m, 2H), 2.13 (td, J=7.2, 2.7 Hz, 2H), 1.60 (m, 2H), 1.48 (m, 4H), 1.12 (d, J=6.2 Hz, 3H), 0.93 (t, J=7.4 Hz, 3H), 0.85 (t, J=8.5 Hz, 3H), 0.83 (t, J=8.1 Hz, 3H). LCMS calcd for $C_{25}H_{34}O_{10}$ 494.22, found 493.3 [M−H].

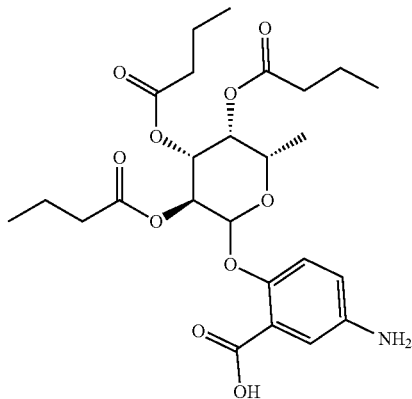 [SMILES: CCCC(=O)O[C@@H]1[C@H](OC(=O)CCC)[C@H](C)OC(Oc2ccc(N)cc2C(=O)O)[C@H]1OC(=O)CCC]

Compound 41: 5-amino-2-(((3S,4R,5R,6S)-3,4,5-tris(butyryloxy)-6-methyltetrahydro-2H-pyran-2-yl)oxy)benzoic acid (3S,4R,5R,6S)-2-hydroxy-6-methyltetrahydro-2H-pyran-3,4,5-triyl tributyrate (500 mg, 1.34 mmol), tert-butyl 5-((tert-butoxycarbonyl)amino)-2-hydroxybenzoate (620 mg, 2.00 mmol) and triphenylphosphine (531 mg, 2.00 mmol) were dissolved in tetrahydrofuran (22.0 mL) and stirred at 0° C. Di-tert-butyl azodicarboxylate (471 mg, 2.00 mmol) was added and stirring was continued at 0° C. for 1 h, then at room temperature overnight. The reaction mixture was concentrated. The crude material was purified by automated chromatography (SiO2, 30% ethyl acetate in hexanes) to afford (3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (213 mg, 24%). [M+NH4]=683, room temperature=2.21. $^1$H NMR (400 MHz, CDCl3) δ 7.58-6.95 (m, 3H), 5.48 (dd, J=10.5, 8.0 Hz, 1H), 5.28 (d, J=3.4 Hz, 1H), 5.10 (dd, J=10.4, 3.4 Hz, 1H), 5.00 (d, J=8.0 Hz, 1H), 3.88 (q, J=6.5 Hz, 1H), 2.55-2.15 (m, 2H), 1.76-1.56 (m, 3H), 1.55 (s, 4H), 1.49 (s, 3H), 1.46 (s, 2H), 1.26-1.14 (m, 2H), 0.99 (t, J=7.4 Hz, 1H), 0.89 (t, J=7.4 Hz, 2H).

(3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (200 mg, 300 μmol) was dissolved in dichloromethane (2.00 mL) at 0° C. To the solution was added hydrochloric acid (4 M in 1,4-dioxane, 158 μL, 631 µmol). The resulting mixture was stirred at 0° C. for 30 min, then at room temperature for 2 h. Solvents were evaporated and the residue was purified by automated reverse phase chromatography (C18, acetonitrile in 10 mM aqueous ammonium formate) After lyophilisation, 5-amino-2-(((3S,4R,5R,6S)-3,4,5-tris(butyryloxy)-6-methyltetrahydro-2H-pyran-2-yl)oxy)benzoic acid (10.0 mg, 13%) was obtained as a white solid. $^1$H NMR (400 MHz, DMSO-d$_6$) δ 6.86 (d, J=9.1 Hz, 1H), 6.74 (d, J=2.9 Hz, 1H), 6.60 (dd, J=9.8, 2.1 Hz, 1H), 5.21-5.06 (m, 4H), 5.01-4.91 (m, 1H), 2.67-2.63 (m, 1H), 2.53 (s, 1H), 2.45-2.07 (m, 7H), 1.60 (dt, J=14.6, 7.3 Hz, 2H), 1.52-1.39 (m, 4H), 1.07 (d, J=6.4 Hz, 3H), 0.92 (t, J=7.4 Hz, 3H), 0.80 (t, J=7.4 Hz, 6H). LCMS calcd for $C_{25}H_{35}NO_{10}$ 509.23, found 508.2 [M−H] at 1.68 min.

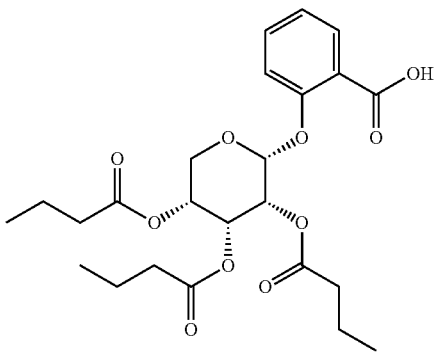 [SMILES: CCCC(=O)O[C@H]1[C@@H](Oc2ccccc2C(=O)O)OC[C@@H](OC(=O)CCC)[C@H]1OC(=O)CCC]

Compound 42: 2-(((3R,4R,5R)-3,4,5-tris(butyryloxy)tetrahydro-2H-pyran-2-yl)oxy)benzoic acid (3R,4R,5R)-2-hydroxytetrahydro-2H-pyran-3,4,5-triyl tributyrate (200 mg, 555 µmol), benzyl 2-hydroxybenzoate (190 mg, 832 µmol) and triphenylphosphine (221 mg, 832 µmol) were dissolved in tetrahydrofuran (4.0 mL) and stirred at 0° C. Di-tert-butyl azodicarboxylate (196 mg, 832 µmol) was added and stirring continued at 0° C. for 1 h, then at room temperature overnight. The reaction mixture was concentrated and purified by automated chromatography (SiO$_2$, ethyl acetate gradient in hexanes) to afford (2R,3R,4R,5R)-2-(2-((benzyloxy)carbonyl)phenoxy)tetrahydro-2H-pyran-3,4,5-triyl tributyrate (229 mg, 72%) as a colorless oil. 1H NMR (400 MHz, CDCl$_3$) δ 7.74 (dd, J=7.7, 1.8 Hz, 1H), 7.46-7.31 (m, 6H), 7.19 (d, J=8.3 Hz, 1H), 7.08 (t, J=7.5 Hz, 1H), 5.57 (broad s, 1H), 5.51 (d, J=3.4 Hz, 1H), 5.31 (dd, J=29.5, 12.5 Hz, 2H), 5.22 (broad s, 1H), 5.15-5.09 (m, 1H), 4.21 (dd, J=11.3, 8.8 Hz, 1H), 3.65 (dd, J=11.3, 4.2 Hz, 1H), 2.50-2.26 (m, 6H), 1.74-1.57 (m, 6H), 1.01-0.84 (m, 9H). LCMS calcd for $C_{31}H_{38}O_{10}$ 570.25, found 588.4 [M+NH$_4$] at 2.19 min.

(2R,3R,4R,5R)-2-(2-((benzyloxy)carbonyl)phenoxy)tetrahydro-2H-pyran-3,4,5-triyl tributyrate (229 mg, 401 µmol) was dissolved in methanol (4.0 mL) at room temperature. The solution was stirred under nitrogen when palladium on carbon (10% wt., 42.7 mg, 40.1 µmol) was added in one portion. The mixture was degassed with hydrogen and allowed to stir under hydrogen for 3 h. The mixture was diluted with dichloromethane and filtered on celite. The crude material was adsorbed on celite and purified by automated reverse phase chromatography (C18, acetonitrile in 10 mM aqueous ammonium formate). After lyophilisation, 2-(((2R,3R,4R,5R)-3,4,5-tris(butyryloxy)tetrahydro-2H-pyran-2-yl)oxy)benzoic acid obtained as an oil (92.0 mg, 48%). $^1$H NMR (400 MHz, DMSO-d$_6$) δ 7.61 (dd, J=7.7, 1.7 Hz, 1H), 7.51-7.44 (m, 1H), 7.18 (d, J=8.4 Hz, 1H), 7.09 (t, J=7.5 Hz, 1H), 5.63 (broad d, J=2.7 Hz, 1H), 5.45 (broad t, J=3.4 Hz, 1H), 5.31 (broad t, J=2.9 Hz, 1H), 5.09 (broad dt, J=6.6, 3.5 Hz, 1H), 4.00 (dd, J=12.0, 6.3 Hz, 1H), 3.81 (dd, J=12.0, 3.2 Hz, 1H), 2.38-2.19 (m, 6H), 1.62-1.44 (m, 6H), 0.86 (td, J=7.4, 2.9 Hz, 9H). UP-LCMS calcd for $C_{24}H_{32}O_{10}$ 480.20, found 503.2 [M+Na] at 1.72 min.

Compound 43: 5-amino-2-(((2R,3R,4S,5R,6R)-3,4,5-tris(butyryloxy)-6-((butyryloxy)methyl)tetrahydro-2H-pyran-2-yl)oxy)benzoic acid Compound 43 was isolated as a minor isomer during the preparation of compound 36.

(2R,3R,4S,5R)-2-((butyryloxy)methyl)-6-hydroxytetrahydro-2H-pyran-3,4,5-triyl tributyrate (239 mg, 519 µmol) was dissolved in N N-dimethylformamide (1 mL). The solution was stirred at room temperature when benzyl 2-fluoro-5-nitrobenzoate (186 mg, 675 µmol) and then 1,4-diazabicyclo[2.2.2]octane (294 mg, 2.59 mmol) were added. Stirring was continued for 2 d and water was added. The aqueous layer was extracted with ethyl acetate. The combined organic layers were washed with brine, dried over anhydrous Na$_2$SO$_4$, filtered and concentrated to give a brown oil. The crude material was adsorbed on celite to be purified by automated chromatography (SiO2, ethyl acetate gradient in hexanes) to afford (3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 45%). LCMS calcd for $C_{36}H_{45}NO_{14}$ 715.28, found 733.6 [M+NH$_4$] at 2.26 min.

(3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 236 µmol) was dissolved in methanol (5.0 mL) at room temperature. The solution was stirred under nitrogen when palladium on carbon (10% wt., 25.1 mg, 23.6 µmol) was added in one portion. Then, the solvent was degassed with hydrogen and the reaction was allowed to stir under hydrogen for 2 h. The mixture was diluted with dichloromethane and filtered on celite. The crude material was purified by automated reverse phase chromatography (C18, 25% to 65% acetonitrile in 10 mM aqueous ammonium formate). After lyophilisation, 5-amino-2-(((2R,3R,4S,5R,6R)-3,4,5-tris(butyryloxy)-6-((butyryloxy)methyl)tetrahydro-2H-pyran-2-yl)oxy)benzoic acid (9 mg, 6%) was obtained as a white solid. $^1$H NMR (400 MHz, DMSO-d$_6$) δ 6.82 (d, J=8.5 Hz, 1H), 6.79 (s, 1H), 6.58 (d, J=8.3 Hz, 1H), 5.56 (d, J=3.6 Hz, 1H), 5.52 (t, J=9.9 Hz, 1H), 5.04 (t, J=9.9 Hz, 1H), 4.93 (dd, J=10.3, 3.6 Hz, 1H), 4.38 (broad s, 1H), 4.10 (dd, J=12.4, 5.1 Hz, 1H), 3.98 (dd, J=12.4, 2.0 Hz, 1H), 2.37-2.15 (m, 8H), 1.56-1.39 (m, 8H), 0.90-0.73 (m, 12H). LCMS calcd for $C_{29}H_{41}NO_{12}$ 595.26, found 613.3 [M+NH$_4$] at 1.84 min.

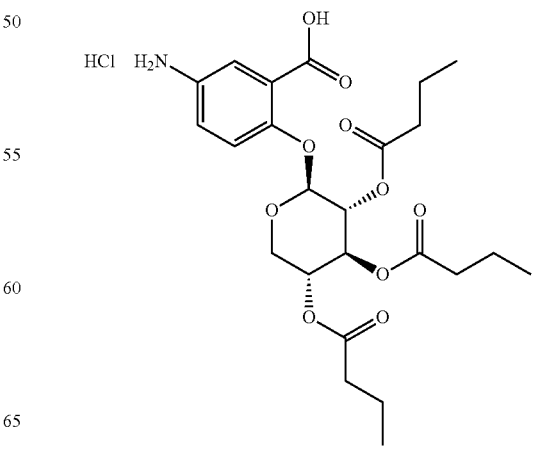

Compound 44: 5-amino-2-(((2S,3R,4S,5R)-3,4,5-tris(butyryloxy)tetrahydro-2H-pyran-2-yl)oxy)benzoic acid hydrochloride Xylose tributyrate (1.87 g, 5.18 mmol, 1 eq), tert-butyl 5-((tert-butoxycarbonyl)amino)-2-hydroxybenzoate (2.4 g, 7.8 mmol, 1.5 eq) and triphenylphosphine (2.05 g, 7.8 mmol, 1.5 eq) were dissolved in anhydrous THF (37.5 mL) under N$_2$ and cooled to 0° C. Di-tert-butyl azodicarboxylate (1.8 g, 7.8 mmol, 1.5 eq) was added and the reaction was stirred at 0° C. for 1 hour under N$_2$. The ice bath was removed and the reaction was stirred at room temperature overnight. The reaction mixture was loaded directly onto silica and dried by rotary evaporation. The solid loaded sample was purified by multiple rounds of column chromatography (gradient: 0-50% ethyl acetate in hexanes) to separate the anomers and yield (2S,3R,4S,5R)-2-(2-(tert-butoxycarbonyl)-4-((tert-butoxycarbonyl)amino)phenoxy)tetrahydro-2H-pyran-3,4,5-triyl tributyrate (45 mg). The purified compound was dissolved in chloroform (1 mL), followed by addition of 4 M HCl in dioxane (1.2 mL). After deprotection was complete as confirmed by LCMS, the solution was concentrated by rotary evaporation and dried under high vacuum overnight to yield the title compound (11 mg, 0.021 mmol, 0.4% yield). LCMS [M−H]$^-$: 494.5. $^1$H NMR (400 MHz, DMSO-d6) δ 6.83-6.75 (m, 2H), 6.64-6.53 (m, 1H), 5.58 (d, J=3.6 Hz, 1H), 5.53 (t, J=9.9 Hz, 1H), 5.03-4.90 (m, 2H), 3.89 (t, J=10.9 Hz, 1H), 3.73 (dd, J=10.9, 5.9 Hz, 1H), 2.38-2.12 (m, 6H), 1.58-1.39 (m, 6H), 0.92-0.76 (m, 9H).

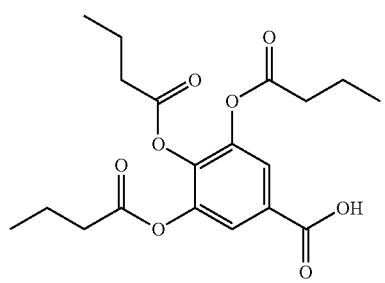 [SMILES: CCCC(=O)Oc1cc(C(=O)O)cc(OC(=O)CCC)c1OC(=O)CCC]

Compound 45: 3,4,5-tris(butyryloxy)benzoic acid

Gallic Acid (400 mg, 2.35 mmol) was dissolved in pyridine (15 eq, 2.83 mL, 35.2 mmol) in a dry round bottom flask. The flask was flushed with N$_2$ and the solution was chilled to 0° C. in an ice bath. Butyric anhydride (6 eq, 2.30 mL, 14.1 mmol) was added dropwise under N$_2$. The resulting stirred solution was allowed to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (C18, 10-90% acetonitrile in water) and fractions were concentrated and fully dried by lyophilization to yield compound 45 (740 mg, 82.8% yield) as a white solid. LCMS [M−H]$^-$: 379.1. $^1$H NMR (400 MHz, DMSO-d6) δ 13.45 (bs, 1H), 7.74 (s, 2H), 2.62-2.55 (m, 6H), 1.70-1.58 (m, 6H), 0.99-0.93 (m, 9H).

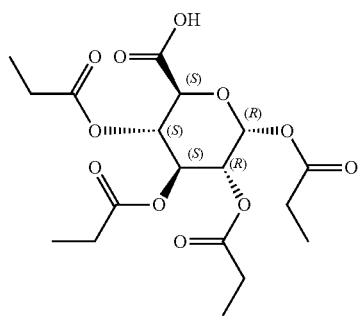

Compound 46: (2S,3S,4S,5R,6R)-3,4,5,6-tetrakis(propanoyloxy)oxane-2-carboxylicacid

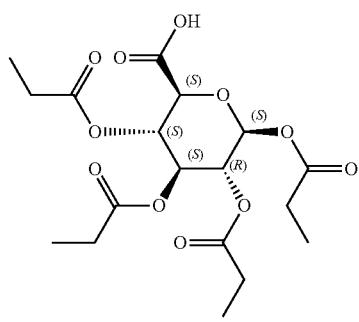

Compound 47: (2S,3S,4S,5R,6S)-3,4,5,6-tetrakis(propanoyloxy)oxane-2-carboxylicacid

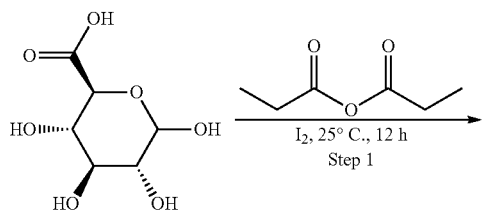

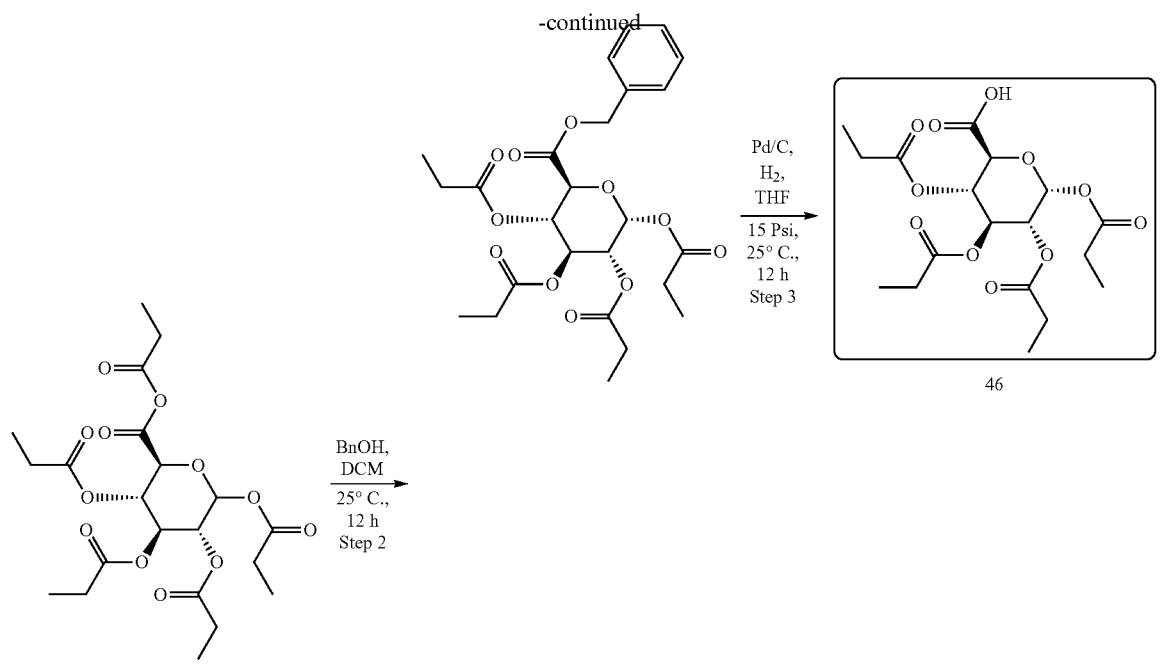

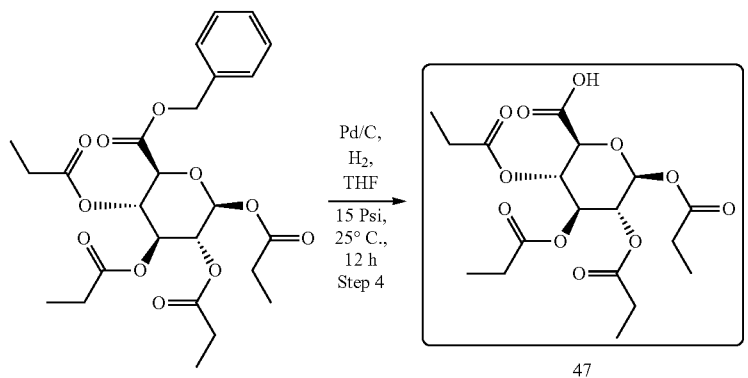

Step 1

To a solution of (2S,3S,4S,5R)-3,4,5,6-tetrahydroxytetrahydropyran-2-carboxylic acid (5 g, 25.75 mmol, 1 eq) in propionic anhydride (25 mL) was added $I_2$ (653.68 mg, 2.58 mmol, 518.79 uL, 0.1 eq). The mixture was stirred at 25° C. for 12 hr. TLC indicated (2S,3S,4S,5R)-3,4,5,6-tetrahydroxytetrahydropyran-2-carboxylic acid was consumed completely. The reaction mixture was concentrated under reduced pressure. Then the residue was taken up in toluene followed by distillation in vacuum. The crude product propionic (2S,3S,4S,5R)-3,4,5,6-tetrakis(propionyloxy) tetrahydro-2H-pyran-2-carboxylic anhydride (7 g, crude) was obtained as a brown liquid.

Step 2

To a solution of propionic (2S,3S,4S,5R)-3,4,5,6-tetrakis (propionyloxy)tetrahydro-2H-pyran-2-carboxylic anhydride (7 g, 16.73 mmol, 1 eq) in DCM (70 mL) was added BnOH (3.62 g, 33.46 mmol, 3.48 mL, 2 eq). The mixture was stirred at 25° C. for 12 hr. TLC indicated (propionic (2S, 3S,4S,5R)-3,4,5,6-tetrakis(propionyloxy)tetrahydro-2H-pyran-2-carboxylic anhydride was consumed completely and one major new spot was detected. The reaction mixture was concentrated under reduced pressure. The residue was purified by column chromatography ($SiO_2$, Petroleum ether/ Ethyl acetate=20/1 to 6:1). Compound benzyl (2S,3S,4S, 5R)-3,4,5,6-tetra(propanoyloxy)tetrahydropyran-2-carboxylate (1.5 g, crude) was obtained as a yellow oil. The residue was purified by prep-HPLC ([water (10 mM $NH_4HCO_3$)-ACN]). The compound 3 for benzyl (2S,3S,4S, 5R,6R)-3,4,5,6-tetra(propanoyloxy) tetrahydropyran-2-carboxylate (30 mg) was obtained as a white solid. The compound 3A benzyl (2S,3S,4S,5R,6S)-3,4,5,6-tetra(propanoyloxy)tetrahydropyran-2-carboxylate (100 mg) was obtained as a white solid. The compound ID was temporary assigned.

Step 3

To a solution of benzyl (2S,3S,4S,5R,6R)-3,4,5,6-tetra (propanoyloxy)tetrahydropyran-2-carboxylate (30 mg, 59.00 umol, 1 eq) in THF (5 mL) was added Pd/C (3 mg, 59.00 umol, 10% purity, 1.00 eq). The suspension was degassed and purged with H₂ for 3 times. The mixture was stirred under H₂ (15 Psi) at 25° C. for 12 hr. LC-MS showed the desired compound was detected. Filtered and concentrated under reduced pressure to give a residue. The residue was purified by prep-HPLC ([water (0.1% TFA)-ACN]). The compound 46 for (2S,3S,4S,5R,6R)-3,4,5,6-tetra (propanoyloxy) tetrahydropyran-2-carboxylic acid (5.3 mg, 12.67 umol, 21.47% yield, 100% purity) was obtained as a yellow solid. The compound ID was temporary assigned. The structure was not further confirmed by 2D NMR. LCMS: (M+18)+: 436.1. @3.215 min. ¹H NMR (400 MHz, CDCl₃): δ6.35 (s, 1H), 5.49 (t, J=9.6 Hz, 1H), 5.22 (t, J=9.8 Hz, 1H), 5.07 (d, J=10.1 Hz, 1H), 4.42 (s, 1H), 2.50-2.36 (m, 2H), 2.34-2.14 (m, 6H), 1.13 (t, J=7.6 Hz, 3H), 1.07-0.97 (m, 9H)

Step 4

To a solution of benzyl (2S,3S,4S,5R,6S)-3,4,5,6-tetra (propanoyloxy)tetrahydropyran-2-carboxylate (50.00 mg, 98.33 umol, 1 eq) in THF (5 mL) was added Pd/C (3 mg, 98.33 umol, 10% purity, 1.00 eq). The suspension was degassed and purged with H₂ for 3 times. The mixture was stirred under H₂ (15 Psi) at 25° C. for 12 hr. LC-MS showed the desired compound was detected. The reaction mixture was filtered and concentrated under reduced pressure. The residue was purified by prep-HPLC ([water (0.1% TFA)-ACN]). The compound 47 for (2S,3S,4S,5R,6R)-3,4,5,6-tetra(propanoyloxy)tetrahydropyran-2-carboxylic acid (11 mg, 26.29 umol, 26.74% yield, 100% purity) was obtained as yellow oil. The compound ID was temporary assigned. The structure was not further confirmed by 2D NMR. LCMS: (M+18)+: 436.1 @ 3.125 min. ¹H NMR (400 MHz, CDCl₃): δ 5.84 (d, J=7.6 Hz, 1H), 5.42-5.27 (m, 2H), 5.19 (t, J=8.3 Hz, 1H), 4.28 (d, J=9.2 Hz, 1H), 2.46-2.24 (m, 8H), 1.18-1.06 (m, 12H)

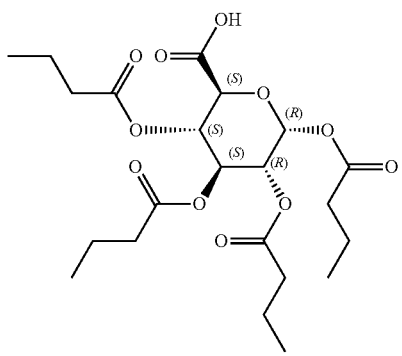

Compound 48: (2S,3S,4S,5R,6R)-3,4,5,6-tetrakis (butanoyloxy)oxane-2-carboxylic acid This compound was prepared according to a modified procedure described for the preparation of compounds 46 and 47. LCMS: (M+Na⁺): 492.2. ¹H-NMR (400 MHz, CDCl₃): δ 6.26 (d, J=3.7 Hz, 1H), 5.49 (t, J=9.9 Hz, 1H), 5.16 (t, J=10.0 Hz, 1H), 5.05 (dd, J=10.2, 3.7 Hz, 1H), 4.12 (d, J=10.3 Hz, 1H), 2.34 (t, J=7.4 Hz, 2H), 2.28-2.09 (m, 6H), 1.69-1.58 (m, 2H), 1.58-1.42 (m, 6H), 0.95-0.78 (m, 12H)

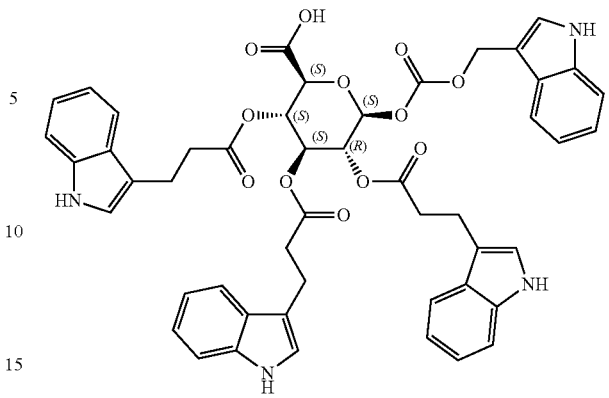

Compound 49: (2S,3S,4S,5R,6S)-3,4,5,6-tetrakis({[3-(1H-indol-3-yl)propanoyl]oxy})oxane-2-carboxylic acid

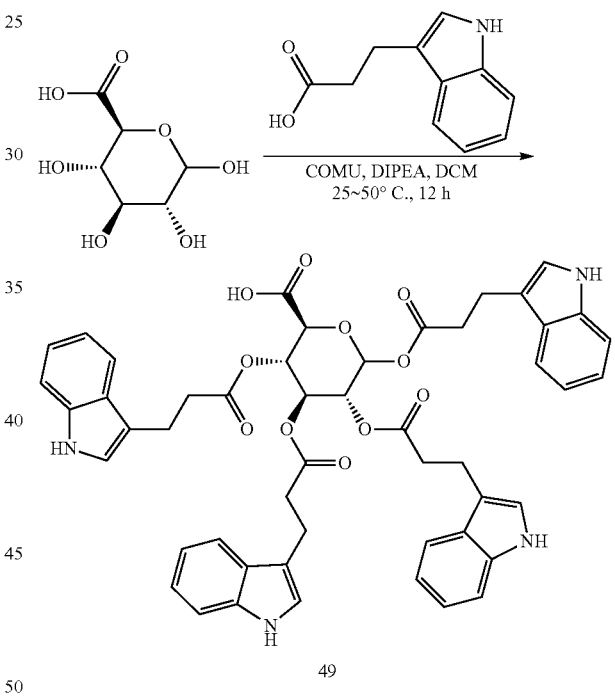

49

To a mixture of (2S,3S,4S,5R)-3,4,5,6-tetrahydroxytetrahydropyran-2-carboxylic acid (0.2 g, 1.03 mmol, 1 eq) and 3-(1H-indol-3-yl)propanoic acid (1.17 g, 6.18 mmol, 6 eq) in DCM (10 mL) was added DIPEA (1.07 g, 8.24 mmol, 1.44 mL, 8 eq) and COMU (2.65 g, 6.18 mmol, 6 eq) in one portion at 25° C. under N₂. The mixture was stirred at 50° C. for 12 hours. LCMS showed the desired mass was detected. The reaction mixture was filtered and concentrated under reduced pressure to give a residue. The residue was purified by prep-HPLC (column: Waters Xbridge Prep OBD C18 150*40 10 u; mobile phase: [water (10 mM NH₄HCO₃)-ACN]; B %: 30%-55%, 11 min) to give (2S, 3S,4S,5R)-3,4,5,6-tetrakis[3-(1H-indol-3-yl)propanoyloxy] tetrahydropyran-2-carboxylic acid (88 mg, 8.77 umol, 8.51e-1% yield, 96.37% purity) as a white solid. LCMS: (M−H⁺) 877.2 @ 1.375 min. LCMS: (M+18) 896.3 @ 2.832 min. ¹H NMR: (400 MHz, Methanol-d4): δ 7.5-6.8 (m, 20H), 5.8 (d, 1H), 5.4-5.3 (m, 1H), 5.3-5.2 (m, 1H), 5.2-5.1 (m, 1H), 4.1 (d, 1H), 3.0-2.0 (m, 16H)

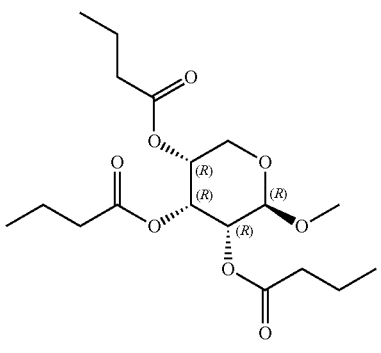

Compound 50: (2R,3R,4R,5R)-3,5-bis(butanoyloxy)-2-methoxyoxan-4-ylbutanoate

This compound was prepared according to a modified procedure described for the preparation of compound 219.

LCMS: (m+H⁺)=375.4. ¹H NMR (400 MHz, DMSO-d6) δ 5.28 (t, 1H), 5.08 (q, 1H), 4.90 (td, 1H), 4.69 (d, 1H), 3.92 (dd, 1H), 3.68 (dd, 1H), 3.34 (s, 3H), 2.39-2.16 (m, 6H), 1.54 (m, 6H), 0.88 (m, 9H).

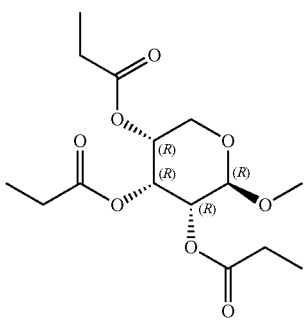

Compound 51: (2R,3R,4R,5R)-2-methoxy-3,5-bis(propanoyloxy)oxan-4-yl propanoate

This compound was prepared according to a modified procedure described for the preparation of compound 219.

LCMS: (m+H+)=355.3. ¹H NMR (400 MHz, DMSO-d6) δ5.26 (t, 1H), 5.07 (q, 1H), 4.94-4.84 (m, 1H), 4.71 (d, 1H), 3.92 (dd, 1H), 3.69 (dd, 1H), 3.35 (s, 3H), 2.45-2.17 (m, 6H), 1.02 (dt, 9H)

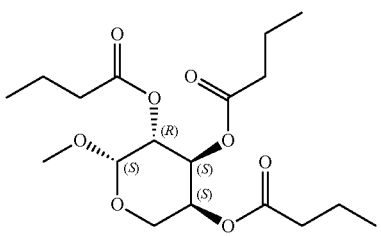

Compound 52: (2S,3R,4S,5S)-3,5-bis(butanoyloxy)-2-methoxyoxan-4-yl butanoate

This compound was prepared according to a modified procedure described for the preparation of compound 219.

LCMS: (M+Na+) 397.3. ¹H NMR (400 MHz, DMSO-d6) 5.27 (dt, 1H), 5.24 (dd, 1H), 5.04 (dd, 1H), 4.90 (d, 1H), 3.89 (dd, 1H), 3.61 (dd, 1H), 3.32 (s, 3H), 2.39-2.13 (m, 6H), 1.65-1.42 (m, 6H), 0.97-0.80 (m, 9H).

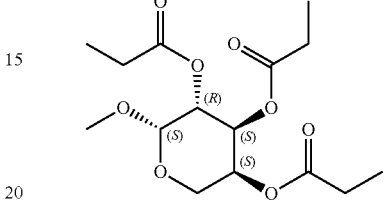

Compound 53: (2S,3R,4S,5S)-2-methoxy-3,5-bis(propanoyloxy)oxan-4-ylpropanoate

This compound was prepared according to a modified procedure described for the preparation of compound 219.

LCMS: (M+Na+) 355.3. ¹H NMR (400 MHz, DMSO-d6) 5.27 (dt, 1H), 5.23 (dd, 1H), 5.04 (dd, 1H), 4.90 (d, 1H), 3.89 (dd, 1H), 3.62 (dd, 1H), 3.32 (s, 3H), 2.45-2.10 (m, 6H), 1.12-0.91 (m, 9H).

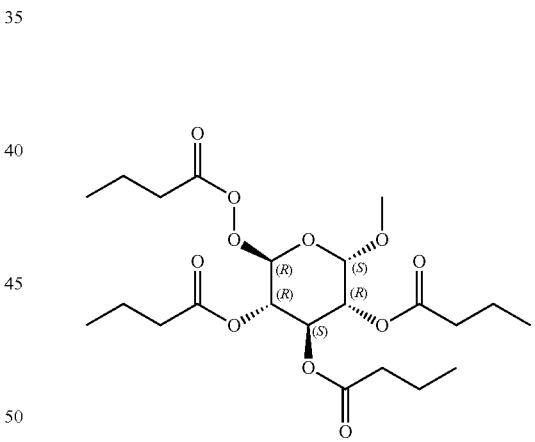

Compound 54: [(2R,3R,4S,5R,6S)-3,4,5-tris(butanoyloxy)-6-methoxyoxan-2-yl]methyl butanoate This compound was prepared according to a modified procedure described for the preparation of compound 219.

LCMS: (M+Na+) 497.2. ¹H NMR (400 MHz, DMSO-d6) δ 5.34 (dd, 1H), 5.00 (t, 1H), 4.92 (d, 1H), 4.83 (dd, 1H), 4.14 (dd, 1H), 4.10-3.88 (m, 2H), 3.34 (s, 3H), 2.35-2.08 (m, 8H), 1.60-1.40 (m, 8H), 0.93-0.78 (m, 12H)

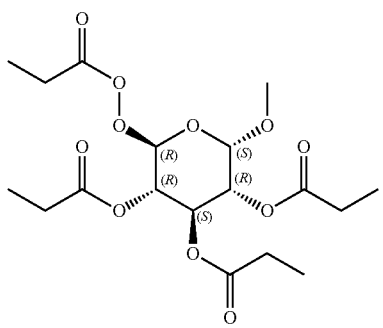

Compound 55: [(2R,3R,4S,5R,6S)-6-methoxy-3,4,5-tris(propanoyloxy)oxan-2-yl]methyl propanoate This compound was prepared according to a modified procedure described for the preparation of compound 219.

LCMS: (M+Na+) 441.2. $^1$H NMR (400 MHz, DMSO-d6) δ 5.32 (dd, 1H), 4.99 (t, 1H), 4.92 (d, 1H), 4.85 (dd, 1H), 4.17 (dd, 1H), 4.06 (dd, 1H), 3.93 (ddd, 1H), 3.34 (s, 3H), 2.39-2.11 (m, 8H), 1.09-0.92 (m, 12H)

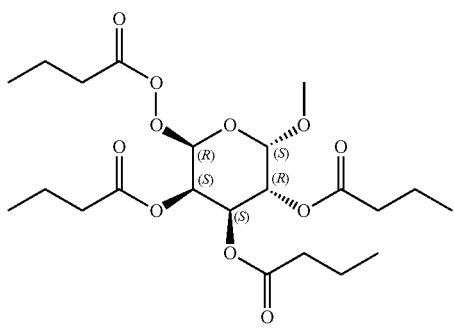

Compound 56: [(2R,3S,4S,5R,6S)-3,4,5-tris(butanoyloxy)-6-methoxyoxan-2-yl]methyl butanoate This compound was prepared according to a modified procedure described for the preparation of compound 219.

LCMS: (M+Na+) 497.2. $^1$H NMR (400 MHz, DMSO-d6) δ 5.40 (dd, 1H), 5.27 (dd, 1H), 5.04 (dd, 1H), 4.97 (d, 1H), 4.22 (t, 1H), 4.15-3.97 (m, 2H), 3.35 (s, 3H), 2.47-2.07 (m, 8H), 1.69-1.38 (m, 8H), 1.01-0.77 (m, 12H)

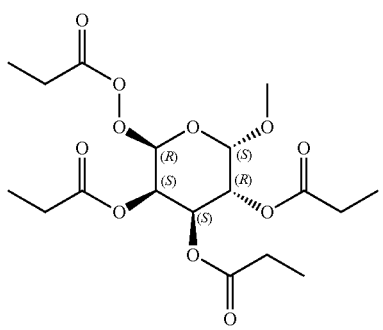

Compound 57: [(2R,3S,4S,5R,6S)-6-methoxy-3,4,5-tris(propanoyloxy)oxan-2-yl]methylpropanoate This compound was prepared according to a modified procedure described for the preparation of compound 219.

LCMS: (M+Na+): 441.1. $^1$H NMR (400 MHz, DMSO-d6) δ 5.40 (dd, 1H), 5.27 (dd, 1H), 5.05 (dd, 1H), 4.98 (d, 1H), 4.22 (ddd, 1H), 4.07 (d, 2H), 3.36 (s, 3H), 2.49-2.11 (m, 8H), 1.15-0.94 (m, 12H)

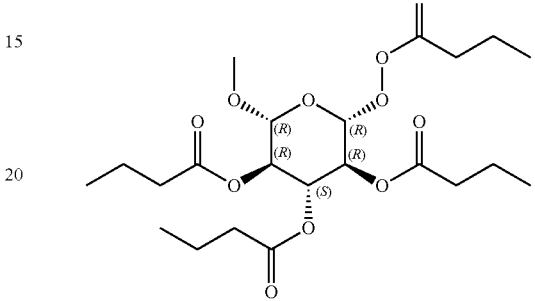

Compound 58: [(2R,3R,4S,5R,6R)-3,4,5-tris(butanoyloxy)-6-methoxyoxan-2-yl]methyl butanoate This compound was prepared according to a modified procedure described for the preparation of compound 219.

LCMS: (M+Na+): 497.1. $^1$H NMR (400 MHz, DMSO-d6) δ 5.33 (t, 1H), 4.96 (t, 1H), 4.81 (dd, 1H), 4.19 (dd, 1H), 4.12-3.97 (m, 2H), 3.39 (s, 3H), 2.38-2.10 (m, 8H), 1.64-1.38 (m, 8H), 0.97-0.77 (m, 12H)

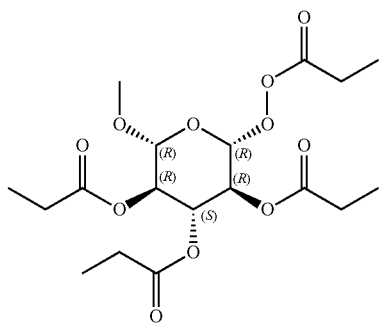

Compound 59: [(2R,3R,4S,5R,6R)-6-methoxy-3,4,5-tris(propanoyloxy)oxan-2-yl]methylpropanoate This compound was prepared according to a modified procedure described for the preparation of compound 219.

LCMS: (M+Na+) 441.1. $^1$H NMR (400 MHz, DMSO-d6) δ 5.31 (t, 1H), 4.95 (t, 1H), 4.80 (dd, 1H), 4.74 (d, 1H), 4.24 (dd, 1H), 4.10-3.99 (m, 2H), 3.39 (s, 3H), 2.41-2.13 (m, 8H), 1.09-0.91 (m, 12H)

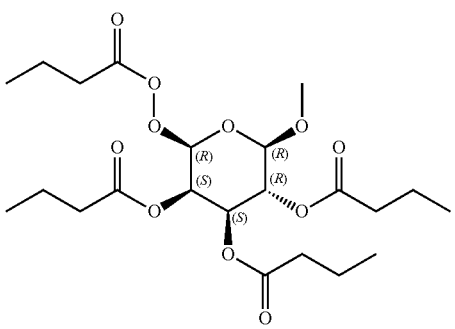

Compound 60: [(2R,3S,4S,5R,6R)-3,4,5-tris(butanoyloxy)-6-methoxyoxan-2-yl]methylbutanoate This compound was prepared according to a modified procedure described for the preparation of compound 219.

LCMS: (M+Na+) 497.1. ¹H NMR (400 MHz, DMSO-d6) δ 5.30 (dd, 1H), 5.22 (dd, 1H), 4.99 (dd, 1H), 4.64 (d, 1H), 4.28-4.20 (m, 1H), 4.15-3.96 (m, 2H), 3.38 (s, 3H), 2.43-2.06 (m, 8H), 1.53 (ddq, 8H), 0.99-0.79 (m, 12H).

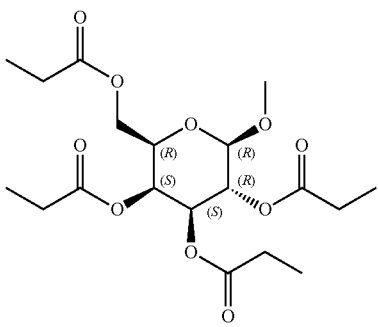

Compound 61: [(2R,3S,4S,5R,6R)-6-methoxy-3,4,5-tris(propanoyloxy)oxan-2-yl]methylpropanoate This compound was prepared according to a modified procedure described for the preparation of compound 219.

LCMS (M+Na): 441.1. ¹H NMR (400 MHz, DMSO-d6) δ 5.30 (dd, 1H), 5.20 (dd, 1H), 4.98 (dd, 1H), 4.65 (d, 1H), 4.24 (td, 1H), 4.18-4.01 (m, 2H), 3.39 (s, 3H), 2.48-2.08 (m, 8H), 1.03 (ddt, 12H)

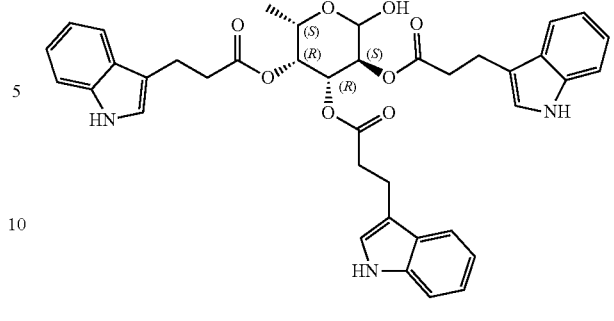

Compound 62: (2S,3R,4R,5S)-6-hydroxy-4,5-bis({[3-(1H-indol-3-yl)propanoyl]oxy})-2-methyloxan-3-yl 3-(1H-indol-3-yl)propanoate This compound was prepared according to a procedure described for compound 37 with the exception that a starting material for compound 62 was used and that the synthesis was stopped at the stage when compound 62 was produced.

LCMS: (M−H): 676.3. ¹H NMR (400 MHz, Chloroform-d) δ 7.77-6.47 (m, 18H), 5.42-5.32 (m, 1H), 5.29-5.22 (m, 1H), 5.12-5.03 (m, 1H), 4.69-4.62 (m, 1H), 4.41-4.35 (m, 1H), 3.87-3.81 (m, 1H), 3.20-3.00 (m, 4H), 2.90-2.75 (m, 4H), 2.74-2.59 (m, 2H), 2.12-1.97 (m, 2H), 1.22-1.07 (m, 3H)

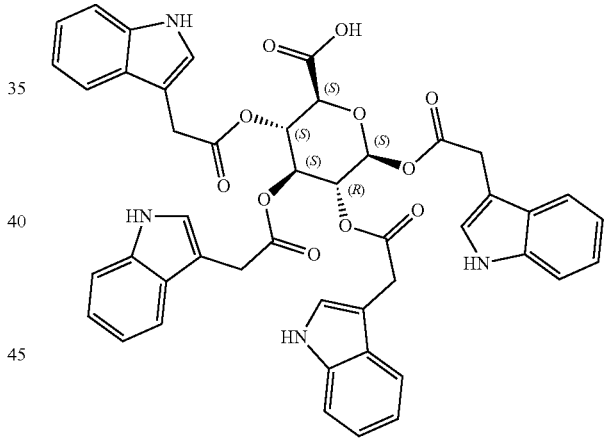

Compound 63: (2S,3S,4S,5R,6S)-3,4,5,6-tetrakis({[2-(1H-indol-3-yl)acetyl]oxy})oxane-2-carboxylicacid

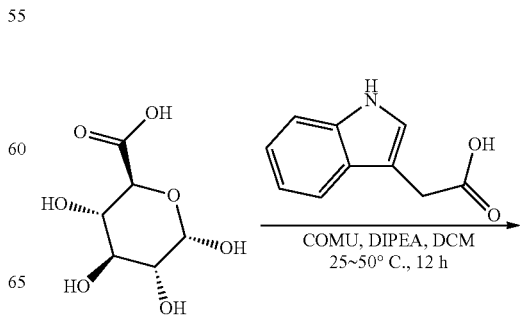

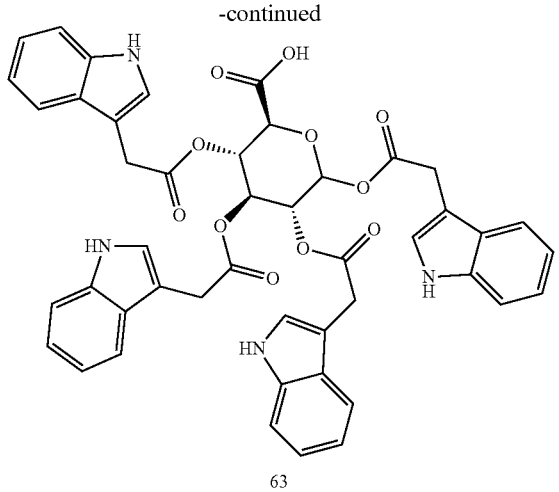

63

To a mixture of (2S,3S,4S,5R,6S)-3,4,5,6-tetrahydroxytetrahydropyran-2-carboxylic acid (200 mg, 1.03 mmol, 1 eq) and 2-(1H-indol-3-yl)acetic acid (1.08 g, 6.18 mmol, 6 eq) in DCM (10 mL) was added COMU (2.65 g, 6.18 mmol, 6 eq) and DIPEA (1.07 g, 8.24 mmol, 1.44 mL, 8 eq) in one portion at 25° C. under N₂. The mixture was stirred at 50° C. for 12 hours. LCMS showed the desired mass was detected. The reaction mixture was filtered and concentrated under reduced pressure to give a residue. The residue was purified by prep-HPLC (column: Waters Xbridge Prep OBD C18 150*40 10 u; mobile phase: [water (10 mM NH₄HCO₃)-MeOH]; B %: 25%-45%, 11 min) to give compound 63 (2S,3S,4S,5R)-3,4,5,6-tetrakis(2-(1H-indol-3-yl)acetoxy)tetrahydro-2H-pyran-2-carboxylic acid (5 mg, 5.48 μmol, 0.532% yield, 90.23% purity) as a light yellow solid. LCMS: (M+18)*840.2 @ 2.594 min. ¹H NMR (400 MHz, Methanol-d4) δ 7.53-6.79 (m, 20H), 5.69 (d, J=8.3 Hz, 1H), 5.39-5.02 (m, 3H), 4.61 (s, 1H), 3.67-3.18 (m, 4H), 3.15-2.90 (m, 4H).

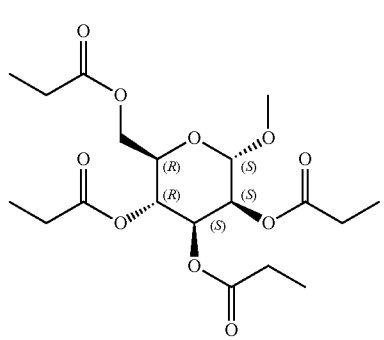

Compound 64: (2S,3S,4R,5R,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 63. ¹H NMR (400 MHz, Chloroform-d) 7.88-6.20 (m, 24H), 5.45-5.20 (m, 3H), 5.15-4.88 (m, 1H), 4.16-3.89 (m, 1H), 3.24-2.99 (m, 4H), 2.99-2.65 (m, 8H), 2.41-1.99 (m, 4H), 1.37-0.91 (m, 3H).

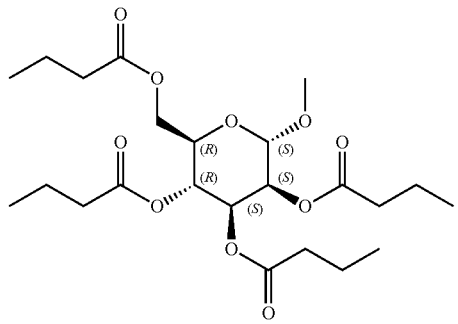

Compound 65: [(2R,3R,4S,5S,6S)-3,4,5-tris(butanoyloxy)-6-methoxyoxan-2-yl]methyl butanoate This compound was prepared according to a modified procedure described for the preparation of compound 219.
LCMS: (M+Na+) 497.2. ¹H NMR (400 MHz, DMSO-d6) 5.28-5.08 (m, 3H), 4.78 (d, 1H), 4.21-4.07 (m, 2H), 3.94 (ddd, 1H), 3.36 (s, 3H), 2.44-2.11 (m, 8H), 1.69-1.40 (m, 8H), 0.89 (m, 12H)

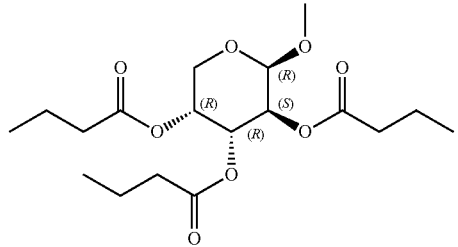

Compound 66: [(2R,3R,4S,5S,6S)-6-methoxy-3,4,5-tris(propanoyloxy)oxan-2-yl]methylpropanoate This compound was prepared according to a modified procedure described for the preparation of compound 219.
LCMS: (M+Na+) 441.1. ¹H NMR (400 MHz, DMSO-d6) δ 5.25-5.15 (m, 1H), 5.14 (m, 2H), 4.80 (d, 1H), 4.20 (dd, 1H), 4.10 (dd, 1H), 3.95 (m, 1H), 3.37 (s, 3H), 2.48-2.18 (m, 8H), 1.14-0.93 (m, 12H)

Compound 67: (2R,3S,4R,5R)-4,5-bis(butanoyloxy)-2-methoxyoxan-3-ylbutanoate

This compound was prepared according to a modified procedure described for the preparation of compound 219.
LCMS: (M+Na+) 397.2. ¹H NMR (400 MHz, DMSO-d6) δ 5.31-5.20 (m, 2H), 5.04 (dd, 1H), 4.90 (d, 1H), 3.89 (dd, 1H), 3.62 (dd, 1H), 3.32 (s, 3H), 2.40-2.13 (m, 6H), 1.65-1.42 (m, 6H), 0.97-0.78 (m, 9H)

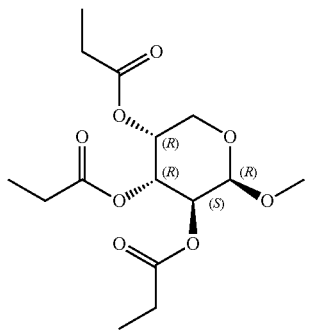

Compound 68: (2R,3S,4R,5R)-2-methoxy-3,5-bis(propanoyloxy)oxan-4-yl propanoate This compound was prepared according to a modified procedure described for the preparation of compound 219.
LCMS: (M+Na+) 355.1. ¹H NMR (400 MHz, DMSO-d6) δ 5.31-5.22 (m, 2H), 5.06 (dd, 1H), 4.92 (d, 1H), 3.91 (dd, 1H), 3.64 (dd, 1H), 3.34 (s, 3H), 2.47-2.12 (m, 6H), 1.13-0.95 (m, 9H)

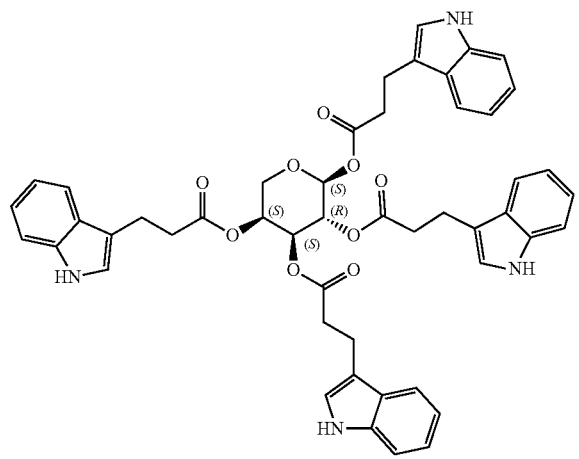

Compound 69: (2S,3R,4S,5S)-3,4,5-tris({[3-(1H-indol-3-yl)propanoyl]oxy})oxan-2-yl 3-(1H-indol-3-yl)propanoate This compound was prepared following a modified procedure described for compound 63. LCMS: (M+H⁺): 835.3.
¹H NMR (400 MHz, Chloroform-d) δ 7.84 (d, J=6.9 Hz, 2H), 7.69 (s, 1H), 7.59-7.45 (m, 5H), 7.34-7.25 (m, 2H), 7.22-7.06 (m, 10H), 7.03 (d, J=2.4 Hz, 1H), 6.92 (d, J=2.3 Hz, 1H), 6.76 (d, J=2.3 Hz, 1H), 6.49 (d, J=2.3 Hz, 1H), 5.68 (d, J=6.9 Hz, 1H), 5.37-5.28 (m, 2H), 5.07 (dd, J=9.2, 3.4 Hz, 1H), 3.95 (dd, J=13.0, 3.7 Hz, 1H), 3.74 (dd, J=13.0, 2.0 Hz, 1H), 3.20-2.57 (m, 12H), 2.55-2.39 (m, 2H), 2.24-1.98 (m, 2H).

Compound 70: (2R,3S,4R,5R,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 63. ¹H NMR (400 MHz, Chloroform-d) 7.78 (s, 1H), 7.74 (s, 1H), 7.66 (s, 1H), 7.54-7.46 (m, 2H), 7.51-7.37 (m, 2H), 7.29 (s, 1H), 7.26-7.16 (m, 2H), 7.16-6.92 (m, 11H), 6.87 (d, J=2.3 Hz, 1H), 6.61 (d, J=2.3 Hz, 1H), 6.30 (d, J=2.4 Hz, 1H), 5.67 (d, J=8.3 Hz, 1H), 5.36 (dd, J=10.5, 8.3 Hz, 1H), 5.27-5.21 (m, 1H), 4.98 (dd, J=10.5, 3.3 Hz, 1H), 3.98-3.86 (m, 1H), 3.18-2.51 (m, 12H), 2.40-2.22 (m, 2H), 1.99-1.76 (m, 2H), 1.21-1.11 (m, 3H)

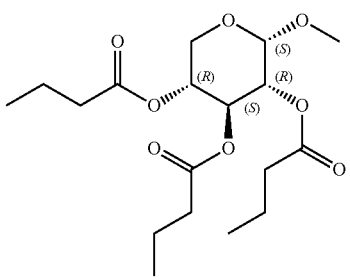

Compound 71: (2S,3R,4S,5R)-4,5-bis(butanoyloxy)-2-methoxyoxan-3-ylbutanoate

This compound was prepared according to a modified procedure described for the preparation of compound 219.
LCMS: (M+Na+) 397.2. ¹H NMR (400 MHz, DMSO-d6) δ 5.37 (t, 1H), 4.97 (ddd, 1H), 4.91 (d, 1H), 4.86 (dd, 1H), 3.80 (dd, 1H), 3.50 (t, 1H), 3.36 (s, 3H), 2.37-2.13 (m, 6H), 1.53 (qd, 6H), 0.89 (td, 9H)

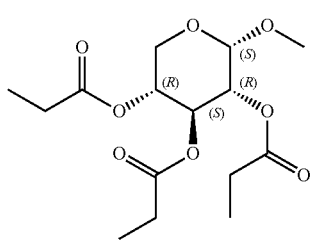

Compound 72: (2S,3R,4S,5R)-2-methoxy-4,5-bis(propanoyloxy)oxan-3-ylpropanoate

This compound was prepared according to a modified procedure described for the preparation of compound 219.

LCMS: (M+Na+) 355.1. $^1$H NMR (400 MHz, DMSO-d$_6$) δ 5.35 (t, 1H), 4.96 (ddd, 1H), 4.91 (d, 1H), 4.87 (dd, 1H), 3.80 (dd, 1H), 3.51 (t, 1H), 3.36 (s, 3H), 2.37-2.23 (m, 6H), 1.02 (td, 9H)

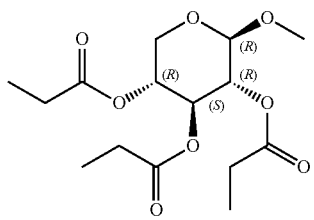

Compound 73: (2R,3R,4S,5R)-2-methoxy-4,5-bis(propanoyloxy)oxan-3-yl propanoate

This compound was prepared according to a modified procedure described for the preparation of compound 219.

LCMS: (M+Na+) 355.1. $^1$H NMR (400 MHz, DMSO-d6) δ 5.24 (t, 1H), 4.90 (td, 1H), 4.81 (dd, 1H), 4.64 (d, 1H), 4.01 (dd, 1H), 3.55 (dd, 1H), 3.40 (s, 3H), 2.38-2.22 (m, 6H), 1.08-0.96 (m, 9H).

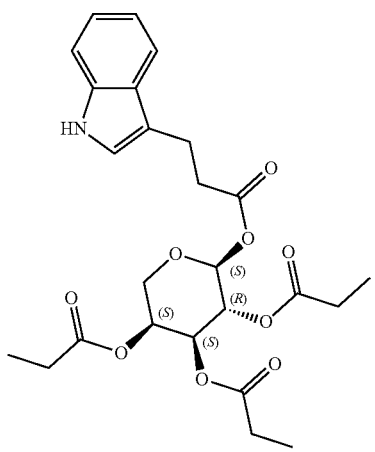

Compound 74: (2S,3R,4S,5S)-3,4,5-tris(propanoyloxy)oxan-2-yl 3-(1H-indol-3-yl)propanoate Step 1

Propionic anhydride (500 mL, 4 mol, 10 eq) was added to L-arabinose (60 g, 0.4 mol, 1 eq) in a 2 L round bottom flask equipped with a stir bar. Pyridine (320 mL, 4 mol, 10 eq) was added to the flask, and the reaction was stirred overnight at room temperature. The reaction was washed with 1M HCl, saturated sodium bicarbonate, and brine. Next the propionic anhydride was removed by rotary evaporation to yield 170 g of crude (2S,3R,4S,5S)-tetrahydro-2H-pyran-2,3,4,5-tetrayl tetrapropionate. Product was taken forward to next step without further purification.

Step 2

Benzylamine (78.5 mL, 720 mmol, 5 equiv) was added to a stirred solution of (2S,3R,4S,5S)-tetrahydro-2H-pyran-2,3,4,5-tetrayl tetrapropionate (62 g, 144 mmol, 1 equiv) in THF (500 mL) at RT. When the TLC indicated complete disappearance of starting material (4-8 h), the reaction was quenched by addition of 1M HCl (375 mL), and the mixture was extracted with ethyl acetate (3×500 mL). The organic phase was dried, pulled through a plug of silica, and concentrated. The crude product was purified by using column chromatography (100% hexanes to 50% Ethyl acetate in hexanes) to yield (3R,4S,5S)-2-hydroxytetrahydro-2H-pyran-3,4,5-triyl tripropionate (16 g, 44.3 mmol, 30.8% yield).

Step 3

Indole-propionic acid (23.0 g, 122 mmol, 1.5 eq), EDC HCl (23.4 g, 122 mmol, 1.5 eq), and DMAP (15 g, 122 mmol, 1.5 eq) were stirred in DCM (200 mL) at room temperature for a few minutes. Compound (3R,4S,5S)-2-hydroxytetrahydro-2H-pyran-3,4,5-triyl tripropionate (26 g, 81.6 mmol, 1 eq) was added and the solution was stirred overnight. The solution was washed with saturated ammonium chloride, saturated sodium bicarbonate, and brine, then loaded onto silica and purified by column chromatography (100% hexanes to 50% Ethyl acetate in hexanes) to yield the title compound (10.7 g, 21.8 mmol, 26.8% yield) as a gooey solid. LCMS (M+Na$^+$): 512.2. $^1$H NMR (400 MHz, DMSO-d$_6$) δ 10.78 (s, 1H), 7.48 (dd, J=7.7, 1.0 Hz, 1H), 7.31 (dd, J=8.1, 1.1 Hz, 1H), 7.10-7.01 (m, 2H), 7.00-6.91 (m, 1H), 5.77 (d, J=7.6 Hz, 1H), 5.28 (dd, J=9.7, 3.6 Hz, 1H), 5.22-5.16 (m, 1H), 5.09 (dd, J=9.7, 7.6 Hz, 1H), 3.98 (dd, J=13.2, 1.7 Hz, 1H), 3.87 (dd, J=13.0, 2.8 Hz, 1H), 2.92 (t, J=7.4 Hz, 2H), 2.70 (td, J=7.8, 7.4, 2.9 Hz, 2H), 2.37 (q, J=7.5 Hz, 2H), 2.27-2.05 (m, 4H), 1.04 (t, J=7.5 Hz, 3H), 0.95 (t, J=7.5 Hz, 3H), 0.89 (t, J=7.5 Hz, 3H).

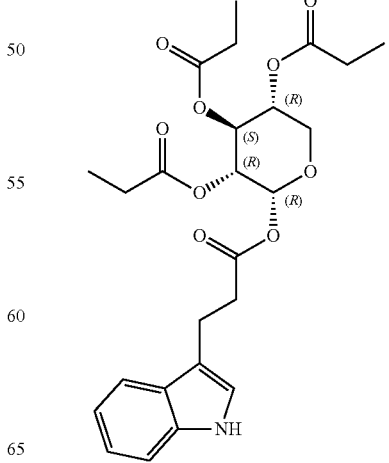

Compound 75: (2R,3R,4S,5R)-3,4,5-tris(propanoyloxy)oxan-2-yl 3-(1H-indol-3-yl)propanoate This compound was prepared following a modified procedure described for compound 74. ¹H NMR (400 MHz, DMSO-d6) δ 10.79 (s, 1H), 7.56-7.43 (m, 1H), 7.31 (m, 1H), 7.13 (d, 1H), 7.05 (ddd, 1H), 6.96 (ddd, 1H), 6.13 (d, 1H), 5.33 (t, 1H), 5.06-4.92 (m, 2H), 3.80 (dd, 1H), 3.52 (t, 1H), 3.05-2.79 (m, 4H), 2.32-2.03 (m, 6H), 0.97 (m, 6H), 0.89 (t, 3H)

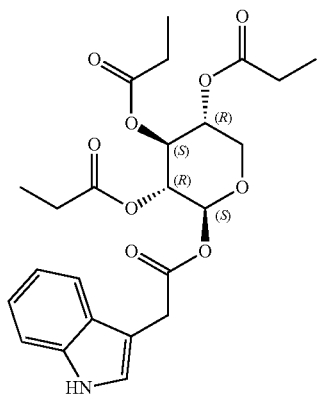

Compound 76: (2S,3R,4S,5R)-2-{[2-(1H-indol-3-yl)acetyl]oxy}-4,5-bis(propanoyloxy)oxan-3-yl propanoate This compound was prepared following a modified procedure described for compound 74. LCMS: (M+Na⁺): 498.2. ¹H NMR (400 MHz, Chloroform-d) 8.07 (s, 1H), 7.60-7.53 (m, 1H), 7.35 (dt, J=8.2, 1.0 Hz, 1H), 7.24-7.16 (m, 2H), 7.16-7.09 (m, 1H), 5.74 (d, J=7.1 Hz, 1H), 5.19 (t, J=8.4 Hz, 1H), 5.05 (dd, J=8.6, 7.0 Hz, 1H), 5.02-4.93 (m, 1H), 4.11 (dd, J=12.0, 5.0 Hz, 1H), 3.81 (d, J=0.9 Hz, 2H), 3.49 (dd, J=12.0, 8.7 Hz, 1H), 2.36-2.17 (m, 4H), 2.12-1.85 (m, 2H), 1.14-1.03 (m, 6H), 0.94 (t, J=7.6 Hz, 3H).

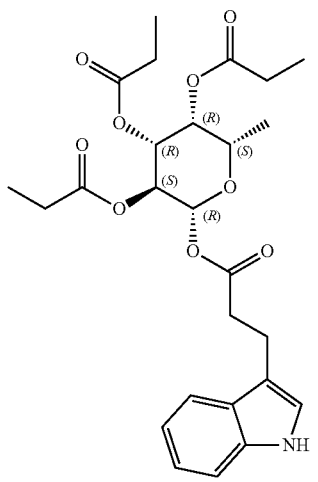

Compound 77: (2R,3S,4R,5R,6S)-6-methyl-3,4,5-tris(propanoyloxy)oxan-2-yl 3-(1H-indol-3-yl)propanoate This compound was prepared following a modified procedure described for compound 74. LCMS: (M+Na⁺): 526.2. ¹H NMR (400 MHz, Chloroform-d) δ 7.97 (s, 1H), 7.57-7.47 (m, 1H), 7.32-7.23 (m, 1H), 7.11 (ddd, J=8.1, 7.1, 1.3 Hz, 1H), 7.04 (ddd, J=8.0, 7.0, 1.1 Hz, 1H), 6.97-6.89 (m, 1H), 5.66 (d, J=8.4 Hz, 1H), 5.28 (dd, J=10.4, 8.3 Hz, 1H), 5.21 (dd, J=3.5, 1.1 Hz, 1H), 5.03 (dd, J=10.4, 3.4 Hz, 1H), 3.89 (qd, J=6.4, 1.2 Hz, 1H), 3.13-2.95 (m, 2H), 2.79-2.61 (m, 2H), 2.49-2.30 (m, 2H), 2.21-1.93 (m, 4H), 1.26-1.09 (m, 6H), 1.00 (t, J=7.5 Hz, 3H), 0.91 (t, J=7.6 Hz, 3H)

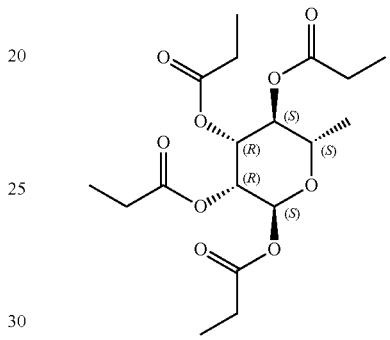

Compound 78: (2S,3R,4R,5S,6S)-6-methyl-3,4,5-tris(propanoyloxy)oxan-2-yl propanoate This compound was prepared according to a modified procedure described for the preparation of compound 219.

LCMS: (M+Na⁺): 411.1. ¹H NMR (400 MHz, Chloroform-d) δ 6.03 (d, J=1.9 Hz, 1H), 5.33 (dd, J=10.1, 3.5 Hz, 1H), 5.27 (dd, J=3.5, 2.0 Hz, 1H), 5.15 (t, J=10.0 Hz, 1H), 4.00-3.88 (m, 1H), 2.51-2.37 (m, 4H), 2.37-2.19 (m, 4H), 1.27-1.04 (m, 15H).

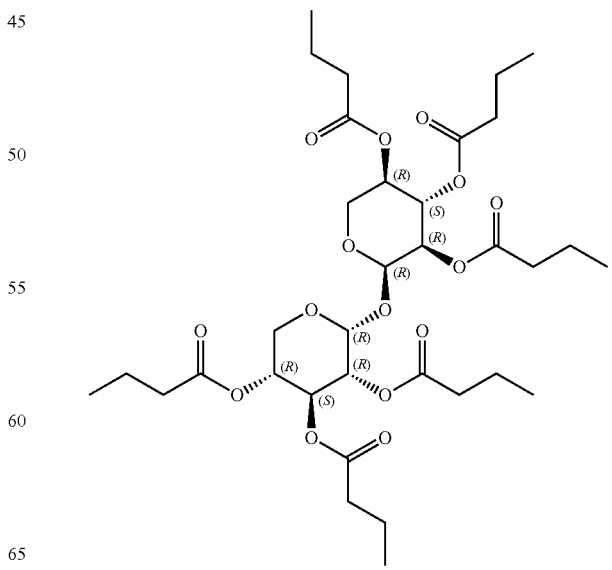

Compound 79: (2R,3R,4S,5R)-4,5-bis(butanoyloxy)-2-{[(2R,3R,4S,5R)-3,4,5-tris(butanoyloxy)oxan-2-yl]oxy}oxan-3-ylbutanoate This compound was prepared according to a modified procedure described for the preparation of compound 219.

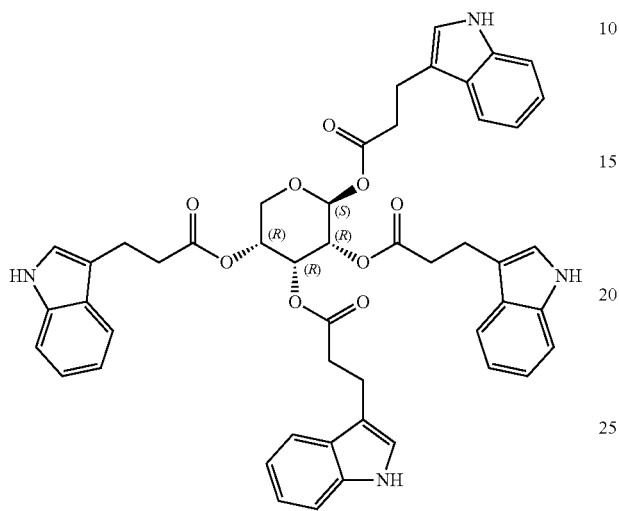

Compound 80: (2S,3R,4R,5R)-3,4,5-tris({[3-(1H-indol-3-yl)propanoyl]oxy})oxan-2-yl 3-(1H-indol-3-yl)propanoate This compound was prepared following a modified procedure described for compound 63. LCMS: (M+H⁺): 835.3. ¹H NMR (400 MHz, Chloroform-d) δ 7.77 (s, 1H), 7.73 (s, 1H), 7.49 (d, J=8.1 Hz, 3H), 7.46-7.38 (m, 2H), 7.25 (t, J=8.4 Hz, 3H), 7.19-6.92 (m, 10H), 6.83 (d, J=2.3 Hz, 1H), 6.77 (d, J=2.3 Hz, 1H), 6.75-6.67 (m, 1H), 6.65-6.60 (m, 1H), 6.03 (d, J=3.7 Hz, 1H), 5.52 (s, 1H), 5.08 (t, J=3.5 Hz, 1H), 5.03-4.94 (m, 1H), 3.76 (t, J=10.4 Hz, 1H), 3.51 (dd, J=11.2, 4.7 Hz, 1H), 3.06-2.86 (m, 8H), 2.67-2.38 (m, 8H).

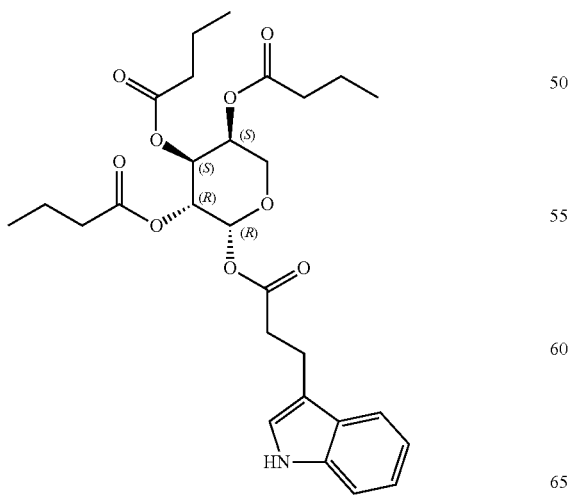

Compound 81: (2R,3R,4S,5S)-4,5-bis(butanoyloxy)-2-{[3-(1H-indol-3-yl)propanoyl]oxy}oxan-3-yl butanoate This compound was prepared following a modified procedure described for compound 74. LCMS: (M+H⁺): 532.2. ¹H NMR (400 MHz, Methanol-d4) 7.56 (d, J=7.8 Hz, 1H), 7.32 (d, J=8.1 Hz, 1H), 7.12-7.05 (m, 2H), 7.05-6.97 (m, 1H), 6.26 (d, J=3.6 Hz, 1H), 5.36-5.26 (m, 2H), 5.21 (dd, J=10.5, 3.6 Hz, 1H), 3.80 (dd, J=13.4, 1.3 Hz, 1H), 3.62 (dd, J=13.4, 1.9 Hz, 1H), 3.21-3.04 (m, 2H), 2.87 (t, J=6.9 Hz, 2H), 2.44-2.34 (m, 2H), 2.22 (t, J=7.2 Hz, 2H), 2.06-1.95 (m, 2H), 1.73-1.61 (m, 2H), 1.64-1.52 (m, 2H), 1.45 (h, J=7.3 Hz, 2H), 0.98 (t, J=7.4 Hz, 3H), 0.91 (t, J=7.4 Hz, 3H), 0.80 (t, J=7.4 Hz, 3H).

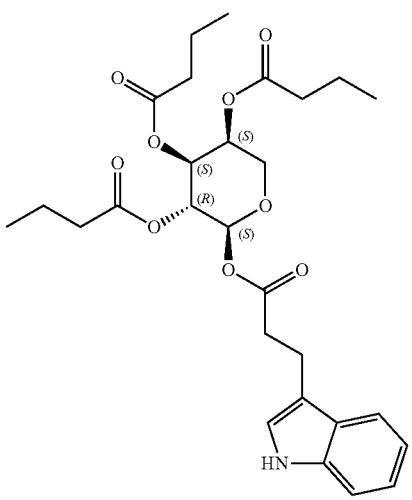

Compound 82: (2S,3R,4S,5S)-4,5-bis(butanoyloxy)-2-{[3-(1H-indol-3-yl)propanoyl]oxy}oxan-3-yl butanoate This compound was prepared following a modified procedure described for compound 74. LCMS: (M+H⁺): 532.2. ¹H NMR (400 MHz, Methanol-d4) δ 7.41 (dt, J=7.9, 1.1 Hz, 1H), 7.21 (dt, J=8.2, 1.0 Hz, 1H), 7.02-6.94 (m, 1H), 6.93-6.85 (m, 2H), 5.63 (d, J=7.2 Hz, 1H), 5.24-5.17 (m, 1H), 5.17-5.05 (m, 2H), 3.83 (dd, J=13.1, 3.3 Hz, 1H), 3.76 (dd, J=13.1, 1.9 Hz, 1H), 3.03-2.89 (m, 2H), 2.73-2.58 (m, 2H), 2.34-1.90 (m, 6H), 1.64-1.53 (m, 2H), 1.52-1.43 (m, 2H), 1.41-1.31 (m, 2H), 0.94-0.84 (m, 3H), 0.84-0.76 (m, 3H), 0.73 (t, J=7.4 Hz, 3H).

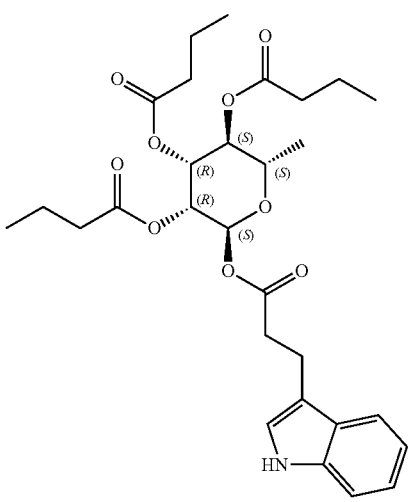

Compound 83: (2S,3R,4R,5S,6S)-4,5-bis(butanoyloxy)-2-{[3-(1H-indol-3-yl)propanoyl]oxy}-6-methyloxan-3-yl butanoate This compound was prepared following a modified procedure described for compound 74.

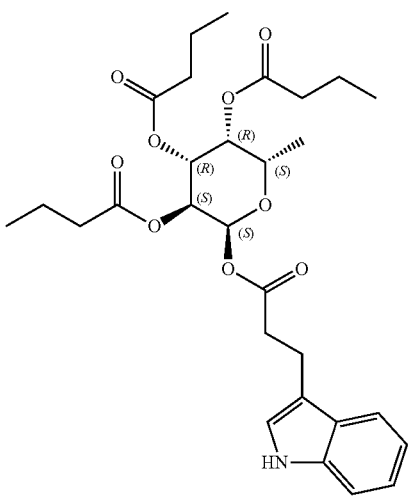

Compound 84: (2S,3S,4R,5R,6S)-4,5-bis(butanoyloxy)-2-{[3-(1H-indol-3-yl)propanoyl]oxy}-6-methyloxan-3-yl butanoate This compound was prepared following a modified procedure described for compound 74. ¹H NMR (400 MHz, Chloroform-d) δ 8.05 (s, 1H), 7.61 (d, J=7.8 Hz, 1H), 7.39-7.32 (m, 1H), 7.19 (ddd, J=8.2, 7.0, 1.3 Hz, 1H), 7.13 (td, J=7.5, 1.2 Hz, 1H), 7.08 (d, J=2.3 Hz, 1H), 6.33 (d, J=3.2 Hz, 1H), 5.40-5.22 (m, 3H), 4.01-3.91 (m, 1H), 3.20-3.08 (m, 2H), 2.84 (t, J=7.3 Hz, 2H), 2.47-2.32 (m, 2H), 2.20 (td, J=7.3, 1.8 Hz, 2H), 2.04 (td, J=7.3, 1.2 Hz, 2H), 1.76-1.41 (m, 6H), 1.04-0.87 (m, 9H), 0.83 (t, J=7.4 Hz, 3H)

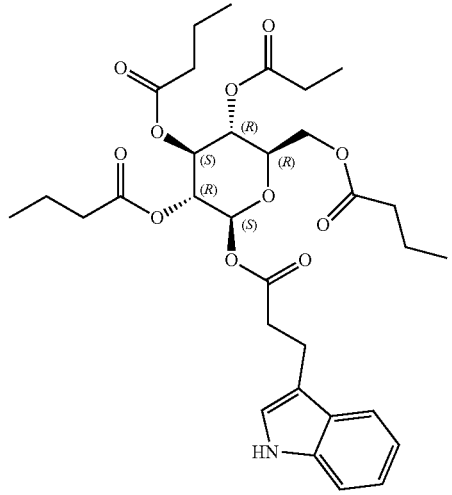

Compound 85: [(2R,3R,4S,5R,6S)-3,4,5-tris(butanoyloxy)-6-{[3-(1H-indol-3-yl)propanoyl]oxy}oxan-2-yl]methyl butanoate This compound was prepared following a modified procedure described for compound 74. ¹H NMR (400 MHz, Chloroform-d) 7.93 (s, 1H), 7.49 (dd, J=7.8, 1.1 Hz, 1H), 7.28 (dt, J=8.1, 1.0 Hz, 1H), 7.12 (ddd, J=8.1, 7.0, 1.3 Hz, 1H), 7.04 (ddd, J=8.1, 7.0, 1.1 Hz, 1H), 6.92 (d, J=2.4 Hz, 1H), 5.68 (d, J=8.2 Hz, 1H), 5.26-5.17 (m, 1H), 5.14-5.05 (m, 2H), 4.14 (qd, J=12.5, 3.4 Hz, 2H), 3.77 (ddd, J=10.0, 4.5, 2.4 Hz, 1H), 3.06-2.97 (m, 2H), 2.78-2.61 (m, 2H), 2.30-2.22 (m, 2H), 2.24-2.09 (m, 4H), 2.03 (td, J=7.4, 2.7 Hz, 2H), 1.63-1.36 (m, 8H), 0.91-0.72 (m, 12H).

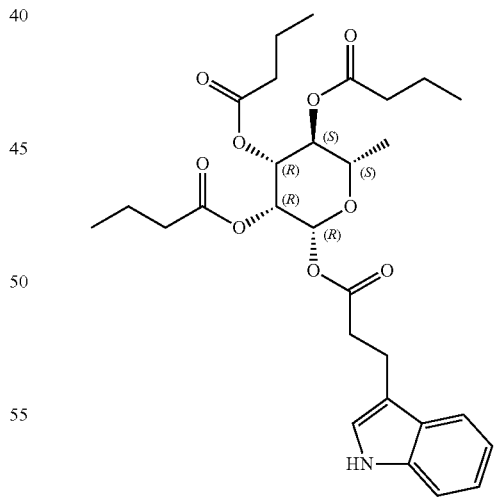

Compound 86: (2R,3R,4R,5S,6S)-4,5-bis(butanoyloxy)-2-{[3-(1H-indol-3-yl)propanoyl]oxy}-6-methyloxan-3-yl butanoate This compound was prepared following a modified procedure described for compound 74.

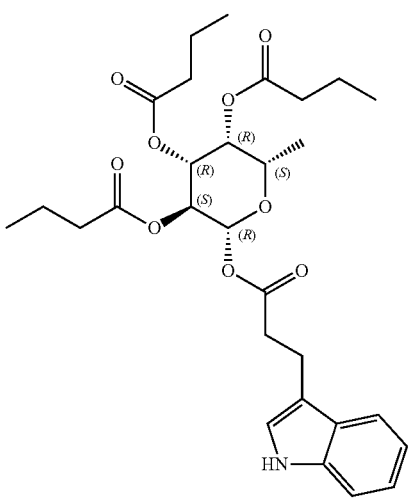

Compound 87: (2R,3S,4R,5R,6S)-4,5-bis(butanoyloxy)-2-{[3-(1H-indol-3-yl)propanoyl]oxy}-6-methyloxan-3-yl butanoate This compound was prepared following a modified procedure described for compound 74. ¹H NMR (400 MHz, Chloroform-d) δ 7.96 (s, 1H), 7.57 (d, J=7.9 Hz, 1H), 7.35 (d, J=8.1 Hz, 1H), 7.23-7.15 (m, 1H), 7.15-7.07 (m, 1H), 7.00 (d, J=2.3 Hz, 1H), 5.73 (d, J=8.4 Hz, 1H), 5.41-5.30 (m, 1H), 5.32-5.27 (m, 1H), 5.10 (dd, J=10.4, 3.4 Hz, 1H), 4.02-3.93 (m, 1H), 3.15-3.00 (m, 2H), 2.87-2.68 (m, 2H), 2.51-2.34 (m, 2H), 2.27-2.16 (m, 2H), 2.16-2.00 (m, 2H), 1.78-1.66 (m, 2H), 1.62-1.43 (m, 4H), 1.27-1.18 (m, 3H), 0.99 (t, J=7.4 Hz, 3H), 0.89 (t, J=7.4 Hz, 3H), 0.83 (t, J=7.4 Hz, 3H)

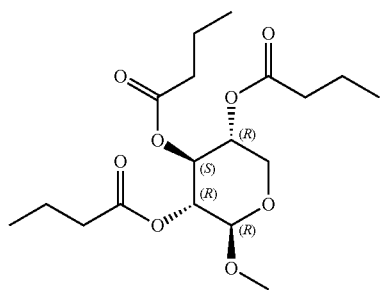

Compound 88: (2R,3R,4S,5R)-4,5-bis(butanoyloxy)-2-methoxyoxan-3-yl butanoate This compound was prepared following a modified procedure described for compounds 46 and 47. LCMS: (M+Na⁺) 397.2. ¹H NMR (400 MHz, DMSO-d6) δ 5.26 (t, 1H), 4.90 (td, 1H), 4.82 (dd, 1H), 4.63 (d, 1H), 4.00 (dd, 1H), 3.54 (dd, 1H), 3.40 (s, 3H), 2.34-2.18 (m, 6H), 1.59-1.48 (m, 6H), 0.97-0.81 (m, 9H)

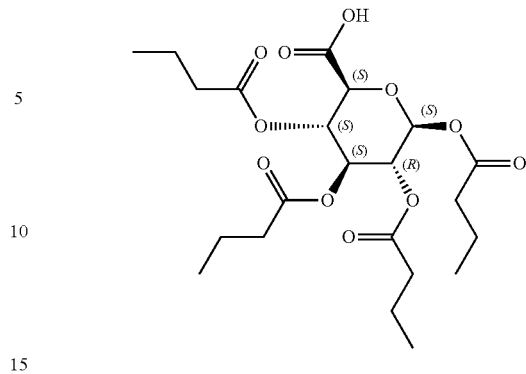

Compound 90: [(2R,3R,4S,5R,6R)-3,4,5-tris(butanoyloxy)-6-{[3-(1H-indol-3-yl)propanoyl]oxy}oxan-2-yl]methyl butanoate This compound was prepared following a modified procedure described for compound 74. ¹H NMR (400 MHz, Chloroform-d) δ 8.04 (s, 1H), 7.54 (dd, J=7.8, 1.2 Hz, 1H), 7.29 (dt, J=8.2, 1.0 Hz, 1H), 7.12 (ddd, J=8.2, 7.0, 1.3 Hz, 1H), 7.09-7.00 (m, 2H), 6.26 (d, J=3.7 Hz, 1H), 5.37 (t, J=9.9 Hz, 1H), 5.05 (t, J=9.9 Hz, 1H), 4.97 (dd, J=10.3, 3.7 Hz, 1H), 3.97 (dd, J=12.5, 3.9 Hz, 1H), 3.86 (dd, J=12.5, 2.3 Hz, 1H), 3.71 (ddd, J=10.3, 4.0, 2.2 Hz, 1H), 3.17-3.00 (m, 2H), 2.81 (t, J=7.2 Hz, 2H), 2.23 (td, J=7.4, 1.7 Hz, 2H), 2.20-2.08 (m, 4H), 2.00-1.87 (m, 2H), 1.62-1.46 (m, 6H), 1.47-1.34 (m, 2H), 0.91-0.80 (m, 9H), 0.74 (t, J=7.4 Hz, 3H).

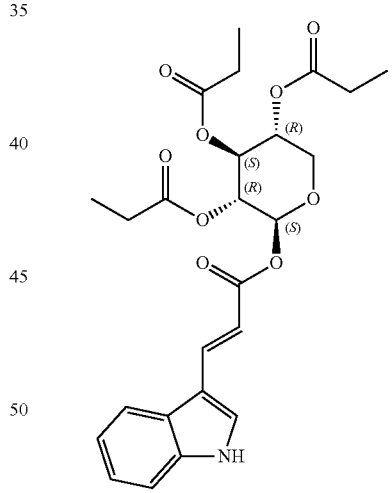

Compound 91: (2S,3R,4S,5R)-3,4,5-tris(propanoyloxy)oxan-2-yl (2E)-3-(1H-indol-3-yl)prop-2-enoate This compound was prepared following a modified procedure described for compound 74. ¹H NMR (400 MHz, Chloroform-d) δ 8.50 (s, 1H), 7.98 (d, J=15.9 Hz, 1H), 7.94-7.88 (m, 1H), 7.54 (d, J=2.8 Hz, 1H), 7.46-7.39 (m, 1H), 7.35-7.24 (m, 2H), 6.41 (d, J=15.9 Hz, 1H), 5.87 (d, J=7.2 Hz, 1H), 5.31 (t, J=8.6 Hz, 1H), 5.21 (dd, J=8.8, 7.2 Hz, 1H), 5.07 (td, J=8.7, 5.2 Hz, 1H), 4.20 (dd, J=11.9, 5.2 Hz, 1H), 3.58 (dd, J=11.9, 9.0 Hz, 1H), 2.38-2.25 (m, 6H), 1.22-1.04 (m, 9H).

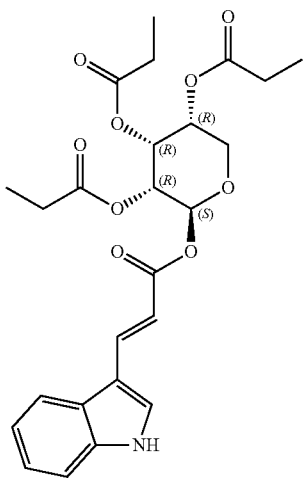

Compound 92: (2S,3R,4R,5R)-3,4,5-tris(propanoyloxy)oxan-2-yl (2E)-3-(1H-indol-3-yl)prop-2-enoate This compound was prepared following a modified procedure described for compound 74. ¹H NMR (400 MHz, Chloroform-d) δ 8.58 (s, 1H), 7.99 (d, J=15.9 Hz, 1H), 7.95-7.89 (m, 1H), 7.55 (d, J=2.8 Hz, 1H), 7.48-7.38 (m, 1H), 7.35-7.24 (m, 2H), 6.44 (d, J=15.9 Hz, 1H), 6.19 (d, J=4.8 Hz, 1H), 5.62 (t, J=3.5 Hz, 1H), 5.27-5.18 (m, 2H), 4.11 (dd, J=12.3, 3.4 Hz, 1H), 3.95 (dd, J=12.4, 5.8 Hz, 1H), 2.39 (ddd, J=9.8, 4.8, 2.2 Hz, 6H), 1.21-1.10 (m, 9H)

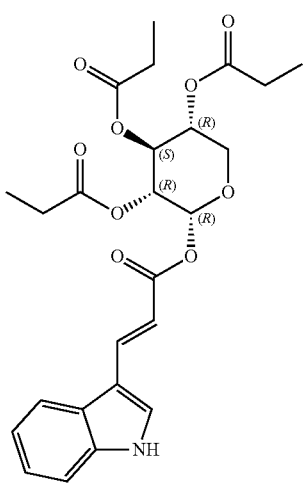

Compound 93: (2R,3R,4S,5R)-3,4,5-tris(propanoyloxy)oxan-2-yl (2E)-3-(1H-indol-3-yl)prop-2-enoate This compound was prepared following a modified procedure described for compound 74.

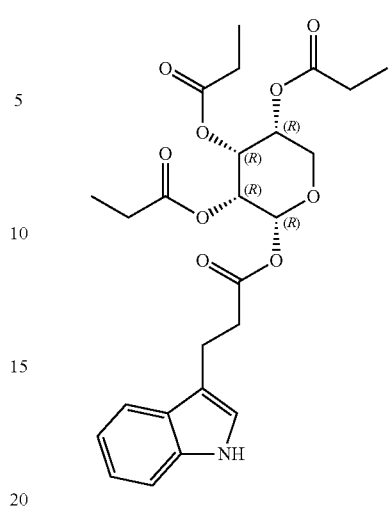

Compound 94: (2R,3R,4R,5R)-3,4,5-tris(propanoyloxy)oxan-2-yl 3-(1H-indol-3-yl)propanoate This compound was prepared following a modified procedure described for compound 74.

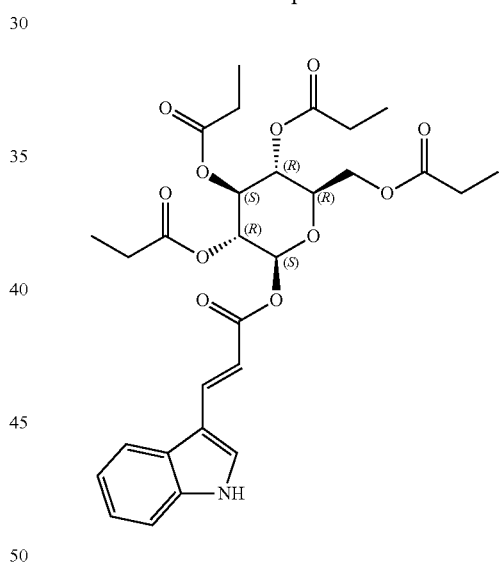

Compound 95: (2S,3R,4S,5R,6R)-3,4,5-tris(propanoyloxy)-6-[(propanoyloxy)methyl]oxan-2-yl (2E)-3-(1H-indol-3-yl)prop-2-enoate This compound was prepared following a modified procedure described for compound 74. ¹H NMR (400 MHz, Chloroform-d) 8.48 (s, 1H), 7.91 (d, J=15.9 Hz, 1H), 7.87-7.79 (m, 1H), 7.47 (d, J=2.9 Hz, 1H), 7.41-7.32 (m, 1H), 7.28-7.16 (m, 2H), 6.33 (d, J=16.0 Hz, 1H), 5.84 (d, J=7.8 Hz, 1H), 5.32-5.19 (m, 2H), 5.15 (t, J=9.5 Hz, 1H), 4.27 (dd, J=12.5, 4.6 Hz, 1H), 4.08 (dd, J=12.5, 2.2 Hz, 1H), 3.86 (ddd, J=10.0, 4.6, 2.2 Hz, 1H), 2.37-2.14 (m, 8H), 1.11-0.95 (m, 12H).

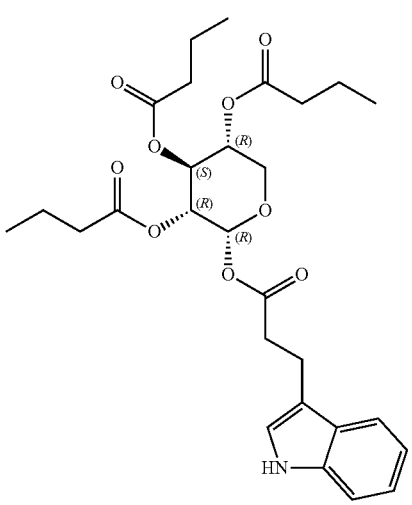

Compound 96: (2R,3R,4S,5R)-4,5-bis(butanoyloxy)-2-{[3-(1H-indol-3-yl)propanoyl]oxy}oxan-3-yl butanoate This compound was prepared following a modified procedure described for compound 74. $^1$H NMR (400 MHz, Methanol-d$_4$) δ 7.58 (dt, J=7.8, 1.1 Hz, 1H), 7.34 (dt, J=8.1, 1.0 Hz, 1H), 7.15-7.07 (m, 2H), 7.03 (ddd, J=8.0, 7.0, 1.1 Hz, 1H), 6.28 (d, J=3.5 Hz, 1H), 5.41-5.28 (m, 2H), 5.23 (dd, J=10.5, 3.6 Hz, 1H), 3.83 (dd, J=13.3, 1.4 Hz, 1H), 3.65 (dd, J=13.3, 2.0 Hz, 1H), 3.23-3.05 (m, 2H), 2.89 (t, J=6.9 Hz, 2H), 2.49-2.31 (m, 2H), 2.24 (t, J=7.2 Hz, 2H), 2.08-1.98 (m, 2H), 1.76-1.54 (m, 4H), 1.54-1.41 (m, 2H), 1.06-0.89 (m, 6H), 0.83 (t, J=7.4 Hz, 3H).

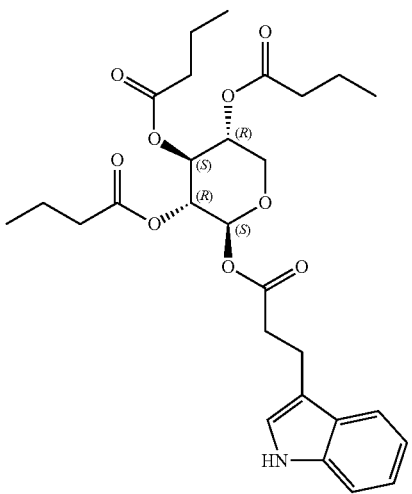

Compound 97: (2S,3R,4S,5R)-4,5-bis(butanoyloxy)-2-{[3-(1H-indol-3-yl)propanoyl]oxy}oxan-3-yl butanoate This compound was prepared following a modified procedure described for compound 74. $^1$H NMR (400 MHz, Methanol-d4) δ 7.56-7.47 (m, 1H), 7.37-7.30 (m, 1H), 7.10 (ddd, J=8.1, 6.9, 1.3 Hz, 1H), 7.06-6.97 (m, 2H), 5.79-5.70 (m, 1H), 5.37-5.29 (m, 1H), 5.29-5.17 (m, 2H), 3.95 (dd, J=13.1, 3.3 Hz, 1H), 3.88 (dd, J=13.1, 1.9 Hz, 1H), 3.15-3.00 (m, 2H), 2.83-2.72 (m, 2H), 2.48-2.34 (m, 2H), 2.22 (t, J=7.3 Hz, 2H), 2.18-2.00 (m, 2H), 1.76-1.65 (m, 2H), 1.68-1.52 (m, 2H), 1.55-1.42 (m, 2H), 1.06-0.96 (m, 3H), 0.99-0.80 (m, 6H).

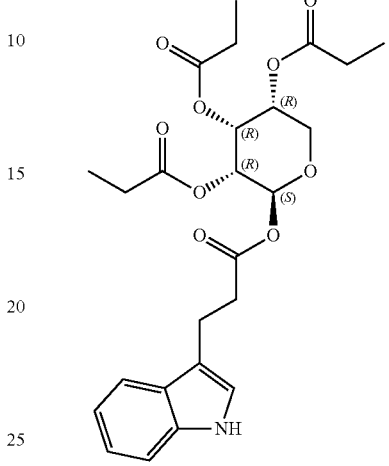

Compound 98: (2S,3R,4R,5R)-3,4,5-tris(propanoyloxy)oxan-2-yl 3-(1H-indol-3-yl)propanoate This compound was prepared following a modified procedure described for compound 74.

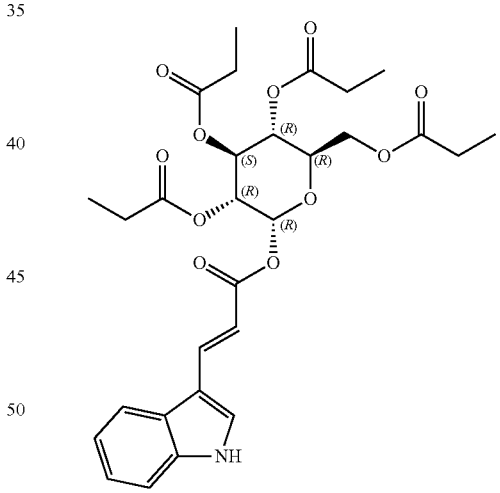

Compound 99: (2R,3R,4S,5R,6R)-3,4,5-tris(propanoyloxy)-6-[(propanoyloxy)methyl]oxan-2-yl (2E)-3-(1H-indol-3-yl)prop-2-enoate This compound was prepared following a modified procedure described for compound 74. $^1$H NMR (400 MHz, Chloroform-d) δ 8.59 (s, 1H), 8.09-7.99 (m, 2H), 7.61 (d, J=2.8 Hz, 1H), 7.52-7.43 (m, 1H), 7.39-7.31 (m, 2H), 6.58-6.49 (m, 2H), 5.68 (t, J=9.9 Hz, 1H), 5.29-5.18 (m, 2H), 4.33 (dd, J=12.4, 4.2 Hz, 1H), 4.26 (ddd, J=10.3, 4.2, 2.1 Hz, 1H), 4.15 (dd, J=12.3, 2.1 Hz, 1H), 2.46-2.25 (m, 8H), 1.20-1.07 (m, 12H).

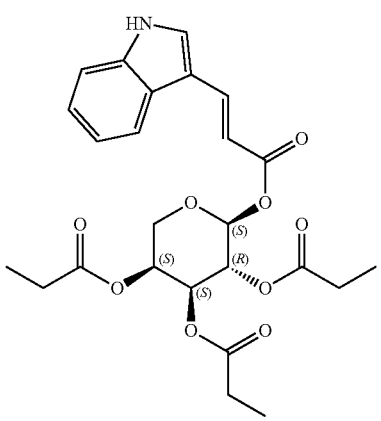

Compound 100: (2S,3R,4S,5S)-3,4,5-tris(propanoyloxy)oxan-2-yl(2E)-3-(1H-indol-3-yl)prop-2-enoate This compound was prepared following a modified procedure described for compound 74.

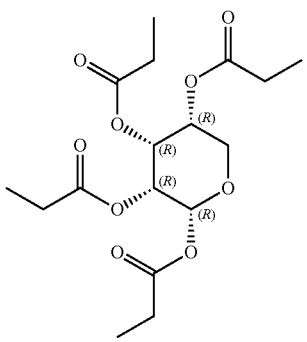

Compound 101: (2R,3R,4R,5R)-3,4,5-tris(propanoyloxy)oxan-2-ylpropanoate

This compound was prepared according to a modified procedure described for the preparation of compound 219.

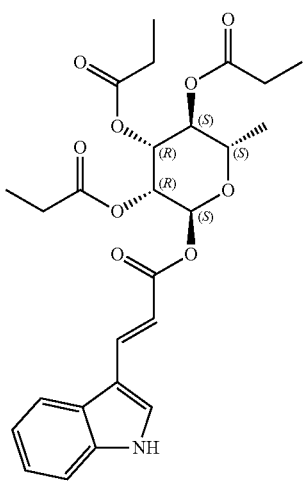

Compound 102: (2S,3R,4R,5S,6S)-6-methyl-3,4,5-tris(propanoyloxy)oxan-2-yl (2E)-3-(1H-indol-3-yl)prop-2-enoate This compound was prepared following a modified procedure described for compound 74.

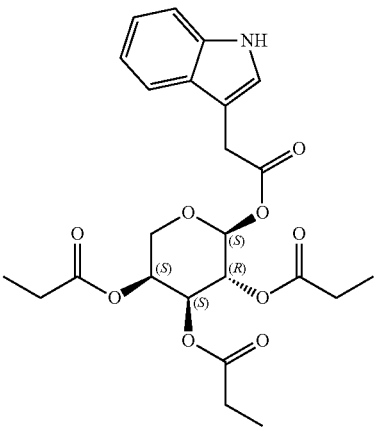

Compound 103: (3S,4S,5R,6S)-6-{[2-(1H-indol-3-yl)acetyl]oxy}-4,5-bis(propanoyloxy)oxan-3-yl propanoate This compound was prepared following a modified procedure described for compound 74.

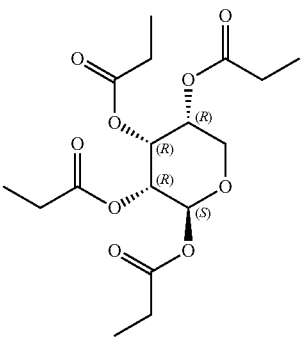

Compound 104: (2S,3R,4R,5R)-3,4,5-tris(propanoyloxy)oxan-2-yl propanoate

This compound was prepared according to a modified procedure described for the preparation of compound 219.

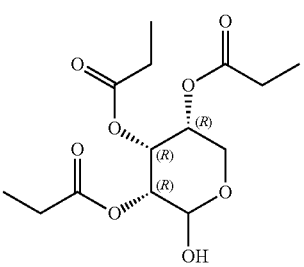

Compound 105: (3R,4R,5R)-2-hydroxy-4,5-bis(propanoyloxy)oxan-3-ylpropanoate

This compound was prepared according to a modified procedure described for the preparation of compound 21.

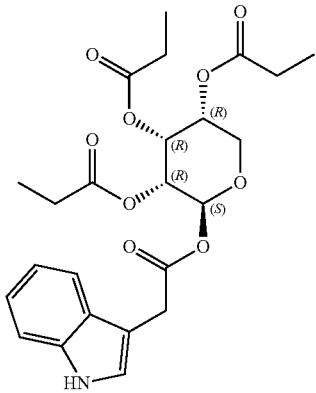

Compound 106: (2S,3R,4R,5R)-2-{[2-(1H-indol-3-yl)acetyl]oxy}-4,5-bis(propanoyloxy)oxan-3-yl propanoate This compound was prepared following a modified procedure described for compound 74.

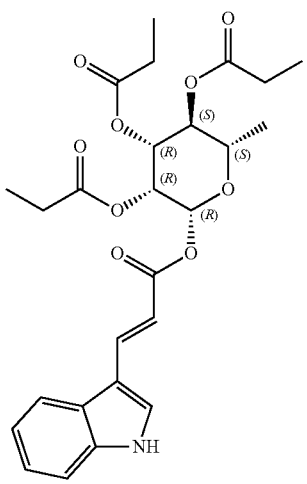

Compound 107: (2R,3R,4R,5S,6S)-6-methyl-3,4,5-tris(propanoyloxy)oxan-2-yl (2E)-3-(1H-indol-3-yl)prop-2-enoate This compound was prepared following a modified procedure described for compound 74.

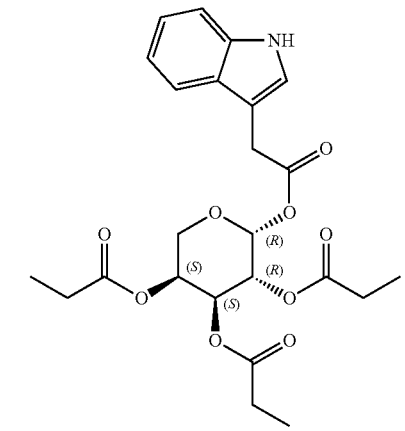

Compound 108: (3S,4S,5R,6R)-6-{[2-(1H-indol-3-yl)acetyl]oxy}-4,5-bis(propanoyloxy)oxan-3-yl propanoate This compound was prepared following a modified procedure described for compound 74.

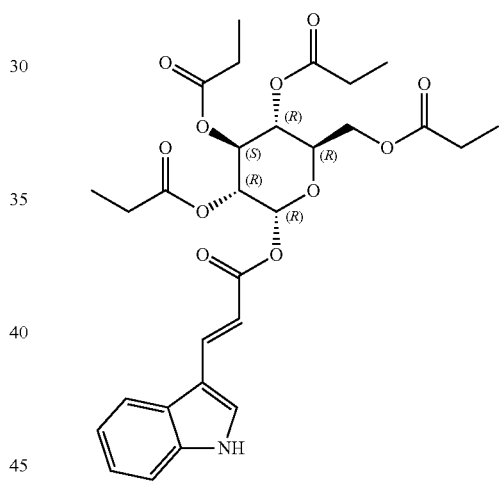

Compound 109: [(2R,3R,4S,5R,6R)-6-{[3-(1H-indol-3-yl)propanoyl]oxy}-3,4,5-tris(propanoyloxy)oxan-2-yl]methyl propanoate This compound was prepared following a modified procedure described for compound 74.

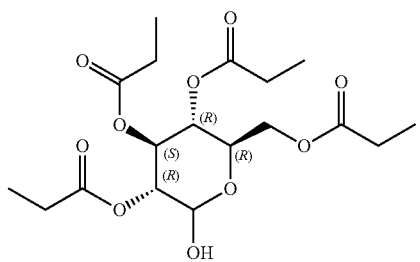

Compound 110: [(2R,3R,4,5R)-6-hydroxy-3,4,5-tris(propanoyloxy)oxan-2-yl]methyl propanoate This compound was prepared according to a modified procedure described for the preparation of compound 21.

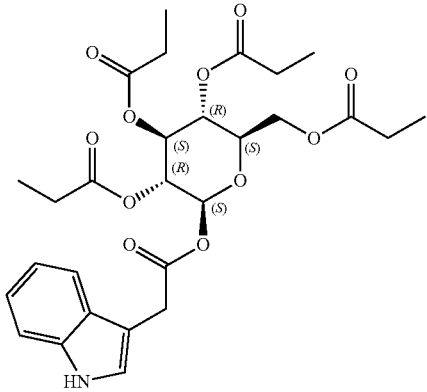

Compound 111: [(2R,3R,4S,5R,6S)-6-{[2-(1H-indol-3-yl)acetyl]oxy}-3,4,5-tris(propanoyloxy)oxan-2-yl]methyl propanoate This compound was prepared following a modified procedure described for compound 74.

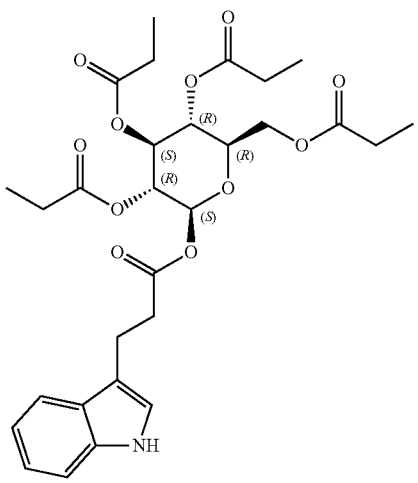

Compound 112: [(2R,3R,4S,5R,6S)-6-{[3-(1H-indol-3-yl)propanoyl]oxy}-3,4,5-tris(propanoyloxy)oxan-2-yl]methyl propanoate This compound was prepared following a modified procedure described for compound 74. LCMS (M+Na$^+$): 598.2.
$^1$H NMR (400 MHz, DMSO-d6) δ 10.78 (d, J=2.4 Hz, 1H), 7.50-7.44 (m, 1H), 7.34-7.27 (m, 1H), 7.09-7.00 (m, 2H), 6.95 (ddd, J=7.9, 6.9, 1.1 Hz, 1H), 5.99 (d, J=8.3 Hz, 1H), 5.45 (t, J=9.6 Hz, 1H), 5.02-4.89 (m, 2H), 4.27-4.15 (m, 2H), 4.03-3.94 (m, 1H), 2.97-2.84 (m, 2H), 2.79-2.63 (m, 2H), 2.34-1.98 (m, 8H), 1.05-0.82 (m, 12H).

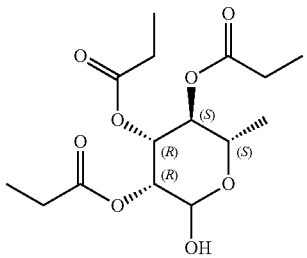

Compound 113: (3R,4R,5S,6S)-2-hydroxy-6-methyl-4,5-bis(propanoyloxy)oxan-3-yl propanoate This compound was prepared according to a modified procedure described for the preparation of compound 21.

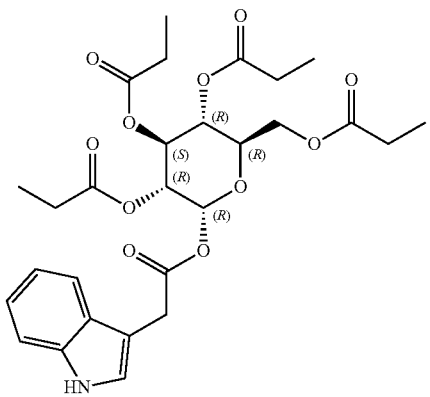

Compound 114: [(2R,3R,4S,5R,6R)-6-{[2-(1H-indol-3-yl)acetyl]oxy}-3,4,5-tris(propanoyloxy)oxan-2-yl]methyl propanoate This compound was prepared following a modified procedure described for compound 74.

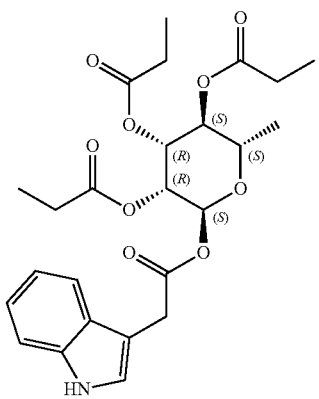

Compound 115: (2S,3R,4R,5S,6S)-2-{[2-(1H-indol-3-yl)acetyl]oxy}-6-methyl-4,5-bis(propanoyloxy)oxan-3-yl propanoate This compound was prepared following a modified procedure described for compound 74.

131

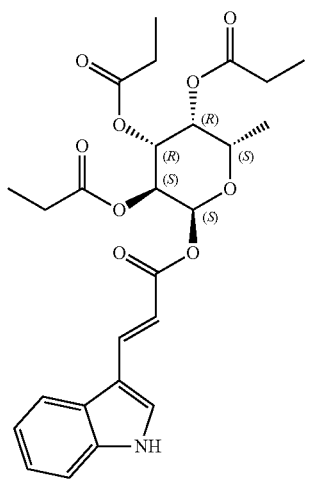

Compound 116: (2S,3S,4R,5R,6S)-6-methyl-3,4,5-tris(propanoyloxy)oxan-2-yl(2E)-3-(1H-indol-3-yl)prop-2-enoate This compound was prepared following a modified procedure described for compound 74.

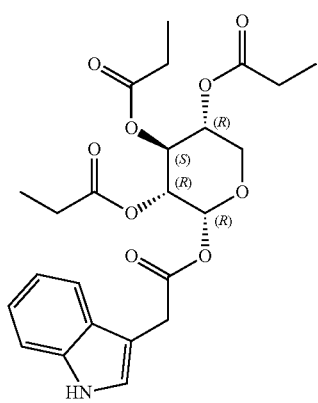

Compound 117: (2R,3R,4S,5R)-2-{[2-(1H-indol-3-yl)acetyl]oxy}-4,5-bis(propanoyloxy)oxan-3-yl propanoate This compound was prepared following a modified procedure described for compound 74. LCMS (M+Na⁺): 498.2. ¹H NMR (400 MHz, Chloroform-d) 8.10 (s, 1H), 7.63-7.56 (m, 1H), 7.33-7.26 (m, 1H), 7.18 (d, J=2.4 Hz, 1H), 7.17-7.06 (m, 2H), 6.21 (d, J=3.6 Hz, 1H), 5.42 (t, J=9.9 Hz, 1H), 4.98-4.87 (m, 2H), 3.82 (s, 2H), 3.74 (dd, J=11.1, 5.9 Hz, 1H), 3.40 (t, J=11.0 Hz, 1H), 2.22 (qd, J=7.6, 1.9 Hz, 4H), 1.96 (qd, J=7.5, 4.2 Hz, 2H), 1.08-0.99 (m, 6H), 0.88 (t, J=7.6 Hz, 3H).

132

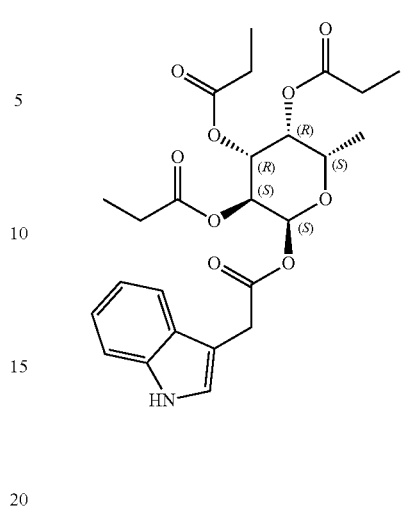

Compound 118: (2S,3S,4R,5R,6S)-2-{[2-(1H-indol-3-yl)acetyl]oxy}-6-methyl-4,5-bis(propanoyloxy)oxan-3-yl propanoate

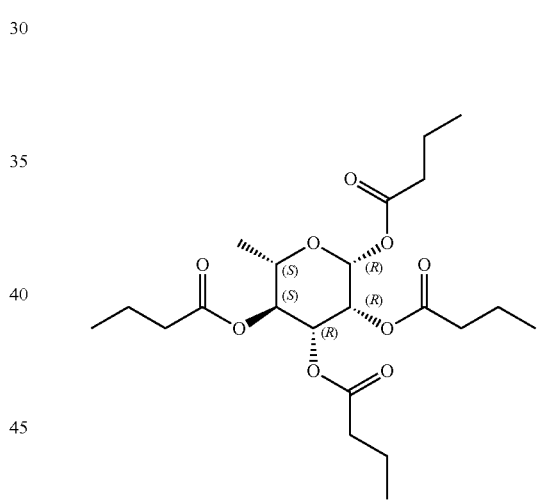

Compound 119: (2R,3R,4R,5S,6S)-3,4,5-tris(butanoyloxy)-6-methyloxan-2-yl butanoate This compound was prepared according to a modified procedure described for the preparation of compound 219. ¹H NMR (400 MHz, DMSO-d6) δ 6.05 (d, J=1.3 Hz, 1H), 5.38 (dd, J=3.5, 1.2 Hz, 1H), 5.31 (dd, J=10.1, 3.4 Hz, 1H), 4.89 (t, J=9.9 Hz, 1H), 3.90-3.81 (m, 1H), 2.41-2.36 (m, 2H), 2.33-2.22 (m, 4H), 2.15 (td, J=7.2, 1.2 Hz, 2H), 1.65-1.56 (m, 2H), 1.55-1.41 (m, 6H), 1.11 (d, J=6.2 Hz, 3H), 0.94 (t, J=7.4 Hz, 3H), 0.88-0.80 (m, 9H)

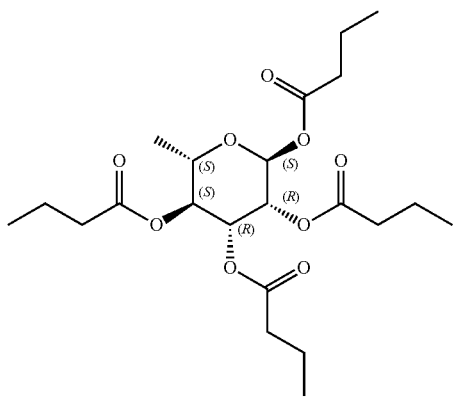

Compound 120: (2S,3R,4R,5S,6S)-3,4,5-tris(butanoyloxy)-6-methyloxan-2-ylbutanoate This compound was prepared according to a modified procedure described for the preparation of compound 219.

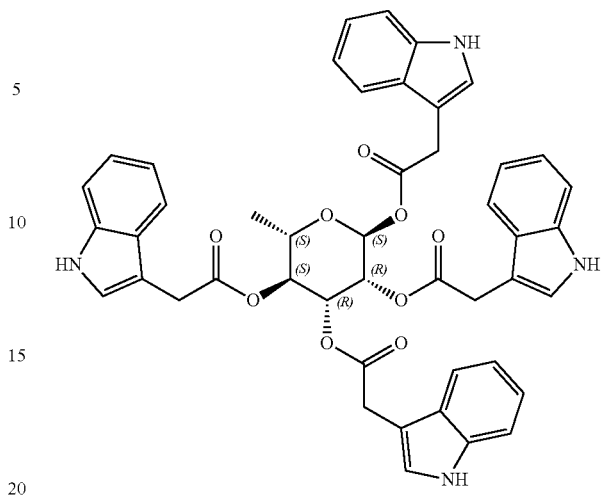

Compound 122: (2S,3R,4R,5S,6S)-3,4,5-tris({[2-(1H-indol-3-yl)acetyl]oxy})-6-methyloxan-2-yl 2-(1H-indol-3-yl)acetate This compound was prepared following a modified procedure described for compound 63.

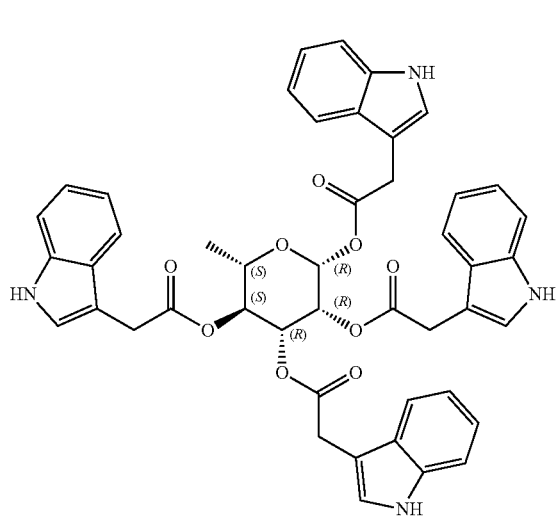

Compound 121: (2R,3R,4R,5S,6S)-3,4,5-tris({[2-(1H-indol-3-yl)acetyl]oxy})-6-methyloxan-2-yl 2-(1H-indol-3-yl)acetate This compound was prepared following a modified procedure described for compound 63.

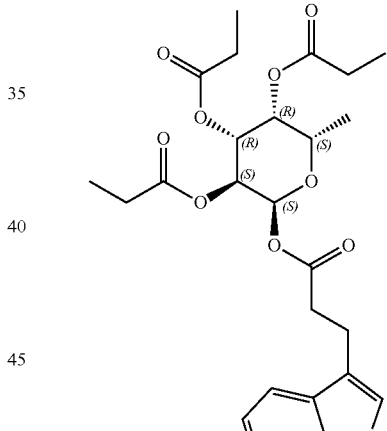

Compound 123: (2S,3S,4R,5R,6S)-6-methyl-3,4,5-tris(propanoyloxy)oxan-2-yl 3-(1H-indol-3-yl)propanoate This compound was prepared following a modified procedure described for compound 74. LCMS (M+Na$^+$): 526.2. $^1$H NMR (400 MHz, Chloroform-d) δ 8.08 (s, 1H), 7.65-7.57 (m, 1H), 7.35 (dt, J=8.1, 1.0 Hz, 1H), 7.24-7.09 (m, 2H), 7.09-7.04 (m, 1H), 6.33 (d, J=2.5 Hz, 1H), 5.36-5.26 (m, 2H), 5.26-5.22 (m, 1H), 4.01-3.91 (m, 1H), 3.20-3.08 (m, 2H), 2.84 (t, J=7.1 Hz, 2H), 2.44 (qd, J=7.6, 0.9 Hz, 2H), 2.24 (q, J=7.5 Hz, 2H), 2.09 (qd, J=7.6, 1.8 Hz, 2H), 1.18 (t, J=7.6 Hz, 3H), 1.09 (t, J=7.6 Hz, 3H), 1.05-0.96 (m, 6H)

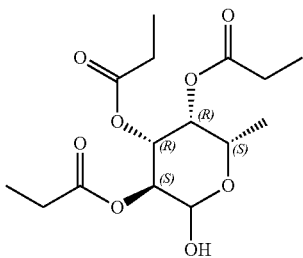

Compound 124: (3S,4R,5R,6S)-2-hydroxy-6-methyl-4,5-bis(propanoyloxy)oxan-3-ylpropanoate This compound was prepared according to a modified procedure described for the preparation of compound 21.

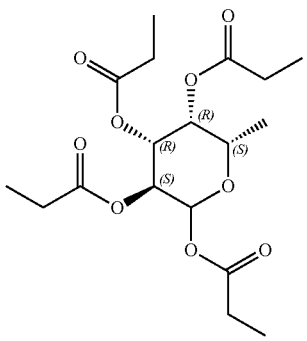

Compound 125: (3S,4R,5R,6S)-6-methyl-3,4,5-tris(propanoyloxy)oxan-2-ylpropanoate This compound was prepared according to a modified procedure described for the preparation of compound 219.

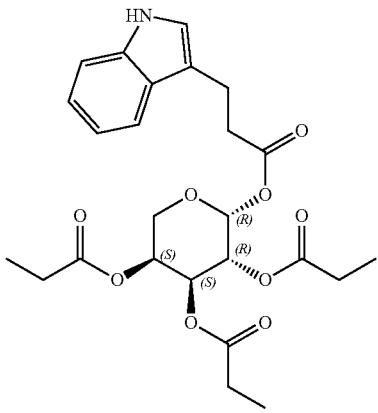

Compound 126: (2R,3R,4S,5S)-3,4,5-tris(propanoyloxy)oxan-2-yl 3-(1H-indol-3-yl)propanoate This compound was prepared following a modified procedure described for compound 74. LCMS (M+Na⁺): 512.2. ¹H NMR (400 MHz, Chloroform-d) 8.00 (s, 1H), 7.57-7.48 (m, 1H), 7.32-7.25 (m, 1H), 7.19 (s, 1H), 7.17-6.93 (m, 3H), 6.28 (d, J=3.1 Hz, 1H), 5.32-5.21 (m, 3H), 3.74 (dd, J=13.2, 1.4 Hz, 1H), 3.62 (dd, J=13.2, 1.9 Hz, 1H), 3.11-3.01 (m, 2H), 2.77 (t, J=7.4 Hz, 2H), 2.35 (q, J=7.5 Hz, 2H), 2.19 (q, J=7.6 Hz, 2H), 2.04 (qd, J=7.6, 1.6 Hz, 2H), 1.15-1.00 (m, 6H), 0.94 (t, J=7.6 Hz, 3H)

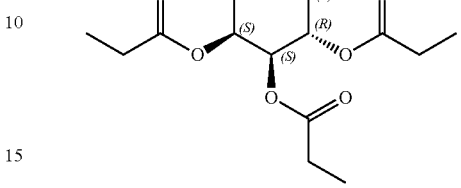

Compound 127: (3S,4S,5R,6R)-6-hydroxy-4,5-bis(propanoyloxy)oxan-3-ylpropanoate

This compound was prepared according to a modified procedure described for the preparation of compound 21.

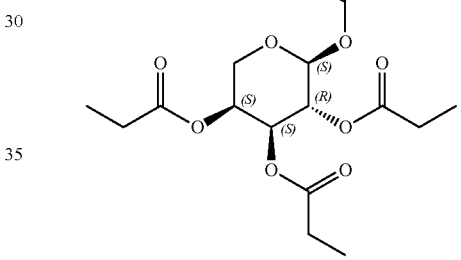

Compound 128: (2S,3R,4S,5S)-3,4,5-tris(propanoyloxy)oxan-2-ylpropanoate

This compound was prepared according to a modified procedure described for the preparation of compound 219.

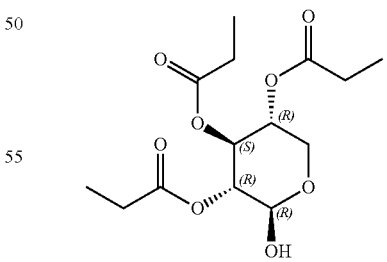

Compound 129: (2R,3R,4S,5R)-2-hydroxy-4,5-bis(propanoyloxy)oxan-3-ylpropanoate

This compound was prepared according to a modified procedure described for the preparation of compound 21.

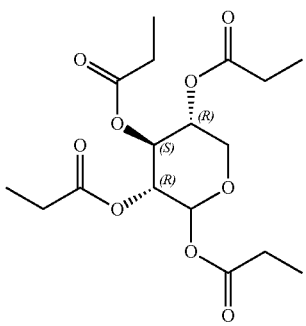

Compound 130: (3R,4S,5R)-3,4,5-tris(propanoyloxy)oxan-2-ylpropanoate

This compound was prepared according to a modified procedure described for the preparation of compound 219.

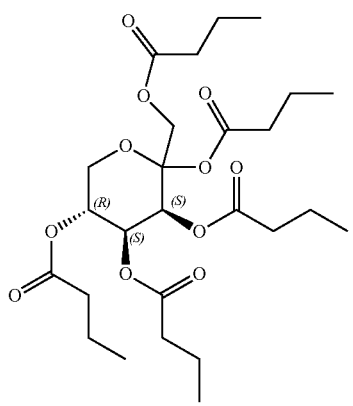

Compound 131: [(3S,4S,5R)-2,3,4,5-tetrakis(butanoyloxy)oxan-2-yl]methyl butanoate This compound was prepared according to a modified procedure described for the preparation of compound 219.

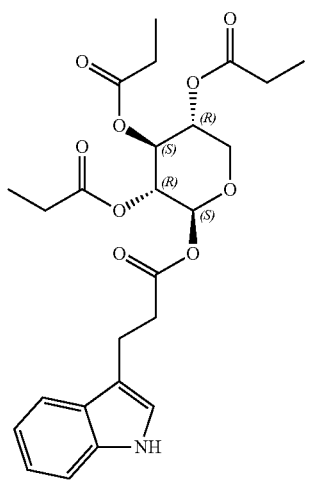

Compound 132: (2S,3R,4S,5R)-3,4,5-tris(propanoyloxy)oxan-2-yl 3-(1H-indol-3-yl)propanoate This compound was prepared following a modified procedure described for compound 74. LCMS: (m+Na$^+$) 512.2. $^1$H NMR (400 MHz, DMSO-d6) δ 10.89-10.66 (m, 1H), 7.52-7.44 (m, 1H), 7.30 (m, 1H), 7.10-7.01 (m, 2H), 6.95 (m, 1H), 5.84 (d, 1H), 5.30 (t, 1H), 4.96-4.84 (m, 2H), 3.97 (dd, 1H), 3.67 (dd, 1H), 2.92 (t, 2H), 2.70 (td, 2H), 2.31-2.10 (m, 6H), 1.05-0.85 (m, 9H)

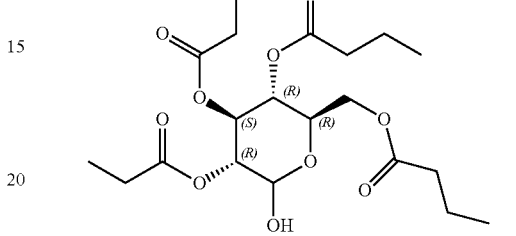

Compound 133: [(2R,3R,4S,5R)-3,4,5-tris(butanoyloxy)-6-hydroxyoxan-2-yl]methylbutanoate

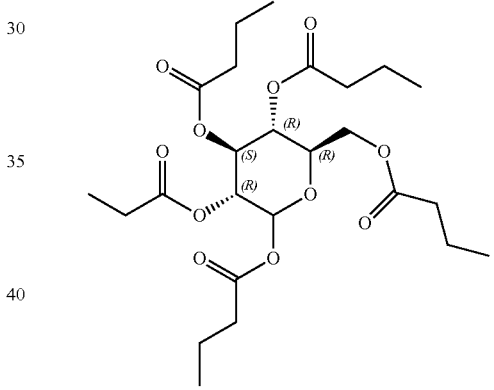

Compound 134: [(2R,3R,4S,5R)-3,4,5,6-tetrakis(butanoyloxy)oxan-2-yl]methyl butanoate

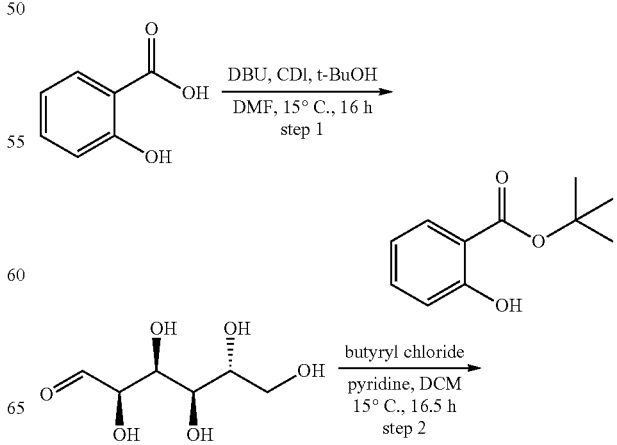

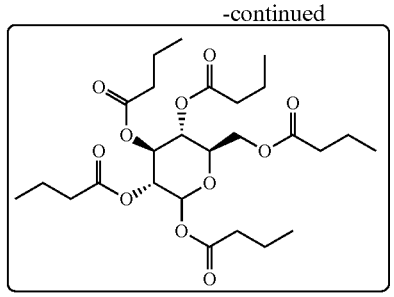

134

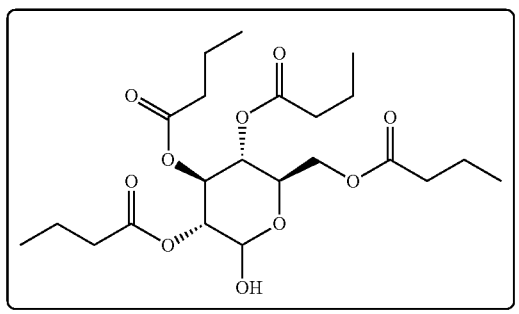

133

Step 1:

To the solution of 2-hydroxybenzoic acid (6 g, 43.44 mmol, 7.50 mL, 1 eq) and CDI (8.45 g, 52.13 mmol, 1.2 eq) in DMF (50 mL) was added DBU (7.94 g, 52.13 mmol, 7.86 mL, 1.2 eq) and t-BuOH (6.47 g, 87.32 mmol, 8.35 mL, 2.01 eq). The mixture was stirred at 15° C. for 16 h. LCMS (ET14826-364-P1A) showed the reaction was completed. The solvent was removed under reduced pressure. The crude product was purified by silica gel chromatography eluted with Petroleum ether/Ethyl acetate=1:0-2:1 to give tert-butyl 2-hydroxybenzoate (5 g, 25.74 mmol, 59.26% yield) as colorless oil showed by $^1$H NMR. LCMS: (M−H$^+$): 193.1 @ 1.988 min Step 2:

To the solution of (2R,3S,4R,5R)-2,3,4,5,6-pentahydroxyhexanal (20 g, 111.02 mmol, 1 eq) in DCM (500 mL) was added butyryl chloride (94.63 g, 888.12 mmol, 92.77 mL, 8 eq) and the mixture was stirred at 15° C. for 0.5 h. Then pyridine (70.25 g, 888.12 mmol, 71.68 mL, 8 eq) was added to the solution dropwise slowly. After the addition, the mixture was stirred at 15° C. for another 16 h. LCMS (ET14826-367-P1A) showed the reaction was completed. The solvent was removed under reduced pressure. The crude product was purified by silica gel chromatography eluted with Petroleum ether/Ethyl acetate=1:0-5:1 to give (3R,4S,5R,6R)-6-((butyryloxy)methyl) tetrahydro-2H-pyran-2,3,4,5-tetrayl tetrabutyrate (58 g, 109.31 mmol, 98.46% yield) as yellow oil showed by $^1$H NMR. LCMS: (M+18): 548.3 @ 1.640 min Step 3:

To the solution of (3R,4S,5R,6R)-6-((butyryloxy)methyl) tetrahydro-2H-pyran-2,3,4,5-tetrayl tetrabutyrate (10 g, 18.85 mmol, 1 eq) in THF (85 mL) and H$_2$O (5 mL) was added methanamine/THF (2 M, 12.25 mL, 1.3 eq). Then the mixture was stirred at 15° C. for 16 h. LCMS (ET14826-370-P1A2) showed most of the starting material was consumed and the desired MS was detected. The solvent was removed under reduced pressure. The crude product was purified by silica gel chromatography eluted with Petroleum ether/Ethyl acetate=10:1-1:1 to give (2R,3R,4S,5R)-2-((bu- tyryloxy)methyl)-6-hydroxytetrahydro-2H-pyran-3,4,5-triyl tributyrate (10 g, 21.50 mmol, 57.03% yield, 99% purity) as yellow oil. LCMS: (M+18): 478.3 @ 1.478 min; LCMS: (M+Na$^+$): 483.1 @ 3.678, 3.742 min

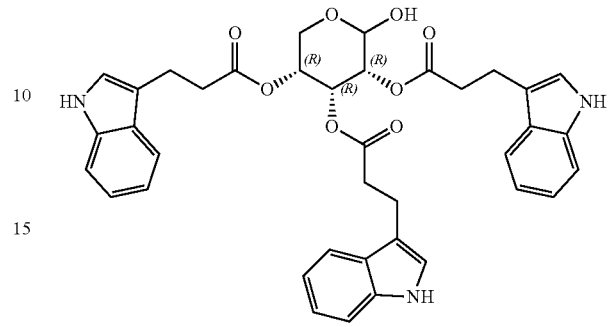

Compound 135: (3R,4R,5R)-6-hydroxy-4,5-bis({[3-(1H-indol-3-yl)propanoyl]oxy})oxan-3-yl 3-(1H-indol-3-yl)propanoate This compound was prepared following a modified procedure described for compound 37 with the exception that the synthesis was stopped at the stage producing the title compound.

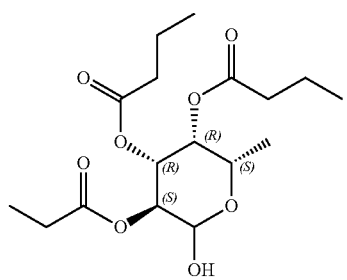

Compound 136: (3S,4R,5R,6S)-4,5-bis(butanoyloxy)-2-hydroxy-6-methyloxan-3-ylbutanoate This compound was prepared according to a modified procedure described for the preparation of compound 21.

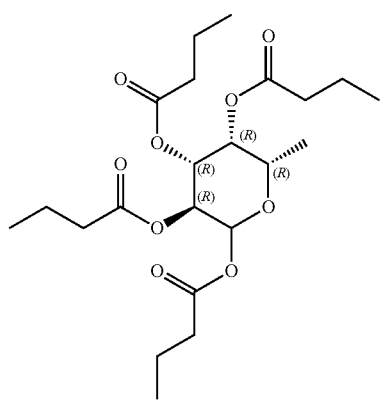

Compound 137: (3S,4R,5R,6S)-3,4,5-tris(butanoyloxy)-6-methyloxan-2-ylbutanoate

This compound was prepared according to a modified procedure described for the preparation of compound 219.

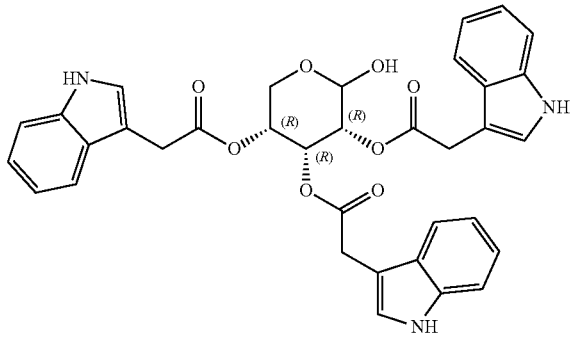

Compound 138: (3R,4R,5R)-6-hydroxy-4,5-bis({[2-(1H-indol-3-yl)acetyl]oxy})oxan-3-yl 2-(1H-indol-3-yl)acetate This compound was prepared following a modified procedure described for compound 37 with the exception that the synthesis was stopped at the stage producing the title compound.

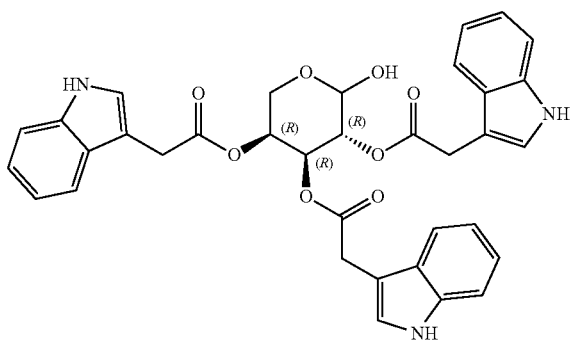

Compound 139: (3S,4S,5R)-6-hydroxy-4,5-bis({[2-(1H-indol-3-yl)acetyl]oxy})oxan-3-yl 2-(1H-indol-3-yl)acetate This compound was prepared following a modified procedure described for compound 37 with the exception that the synthesis was stopped at the stage producing the title compound.

Compound 140: (2S,3R,4R,5R)-3,4,5-tris({[2-(1H-indol-3-yl)acetyl]oxy})oxan-2-yl 2-(1H-indol-3-yl)acetate This compound was prepared following a modified procedure described for compound 74.

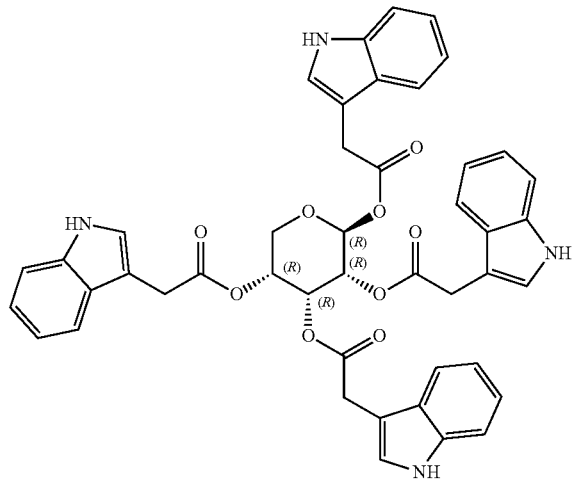

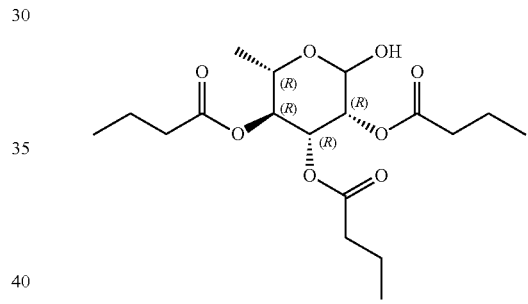

Compound 141: (2S,3S,4R,5R)-4,5-bis(butanoyloxy)-6-hydroxy-2-methyloxan-3-yl butanoate This compound was prepared according to a modified procedure described for the preparation of compound 21.

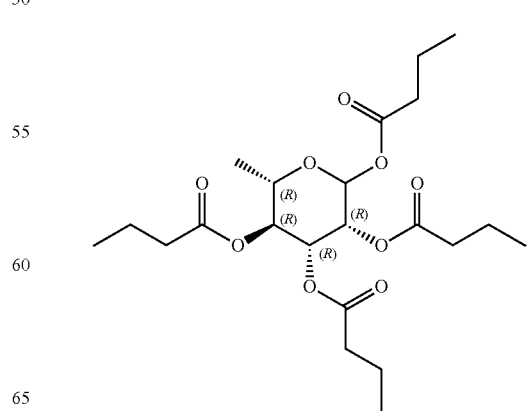

Compound 142: (3R,4R,5S,6S)-3,4,5-tris(butanoyloxy)-6-methyloxan-2-ylbutanoate

This compound was prepared according to a modified procedure described for the preparation of compound 219.

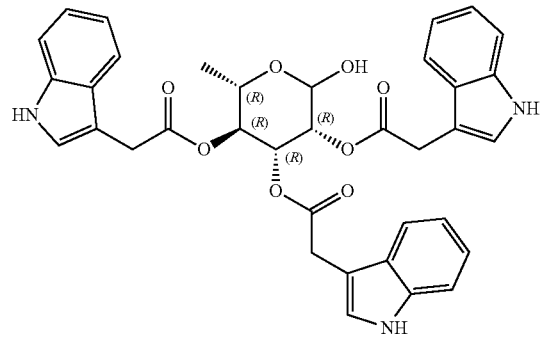

Compound 143: (2S,3S,4R,5R)-6-hydroxy-4,5-bis({[2-(1H-indol-3-yl)acetyloxy})-2-methyloxan-3-yl 2-(1H-indol-3-yl)acetate This compound was prepared following a modified procedure described for compound 37 with the exception that the synthesis was stopped at the stage producing the title compound.

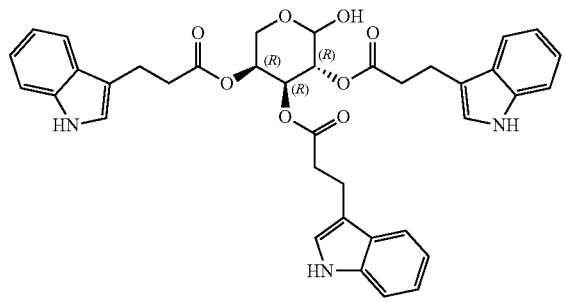

Compound 144: (3S,4S,5R)-6-hydroxy-4,5-bis({[3-(1H-indol-3-yl)propanoyl]oxy})oxan-3-yl 3-(1H-indol-3-yl)propanoate This compound was prepared following a modified procedure described for compound 37 with the exception that the synthesis was stopped at the stage producing the title compound.

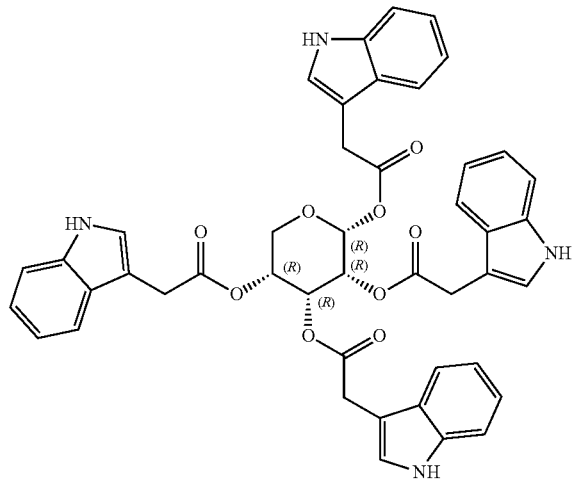

Compound 145: (2R,3R,4R,5R)-3,4,5-tris({[2-(1H-indol-3-yl)acetyl]oxy})oxan-2-yl 2-(1H-indol-3-yl) acetate This compound was prepared following a modified procedure described for compound 63.

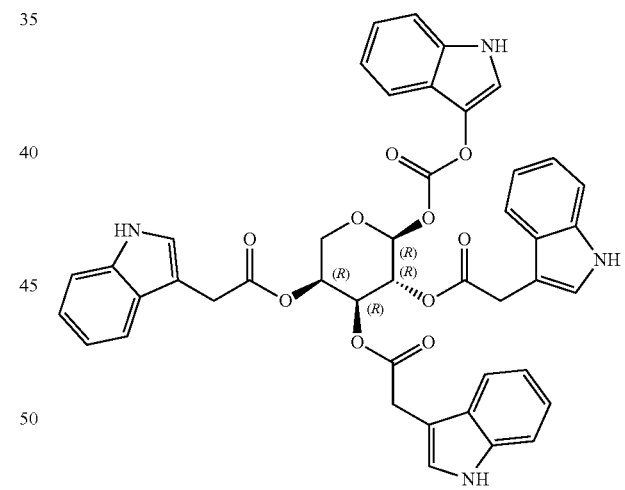

Compound 146: (2S,3R,4S,5S)-3,4,5-tris({[2-(1H-indol-3-yl)acetyl]oxy})oxan-2-yl 2-(1H-indol-3-yl) acetate This compound was prepared following a modified procedure described for compound 63.

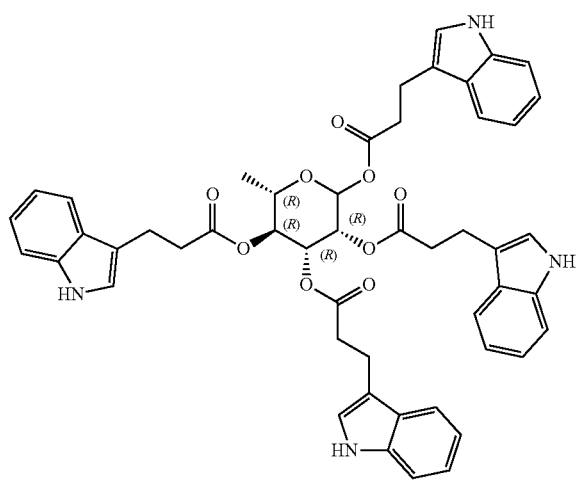

Compound 147: (3R,4R,5S,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 63.

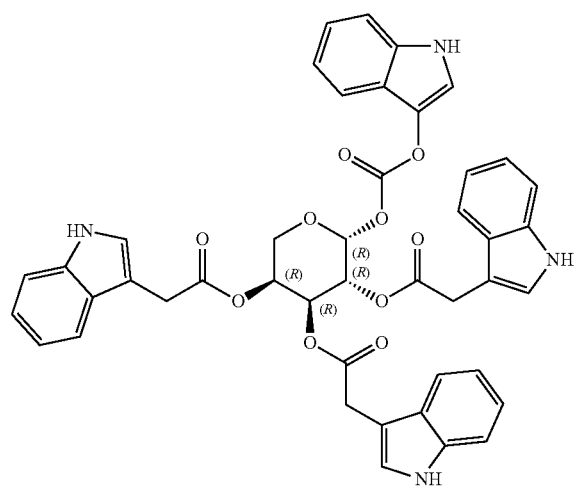

Compound 148: (2R,3R,4S,5S)-3,4,5-tris({[2-(1H-indol-3-yl)acetyl]oxy})oxan-2-yl 2-(1H-indol-3-yl)acetate This compound was prepared following a modified procedure described for compound 63.

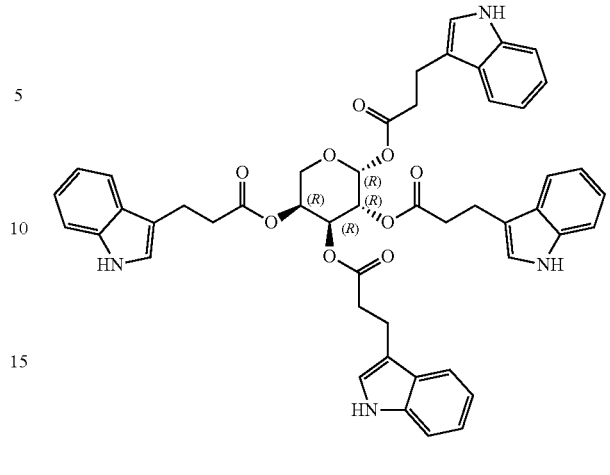

Compound 149: (2R,3R,4S,5S)-3,4,5-tris({[3-(1H-indol-3-yl)propanoyl]oxy})oxan-2-yl 3-(1H-indol-3-yl)propanoate This compound was prepared following a modified procedure described for compound 63. LCMS (M+H$^+$): 835.3. $^1$H NMR (400 MHz, Chloroform-d) δ 7.68 (d, J=7.1 Hz, 2H), 7.57 (d, J=10.5 Hz, 2H), 7.54-7.48 (m, 2H), 7.48-7.41 (m, 2H), 7.20-6.98 (m, 12H), 6.92 (dd, J=13.6, 2.4 Hz, 2H), 6.60 (d, J=2.3 Hz, 1H), 6.49 (d, J=2.3 Hz, 1H), 6.27 (d, J=3.6 Hz, 1H), 5.32 (dd, J=10.7, 3.5 Hz, 1H), 5.25 (s, 1H), 5.24-5.17 (m, 1H), 3.75 (d, J=13.2 Hz, 1H), 3.59 (dd, J=13.2, 2.0 Hz, 1H), 3.13-2.94 (m, 4H), 2.90-2.67 (m, 8H), 2.31-2.02 (m, 4H)

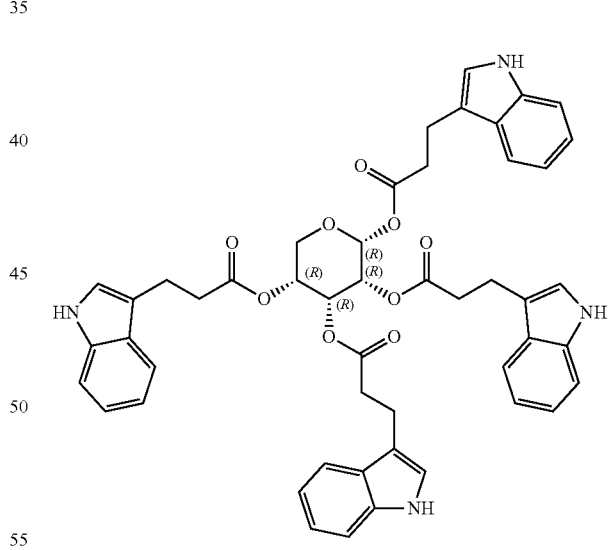

Compound 150: (2R,3R,4R,5R)-3,4,5-tris({[3-(1H-indol-3-yl)propanoyl]oxy})oxan-2-yl 3-(1H-indol-3-yl)propanoate This compound was prepared following a modified procedure described for compound 63. LCMS (M+H$^+$): 835.3. $^1$H NMR (400 MHz, Chloroform-d) δ 7.79 (d, J=15.3 Hz, 3H), 7.69 (s, 1H), 7.53-7.43 (m, 4H), 7.27-7.14 (m, 4H), 7.14-7.06 (m, 4H), 7.02 (t, J=7.4 Hz, 4H), 6.82 (s, 2H), 6.76 (s, 2H), 5.97 (s, 1H), 5.17 (d, J=4.7 Hz, 1H), 5.06 (t, J=6.1

Hz, 1H), 4.04 (s, 1H), 4.01-3.93 (m, 1H), 3.81 (dd, J=12.1, 5.7 Hz, 1H), 3.03-2.88 (m, 8H), 2.65-2.56 (m, 6H), 2.44 (t, J=7.5 Hz, 2H)

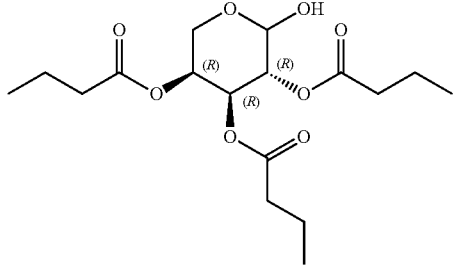

Compound 151: (3S,4S,5R)-4,5-bis(butanoyloxy)-6-hydroxyoxan-3-ylbutanoate

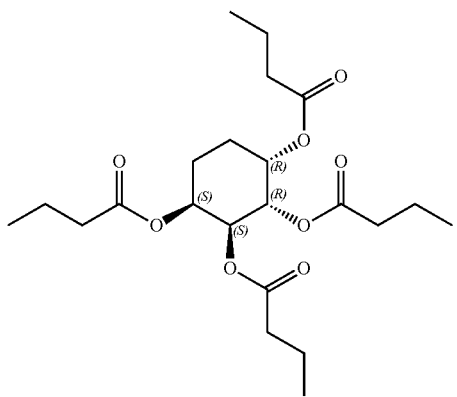

Compound 152: (2R,3R,4S,5S)-3,4,5-tris(butanoyloxy)oxan-2-yl butanoate

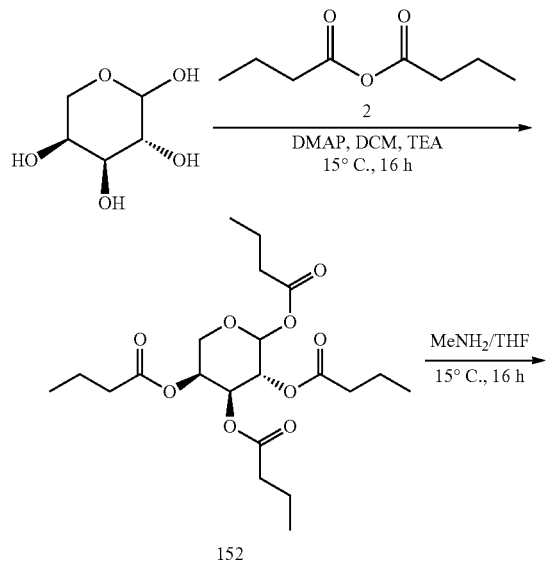

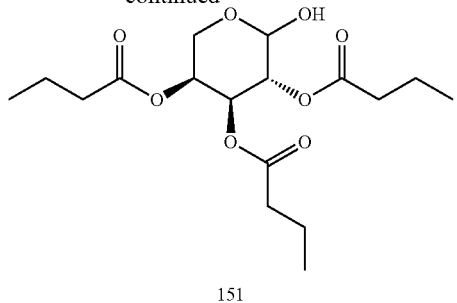

151

Step 1:

To the solution of (3R,4S,5S)-tetrahydro-2H-pyran-2,3,4,5-tetraol (10 g, 66.61 mmol, 1 eq), TEA (53.92 g, 532.87 mmol, 74.17 mL, 8 eq) and DMAP (1.63 g, 13.32 mmol, 0.2 eq) in DCM (100 mL) was added butyric anhydride (52.69 g, 333.05 mmol, 54.48 mL, 5 eq) at 0° C. Then the solution was stirred 0° C. for 1 h and stirred at 15° C. for another 15 h. TLC showed the reaction was completed. The solvent was removed under reduced pressure. The crude product was purified by silica gel chromatography eluted with Petroleum ether/Ethyl acetate=1:0 to give compound 152 (3R,4S,5S)-tetrahydro-2H-pyran-2,3,4,5-tetrayl tetrabutyrate (28 g, 65.04 mmol, 97.65% yield, 100% purity) as yellow oil. LCMS: (M+Na$^+$): 453 @ 1.592 min. $^1$H NMR (400 MHz, Chloroform-d) δ 6.4 (m, 1H), 5.4-5.3 (m, 3H), 4.1-3.8 (m, 2H), 3.7-3.3 (m, 2H), 2.4-2.2 (m, 8H), 1.7-1.6 (m, 8H), 1.0-0.9 (m, 12H).

Step 2:

To the solution of compound 152 (3R,4S,5S)-tetrahydro-2H-pyran-2,3,4,5-tetrayl tetrabutyrate (25 g, 58.07 mmol, 1 eq) in THF (200 mL) and H$_2$O (10 mL) was added methanamine/THF (2 M, 37.75 mL, 1.3 eq). Then the mixture was stirred at 15° C. for 16 h. LCMS showed the desired MS. The solvent was removed under reduced pressure. The crude product was purified by silica gel chromatography eluted with Petroleum ether/Ethyl acetate=1:0-2:1 to give compound 151 (3R,4S,5S)-2-hydroxytetrahydro-2H-pyran-3,4,5-triyl tributyrate (14 g, 38.85 mmol, 33.45% yield) as yellow oil. LCMS: (M+H$_2$O$^+$): 378 @2.833, 2.934 min. $^1$H NMR (400 MHz, Chloroform-d) δ 5.5-5.4 (m, 1H), 5.4-5.3 (m, 1H), 5.3-5.1 (m, 2H), 4.6 (m, 1H) 4.3-4.0 (m, 1H), 3.7-3.6 (m, 1H), 2.4-2.3 (m, 6H), 1.7-1.6 (m, 6H), 1.0-0.9 (m, 9H)

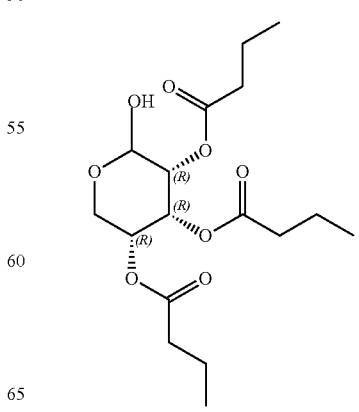

152

Compound 153: (3R,4R,5R)-4,5-bis(butanoyloxy)-2-hydroxyoxan-3-yl butanoate

This compound was prepared according to a modified procedure described for the preparation of compound 21.

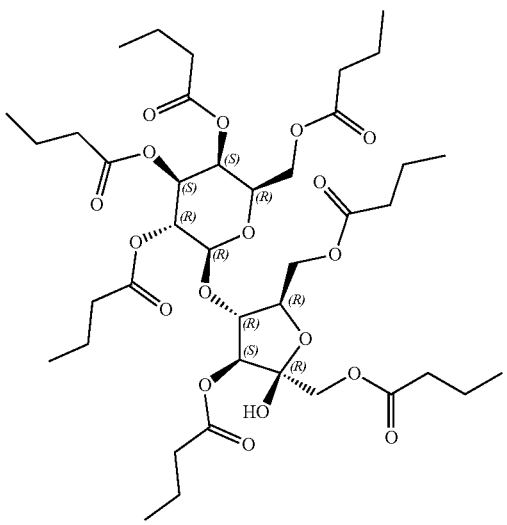

Compound 154: [(2R,3R,4S,5R)-4-(butanoyloxy)-5-[(butanoyloxy)methyl]-5-hydroxy-3-{[(2S,3R,4S,5S,6R)-3,4,5-tris(butanoyloxy)-6-[(butanoyloxy)methyl]oxan-2-yl]oxy}oxolan-2-yl]methyl butanoate This compound was prepared according to a modified procedure described for the preparation of compound 219.

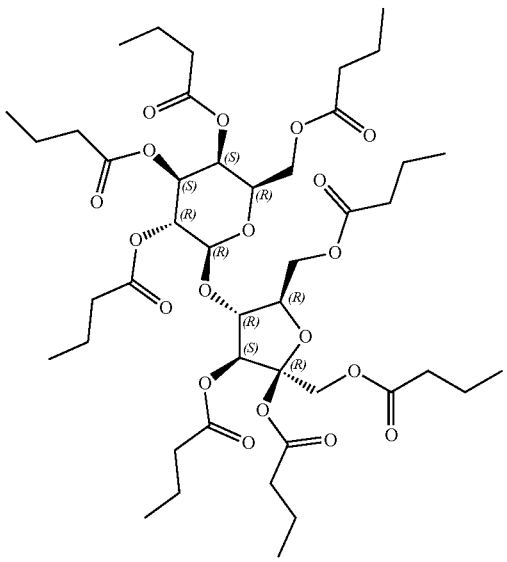

Compound 155: [(2R,3R,4S,5S)-4,5-bis(butanoyloxy)-5-[(butanoyloxy)methyl]-3-{[(2S,3R,4S,5S,6R)-3,4,5-tris(butanoyloxy)-6-[(butanoyloxy)methyl]oxan-2-yl]oxy}oxolan-2-yl]methyl butanoate This compound was prepared according to a modified procedure described for the preparation of compound 219.

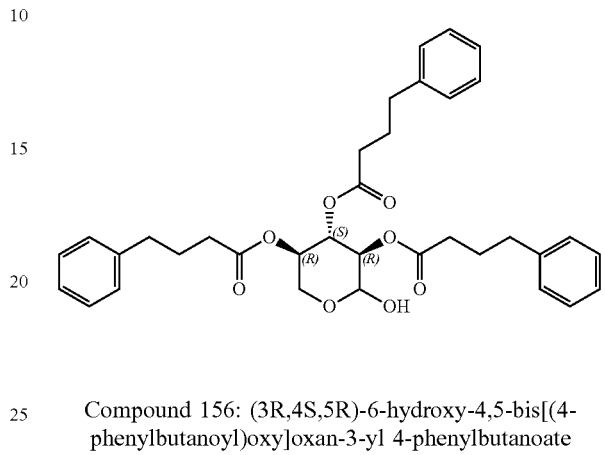

Compound 156: (3R,4S,5R)-6-hydroxy-4,5-bis[(4-phenylbutanoyl)oxy]oxan-3-yl 4-phenylbutanoate This compound was prepared according to the description in WO 2018/226732. $^1$H NMR (CDCl$_3$): δ 7.0-7.2 (m, 15H) 5.5 (dd, 1H), 5.4 (m, 1H), 4.8-5.0 (m, 2H), 4.1 (brs, 1H), 3.8, (dd, 2H), 2.5-2.6 (m, 6H), 2.2-2.3 (m, 6H), 1.8-0.9 (m, 6H) ppm

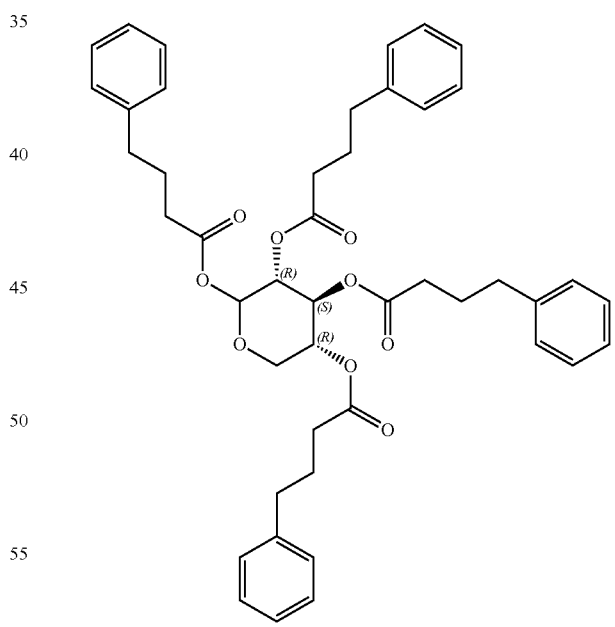

Compound 157: (3R,4S,5R)-4,5,6-tris[(4-phenylbutanoyl)oxy]oxan-3-yl 4-phenylbutanoate This compound was prepared according to a modified procedure described for the preparation of compound 219.

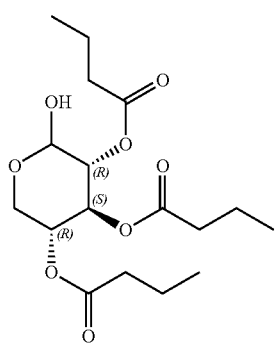

Compound 158:
(3R,4S,5R)-4,5-bis(butanoyloxy)-2-hydroxyoxan-3-yl butanoate

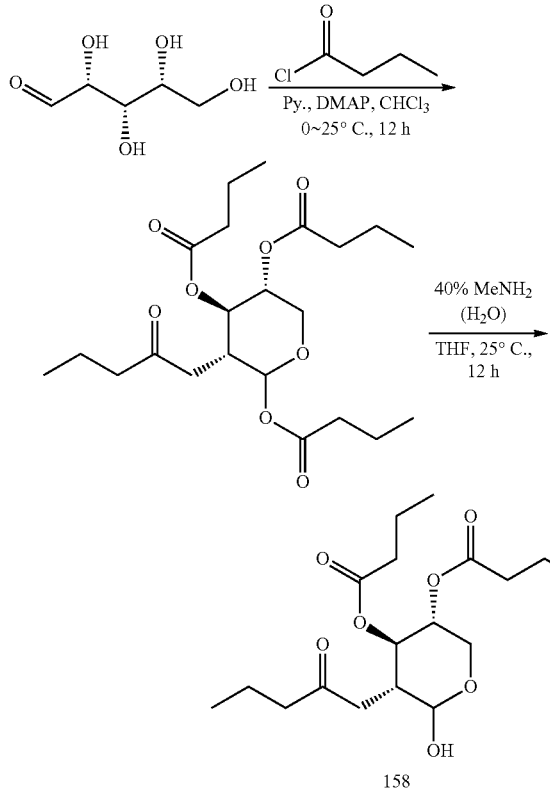

Step 1

To a solution of pyridine (316.13 g, 4.00 mol, 322.58 mL, 6 eq) in CHCl$_3$ (1 L) was added butanoyl chloride (425.83 g, 4.00 mol, 417.48 mL, 6 eq) and DMAP (2.44 g, 19.98 mmol, 0.03 eq) at 0° C. (2R,3S,4R)-2,3,4,5-tetrahydroxypentanal (100 g, 666.09 mmol, 1 eq) was added into the mixture at 0° C. and the mixture was stirred at 25° C. for 12 h. TLC showed the starting reactant consumed. The mixture reaction was concentrated. The residue was purified by column chromatography (SiO$_2$, Petroleum ether/Ethyl acetate=20/1 to 10:1 to 3/1). [(3R,4S,5R)-4,5,6-tri(butanoyloxy)tetrahydropyran-3-yl]butanoate (165 g, 325.79 mmol, 48.91% yield, 85% purity) was obtained as colorless oil.

Step 2

To a solution of [(3R,4S,5R)-4,5,6-tri(butanoyloxy)tetrahydropyran-3-yl] butanoate (55 g, 127.76 mmol, 1 eq) in THF (800 mL) was added MeNH$_2$ in H$_2$O (14.88 g, 191.64 mmol, 40% purity, 1.5 eq). The mixture was stirred at 25° C. for 12 h. TLC showed the starting reactant consumed. The mixture reaction was concentrated. The residue was purified by column chromatography (SiO$_2$, Petroleum ether/Ethyl acetate=10/1 to 5:1). [(3R,4S,5R)-4,5-di(butanoyloxy)-6-hydroxy-tetrahydropyran-3-yl] butanoate (50 g, 124.86 mmol, 48.87% yield, 90% purity) was obtained. The compound was combined with other batches. In total, 99 g was obtained as a yellow solid. LCMS: (M+Na$^+$): 383.1 @ 3.490 min. $^1$H NMR (400 MHz, DMSO-d$_6$) δ 7.2-7.0 (m, 1H), 5.4-5.1 (m, 2H), 4.9-4.7 (m, 2H), 3.7-3.3 (m, 2H), 2.4-2.2 (m, 6H), 1.5-1.4 (m, 6H), 0.9-0.8 (m, 9H)

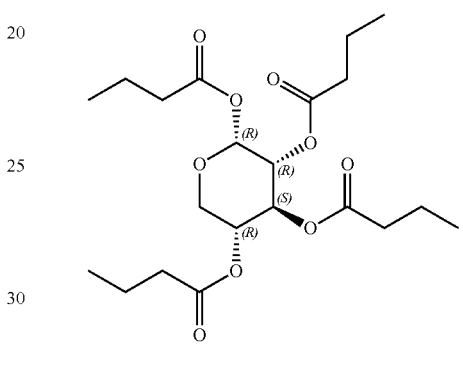

Compound 159: (2R,3R,4S,5R)-3,4,5-tris(butanoyloxy)oxan-2-ylbutanoate

This compound was prepared according to a modified procedure described for the preparation of compound 219.

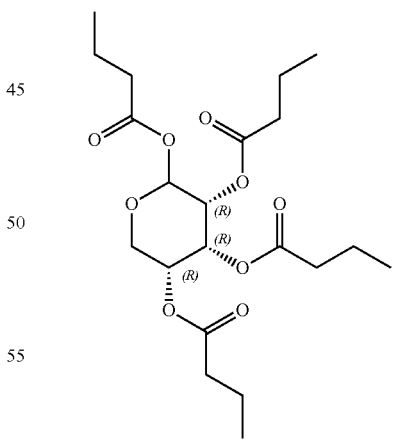

Compound 160:
(3R,4R,5R)-3,4,5-tris(butanoyloxy)oxan-2-yl butanoate

This compound was prepared according to a modified procedure described for the preparation of compound 219.

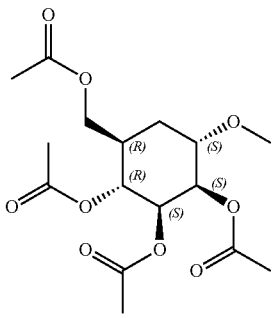

Compound 161: (2R,3R,4S,5S,6S)-2-(acetoxymethyl)-6-methoxytetrahydro-2H-pyran-3,4,5-triyl triacetate This compound was prepared according to a modified procedure described for the preparation of compound 219. LCMS: (m+Na⁺) 385.1. ¹H NMR (400 MHz, DMSO-d6) δ 5.16-5.07 (m, 3H), 4.79 (d, 1H), 4.17 (dd, 1H), 4.07 (dd, 1H), 3.95-3.87 (m, 1H), 3.36 (s, 3H), 2.12 (s, 3H), 2.04 (d, 6H), 1.95 (s, 3H)

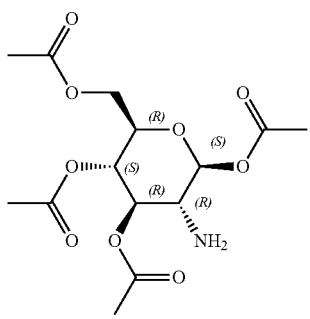

Compound 162: (2S,3R,4R,5S,6R)-6-(acetoxymethyl)-3-aminotetrahydro-2H-pyran-2,4,5-triyltriacetate Stir Boc-protected glucosamine in acetic anhydride and purify. Then, deprotect with HCl in dioxane to yield the title compound as the HCl salt. LCMS: (M+Na⁺): 370.1. ¹H NMR (400 MHz, DMSO-de) δ 8.94-8.54 (m, 3H), 6.01-5.82 (m, 1H), 5.42-5.27 (m, 1H), 4.94 (t, J=9.6 Hz, 1H), 4.20 (dd, J=12.5, 4.4 Hz, 1H), 4.13-3.92 (m, 2H), 3.67-3.51 (m, 1H), 2.18 (s, 3H), 2.08-1.95 (m, 9H)

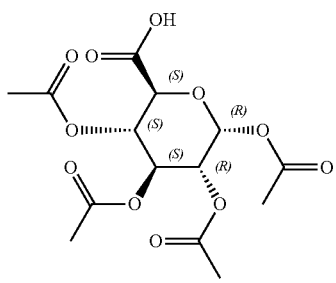

Compound 163: (2S,3S,4S,5R,6R)-3,4,5,6-tetraacetoxytetrahydro-2H-pyran-2-carboxylicacid This compound was prepared following a modified procedure described for compounds 46 and 47. LCMS: (M+NH₄): 380.1. ¹H NMR (400 MHz, Chloroform-d) δ 6.40 (s, 1H), 5.52 (t, J=9.5 Hz, 1H), 5.32-5.22 (m, 1H), 5.16-5.08 (m, 1H), 4.46 (d, J=9.7 Hz, 1H), 2.20 (s, 3H), 2.08-2.00 (m, 9H).

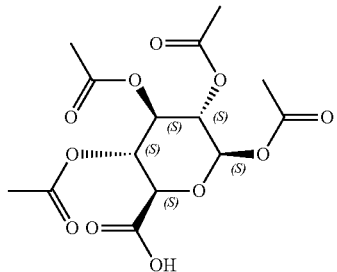

Compound 164: (2,3,4,5R,6)-3,4,5,6-tetraacetoxytetrahydro-2H-pyran-2-carboxylic acid This compound was prepared following a modified procedure described for compounds 46 and 47. LCMS: (M+NH₄+): 380.0. ¹H NMR (400 MHz, Chloroform-d) δ 5.81 (d, J=7.6 Hz, 1H), 5.39-5.26 (m, 2H), 5.22-5.10 (m, 1H), 4.32-4.22 (m, 1H), 2.14 (s, 3H), 2.12-2.03 (m, 9H).

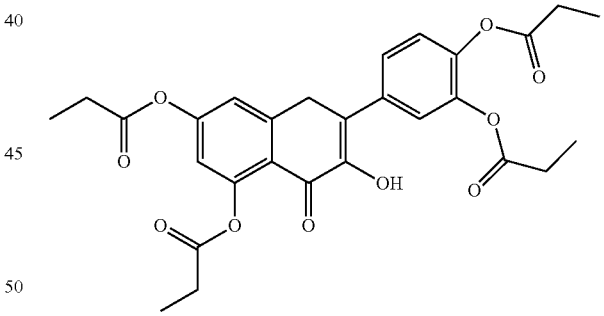

Compound 165: 2-[3,4-bis(propanoyloxy)phenyl]-3-hydroxy-4-oxo-7-(propanoyloxy)-4H-chromen-5-yl propanoate This compound was prepared following a modified procedure described for compound 26. ¹H NMR (400 MHz, Chloroform-d) δ 12.10 (s, 1H), 7.88-7.58 (m, 2H), 7.36 (d, J=8.3 Hz, 1H), 6.86 (d, J=2.0 Hz, 1H), 6.59 (d, J=2.0 Hz, 1H), 2.87-2.37 (m, 8H), 1.41-1.12 (m, 12H)

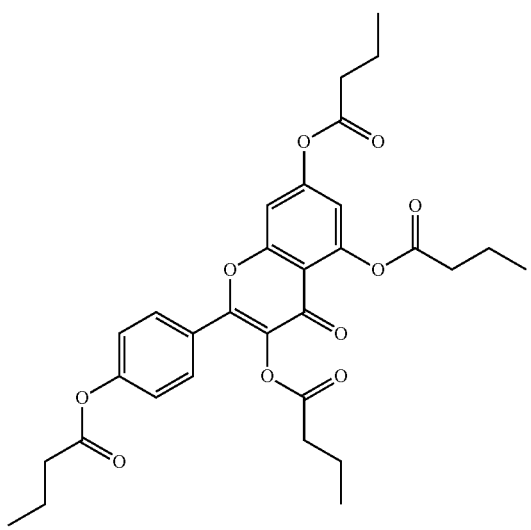 [SMILES: CCCC(=O)Oc1ccc(-c2oc3cc(OC(=O)CCC)cc(OC(=O)CCC)c3c(=O)c2OC(=O)CCC)cc1]

Compound 166: 4-[3,5,7-tris(butanoyloxy)-4-oxo-4H-chromen-2-yl]phenyl butanoate

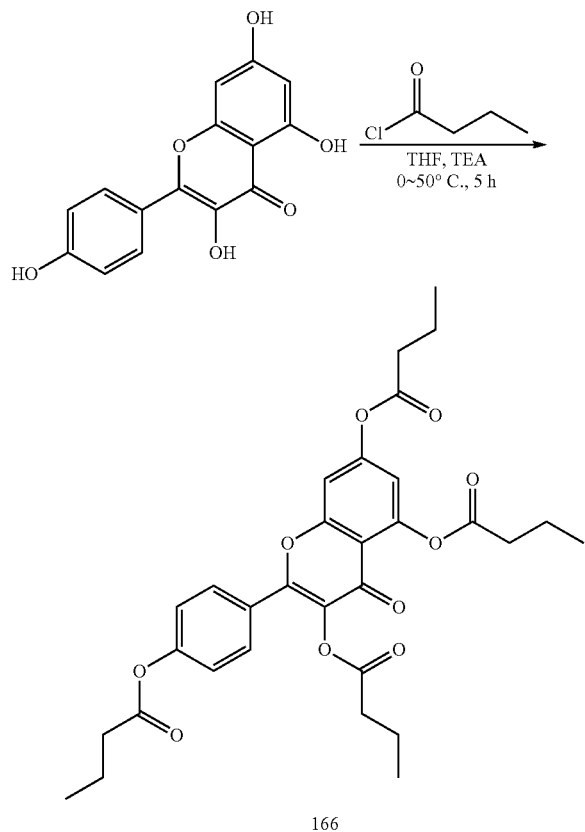

166

To a mixture of 3,5,7-trihydroxy-2-(4-hydroxyphenyl)chromen-4-one (500 mg, 1.75 mmol, 1 eq), TEA (883.80 mg, 8.73 mmol, 1.22 mL, 5 eq) in THF (20 mL) was added butanoyl chloride (930.62 mg, 8.73 mmol, 912.37 uL, 5 eq) slowly at 0° C. And then the mixture was stirred at 50° C. for 5 hr under $N_2$ atmosphere. LC-MS showed reactant was consumed completely and one main peak with desired mass was detected. The reaction mixture was quenched by addition $H_2O$ 200 mL at 25° C. and then extracted with EtOAc 180 mL (60 mL*3). The combined organic layers were washed with brine 20 mL, dried over $Na_2SO_4$, filtered and concentrated under reduced pressure to give a residue. The residue was purified by column chromatography ($SiO_2$, Petroleum ether/Ethyl acetate=5/1 to 3:1). [4-[3,5,7-tri(butane-yloxy)-4-oxo-chromen-2-yl]phenyl]butanoate (437 mg, 734.02 umol, 42.02% yield, 95.17% purity) was obtained as a white solid. LCMS: (M+H$^+$) 567.2 @ 1.577 min; LCMS: (M+H$^+$) 567.2 @ 3.520 min. $^1$H NMR (400 MHz, Chloroform-d) δ 12.10 (s, 1H), 7.88-7.58 (m, 2H), 7.36 (d, J=8.3 Hz, 1H), 6.86 (d, J=2.0 Hz, 1H), 6.59 (d, J=2.0 Hz, 1H), 2.87-2.37 (m, 8H), 1.41-1.12 (m, 12H)

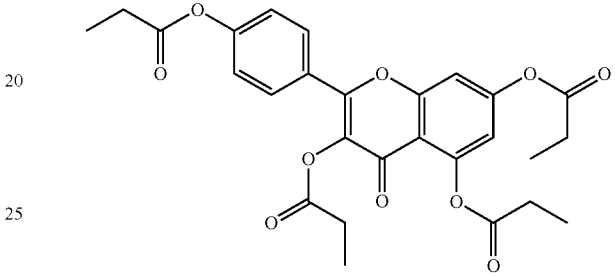

Compound 167: 4-[4-oxo-3,5,7-tris(propanoyloxy)-4H-chromen-2-yl]phenyl propanoate This compound was prepared following a modified procedure described for compound 27. LCMS: (M+H$^+$) 511.2. $^1$H NMR (400 MHz, Chloroform-d) δ 7.88-7.80 (m, 2H), 7.32 (d, J=2.2 Hz, 1H), 7.28-7.21 (m, 2H), 6.86 (d, J=2.2 Hz, 1H), 2.77 (q, J=7.5 Hz, 2H), 2.68-2.58 (m, 6H), 1.33-1.23 (m, 9H), 1.21 (t, J=7.5 Hz, 3H)

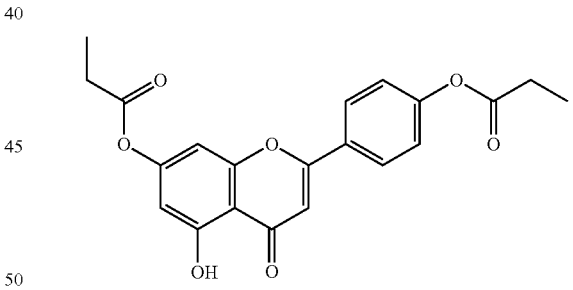

Compound 168: 5-hydroxy-4-oxo-2-[4-(propanoyloxy)phenyl]-4H-chromen-7-yl propanoate Propionic anhydride (641 uL, 5.03 mmol) was added dropwise to a stirred solution of 5,7-dihydroxy-2-(4-hydroxyphenyl)-4H-chromen-4-one (170 mg, 0.63 mmol) in 1 mL pyridine at 0° C. under nitrogen. The reaction was stirred at room temperature for 16 hours then diluted with 20 mL ethyl acetate. The organic layer was washed with 10 mL 1M HCl twice followed by brine, dried over $MgSO_4$, filtered and concentrated. The residue was dissolved in DMSO and purified by reverse phase flash chromatography (10-90% acetonitrile in water). Fraction was concentrated by lyophilization to yield 5-hydroxy-4-oxo-2-[4-(propanoyloxy)phenyl]-4H-chromen-7-yl propanoate (48 mg, 20% yield) as a white solid. LCMS: (M+H) 383.1. ¹H NMR (400 MHz, DMSO-d6) 12.83 (s, 1H), 8.21-8.15 (m, 2H), 7.40-7.34 (m, 2H), 7.14 (s, 1H), 7.11 (d, 1H), 6.68 (d, 1H), 2.65 (qd, 4H), 1.16 (t, 6H)

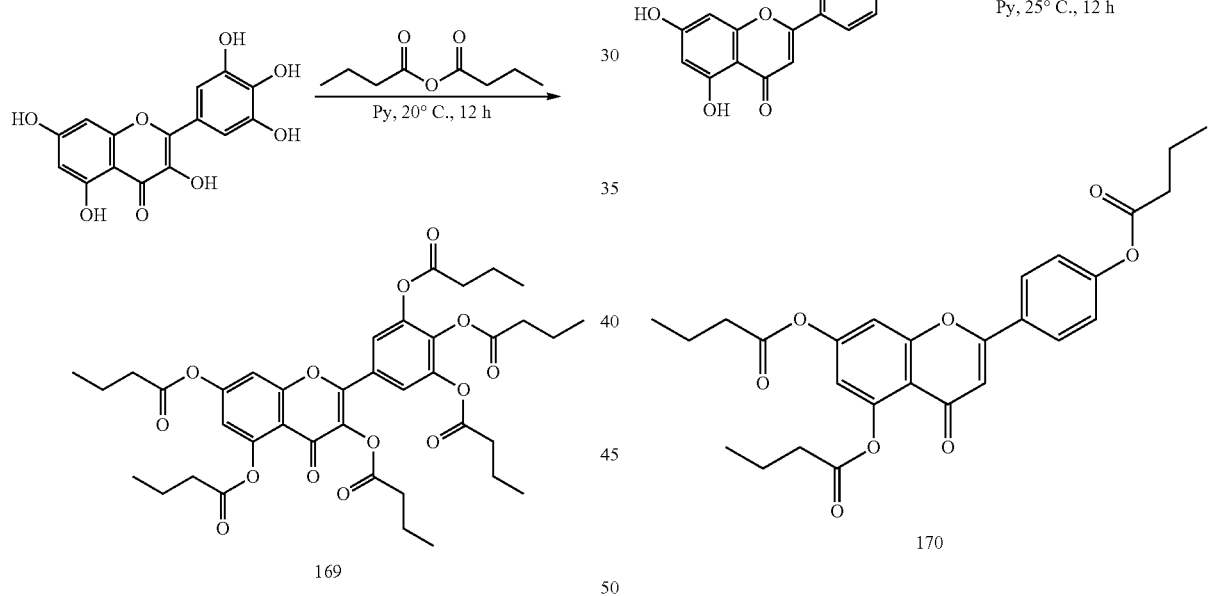

Compound 169: 3,5-bis(butanoyloxy)-4-oxo-2-[3,4,5-tris(butanoyloxy)phenyl]-4H-chromen-7-yl butanoate

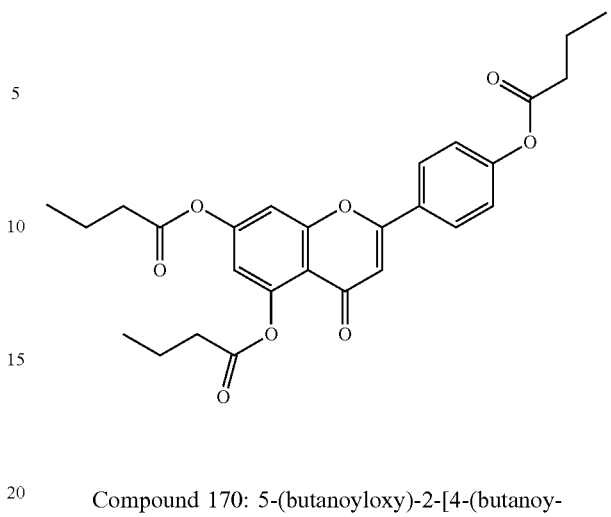

Compound 170: 5-(butanoyloxy)-2-[4-(butanoyloxy)phenyl]-4-oxo-4H-chromen-7-yl butanoate A mixture of 3,5,7-trihydroxy-2-(3,4,5-trihydroxyphenyl) chromen-4-one (0.2 g, 628.47 umol, 1 eq), butanoyl butanoate (795.36 mg, 5.03 mmol, 822.50 uL, 8 eq) in Pyridine (5 mL) was degassed and purged with $N_2$ for 3 times, and then the mixture was stirred at 20° C. for 12 hr under $N_2$ atmosphere. TLC indicated the reaction was completed and one new spot formed. The reaction mixture was washed with $H_2O$ (5 mL), filtered and the filter cake was concentrated under reduced pressure to give a residue. Compound [3,5-di(butanoyloxy)-4-oxo-2-[3,4,5-tri(butanoyloxy)phenyl]chromen-7-yl] butanoate (0.378 g, 501.43 umol, 79.79% yield, 98% purity) was obtained as off-white solid. LCMS: (M+H⁺) 739.2 @ 3.587 min. ¹H NMR (400 MHz, Chloroform-d) δ 7.62 (s, 2H), 7.35 (d, J=2.2 Hz, 1H), 6.88 (d, J=2.2 Hz, 1H), 2.74 (t, J=7.5 Hz, 2H), 2.69-2.52 (m, 10H), 1.91-1.70 (m, 12H), 1.12-0.98 (m, 18H).

To a solution of 5,7-dihydroxy-2-(4-hydroxyphenyl) chromen-4-one (500 mg, 1.85 mmol, 1 eq) in Py. (5 mL) was added butanoyl butanoate (1.76 g, 11.10 mmol, 1.82 mL, 6 eq) at 25° C. The mixture was stirred at 25° C. for 12 hr. LCMS showed the desired compound was detected. The reaction mixture was concentrated under reduced pressure to give a residue. The residue were washed with $H_2O$ (20 mL) and petroleum ether (20 mL), and concentrated under reduced pressure to give a residue. Compound [4-[5,7-di(butanoyloxy)-4-oxo-chromen-2-yl]phenyl] butanoate (167 mg, 340.60 umol, 18.41% yield, 98% purity) was obtained as a yellow solid. LCMS: (M+H⁺) 481.1 @ 3.244 min. ¹H NMR (400 MHz, Chloroform-d) δ 7.92-7.83 (m, 2H), 7.34 (d, J=2.3 Hz, 1H), 7.28-7.22 (m, 2H), 6.83 (d, J=2.2 Hz, 1H), 6.62 (s, 1H), 2.72 (t, J=7.5 Hz, 2H), 2.58 (td, J=7.4, 1.8 Hz, 4H), 1.87-1.74 (m, 6H), 1.12-1.02 (m, 9H)

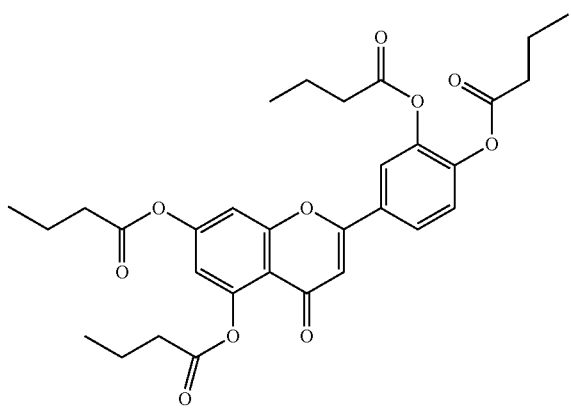 [SMILES: CCCC(=O)Oc1cc(OC(=O)CCC)c2c(=O)cc(-c3ccc(OC(=O)CCC)c(OC(=O)CCC)c3)oc2c1]

Compound 171: 2-[3,4-bis(butanoyloxy)phenyl]-5-(butanoyloxy)-4-oxo-4H-chromen-7-yl butanoate

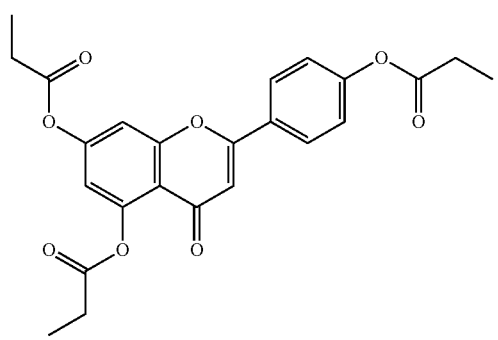 [SMILES: CCC(=O)Oc1ccc(-c2cc(=O)c3c(OC(=O)CC)cc(OC(=O)CC)cc3o2)cc1]

Compound 172: 4-oxo-7-(propanoyloxy)-2-[4-(propanoyloxy)phenyl]-4H-chromen-5-yl propanoate

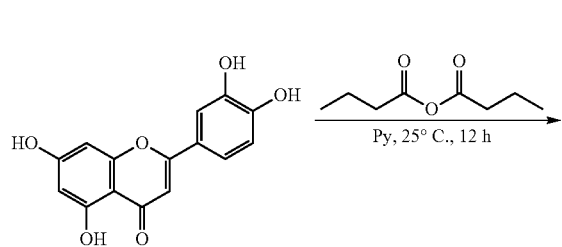

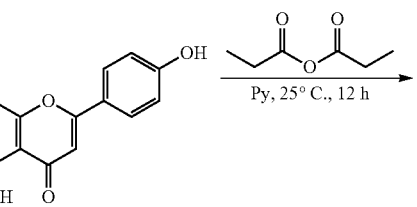

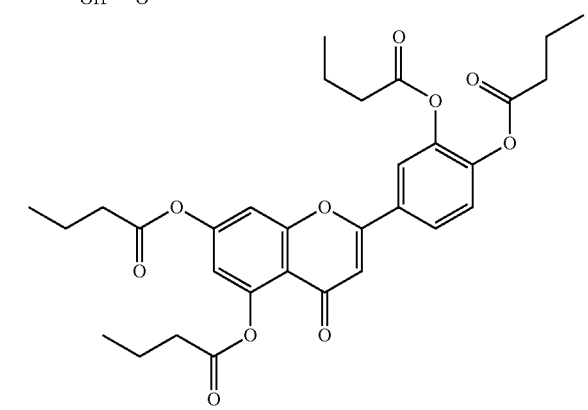

171

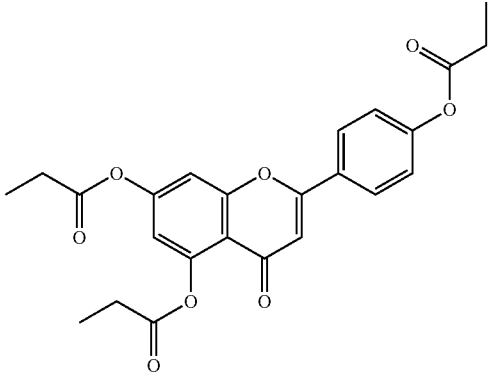

172

To a solution of 2-(3,4-dihydroxyphenyl)-5,7-dihydroxy-chromen-4-one (500 mg, 1.75 mmol, 1 eq) in Pyridine (10 mL) was added butanoyl butanoate (2.21 g, 13.97 mmol, 2.29 mL, 8 eg) at 25° C. The mixture was stirred at 25° C. for 12 hr. LCMS showed the desired compound was detected. The reaction mixture was concentrated under reduced pressure to give a residue. The residue were washed with H$_2$O (20 mL) and petroleum ether (20 mL), and concentrated under reduced pressure to give a residue. Compound [2-butanoyloxy-4-[5,7-di(butanoyloxy)-4-oxo-chromen-2-yl]phenyl] butanoate (155 mg, 270.83 umol, 15.50% yield, 99% purity) was obtained as a yellow solid. LCMS: (M+H$^+$) 567.1 @3.385 min. $^1$H NMR (400 MHz, Chloroform-d) δ 7.76-7.66 (m, 2H), 7.40-7.32 (m, 2H), 6.83 (d, J=2.2 Hz, 1H), 6.60 (s, 1H), 2.72 (t, J=7.5 Hz, 2H), 2.62-2.51 (m, 6H), 1.91-1.72 (m, 8H), 1.11-1.01 (m, 12H).

To a solution of 5,7-dihydroxy-2-(4-hydroxyphenyl)chromen-4-one (500 mg, 1.85 mmol, 1 eq) in Pyridine (5 mL) was added propanoyl propanoate (1.44 g, 11.10 mmol, 1.43 mL, 6 eq) at 25° C. The mixture was stirred at 25° C. for 12 hr. LCMS showed the desired compound was detected. The reaction mixture was concentrated under reduced pressure to give a residue. The residue were washed with H$_2$O (20 mL) and petroleum ether (20 mL), and concentrated under reduced pressure to give a residue. Compound [4-[4-oxo-5,7-di(propanoyloxy)chromen-2-yl]phenyl] propanoate (156 mg, 351.73 umol, 19.01% yield, 98.85% purity) was obtained as a yellow solid. LCMS: (M+H$^+$) 439.1 @ 3.130 min. $^1$H NMR (400 MHz, Chloroform-d) δ 7.94-7.86 (m, 2H), 7.38 (d, J=2.2 Hz, 1H), 7.32-7.24 (m, 2H), 6.87 (d, J=2.2 Hz, 1H), 6.64 (s, 1H), 2.80 (q, J=7.5 Hz, 2H), 2.66 (qd, J=7.5, 1.8 Hz, 4H), 1.38-1.26 (m, 9H)

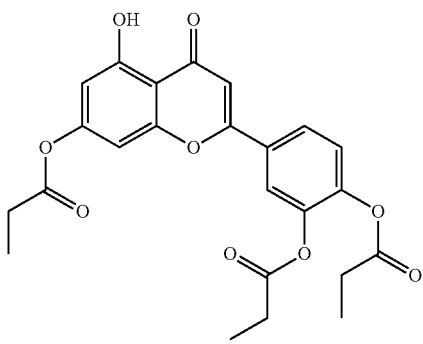 [SMILES: CCC(=O)Oc1cc(O)c2c(=O)cc(-c3ccc(OC(=O)CC)c(OC(=O)CC)c3)oc2c1]

Compound 173: [4-[4-oxo-5,7-di(propanoyloxy)chromen-2-yl]-2-propanoyloxy-phenyl]propanoate Propionic anhydride (1.33 mL, 10.4 mmol) was added dropwise to a stirred solution of luteolin (0.3 g, 1.04 mmol) in anhydrous pyridine (2.5 mL, 31.2 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HCl (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield compound 173 (0.073 g, 15% yield) as an off-white solid. 1H-NMR (DMSO-d6, 400 MHz): δ 12.75 (s, 1H), 8.07 (m, 2H), 7.5 (m, 1H), 7.15 (s, 1H), 7.12 (d, 1H), 6.66 (d, 1H), 2.59-2.66 (m, 6H), 1.11-1.17 (m, 9H)

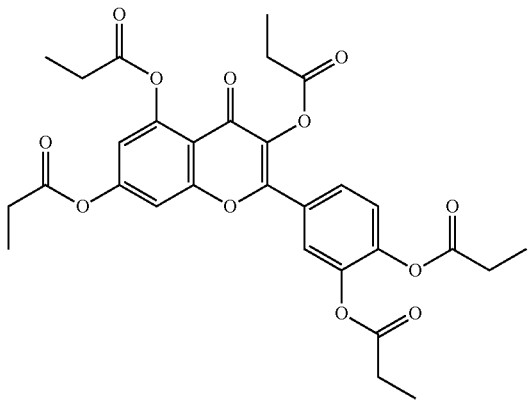 [SMILES: CCC(=O)Oc1cc(OC(=O)CC)c2c(=O)c(OC(=O)CC)c(-c3ccc(OC(=O)CC)c(OC(=O)CC)c3)oc2c1]

Compound 174: [4-[4-oxo-3,5,7-tri(propanoyloxy)chromen-2-yl]-2-propanoyloxy-phenyl]propanoate Propionic anhydride (2.1 mL, 16.5 mmol) was added dropwise to a stirred solution of quercetin (0.5 g, 1.65 mmol) in anhydrous pyridine (3.98 mL, 49.5 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HCl (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 174 (0.1 g, 10% yield) as a white solid. $^1$H NMR (DMSO-d6, 400 MHz): δ 7.85 (m, 2H), 7.66 (d, 1H), 7.54 (d, 1H), 7.18 (d, 1H), 2.62-2.89 (m, 10H), 1.09-1.19 (m, 20H)

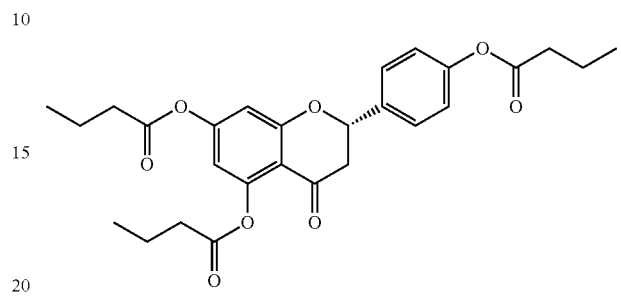

Compound 175: (S)-2-(4-(butyryloxy)phenyl)-4-oxochromane-5,7-diyl dibutyrate

To a solution of 5,7-dihydroxy-2-(4-hydroxyphenyl)chroman-4-one (0.500 g) in pyridine (10 mL), was added butanoyl butanoate (1.02 g). The reaction mixture was stirred at 15° C. for 12 h. The mixture was concentrated. The residue was purified by column chromatography ($SiO_2$, petroleum ether/ethyl acetate gradient) to give compound 175 (0.325 g, 34% yield) as a white solid. LCMS: 500.2 $(M+H_2O^+)$ $^1$H NMR (400 MHz, $CDCl_3$) δ 7.463 (d, 2H), 7.158 (d, 2H), 6.786 (d, 1H), 6.536 (d, 1H), 5.483 (m, 1H), 3.031 (m, 1H), 2.662 (m, 1H), 2.586-2.524 (m, 6H), 1.837-1.785 (m, 6H), 1.089-1.021 (m, 9H)

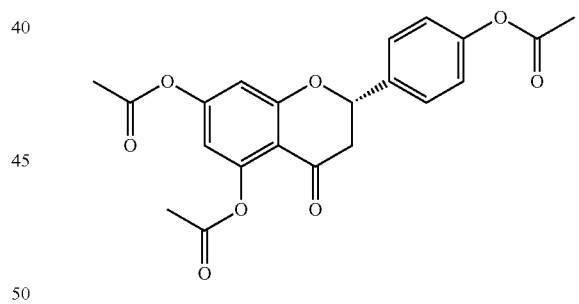

Compound 176: (S)-2-(4-acetoxyphenyl)-4-oxochromane-5,7-diyl diacetate 5,7-dihydroxy-2-(4-hydroxyphenyl)chroman-4-one (0.500 g) was dissolved with pyridine (10 mL), and then acetyl acetate (0.844 g) was added to the mixture reaction. The reaction mixture was stirred at 15° C. for 12 h. The mixture reaction was concentrated under reduced pressure. The residue was purified by column chromatography ($SiO_2$, petroleum ether/ethyl acetate gradient) to give compound 176 (0.300 g, 39% yield) as a white solid. LCMS: 416.1 $(M+H_2O^+)$$^1$H NMR (400 MHz, $CDCl_3$) δ 7.468 (d, 2H), 7.166 (d, 2H), 6.793 (d, 1H), 6.551 (d, 1H), 5.497 (dd, 1H), 3.039 (dd, 1H), 2.783 (dd, 1H), 2.393 (s, 3H), 2.326 (s, 3H), 2.308 (s, 3H).

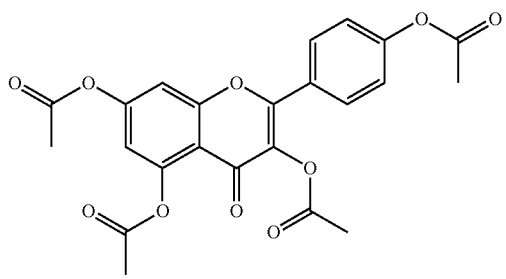 [SMILES: CC(=O)Oc1ccc(-c2oc3cc(OC(C)=O)cc(OC(C)=O)c3c(=O)c2OC(C)=O)cc1]
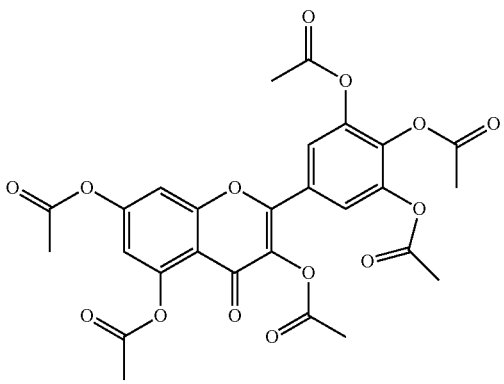 [SMILES: CC(=O)Oc1cc(OC(C)=O)c2c(=O)c(OC(C)=O)c(-c3cc(OC(C)=O)c(OC(C)=O)c(OC(C)=O)c3)oc2c1]

Compound 177: [4-(3,5,7-triacetoxy-4-oxo-chromen-2-yl)phenyl] acetate

To a mixture of 3,5,7-trihydroxy-2-(4-hydroxyphenyl)chromen-4-one (2 g) in pyridine (15 mL) was added acetyl acetate (30 g), and then the mixture was stirred at 15° C. for 12 hr under $N_2$ atmosphere. The solvent was removed under reduced pressure and the residue was poured into crushed ice with vigorous stirring. The solid precipitate was collected by filtration and washed with cold water and then with methanol. Compound 177 (2.1 g, 65% yield) was obtained as a white solid. LCMS: 455.0 (M+H$^+$)$^1$H NMR (400 MHz, CDCl$_3$) δ 7.858 (d, 2H), 7.339 (d, 1H), 7.278-7.257 (m, 2H), 6.883 (d, 1H), 2.447 (s, 3H), 2.357 (s, 6H), 2.333 (s, 3H)

Compound 178: [3,5-diacetoxy-4-oxo-2-(3,4,5-triacetoxyphenyl)chromen-7-yl] acetate To a solution of 3,5,7-trihydroxy-2-(3,4,5-trihydroxyphenyl)chromen-4-one (1 g) in pyridine (10 mL) was added acetyl acetate (15.26 g), then the mixture was stirred at 15° C. for 16 h. The solvent was removed and the mixture was poured into ice water under stirring. The solid was filtered, washed with water and dried in vacuum to give compound 178 (1.1 g, 61% yield) as a gray solid. LCMS 571.1 (M+H$^+$) $^1$H NMR (400 MHz, CDCl$_3$) δ 7.260 (s, 2H), 7.349 (d, 1H), 6.886 (d, 1H), 2.441 (s, 3H), 2.372 (s, 3H), 2.353 (s, 3H), 2.341 (s, 3H), 2.333 (s, 6H)

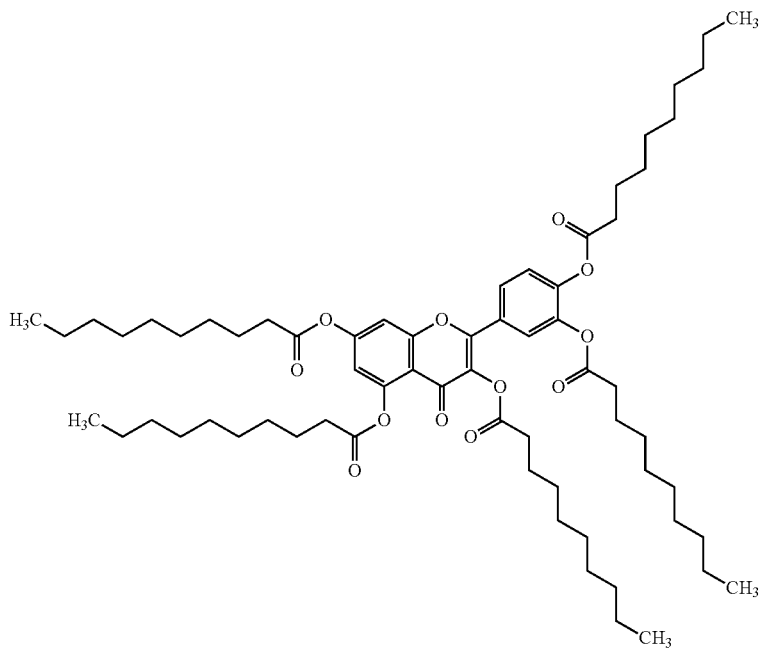 [SMILES: CCCCCCCCCC(=O)Oc1cc(OC(=O)CCCCCCCCC)c2c(=O)c(OC(=O)CCCCCCCCC)c(-c3ccc(OC(=O)CCCCCCCCC)c(OC(=O)CCCCCCCCC)c3)oc2c1]

Compound 179: [2-decanoyloxy-4-[3,5,7-tris(decanoyloxy)-4-oxo-chromen-2-yl] phenyl] decanoate To a mixture of 2-(3,4-dihydroxyphenyl)-3,5,7-trihydroxy-chromen-4-one (1 g) and decanoyl chloride (6.31 g) in THF (50 mL) was added TEA (3.35 g) at 25° C., then the mixture was stirred at 55° C. for 12 h. A portion of the solvent was removed in vacuum and the precipitate was collected by filtration to give compound 179 (2.47 g, 69%) as a white solid. $^1$H NMR (400 MHz, CDCl$_3$). δ 7.772-7.669 (m, 2H), 7.343-7.321 (m, 2H), 6.685 (s, 1H), 2.736 (t, 2H), 2.610-2.551 (m, 8H), 1.762 (m, 10H), 1.557-1.295 (m, 50H), 0.899 (m, 15H)

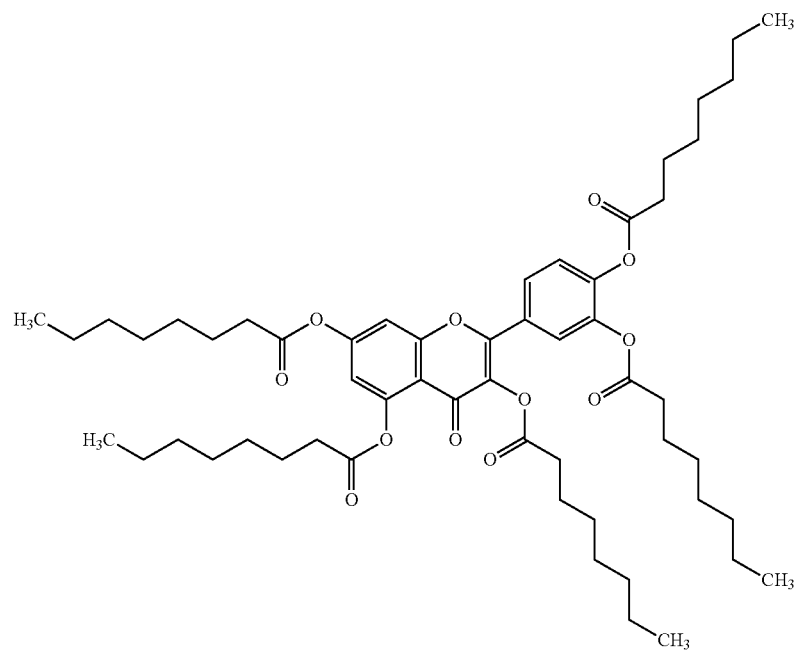 [SMILES: CCCCCCCC(=O)Oc1cc(OC(=O)CCCCCCC)c2c(=O)c(OC(=O)CCCCCCC)c(-c3ccc(OC(=O)CCCCCCC)c(OC(=O)CCCCCCC)c3)oc2c1]

Compound 180: [2-octanoyloxy-4-[3,5,7-tri(octanoyloxy)-4-oxo-chromen-2-yl] phenyl] octanoate To a mixture of 2-(3,4-dihydroxyphenyl)-3,5,7-trihydroxy-chromen-4-one (0.32 g) and octanoyl chloride (1.72 g) in THF (20 mL) was added TEA (1.07 g) at 25° C. Then the mixture was stirred at 55° C. for 12 h. A portion of the solvent was removed in vacuum and the precipitate was collected by filtration to give compound 180 (0.20 g, 20%) as a white solid. $^1$H NMR (400 MHz, CDCl$_3$). δ 7.709-7.655 (m, 2H), 7.329-7.301 (m, 2H), 6.837 (s, 1H), 2.723 (t, 2H), 2.612-2.539 (m, 8H), 1.751 (m, 10H), 1.412-1.309 (m, 40H), 0.896 (m, 15H).

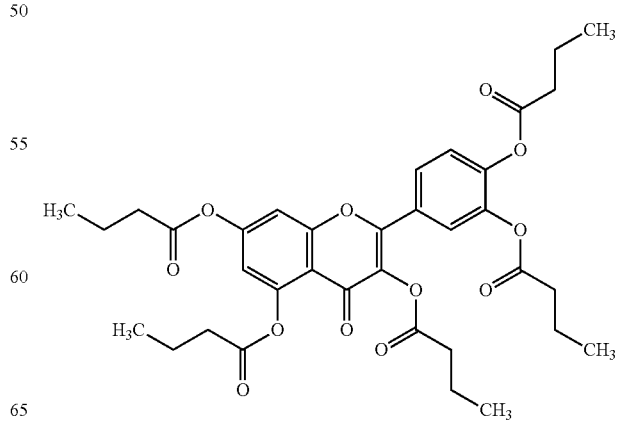

Compound 181: [2-butanoyloxy-4-[3,5,7-tri(butanoyloxy)-4-oxo-chromen-2-yl]phenyl] butanoate To a mixture of 2-(3,4-dihydroxyphenyl)-3,5,7-trihydroxy-chromen-4-one (1 g) and butanoyl chloride (3.53 g) in THF (40 mL) was added triethylamine (TEA) (3.35 g) at 25° C., then the mixture was stirred at 55° C. for 12 h. The reaction mixture was concentrated in vacuum and purified by reverse phase prep-HPLC (C18, water (0.05% HCl)-ACN gradient) to give compound 181 (1.13 g, 52% yield) as a colorless solid. LCMS: 653.3 (M+H⁺) ¹H NMR (400 MHz, CDCl₃). δ 7.666-7.608 (m, 2H), 7.292-7.210 (m, 2H), 6.880 (s, 1H), 2.542 (t, 2H), 2.535-2.484 (m, 8H), 1.753 (m, 10H), 1.020-0.997 (m, 12H), 0.949 (t, 3H).

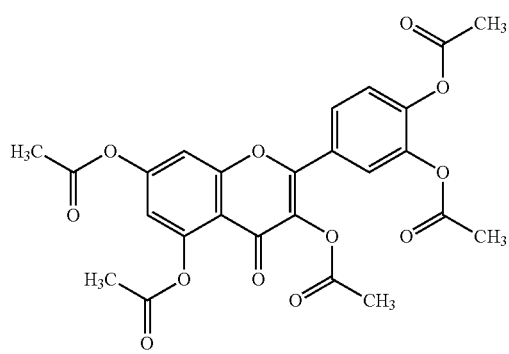 [SMILES: CC(=O)Oc1cc(OC(C)=O)c2c(=O)c(OC(C)=O)c(-c3ccc(OC(C)=O)c(OC(C)=O)c3)oc2c1]

Compound 182: [2-acetoxy-4-(3,5,7-triacetoxy-4-oxo-chromen-2-yl)phenyl]acetate To a mixture of 2-(3,4-dihydroxyphenyl)-3,5,7-trihydroxy-chromen-4-one (1 g) and acetic anhydride (2.36 g) in THF (40 mL) was added K₂CO₃ (3.2 g) at 25° C., then the mixture was stirred at 55° C. for 12 h. Additional acetic anhydride was added (3 equiv.) and the mixture and stirred for another 3 h. The reaction mixture was concentrated in vacuum and purified by reverse phase prep-HPLC (C18; water (0.05% HCl)-ACN gradient) to give compound 182 (0.837 g, 49%) as a white solid. LCMS: 513.2 (M+H⁺) ¹H NMR (400 MHz, CDCl₃). δ 7.742-7.703 (m, 2H), 7.373-7.346 (m, 2H), 6.888 (s, 1H), 2.443, (s, 3H), 2.356 (s, 6H), 2.350 (s, 6H).

Compound 183: 5-amino-2-[(2S,3R,4S,5R)-3,4,5-tri(butanoyloxy)tetrahydropyran-2-yl]oxy-benzoic acid Step 1

5-Amino salicylic acid (10.0 g) was dissolved in a mixture of dioxane (100 mL), water (100 mL), and NaOH (2.60 g), and the resulting solution was cooled in an ice-bath. Di-tert-butyl dicarbonate (Boc anhydride) (15.60 g) was added, and the mixture was warmed to room temperature and stirred for 1.0 h. The solution was concentrated to 60 mL, diluted with ethyl acetate (100 mL), and the resulting mixture was cooled in an ice-bath. The mixture was acidified with aq. KHSO₄ to pH 2-3. The aqueous layer was extracted with EtOAc. The organic phase was washed with water, brine, dried over Na₂SO₄, filtered, and concentrated to afford 5-(tert-butoxycarbonylamino)-2-hydroxy-benzoic acid (7.0 g, 42%).

Step 2

5-(tert-butoxycarbonylamino)-2-hydroxy-benzoic acid (3 g) was dissolved in DMF, and the resulting solution was cooled to 0° C. 1,1'-Carbonyldiimidazole (CDI) was added, and the mixture was stirred at room temperature for 2 h. Then, tert-butylalcohol (1.7 g) and DBU (2.1 g) were added. The reaction was stirred at room temperature overnight. The reaction mixture was poured onto ice-water, and the solid product, tert-butyl 5-(tert-butoxycarbonylamino)-2-hydroxy-benzoate, was collected by filtration (3.0 g, 81.9%).

Step 3

To a mixture of tert-butyl 5-(tert-butoxycarbonylamino)-2-hydroxy-benzoate, [(3R,4S,5R)-4,5-di(butanoyloxy)-6-hydroxy-tetrahydropyran-3-yl] butanoate (1.2 g) and triphenylphosphene (1.2 g) in THF (50 mL) was added di-t-butyl azodicarboxylate (DTAD) (1.1 g), and the mixture was stirred overnight at room temperature. The product was purified by reverse phase chromatography using acetonitrile-water to afford tert-butyl 5-(tert-butoxycarbonylamino)-2-[(3R,4S,5R)-3,4,5-tri(butanoyloxy)tetrahydropyran-2-yl]oxy-benzoate as sticky solid (0.6 g, 30%).

Step 4

Tert-butyl 5-(tert-butoxycarbonylamino)-2-[(3R,4S,5R)-3,4,5-tri(butanoyloxy)tetrahydropyran-2-yl]oxy-benzoate (600 mg) was added to 4M HCl in dioxane (15 mL) and stirred at room temperature overnight. After the consumption of the starting material, the organic phase was evaporated, and the residue was co-evaporated with heptane and dichloromethane twice more. The solid obtained was dried under high vacuum to afford compound the title product as dark brown solid (200 mg, 43.8%). Fractionation of the product afforded two anomeric isomers (compounds 185 and 186). ¹H NMR (DMSO d6): Isomer 1: δ 7.62 (d, 1H), 7.45 (dd, 1H), 7.38 (d, 1H), 6 (d, 1H), 5.6 (t, 1H), 5.0-5.1 (m, 1H), 4.7-4.75 (m, 1H), 3.6-3.8 (m, 1H), 3.45-3.6 (1H), 2.1-2.3 (m, 6H), 1.4-1.6 (m, 6H), 0.75-0.85 (m, 9H). Isomer 2: δ 7.82 (d, 1H), 7.5 (dd, 1H), 7.05 (d, 1H), 5.5 (d, 1H), 5.3 (t, 1H), 5.1-5.15 (m, 1H), 4.9-5.0 (m, 1H), 4.0-4.08 (m, 1H), 3.7-3.8 (1H), 2.1-2.3 (m, 6H), 1.4-1.6 (m, 6H), 0.75-0.85 (m, 9H) ppm

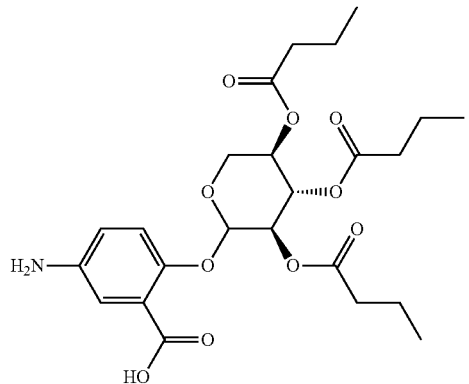

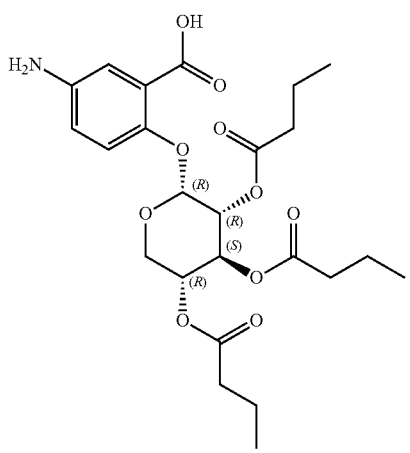

Compound 184: 5-amino-2-[(2R,3R,4S,5R)-3,4,5-tri(butanoyloxy)tetrahydropyran-2-yl]oxy-benzoic acid This compound was prepared according to a modified procedure described for the preparation of compound 183. LCMS [M−H]⁻: 494.5. ¹H NMR (400 MHz, DMSO-d6) δ 6.83-6.75 (m, 2H), 6.64-6.53 (m, 1H), 5.58 (d, J=3.6 Hz, 1H), 5.53 (t, J=9.9 Hz, 1H), 5.03-4.90 (m, 2H), 3.89 (t, J=10.9 Hz, 1H), 3.73 (dd, J=10.9, 5.9 Hz, 1H), 2.38-2.12 (m, 6H), 1.58-1.39 (m, 6H), 0.92-0.76 (m, 9H).

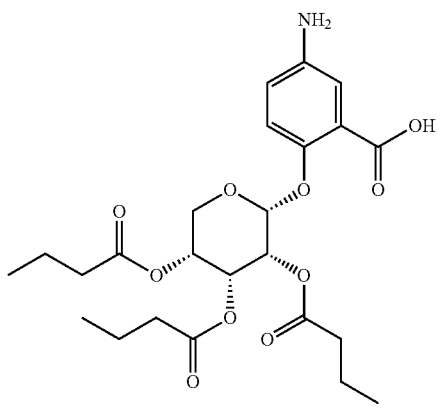 [SMILES: CCCC(=O)O[C@H]1[C@@H](Oc2ccc(N)cc2C(=O)O)OC[C@@H](OC(=O)CCC)[C@H]1OC(=O)CCC]

Compound 185: 5-amino-2-(((2R,3R,4R,5R)-3,4,5-tris(butyryloxy)tetrahydro-2H-pyran-2-yl)oxy)benzoic acid Step 1. Ribose tetrabutyrate To a stirred solution of D-(+)-ribose 1 (5 g) in anhydrous pyridine (24.2 mL) was added solution of butyryl chloride (23.70 g) in dichloromethane (50 mL) at 0-5° C. The reaction mixture was brought to room temperature and stirred for 16 h. The mixture was diluted with dichloromethane (100 ml) and washed successively with water (100 mL), 2N aqueous HCl (300 mL), saturated sodium bicarbonate solution (300 mL) and brine (100 mL). The organic layer was dried over sodium sulfate and concentrated under reduced pressure. The residue was purified by column chromatography over silica gel (5-10% EtOAc-hexane gradient) to afford ribose tetrabutyrate as a colorless oil (7.5 g, 52%, mixture of a/anomers).

Step 2. Ribose tributyrate

Ammonium hydroxide (11 mL) was added slowly to a mixture of ribose tetrabutyrate 2 (7.5 g) in acetonitrile (60 mL) at room temperature and the resulting reaction mixture was stirred for 5 h. The mixture was diluted with MTBE (75 mL) and stirred for 15 minutes. The organic layer was separated and concentrated under reduced pressure and the residue was partitioned between MTBE (100 mL) and water (75 mL). The MTBE layer was separated, dried over sodium sulfate and concentrated under reduced pressure. The residue was purified by column chromatography [using silica gel 100-200 mesh and 10-20% EtOAc-Hexane as eluting solvent] to afford ribose tributyrate as a colorless oil (1.1 g, 17%).

Step 3.
5-tert-butoxycarbonylamino-2-hydroxy-benzoic acid

To the stirred solution of 5-amino salicylic acid 4 (5 g) in 1,4-dioxane and water (1:1; 100 mL) was added NaOH (1.3 g) and Boc-anhydride (7.83 g) at 0° C. and the resulting reaction mixture was stirred at room temperature for 1 h. The reaction mixture was concentrated under reduced pressure, the residue was diluted with EtOAc (50 mL) and the pH was adjusted to ~3-4 by dropwise addition of 0.5N aqueous HCl at 0° C. The organic layer was separated, and the aqueous layer was extracted with EtOAc (50 mL). The combined organic layer was dried over sodium sulfate and concentrated under reduced pressure to provide 5-tert-butoxycarbonylamino-2-hydroxy-benzoic acid as off white solid (5.3 g, 64%).

Step 4.
5-tert-butoxycarbonylmethyl-2-hydroxy-benzoic acid tert-butyl ester

To a stirred solution of 5-tert-butoxycarbonylamino-2-hydroxy-benzoic acid 5 (5.3 g) in DMF (50 mL) was added CDI (3.39 g) at 0-5° C. and the mixture was stirred for 2 h. tert-Butanol (4.025 mL) and DBU (2.54 mL) were then added and the mixture was stirred at room temperature for 16 h. The mixture was diluted with water (100 mL) and extracted with EtOAc (200 mL). The organic layer was separated, dried over sodium sulfate and concentrated under reduced pressure. The residue was purified by column chromatography using silica gel [100-200 mesh; under gradient elution of 5-10% EtOAc-Hexane] to afford 5-tert-butoxycarbonylmethyl-2-hydroxy-benzoic acid tert-butyl ester as off white solid (2 g, 31%).

Step 5. (2R,3R,4R,5R)-2-(2-(tert-butoxycarbonyl)-4-((tert-butoxycarbonyl)amino)phenoxy)tetrahydro-2H-pyran-3,4,5-triyl tributyrate hydroxy-benzoic acid tert-butyl ester 6 (0.850 g) and ribose tributyrate (1.04 g) in THF (5 mL) was sequentially added triphenylphosphine (1.03 g) and di-tert-butyl azodicarboxylate (0.948 g) at room temperature and the mixture was stirred for 16 h. The mixture was concentrated under reduced pressure and the residue was purified by column chromatography over silica gel (5 to 18% EtOAc-Hexane gradient) to afford of crude (2R,3R,4R,5R)-2-(2-(tert-butoxycarbonyl)-4-((tert-butoxycarbonyl)amino)phenoxy)tetrahydro-2H-pyran-3,4,5-triyl tributyrate (1.3 g) which was used directly in the next step.

Step 6. 5-amino-2-[(2R,3R,4R,5R)-3,4,5-tri(butanoyloxy)tetrahydropyran-2-yl]oxy-benzoic acid To a stirred solution of crude (2R,3R,4R,5R)-2-(2-(tert-butoxycarbonyl)-4-((tert-butoxycarbonyl)amino)phenoxy)tetrahydro-2H-pyran-3,4,5-triyl tributyrate (1.3 g, crude from above experiment) in 1,4-dioxane (7 mL) was added 4N HCl in 1,4-dioxane (10 mL) at 0° C. and the resulting reaction mixture was stirred at room temperature for 16 h. Then reaction mixture was concentrated under reduced pressure and the residue was purified by reverse phase prep-HPLC to provide 5-amino-2-[(2R,3R,4R,5R)-3,4,5-tri(butanoyloxy)tetrahydropyran-2-yl]oxy-benzoic acid (0.05 g). LCMS: 496.5 (M+H$^+$) $^1$H NMR (400 MHz, DMSO-d6): δ 6.919-6.898 (m, 2H), 6.658 (m, 1H), 5.431 (m, 1H), 5.350 (m, 1H), 5.234 (m, 1H), 5.161 (m, 1H), 4.213 (m 1H), 3.749 (m, 1H), 2.497-2.268 (m, 4H), 2.197 (m, 1H), 1.620-1.487 (m, 6H), 0.926-0.888 (m, 9H) ppm

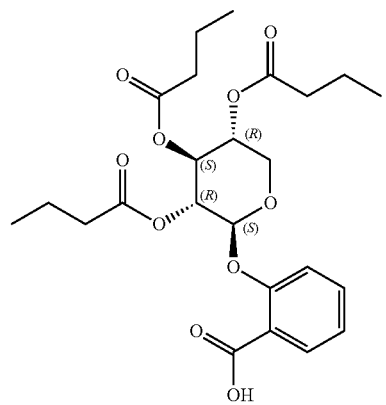

Compound 186: 2-{[(2R,3R,4S,5R)-3,4,5-tris(butanoyloxy)oxan-2-yl]oxy}benzoic acid

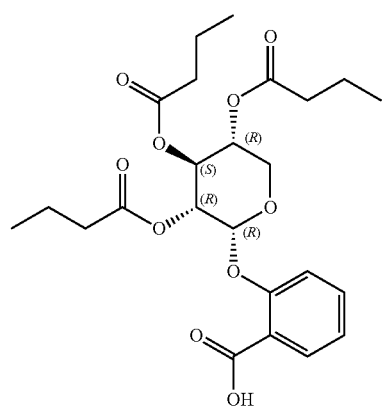

Compound 187: 2-{[(2R,3R,4,5R)-3,4,5-tris(butanoyloxy)oxan-2-yl]oxy}benzoic acid

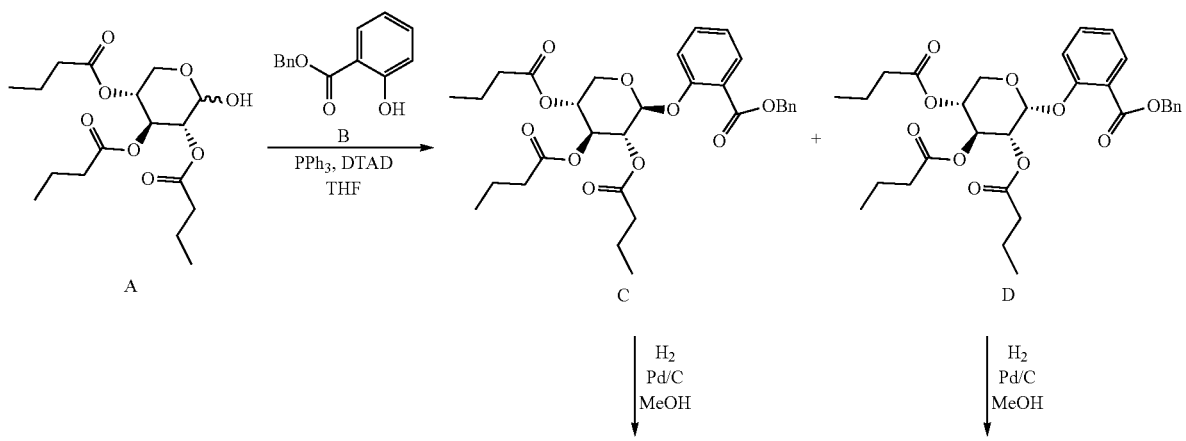

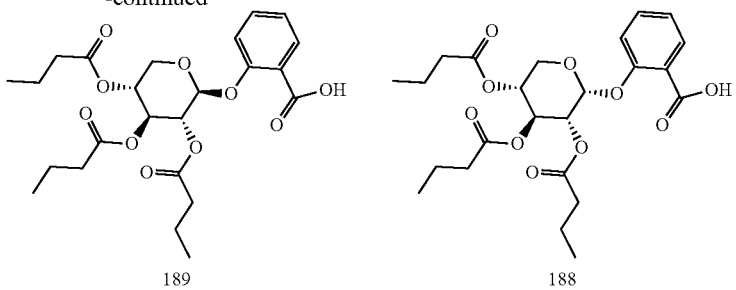

Step 1

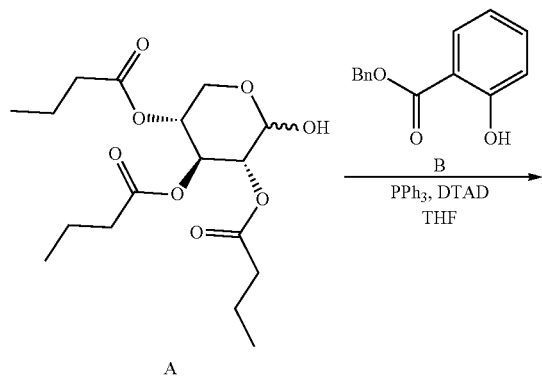

| S.N. | Materials | MW/d | Amount/mmol | Equiv/Vol |
|---|---|---|---|---|
| 1 | Xylose Tributyrate (X3B) A | 360 | 12 g/33.3 | 1.0 |
| 2 | Compound B | 228 | 11.4 g/50 | 1.5 |
| 3 | Triphenylphosphine | 262 | 13.1 g/50 | 1.5 |
| 4 | Di-t-butyl azodicarboxylate (DTAD) | 230 | 11.5 g/50 | 1.5 |
| 5 | THF | | 240 mL | 20 Vol |

Compound A, B and TPP were dissolved in THF and stirred at 0° C. To this mixture was added DTAD and stirring was continued at 0° C. for 1 h, then at room temperature overnight. The reaction mixture was concentrated. NMR of the crude product showed a mixture of C and D (ratio 1:0.9). Multiple purifications by column chromatography using 0-30% ethyl acetate in hexanes provided the desired p isomer C (7 g, 32%) and a isomer D (4.6 g, 21%).

Step 2A:

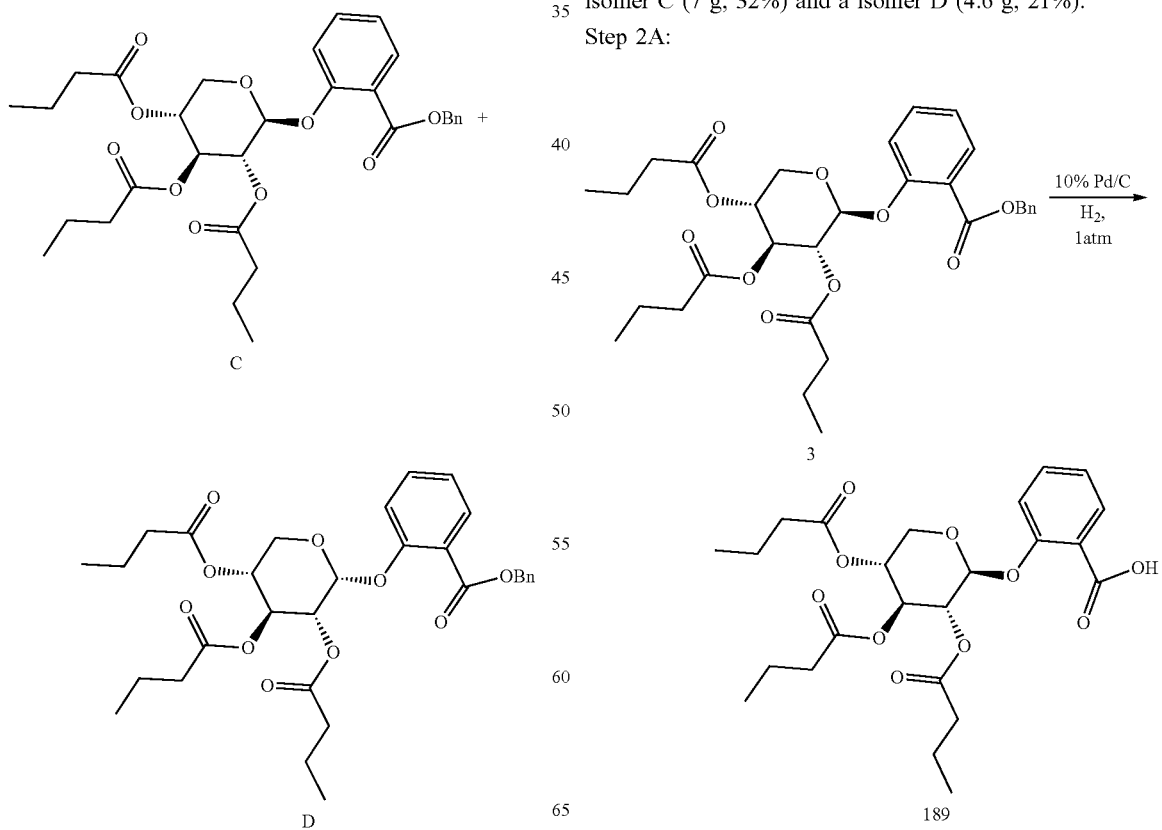

| S.N. | Materials    | MW/d | Amount/mmol | Equiv/Vol |
|------|--------------|------|-------------|-----------|
| 1    | Compound C   | 570  | 4.2 g/7.37  | 1.0       |
| 2    | 10% Pd/C     |      | 200 mg      |           |
| 3    | MeOH         |      | 50 mL       | 12 Vol    |

Compound C was dissolved in methanol and stirred at room temperature. To this mixture was added 10% Pd/C. The suspension was stirred under a hydrogen atmosphere at room temperature overnight. The reaction mixture was filtered through Celite and washed with methanol. The combined filtrate and washing were concentrated. The residue was purified by ISCO using 0-5% MeOH in DCM to give 2.1 g (60%) of pure product 187 and 850 mg of impure product.

Step 2B:

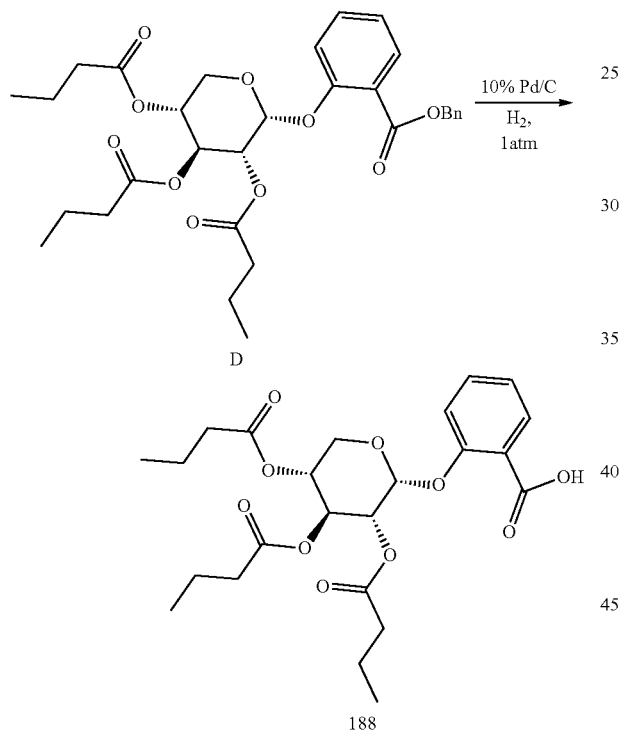

| S.N. | Materials    | MW/d | Amount/mmol | Equiv/Vol |
|------|--------------|------|-------------|-----------|
| 1    | Compound 4   | 570  | 2.8 g/4.9   | 1.0       |
| 2    | 10% Pd/C     |      | 150 mg      |           |
| 3    | MeOH         |      | 40 mL       | 14 Vol    |

Compound 4 was dissolved in methanol and stirred at room temperature. To this mixture was added 10% Pd/C. The suspension was stirred under hydrogen atmosphere at room temperature overnight. The reaction mixture was filtered through Celite and washed with methanol. The combined filtrate and washing were concentrated. The residue was purified by ISCO using 0-5% MeOH in DCM to give 936 mg (40%) of pure product 186.

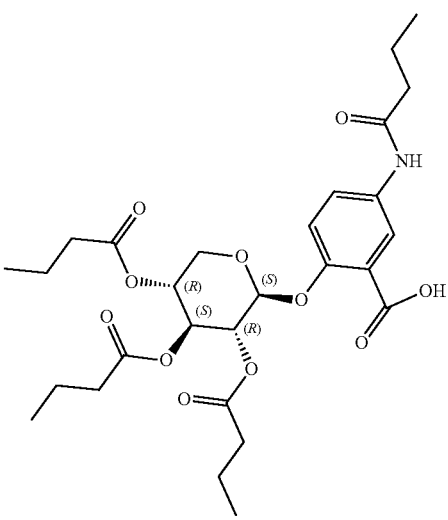

Compound 188:5-butanamido-2-{[(2S,3R,4S,5R)-3,4,5-tris(butanoyloxy)oxan-2-yl]oxy}benzoic acid Compound 183 in metabolic application (50 mg, 0.10 mmol, 1 equiv) was dissolved in 0.25 mL of DCM, followed by addition of butyric anhydride (0.05 mL, 0.3 mmol, 3 equiv). The reaction was stirred at room temperature for 40 minutes, then purified by column chromatography (0-100% EtOAc in hexanes) to yield the title compound as a white solid (42.5 mg, 0.075 mmol, 75% yield). $^1$H NMR (400 MHz, DMSO-d) δ 12.71 (s, 1H), 9.90 (s, 1H), 7.86 (d, J=2.8 Hz, 1H), 7.65 (dd, J=9.0, 2.7 Hz, 1H), 7.10 (d, J=9.0 Hz, 1H), 5.36 (d, J=7.2 Hz, 1H), 5.29 (t, J=9.0 Hz, 1H), 5.04 (dd, J=9.2, 7.2 Hz, 1H), 4.94 (td, J=9.2, 5.4 Hz, 1H), 4.04 (dd, J=11.5, 5.4 Hz, 1H), 3.70 (dd, J=11.6, 9.4 Hz, 1H), 2.33-2.11 (m, 8H), 1.65-1.41 (m, 8H), 0.93-0.77 (m, 12H).

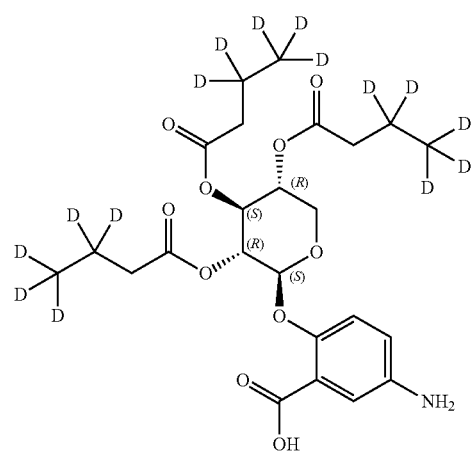

Compound 189:5-amino-2-{[(2S,3R,4S,5R)-3,4,5-tris[(3,3,4,4,4-$^2$H$_5$)butanoyloxy]oxan-2-yl]oxy}benzoic acid This compound was prepared as described for compound 183 with the exception that starting materials appropriately enriched in deuterium. LCMS: (M+H$^+$) 511.3. 1H NMR (400 MHz, DMSO-d6) δ 12.41 (s, 1H), 6.86 (d, 1H), 6.81 (d, 1H), 6.64 (dd, 1H), 5.27 (t, 1H), 5.14 (d, 1H), 5.00 (dd, 1H), 4.92 (td, 1H), 4.02 (dd, 1H), 3.63 (dd, 1H), 2.33-2.14 (m, 6H)

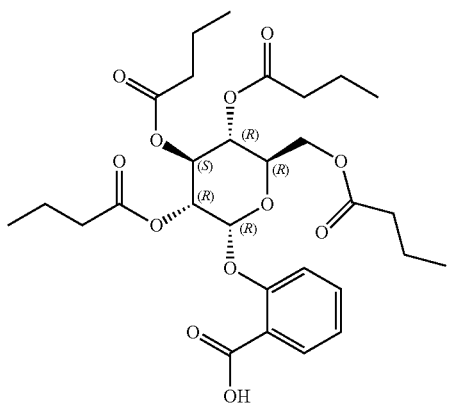

Compound 190: 2-{[(2R,3R,4S,5R,6R)-3,4,5-tris(butanoyloxy)-6-[(butanoyloxy)methyl]oxan-2-yl]oxy}benzoic acid This compound was prepared according to a modified procedure for the preparation of compound 41.

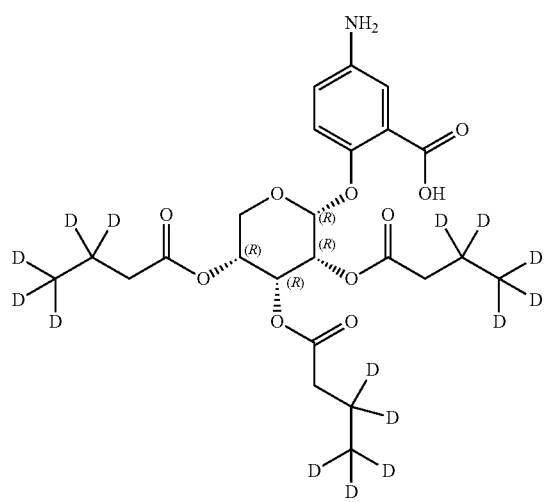

Compound 191: 5-amino-2-{[(2R,3R,4R,5R)-3,4,5-tris[(3,3,4,4,4-$^{2}$H$_{5}$)butanoyloxy]oxan-2-yl]oxy}benzoic acid This compound was prepared according to a modified procedure for the preparation of compound 41.

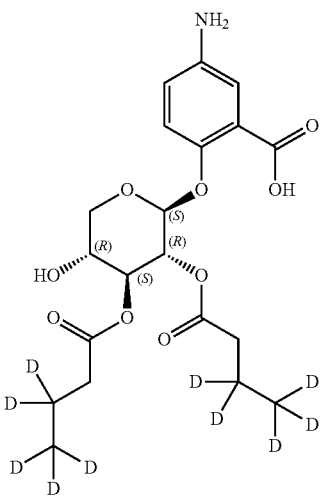

Compound 192: 5-amino-2-{[(2S,3R,4S,5R)-3,4-bis[(3,3,4,4,4-$^{2}$H$_{5}$)butanoyloxy]-5-hydroxyoxan-2-yl]oxy}benzoic acid This compound was prepared according to a modified procedure for the preparation of compound 32. LCMS: (M−H−) 434.2. $^{1}$H NMR (400 MHz, Chloroform-d) δ 7.46 (d, 1H), 7.04 (d, 1H), 6.85 (dd, 1H), 5.35 (d, 1H), 5.15 (dd, 1H), 5.06 (t, 1H), 4.17 (dd, 1H), 3.84 (td, 1H), 3.61 (dd, 1H), 2.41 (s, 2H), 2.36 (s, 2H)

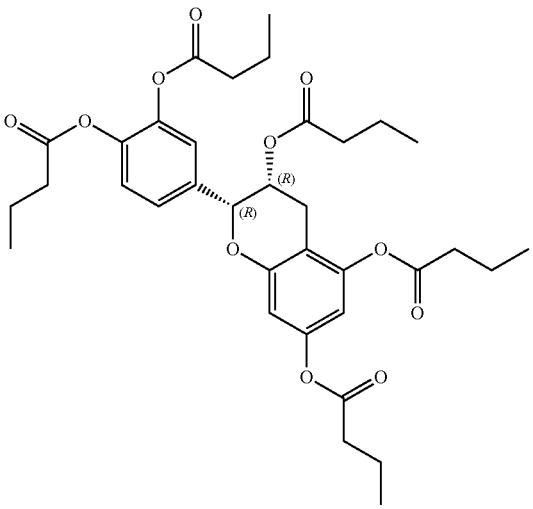

Compound 193: (2R,3R)-2-[3,4-bis(butanoyloxy)phenyl]-5,7-bis(butanoyloxy)-3,4-dihydro-2H-1-benzopyran-3-ylbutanoate

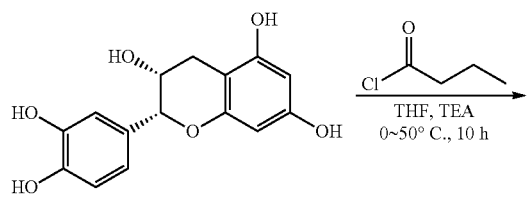

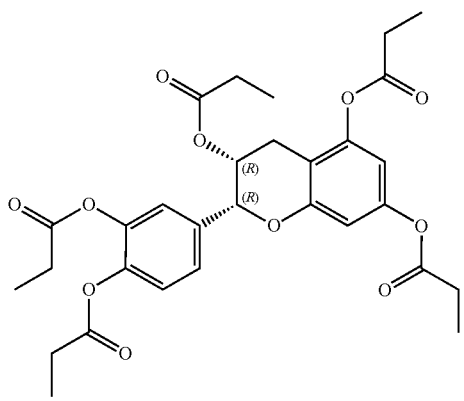

Compound 194: (2R,3R)-2-[3,4-bis(propanoyloxy)phenyl]-5,7-bis(propanoyloxy)-3,4-dihydro-2H-1-benzopyran-3-yl propanoate

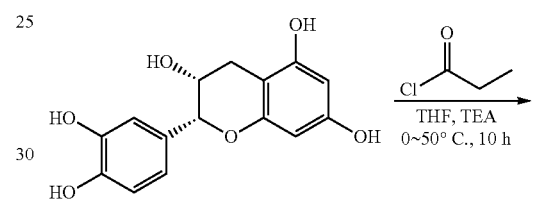

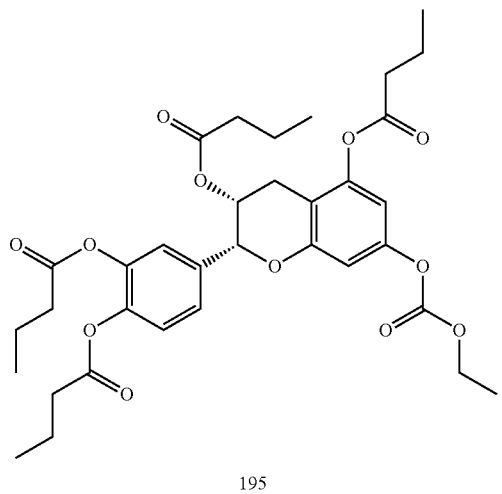

195

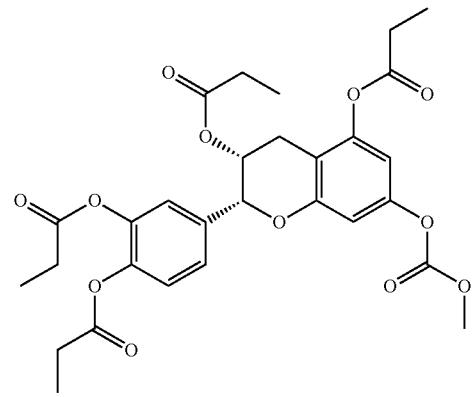

196

A mixture of (2R,3R)-2-(3,4-dihydroxyphenyl)chromane-3,5,7-triol (300 mg, 1.03 mmol, 1 eq) and TEA (627.50 mg, 6.20 mmol, 863.13 uL, 6 eq) in THF (8 mL) was cooled to 0° C. and stirred under $N_2$. Then butanoyl chloride (110.12 mg, 1.03 mmol, 107.96 uL, 1.00 eq) was dropped to the mixture and then heated to 50° C. and stirred for 10 hours. LCMS showed desired compound was detected. The reaction mixture was concentrated under reduced pressure to give a residue. The residue was purified by prep-HPLC (column: Phenomenex Luna C18 200*40 mm*10 um; mobile phase: [water (0.05% HCl)-ACN]; B %: 70%-90%, 10 min) to give WX-0637 (2R,3R)-2-(3,4-bis(butyryloxy)phenyl)chroman-3,5,7-triyl tributyrate (154 mg, 216.61 umol, 20.96% yield, 90.12% purity) as a white solid. LCMS: (M+H$^+$) 641.4 @ 1.476 min; LCMS: (M+Na$^+$) 663.3 @ 2.346 min. $^1$H NMR (400 MHz, Chloroform-d) δ 7.32 (d, J=2.0 Hz, 1H), 7.30-7.23 (m, 1H), 7.19 (d, J=8.4 Hz, 1H), 6.67 (d, J=2.3 Hz, 1H), 6.54 (d, J=2.3 Hz, 1H), 5.43-5.37 (m, 1H), 5.12 (s, 1H), 2.97 (dd, J=17.8, 4.5 Hz, 1H), 2.86 (dd, J=17.9, 2.3 Hz, 1H), 2.57-2.47 (m, 8H), 2.14 (t, J=7.4 Hz, 2H), 1.77 (hd, J=7.4, 2.3 Hz, 8H), 1.44 (h, J=7.3 Hz, 2H), 1.08-0.99 (m, 12H), 0.74 (t, J=7.4 Hz, 3H)

A mixture of (2R,3R)-2-(3,4-dihydroxyphenyl)chromane-3,5,7-triol (300 mg, 1.03 mmol, 1 eq) and TEA (627.50 mg, 6.20 mmol, 863.13 uL, 6 eq) in THF (8 mL) was cooled to 0° C. and stirred under $N_2$. Then propanoyl chloride (573.76 mg, 6.20 mmol, 573.76 uL, 6 eq) was dropped to the mixture and the mixture heated to 50° C. and stirred for 10 hours. LCMS showed desired compound was detected. The reaction mixture was concentrated under reduced pressure to give a residue. The residue was purified by prep-HPLC (column: Phenomenex Luna C18 200*40 mm*10 um; mobile phase: [water (0.05% HCl)-ACN]; B %: 55%-75%, 10 min) to give [2-propanoyloxy-4-[(2R,3R)-3,5,7-tri(propanoyloxy)chroman-2-yl]phenyl] propanoate (151 mg, 258.48 umol, 25.01% yield, 97.67% purity) as a white solid. LCMS: (M+H$^+$) 571.3 @ 1.342 min; LCMS: (M+Na$^+$) 593.3 @ 2.147 min. $^1$H NMR (400 MHz, Chloroform-d) δ 7.33 (d, J=2.0 Hz, 1H), 7.30-7.23 (m, 1H), 7.19 (d, J=8.4 Hz, 1H), 6.67 (d, J=2.3 Hz, 1H), 6.56 (d, J=2.3 Hz, 1H), 5.43-5.37 (m, 1H), 5.12 (s, 1H), 2.97 (dd, J=17.8, 4.5 Hz, 1H), 2.86 (dd, J=17.9, 2.3 Hz, 1H), 2.63-2.51 (m, 8H), 2.18 (q, J=7.5 Hz, 2H), 1.30-1.20 (m, 12H), 0.95 (t, J=7.5 Hz, 3H).

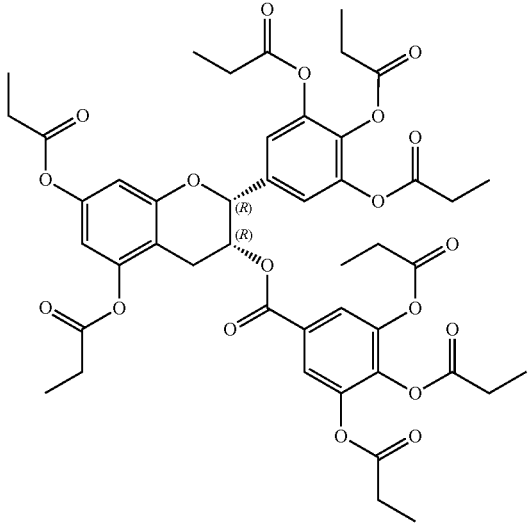

Compound 195: [(2R,3R)-5,7-di(propanoyloxy)-2-[3,4,5-tri(propanoyloxy)phenyl]chroman-3-yl]3,4,5-tri(propanoyloxy)benzoate Propionic anhydride (2.78 mL, 21.8 mmol) was added dropwise to a stirred solution of epigallocatechin gallate (0.5 g, 1.09 mmol) in anhydrous pyridine (2.61 mL, 32.6 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HCl (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 197 (0.695 g, 70% yield) as a white solid. $^1$H NMR (DMSO-d6, 400 MHz): δ 7.54 (s, 2H), 7.38 (s, 2H), 6.79 (m, 1H), 6.66 (m, 1H), 5.66 (m, 1H), 5.54 (s, 1H), 3.13-3.17 (m, 1H), 2.96 (d, 1H), 2.5-2.65 (m, 16H), 1.0-1.2 (m, 24H)

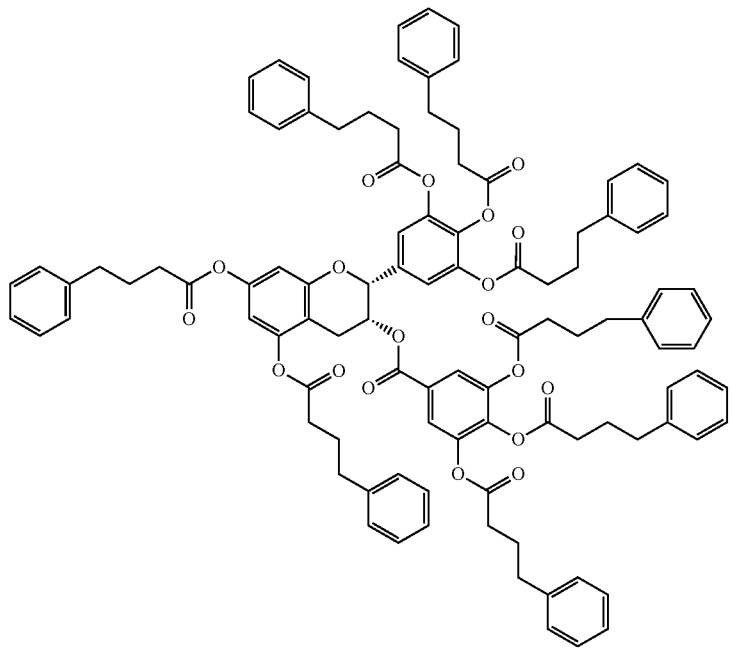 [SMILES: O=C(CCCc1ccccc1)Oc1cc(OC(=O)CCCc2ccccc2)c2c(c1)O[C@H](c1cc(OC(=O)CCCc3ccccc3)c(OC(=O)CCCc3ccccc3)c(OC(=O)CCCc3ccccc3)c1)[C@H](OC(=O)c1cc(OC(=O)CCCc3ccccc3)c(OC(=O)CCCc3ccccc3)c(OC(=O)CCCc3ccccc3)c1)C2]

Compound 196: [(2R,3R)-5,7-bis(4-phenylbutanoyloxy)-2-[3,4,5-tris(4-phenylbutanoyloxy)phenyl]chroman-3-yl] 3,4,5-tris(4-phenylbutanoyloxy)benzoate Step 1:

To a solution of 4-phenylbutanoic acid (3 g, 18.27 mmol) and SOCl$_2$ (10.87 g, 91.35 mmol, 6.63 mL) in dichloromethane (50 mL) is added one drop of DMF, then the mixture stirred at 20° C. for 5 h. The solvent is removed in vacuum and toluene (20 mL) added to the mixture. The mixture is concentrated in vacuo to afford 4-phenylbutanoyl chloride (3.5 g, crude).

Step 2:

To a solution of [(2R,3R)-5,7-dihydroxy-2-(3,4,5-trihydroxyphenyl)chroman-3-yl] 3,4,5-trihydroxybenzoate (1 g, 2.18 mmol) and K$_2$CO$_3$ (4.52 g, 32.72 mmol) in acetonitrile (100 mL) was added a solution of 4-phenylbutanoyl chloride (7.97 g, 43.63 mmol) in acetonitrile (10 mL), then the mixture was stirred at 20° C. for 10 h. The mixture was filtered, and the filtrate was concentrated in vacuum. The crude product was purified by silica gel chromatography (petroleum ether/ethyl acetate=20:1-1:1) to afford compound 198 (2.2 g, 1.28 mmol, 58.7% yield) as a white solid. LC/MS (M+H$_3$O$^+$): 1645.1

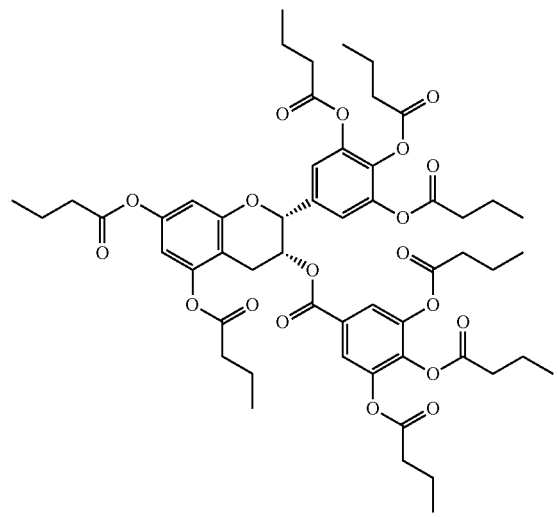

Compound 198: [(2R,3R)-5,7-di(butanoyloxy)-2-[3,4,5-tri(butanoyloxy)phenyl]chroman-3-yl] 3,4,5-tri(butanoyloxy)benzoate Butyryl chloride (6.03 mL) was added to a stirred solution of epigallocatechin gallate (2.0 g) and pyridine (6.28 mL) in dichloromethane (20 mL) over 2 h between −5° C. to 5° C. The resulting mixture was stirred overnight at room temperature. The reaction mixture was then diluted with dichloromethane (100 mL), washed sequentially with water (50 mL), 2N HCl (50 mL), saturated sodium bicarbonate (50 mL), and brine. The organic layer was evaporated in vacuo, and the resulting crude material was purified by flash chromatography (30% ethyl acetate/heptane) to give compound 198 (800 mg, 18%). $^1$H NMR (CDCl$_3$): δ 7.6 (s, 2H), 7.22 (s, 2H), 6.78 (s, 1H), 6.6 (s, 1H), 5.62 (t, 1H), 5.18 (s, 1H), 2.98-3.02 (m, 2H), 2.4-2.6 (m, 16H), 1.6-1.8 (m, 16H), 0.92-1.02 (m, 24H).

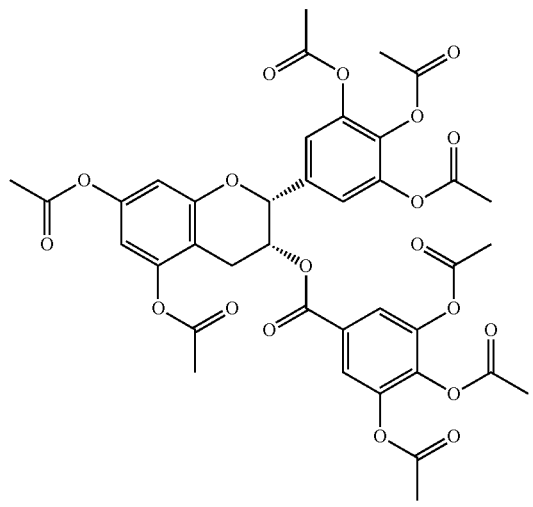 [SMILES: CC(=O)Oc1cc(OC(C)=O)c2c(c1)O[C@H](c1cc(OC(C)=O)c(OC(C)=O)c(OC(C)=O)c1)[C@H](OC(=O)c1cc(OC(C)=O)c(OC(C)=O)c(OC(C)=O)c1)C2]

Compound 197: [(2R,3R)-5,7-diacetoxy-2-(3,4,5-triacetoxyphenyl)chroman-3-yl] 3,4,5-triacetoxybenzoate Acetic anhydride (6.1 mL) was added dropwise to epigallocatechin gallate (2.0 g) in pyridine (20 mL) at 0° C., and the resulting mixture was stirred overnight at room temperature. Water was added to the reaction mixture, and the solid was filtered and washed with aq. 1N HCl (10 mL) and heptane (20 mL). The solid was then dissolved in dichloromethane and passed through a silica gel filter column with dichloromethane as a mobile phase to furnish compound 199 (1.0 g, 28%) upon evaporation of volatiles. $^1$H NMR (CDCl$_3$): δ 7.6 (s, 2H), 7.2 (s, 2H), 6.75 (s, 1H), 6.6 (s, 1H), 5.6 (t, 1H), 5.19 (s, 1H), 2.98-3.02 (m, 2H), 2.18-2.28 (m, 24H).

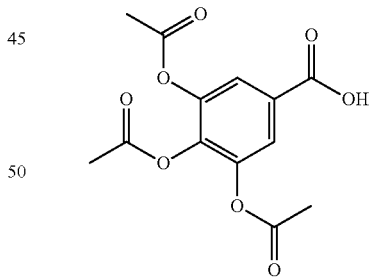

Compound 199: 3,4,5-triacetoxybenzoic acid

Acetic anhydride (1.65 mL, 17.6 mmol) was added dropwise to a stirred solution of gallic acid (0.300 g, 1.76 mmol) in anhydrous pyridine (1.41 mL, 17.6 mmol) at 0° C. under N$_2$ atmosphere. The resulting stirred solution was left to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% acetonitrile in water) and fractions were concentrated by rotary evaporation to yield compound 201 (0.259 g, 49.7% yield) as a white solid. ¹H-NMR (DMSO-d6, 400 MHz): δ 13.44 (s, 1H), 7.75 (s, 1H), 2.33 (s, 3H), 2.30 (s, 6H). LC-MS: 319.0 (M+Na)+

Compound 201: 3,4,5-tris(propanoyloxy)benzoic acid

This compound was prepared following a modified procedure described for compound 199. LCMS (M–H–) 337.1. ¹H NMR (400 MHz, DMSO-d6) δ 13.43 (s, 1H), 7.75 (s, 2H), 2.62 (m, 6H), 1.13 (m, 9H)

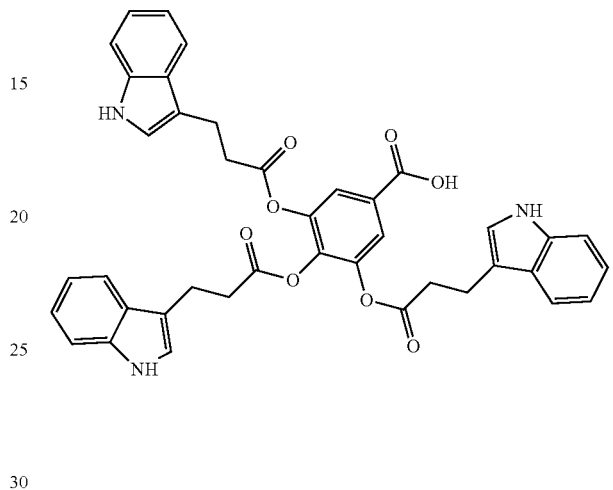

Compound 202: 3,4,5-tris({[3-(1H-indol-3-yl)propanoyl]oxy})benzoic acid

This compound was prepared following a modified procedure described for compound 199. LCMS: (m+H⁺) 684.2. ¹H NMR (400 MHz, DMSO-d6) δ 13.48 (s, 1H), 10.85 (d, 3H), 7.70 (s, 2H), 7.50 (dd, 3H), 7.38-7.29 (m, 3H), 7.13 (dd, 3H), 7.10-7.02 (m, 3H), 6.94 (m, 3H), 3.00 (m, 6H), 2.83 (m, 6H)

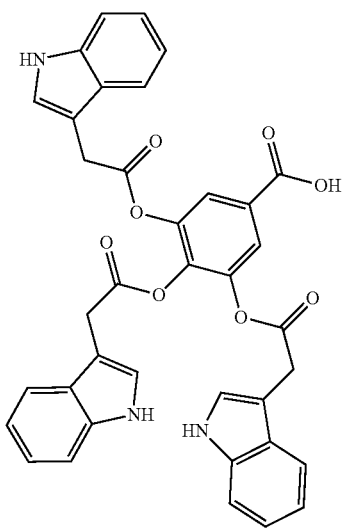 [SMILES: O=C(Cc1c[nH]c2ccccc12)Oc1cc(C(=O)O)cc(OC(=O)Cc2c[nH]c3ccccc23)c1OC(=O)Cc1c[nH]c2ccccc12]

Compound 200: 3,4,5-tris({[2-(1H-indol-3-yl)acetyl]oxy})benzoic acid

This compound was prepared following a modified procedure described for compound 63. LCMS: (M+H⁺) 642.2. ¹H NMR (400 MHz, DMSO-d6) δ 11.06 (dd, 3H), 7.65 (s, 2H), 7.46 (dd, 3H), 7.37 (dd, 3H), 7.22 (dd, 3H), 7.14-7.07 (m, 3H), 7.05-6.97 (m, 3H), 3.71 (s, 4H), 3.43 (s, 2H)

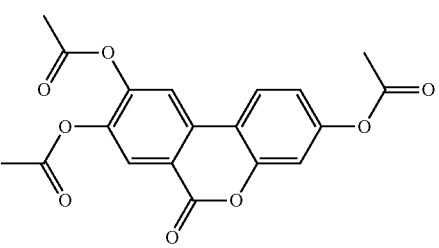

Compound 203: 6-oxo-6H-benzo[c]chromene-3,8,9-triyl triacetate

To a mixture of 3,8,9-trihydroxybenzo[c]chromen-6-one (0.3 g, 1.23 mmol, 1 eq) and acetyl acetate (501.67 mg, 4.91 mmol, 460.25 uL, 4 eq) in DCM (10 mL) was added triethylamine (TEA) (372.94 mg, 3.69 mmol, 512.98 uL, 3 eq). The mixture was stirred at 25° C. for 10 hours. TLC indicated one new spot was detected. The reaction mixture

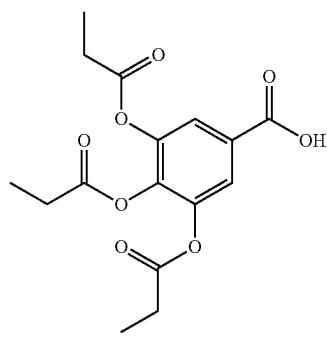 [SMILES: CCC(=O)Oc1cc(C(=O)O)cc(OC(=O)CC)c1OC(=O)CC]

was quenched by addition water 10 mL and extracted with EtOAc (10 mL×3). The combined organic layers were washed with brine 20 mL, dried over Na$_2$SO$_4$, filtered and concentrated under reduced pressure to give the residue. The residue was purified by column chromatography (SiO$_2$, Petroleum ether/Ethyl acetate=3/1 to 1:1). Compound (8,9-diacetoxy-6-oxo-benzo[c]chromen-3-yl) acetate (0.36 g) was obtained as a gray solid. LCMS: (M+H$^+$): 371.0 $^1$H NMR (400 MHz, CDCl$_3$) δ 8.2 (s, 1H), 9.9 m, 2H), 7.1 (m, 2H), 2.3 (s, 9H).

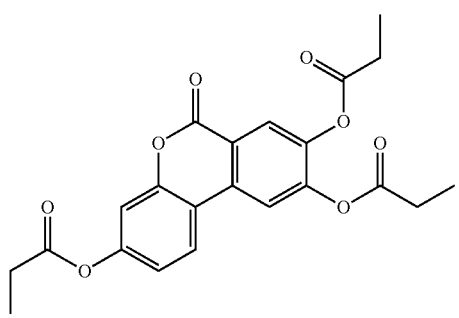 [SMILES: CCC(=O)Oc1ccc2c(c1)oc(=O)c1cc(OC(=O)CC)c(OC(=O)CC)cc12]

Compound 204: [6-oxo-8,9-di(propanoyloxy)benzo[c]chromen-3-yl] propanoate

Propionic anhydride (2.61 mL, 20.4 mmol) was added dropwise to a stirred solution of urolithin C (0.5 g, 2.04 mmol) in anhydrous pyridine (4.92 mL, 61.2 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HCl (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 204 (0.05 g, 6% yield) as a pink solid. $^1$H NMR (DMSO-d6, 400 MHz): δ 8.4 (s, 1H), 8.35 (d, 1H), 8.14 (s, 1H), 7.31 (d, 1H), 7.23 (m, 1H), 2.73-2.63 (m, 6H), 1.21-1.14 (m, 9H) ppm Compound 205: [8,9-di(octanoyloxy)-6-oxo-benzo[c]chromen-3-yl] octanoate To a solution of 3,8,9-trihydroxybenzo[c]chromen-6-one (0.3 g) in acetonitrile (10 mL) was added K$_2$CO$_3$ (0.68 g) followed by octanoyl chloride (0.8 g). The resulting mixture was stirred at 50° C. for 24 hours. Additional octanoyl chloride (0.8 g) was added and the mixture was stirred at 50° C. for 12 hours. The reaction mixture was quenched by addition of water (10 mL) and extracted three times with ethyl acetate (10 mL). The combined organic layers were dried over Na$_2$SO$_4$, filtered and concentrated under reduced pressure. The residue was purified by column chromatography (SiO$_2$, petroleum ether/ethyl acetate, 9:1 to 1:1) to give [8,9-di(octanoyloxy)-6-oxo-benzo[c]chromen-3-yl]octanoate (0.45 g, 55.5%) as a white solid. $^1$H NMR (400 MHz, CDCl$_3$): δ 8.186 (s, 1H), 7.926 (d, 1H), 7.908 (s, 1H), 7.157-7.096 (m, 2H), 2.621-2.573 (m, 6H), 1.79-1.75 (6H, m), 1.5-1.25 (m, 24H), 0.916-0.878 (m, 9H) ppm

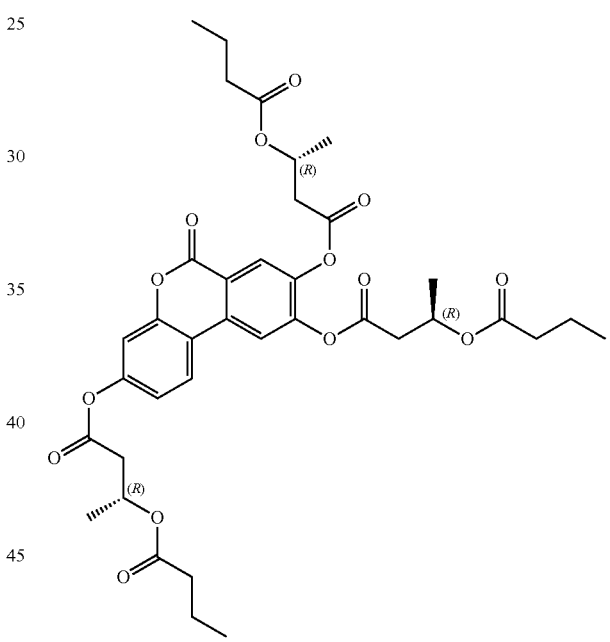

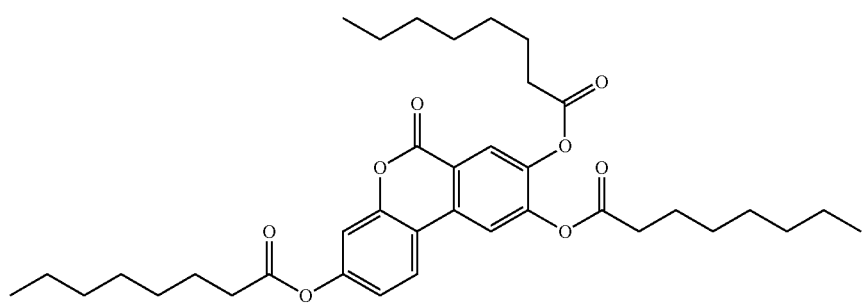 [SMILES: CCCCCCCC(=O)Oc1ccc2c(c1)oc(=O)c1cc(OC(=O)CCCCCCC)c(OC(=O)CCCCCCC)cc12]

189

Compound 206: 8,9-bis({[(3R)-3-(butanoyloxy)butanoyl]oxy})-6-oxo-6H-benzo[c]chromen-3-yl (3R)-3-(butanoyloxy)butanoate This compound was prepared following a modified procedure described for compound 203.

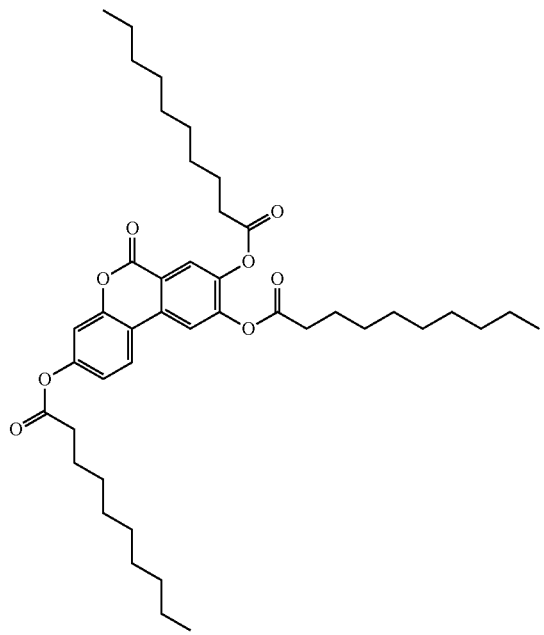 [SMILES: CCCCCCCCCC(=O)Oc1ccc2c(c1)oc(=O)c1cc(OC(=O)CCCCCCCCC)c(OC(=O)CCCCCCCCC)cc12]

Compound 207: 8,9-bis(decanoyloxy)-6-oxo-6H-benzo[c]chromen-3-yl decanoate

This compound was prepared following a modified procedure described for compound 203.

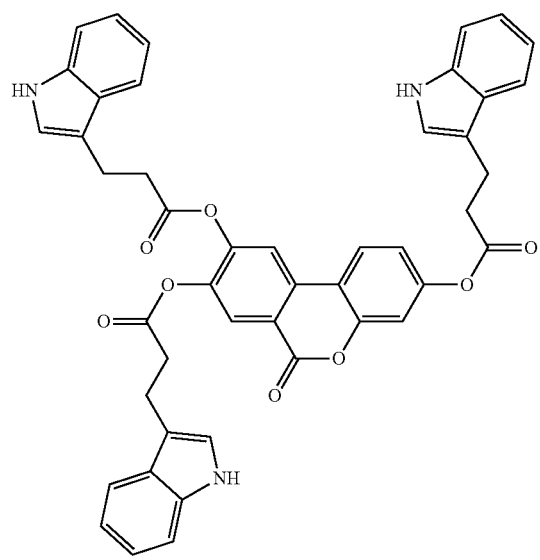 [SMILES: O=C(CCc1c[nH]c2ccccc12)Oc1ccc2c(c1)oc(=O)c1cc(OC(=O)CCc3c[nH]c4ccccc34)c(OC(=O)CCc3c[nH]c4ccccc34)cc12]

190

Compound 208: 8,9-bis({[3-(1H-indol-3-yl)propanoyl]oxy})-6-oxo-6H-benzo[c]chromen-3-yl 3-(1H-indol-3-yl)propanoate This compound was prepared following a modified procedure described for compound 63.

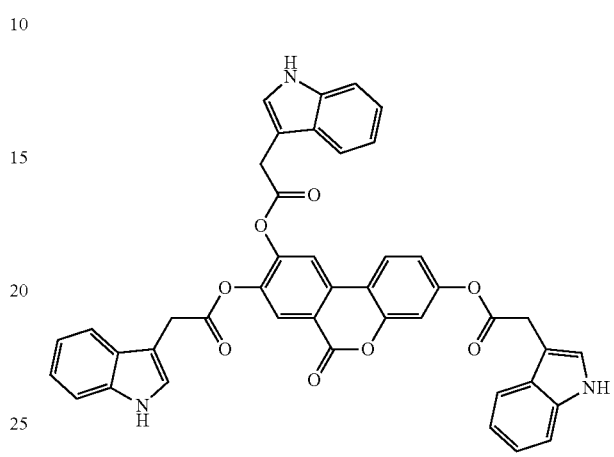

Compound 209: 8,9-bis({[2-(1H-indol-3-yl)acetyl]oxy})-6-oxo-6H-benzo[c]chromen-3-yl 2-(1H-indol-3-yl)acetate This compound was prepared following a modified procedure described for compound 63.

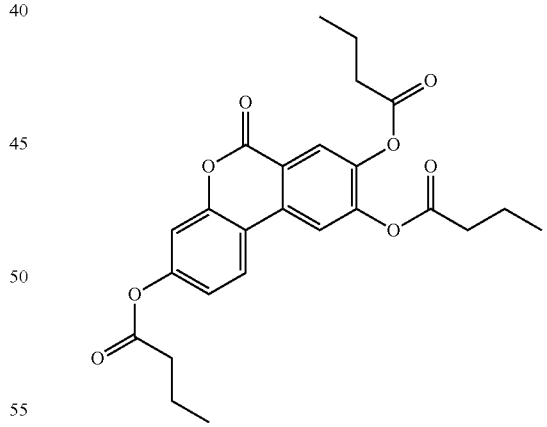

Compound 210: 8,9-bis(butanoyloxy)-6-oxo-6H-benzo[c]chromen-3-yl butanoate

This compound was prepared following a modified procedure described for compound 203.

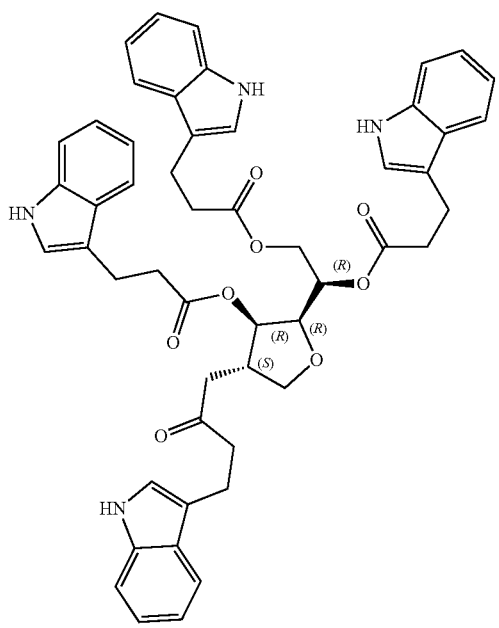

Compound 211: (1R)-1-[(2R,3R,4S)-3,4-bis({[3-(1H-indol-3-yl)propanoyl]oxy})oxolan-2-yl]-2-{[3-(1H-indol-3-yl)propanoyl]oxy}ethyl 3-(1H-indol-3-yl)propanoate This compound was prepared following a modified procedure described for compound 63.

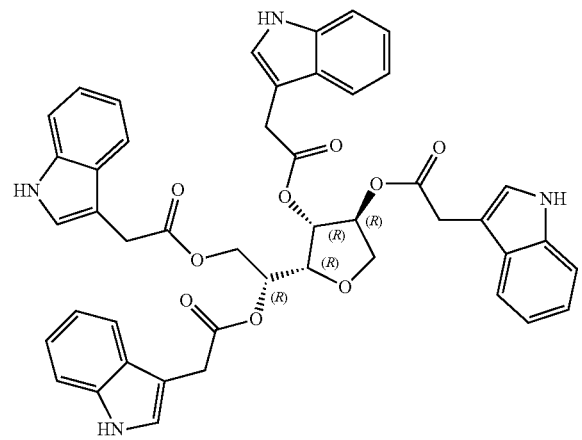

Compound 212: (1R)-1-[(2R,3R,4S)-3,4-bis({[2-(1H-indol-3-yl)acetyl]oxy})oxolan-2-yl]-2-{[2-(1H-indol-3-yl)acetyl]oxy}ethyl 2-(1H-indol-3-yl)acetate This compound was prepared following a modified procedure described for compound 63.

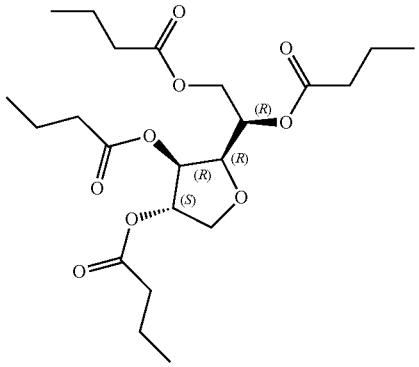

Compounds 213: (1R)-1-[(2R,3R,4S)-3,4-bis(butanoyloxy)oxolan-2-yl]-2-(butanoyloxy)ethyl butanoate This compound was prepared following a modified procedure described for compound 203.

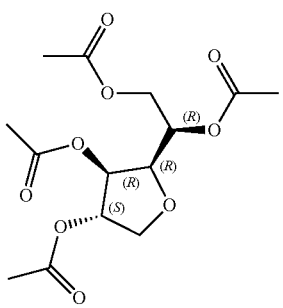

Compound 214: (1R)-2-(acetyloxy)-1-[(2R,3R,4S)-3,4-bis(acetyloxy)oxolan-2-yl]ethyl acetate This compound was prepared following a modified procedure described for compound 203.

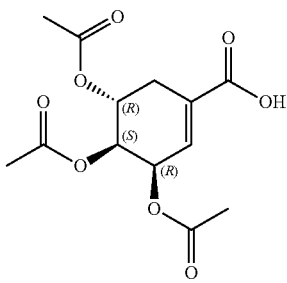

Compound 215: (3R,4S,5R)-3,4,5-triacetoxycyclohex-1-ene-1-carboxylic acid

Acetic anhydride (1.61 mL, 17.2 mmol) was added dropwise to a stirred solution of shikimic acid (0.300 g, 1.72 mmol) in anhydrous pyridine (1.38 mL, 17.2 mmol) at 0° C. under $N_2$ atmosphere. The resulting stirred solution was left to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% acetonitrile in water) and fractions were concentrated by rotary evaporation to yield compound 43 (0.18 g, 34.8% yield) as a white solid. $^1$H-NMR (DMSO-d6, 400 MHz): δ 12.90 (s, 1H), 6.61 (dt, 1H), 5.60 (m, 1H), 5.18 (dd, 1H), 5.12 (dt, 1H), 2.76 (m, 1H), 2.35 (m, 1H), 2.04 (s, 5H), 2.01 (s, 3H). LC-MS: 299.1 (M−H)$^−$

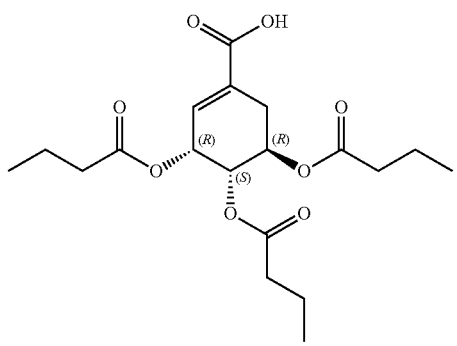

Compound 218: (3R,4S,5R)-3,4,5-tris(butanoyloxy)cyclohex-1-ene-1-carboxylicacid

This compound was prepared following a modified procedure described for compound 215.

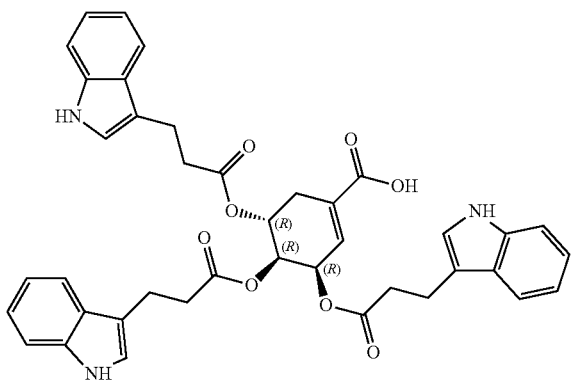

Compound 216: (3R,4S,5R)-3,4,5-tris({[3-(1H-indol-3-yl)propanoyl]oxy})cyclohex-1-ene-1-carboxylic acid This compound was prepared following a modified procedure described for compound 63.

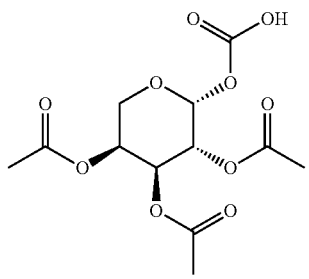

Compound 219: (2R,3R,4S,5S)-tetrahydro-2H-pyran-2,3,4,5-tetrayltetraacetate

L-Arabinose (50 g), N,N-dimethylpyridin-4-amine (6 g), and triethylamine (367 mL) were dissolved in 700 mL DCM and stirred at 0° C. under N$_2$. Acetic anhydride (217 mL) was added dropwise over 30 minutes and the reaction mixture was stirred overnight. The solvent was removed under reduced pressure and the residue was redissolved in ethyl acetate, washed with 1M HCl, H$_2$O and brine, dried over MgSO$_4$ and evaporated. Purification on normal phase with 0-100% ethyl acetate in hexanes gave Compound 53 as a waxy/amorphous solid (50% yield). 1H-NMR (DMSO-CDCl$_3$, 400 MHz): δ 6.35 (d, 1H), 5.37 (m, 3H), 4.06 (dd, 1H), 3.82 (dd, 1H), 2.155 (s, 3H) 2.15 (s, 3H), 2.02 (s, 6H). LC-MS: 341.1 (M+Na)$^+$ Example 2. In Vitro Assays Acylated active agents disclosed herein may be stable under a range of physiological pH levels and cleaved selectively at a desired site of action (for example, in the GI tract, e.g., in the stomach, small intestine, or large intestine) by enzymes present in the local microenvironment. Acylated active agents are tested for chemical stability at a range of pH levels as well as their ability to be degraded in representative in vitro systems. Data for select acylated active agents are shown below.

Assay 1. Stability of acylated active agents in Simulated Gastric Fluid (SGF). This assay was used to assess the stability of an acylated active agent in a stomach.

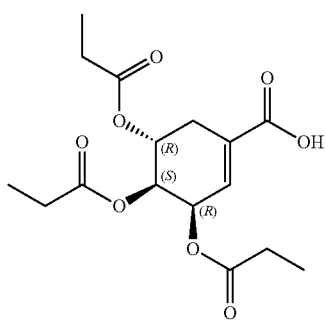

Compound 217: (3R,4S,5R)-3,4,5-tris(propanoyloxy)cyclohex-1-ene-1-carboxylic acid This compound was prepared following a modified procedure described for compound 215.

Medium was prepared by dissolving 2 g of sodium chloride in 0.6 L in ultrapure water (MilliQ®, Millipore Sigma, Darmstadt, Germany). The pH was adjusted to 1.6 with 1N hydrochloric acid, and the volume was then adjusted to 1 L with purified water.

60 mg FaSSIF powder (Biorelevant™, London, UK) were dissolved in 500 mL buffer (above). Pepsin was added (0.1 mg/mL) (Millipore Sigma, Darmstadt, Germany), and the solution was stirred. The resulting SGF media were used fresh for each experiment.

Test compounds were dissolved in DMSO stock to 1 mM. An aliquot of the DMSO stock solution was removed and diluted in the SGF Media in 15 mL falcon tubes to generate a total compound concentration of 1 µM. A 1 mL aliquot was immediately removed and diluted once with 1 volume of acetonitrile for T0 timepoint. The mixture was sealed and mixed at 37° C. in an incubator. Aliquots (1 mL) were removed at regular intervals and immediately quenched by the addition of 1 volume of acetonitrile. The resulting samples were analyzed by LC/MS to determine degradation rates in SGF.

Assay 2. Stability of acylated active agents in Simulated Intestinal Fluid (SIF). This assay was used to assess the stability of an acylated active agent in a small intestine.

Phosphate buffer was prepared by dissolving 0.42 g of sodium hydroxide pellets and 3.95 g of monobasic sodium phosphate monohydrate and 6.19 g of sodium chloride in ultrapure water (MilliQ®, Millipore Sigma, Darmstadt, Germany). The pH was adjusted to 6.7 using aq. HCl and aq. NaOH, as necessary, and the solution was diluted with ultrapure water to produce 1 L of the pH 6.7 buffer.

112 mg FaSSIF powder (Biorelevant™, London, UK) was dissolved in 50 mL of the pH 6.7 buffer. 2 to 3 mL of the resulting solution were then added to 500 mg pancreatin (Millipore Sigma, Darmstadt, Germany). The resulting mixture was agitated by finger tapping the vessel containing the mixture until milky suspension formed. At this time, the remainder of the 50 mL FaSSiF/pH 6.7 buffer solution was added. The resulting suspension was flipped upside down 10 times to produce SIF, which was used fresh.

Test compounds were dissolved in DMSO stock to 1 mM. An aliquot of the DMSO stock solution was removed and diluted in the SIF media in 15 mL falcon tubes to produce a mixture with a tested compound concentration of 1 µM. A 1 mL aliquot was immediately removed and diluted once with 1 volume of acetonitrile for T0 timepoint. The mixture was sealed and agitated at 37° C. in an incubator. Aliquots (1 mL) were removed at regular intervals and immediately quenched by the addition of 1 volume of acetonitrile. The resulting samples were analyzed by LC/MS to determine degradation rates.

Assay 3. In vitro Colonic Material Stability Assay. This assay was used to assess the stability of an acylated active agent in a large intestine. All experiments were performed in an anaerobic chamber containing 90% nitrogen, 5% hydrogen and 5% carbon dioxide. Colonic material was resuspended as a slurry (15% w/v final concentration) in pre-reduced, anaerobically sterilized dilution blanks (Anaerobe Systems AS-908). The colonic material was then inoculated into 96 well plates containing YCFAC media (Anaerobe Systems AS-680) or other suitable media (6.7 µL slurry into 1 mL total media). Compounds or groups of compounds were added to each individual well to reach final analyte concentration of 1 or 10 µM, and the material was mixed by pipetting. Sample was removed after set timepoints (0, 120, 240, 480, 1440, 2880 minutes after initiation of the assay), quenched with acetonitrile containing internal standard, and analyzed by LC/MS.

Buffer Assay. Stability of acylated active agents in a buffer. This assay provides for the assessment of the stability of an acylated active agent at different physiological pH levels.

Compounds are diluted in DMSO, and added in the appropriate quantity to phosphate buffer (pH levels 2, 4, 6, and 8) to reach a total sample concentration of 2 µM. Compounds are incubated at RT, and aliquots are removed at time points 0, 60, 120, 360 and 1440 minutes and analyzed for purity by LC/MS/MS.

TABLE 1

| Compound | Assay 1 (SGF) (% Remaining @ 1 hour) | Assay 2 (SIF) (% @ Remaining 4 hours) | Assay 3 (% Remaining at 24 h) |
|---|---|---|---|
| 1 |  | C | B |
| 2 | C | A | A |
| 4 | C | A |  |
| 5 |  | B |  |
| 8 | C | A |  |
| 9 | C | A |  |
| 10 | B | A |  |
| 11 | C |  |  |
| 12 | C | A |  |
| 13 | B | A |  |
| 14 | C | A | C |
| 16 |  | C | C |
| 17 |  | A |  |
| 18 | C | B | C |
| 19 | C | B | B |
| 21 | C | C | B |
| 22 | C | B | B |
| 23 |  | B | C |
| 25 | C | C |  |
| 26 | C | A |  |
| 27 | C | B |  |
| 28 | C |  |  |
| 29 | C |  | C |
| 31 | C | A |  |
| 32 |  | B | C |
| 36 |  | C | C |
| 38 |  | C | C |
| 39 | C | B | C |
| 40 | C | C | C |
| 41 | C | C |  |
| 42 |  | C |  |
| 45 |  | A | A |
| 46 | C | A | A |
| 47 | C | A | A |
| 48 |  |  |  |
| 49 | Run 1: B, Run 2: C | A | A |
| 50 | C | A | A |
| 51 | C | C | B |
| 52 | B | B | B |
| 53 | C | B | C |
| 54 | B | A | A |
| 55 | C | A | A |
| 56 |  | A | A |
| 57 | C | A | A |
| 58 |  | A | A |
| 59 |  | A | A |
| 60 |  | A | A |
| 61 |  | A | A |
| 62 | C | A | C |
| 64 |  | A | A |
| 68 | C | A | B |
| 69 | B | A | A |
| 70 | B | A | Run 1: A, Run 2: B |
| 71 | B | A | A |
| 72 | C | B | A |
| 73 | C | A | A |
| 74 | C | A | A |

TABLE 1-continued

| Compound | Assay 1 (SGF) (% Remaining @ 1 hour) | Assay 2 (SIF) (% @ Remaining 4 hours) | Assay 3 (% Remaining at 24 h) |
|---|---|---|---|
| 75 | C | | |
| 76 | C | A | A |
| 77 | C | C | A |
| 78 | B | A | A |
| 80 | C | A | A |
| 81 | B | A | |
| 83 | C | A | A |
| 84 | C | A | A |
| 85 | B | A | A |
| 86 | B | | A |
| 87 | B | | A |
| 88 | | A | A |
| 90 | C | B | A |
| 91 | C | A | A |
| 92 | C | A | A |
| 93 | C | A | A |
| 94 | C | A | A |
| 95 | B | | |
| 96 | C | A | A |
| 97 | B | | A |
| 98 | B | A | A |
| 99 | B | | A |
| 100 | B | | A |
| 101 | C | A | A |
| 102 | C | B | A |
| 103 | C | A | A |
| 104 | C | A | A |
| 105 | C | B | B |
| 106 | C | A | A |
| 107 | B | A | B |
| 108 | C | A | A |
| 109 | C | A | A |
| 110 | C | A | |
| 111 | C | A | A |
| 112 | C | A | A |
| 113 | C | A | C |
| 114 | C | A | A |
| 115 | C | A | A |
| 116 | C | | |
| 117 | C | A | A |
| 118 | C | A | |
| 119 | | A | |
| 120 | | A | |
| 121 | | A | |
| 122 | | A | |
| 123 | Batch 1: C; Batch 2: B | C | A |
| 124 | C | A | |
| 125 | C | A | |
| 126 | C | A | A |
| 127 | C | B | |
| 128 | C | | |
| 129 | C | A | |
| 130 | C | A | |
| 131 | | A | |
| 132 | C | | |
| 136 | C | A | |
| 141 | | C | |
| 147 | | | A |
| 149 | B | A | A |
| 150 | | A | A |
| 151 | C | A | |
| 158 | | A | A |
| 159 | | C | |
| 161 | C | C | B |
| 162 | C | A | C |
| 163 | C | C | B |
| 165 | B | A | A |
| 166 | B | A | A |
| 167 | B | A | A |
| 168 | B | A | A |
| 169 | C | C | |
| 170 | B | A | A |
| 171 | C | A | |
| 172 | C | A | B |
| 173 | C | A | |
| 174 | C | | |
| 175 | | A | |
| 176 | | A | |
| 177 | C | | |
| 181 | C | A | |
| 182 | | A | |
| 183 | | B | B |
| 184 | | B | |
| 185 | C | B | B |
| 186 | C | A | A |
| 188 | | A | |
| 189 | | | B |
| 192 | | | B |
| 193 | C | A | A |
| 194 | B | A | A |
| 195 | C | | |
| 197 | | | A |
| 198 | | | Runs 1 and 2: C; Run 3: B |
| 199 | C | B | |
| 200 | C | A | A |
| 201 | C | A | A |
| 202 | A | C | |
| 203 | | B | |
| 204 | C | A | |
| 208 | | B | B |
| 210 | | | A |
| 215 | | | B |
| 216 | B | B | |
| 217 | | | B |
| 218 | | | B |
| 219 | C | A | A |

In Table 1, A: <25% of the tested compound remaining; B: 25-75% of the tested compound remaining; and C: >75% of the tested compound remaining.

Table 1 shows that, for example, compounds 2, 4, 8-10, 12-14, 18, 19, 22, 26, 27, 31, 39, and 221 can be selectively delivered to the upper intestine.

Example 3. In Vivo Evaluation of an Acylated Active Agent

Acylated active agents disclosed herein may be useful in modulating autoimmunity markers and for treating autoimmune disorders. This example demonstrates the capability of an exemplary acylated active agent, compound 2, to induce CD4$^+$CD25$^+$ Treg cells (an autoimmunity marker) in a subject.

C57BU6 mice were divided into seven cohorts, as listed in Table 2.

TABLE 2

| Model | Treatment* | # of animals | Dose** | Frequency | Route |
|---|---|---|---|---|---|
| HFD-fed C57BL/6 mice | ND | 10 | | Ad libitum | Diet |
| | HFD | 10 | | Ad libitum | Diet |
| | HFD + Acetate | 10 | 5% | Ad libitum | Diet |
| | HFD + EGCG | 10 | 1% | Ad libitum | Diet |
| | HFD + Acetate + EGCG | 10 | 5% + 1% | Ad libitum | Diet |
| | Compound 2 (EGCG-8A) | 10 | 6% | Ad libitum | Diet |
| | HFD + rosiglitazone | 10 | 0.45 mg/g | Ad libitum | Diet |

*In Table 2, ND means normal diet, HFD means high-fat diet, and EGCG means epigallocatechin gallate.
**In Table 2, dose percentages refer to weight percentage relative to the high fat diet.

The results of this study are illustrated in the FIG. 1, which shows a synergistic anti-inflammatory effect of Compound 2 in animals fed a high-fat diet, as compared to the administration of EGCG, acetate, or their combination as separate compounds.

Example 4. Impact of Compounds on Inflammatory Signals in Primary Human Peripheral Blood Mononuclear Cells (PBMCs)

Human donor blood (8 mL) was collected in sodium citrate CPT tubes and centrifuged at 1,600×g for 20 minutes at room temperature. Buffy coat containing PBMCs was collected and transferred to a 50 mL conical tube containing 30 mL of RPMI-1640 medium at room temperature (supplemented with penicillin-streptomycin). PBMCs samples were centrifuged at 400×g for 10 minutes at 10° C. The pelleted PBMCs were washed twice in 10 ml of RPMI-1640 medium (supplemented with penicillin-streptomycin), then resuspended in RPMI-1640 medium (supplemented with penicillin-streptomycin, fetal bovine serum, and L-Glutamine). PBMCs were filtered through a 70 micron mesh to remove any cellular debris. The volume was adjusted to achieve 1.66×10$^6$ cells/mL, from which 180 µl (300,000 PBMCs) were added into each well in a 96-well plate (sterile, tissue culture treated, round bottom). PBMCs in a 96-well plate were rested for 30 minutes in a 37° C., 5% CO$_2$ incubator, then subsequently treated with 10 µl of indicated compound. After 2 hours 10 µL of LPS (0111:B4) 1 mg/mL was added to test wells. After 24 hours of incubation at 37° C., 5% CO$_2$ 100 µL of cell supernatant was collected and transferred to a 96-well plate (non-tissue treated, flat bottom). The plate was centrifuged at 350×g for 5 minutes at room temperature, and then the clear supernatant transferred to a new 96-well plate (non-tissue treated, flat bottom). The remaining cells were tested for viability using CellTiter-Glo® Luminescent Cell Viability Assay (Promega). The supernatant was analyzed for TNFα, IL-6 and IL-1β (kit LXSAHM-03; R&D Systems), using Luminex Immunoassay Technology (MAG-PIX System). Cytokine levels of LPS treated DMSO control samples were set to 100%, and compound treated samples were expressed relative to this (Table 3).

TABLE 3

| Compound | Concentration (uM) | TNFα % of DMSO control | IL6 % DMSO control | IL1β % DMSO control |
|---|---|---|---|---|
| Propionate | 100 | + | + | + |
| Arabinose | 100 | + | + | = |
| butanediol | 100 | = | = | = |
| Beta-hydroxybutyrate (BHB) | 100 | − | = | − |
| Butyrate | 100 | ++ | + | − |
| Acetate | 100 | = | = | = |
| Quercitin | 100 | + | + | + |

(−) >110% DMSO;
(=) 90% > <110% DMSO
(+) 50% > <90% DMSO
(++) <50% DMSO

These data demonstrate that acylated active agents (e.g., those including propionate, butyrate, arabinose, and/or quercetin) can modulate autoimmunity markers (e.g., reduce TNFα, IL6, and/or IL10 levels).

Example 5. In Vivo Assessment of Compounds in DSS Colitis

Figure 2:
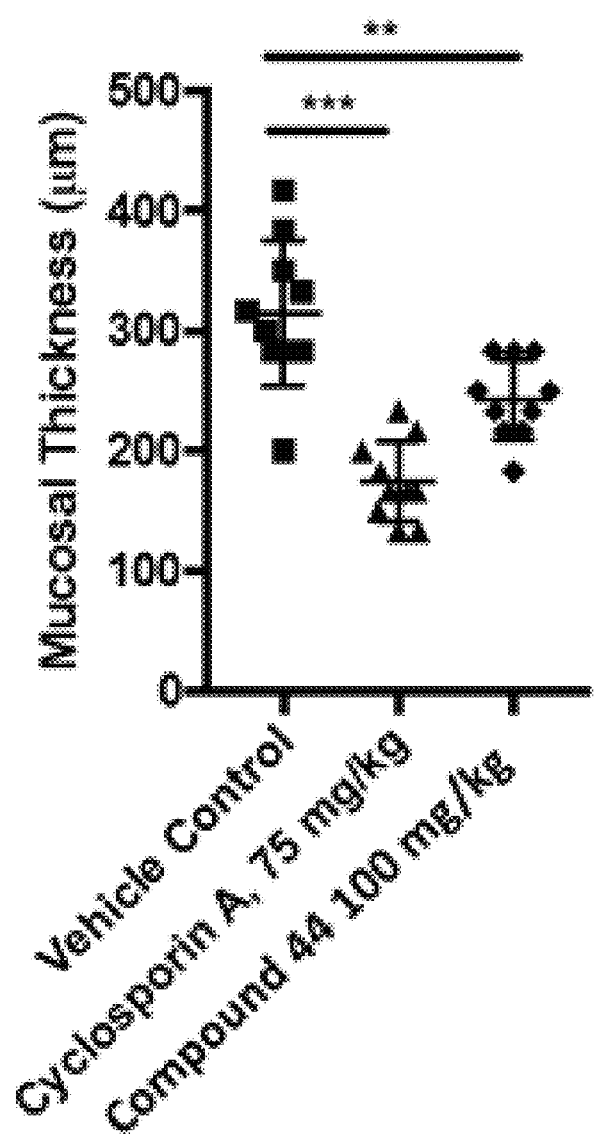
FIG. 2 is a chart showing changes in the mucosal thickness in mice following the treatment with a vehicle control (methylcellulose), cyclosporine A, or compound 44.

Specific pathogen-free female Swiss Webster mice, 6-8 weeks old, weighing 16-20 g were obtained from Harlan. Mice were randomized into treatment groups (n=10) based on body weight on study day −2. From study day 0 through 5, all groups were given 3% dextran sulfate sodium (DSS, Spectrum, Lot #2DC0020) in drinking water. On study day 5 through, drinking water was switched to water without DSS until the study end on day 7. From study day 0 through 7, the negative control (vehicle), positive control (cyclosporine A), and the treatment groups were given vehicle (1% Methylcellulose (Sigma, 400 cP)), cyclosporine A (70 mg/kg), and compound 44 (100 mg/kg) once a day until study day 7 via oral gavage. On study day 7, animals were anesthetized with Isoflurane and bled to exsanguination followed by cervical dislocation. The entire colon was removed and the overall efficacy of compound 44 was assessed based on colon histopathology. At the end of the study, colon histopathology showed significant reduction in mucosal thickness by compound 44 compared to the vehicle control (FIG. 2). Statistical analysis was performed with GraphPad Prism (GraphPad Software). Mann-Whitney U test was used to assess significance between the vehicle control and each treatment group.

This data is relevant to immune mediated IBD, driven primarily though T cell biology. A positive result in this pharmacology in vivo study suggests efficacy in human IBD.

Example 6: Adoptive T-cell Transfer Study

Figure 3A:
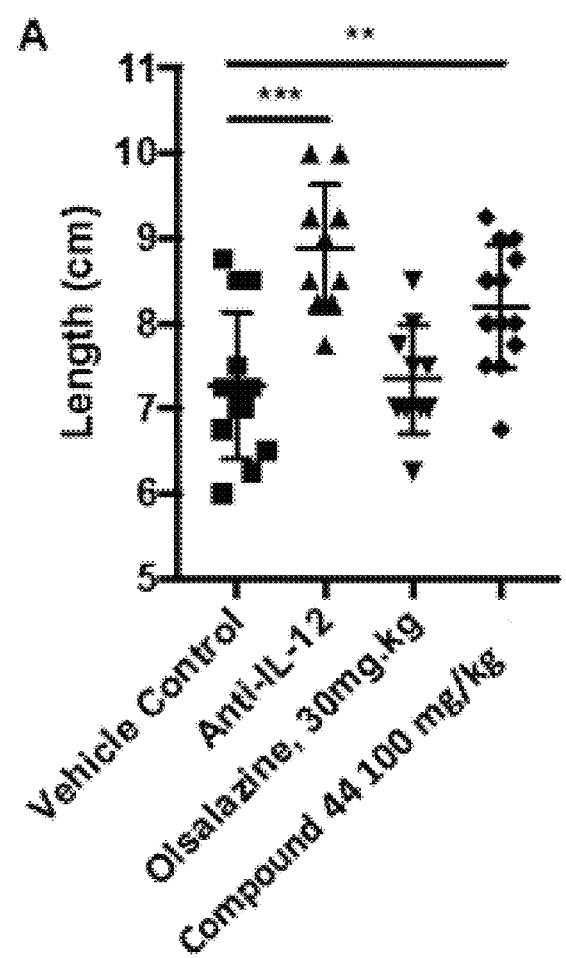
FIG. 3A is a chart showing the colon lengths measured in colon samples from adoptive T-cell transfer mice treated with a vehicle (methyl-cellulose), anti-IL12 antibody (positive control), olsalazine (positive treatment group), or compound 44 (test treatment group). Data are presented as mean±SEM; *p<0.05 and **p<0.01 were considered to be statistically significant.
Figure 3B:
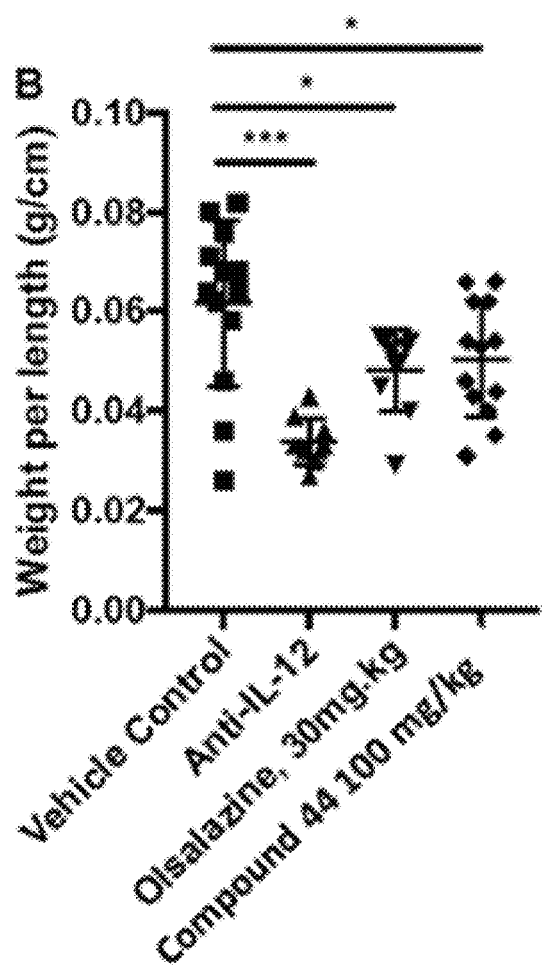
FIG. 3B is a chart showing the colon weight per unit length measured in colon samples from mice treated with a vehicle (methyl-cellulose), anti-IL12 antibody (positive control), olsalazine (positive treatment group), or compound 44 (test treatment group). Data are presented as mean±SEM; *p<0.05 and ***p<0.001 were considered to be statistically significant.

On study day 0, naïve T-cells were obtained from the spleen of 11 to 12 week-old Balb/C mice using the SCID Cell Separation Protocol with the following labelling scheme; CD4$^+$CD45RB$^{high}$CD25− and CD4$^+$CD45RB$^{low}$CD25+ cell (APC CD4 Antibody (100412), FITC CD45R$^B$ Antibody (103306), PE CD25 Antibody (101904), from BioLegend, San Diego, Calif., and CD4 cell enrichment kit: 19752A, Stemcell Technologies, Cambridge, Mass.) and the 4×10$^5$ of CD4$^+$CD45RB$^{high}$CD25− cells were transferred 6-7 weeks old CB-17 SCID mice. Recipient mice were randomized based on their body weight (n=12 mice/group), and received 200 ml of vehicle (0.5% methyl-cellulose) (vehicle control), 0.5 mg per mouse of anti-IL-12 (positive control), 30 mg/kg of olsalazine (positive treatment group), and 100 mg/kg of compound 44 (compound treatment group) through day 42. On day 42, animals were anesthetized with Isoflurane and bled to exsanguination followed by cervical dislocation. The entire colon was removed and the overall efficacy of compound 44 was assessed based on colon length and weight per length. At the end of the study, colon length (FIG. 3A) and weight per length (FIG. 3B) were significant increased and reduced, respectively by compound 44 compared to the vehicle control, whereas olsalazine significantly increased the colon weight per length, but not the colon length. Statistical analysis was performed with GraphPad Prism (GraphPad Software). Mann-Whitney U test was used to assess significance between the vehicle control and each treatment group.

This data is relevant to immune mediated IBD, driven primarily though T cell biology. A positive result in this pharmacology in vivo study suggests efficacy in human IBD.

Example 7: Neutrophil Chemokine Production Assay

A volume 25 mL of human blood was layered over 15 mL of Histopaque-1077 and centrifuged at 500 g, RT, for 30 min with no break applied to the centrifuge. The PBMC band and Histopaque-1077 layer were removed leaving behind the bottom red layer which was mixed with 40 mL of 1× red blood cell (RBC) lysis buffer (Sigma-Aldrich) was and split into two 50 mL tubes. The volume for both fractions was brought to 50 mL with RBC lysis buffer, mixed by inversion, and then incubated at RT for 10 min. Solutions were centrifuged at 250 g, for 10 min at RT and the supernatant liquids removed. The reddish pellets were re-suspended in 1 mL of RBC lysis buffer and combined. The cell suspension was incubated for 5 min at RT in RBC lysis buffer. After incubation 45 mL of Hanks Balanced Salt Solution with no calcium, magnesium or phenol red (HBSS−) was added, the cell suspension was spun (250 g for 10 min at RT), and supernatant liquids were removed. The white pellet was re-suspended in 1 mL of HBSS−, and cell counts were determined. The neutrophil cell suspension was brought to a concentration of 1.11e6 cells/mL in RPMI complete (Sigma-Aldrich), and 180 µL of cell suspension was transferred to all wells within a sterile 96-well tissue culture treated plate resulting in 2.0e5 cells/well. Test compounds were brought to a 20× concentration in RPMI with 2% DMSO, and 10 µL of compound solutions were added to wells respective for each compound and incubated for 30 min. After incubation, 10 µL of 2 µg/mL LPS solution in RPMI complete was added to each well except for control wells, which received an additional 10 µL of media. Cells were incubated for 12 h (37° C., 5% $CO_2$), after which plates were centrifuged at 250 g, RT, for 5 min and supernatant liquids were obtained and stored at −80° C. until analyzed via Luminex® Multiplex Assay for various chemokines and cytokines. Three data points were acquired from two different blood donors and averaged. Statistical analysis was performed using a two-tailed t-test comparing chemokine/cytokines production in the presence of each individual compound to the DMSO+ LPS positive control.

TABLE 4

| Compound | Conc. (µM) | % IL-8 (Vehicle + LPS = 100%) | % MIP-1α (Vehicle + LPS = 100%) | % MIP-1β (DMSO + LPS = 100%) |
| --- | --- | --- | --- | --- |
| acetate | 500.0 | − | + | + |
| acetate | 1000.0 | − | ++ | + |
| acetate | 3000.0 | +++ | +++ | +++ |
| L-arabinose | 500.0 | − | − | − |
| L-arabinose | 1000.0 | − | − | − |
| EGCG | 0.1 | − | − | − |
| EGCG | 1.0 | − | − | − |
| quercetin | 0.1 | − | − | − |
| quercetin | 1.0 | − | − | − |
| butanediol | 100.0 | − | − | + |
| butanediol | 500.0 | − | − | + |
| beta-hydroxybutyric acid | 200.0 | − | − | + |
| beta-hydroxybutyric acid | 2000.0 | + | ++ | + |
| butyrate | 500.0 | ++ | +++ | +++ |
| butyrate | 1000.0 | ++ | +++ | +++ |
| propionate | 500.0 | − | +++ | +++ |
| propionate | 1000.0 | ++ | +++ | +++ |
| propionate | 3000.0 | +++ | +++ | +++ |

Vehicle + LPS = 100%
− = >90% Vehicle
+ = <90% Vehicle
++ = <70% Vehicle
+++ = <50% Vehicle Neutrophils are the first response from the innate immune system. There is a clear link between neutrophil presence and disease activity in ulcerative colitis. IL-8/MIP1a and b are important CC chemokines produced from neutrophils. Compounds indicated in Table 4 reduce neutrophil production of these mediators and, therefore, may be useful in a variety of autoimmune disorders, e.g., inflammatory bowel disease, rheumatoid arthritis, and scleroses.

Example 8: Investigating AhR Activation in Caco-2 Cells Through CYP1A1 mRNA Expression Caco-2 cells from American Type Culture Collection (ATCC) were plated in a sterile tissue culture treated 96-well plate (ThermoFisher) at $8.0 \times 10^5$ cells per well, and grown overnight at 37° C., 5% $CO_2$ in DMEM complete (Gibco) in order to achieve confluence. After the incubation medium was aspirated off of the Caco-2 monolayers, tissues were then washed with 200 µL of warmed PBS solution, and subsequently 190 µL of pre-warmed growth medium was added to each well. Compounds of interest were diluted at a 20× concentration in growth medium containing 2% DMSO, and 10 µL of compound solutions were added to respective wells in triplicate. Compounds where incubated overnight at 37° C., 5% $CO_2$. 2-(1'H-indole-3'-carbonyl)-thiazole-4-carboxylic acid methyl ester (ITE) was used as the positive control for AhR activation at 1 and 100 µM concentrations. At the end of the incubation, medium was aspirated off of the Caco-2 cells, and the cells washed with 100 µL of cold PBS solution. RNA was extracted via the TaqMan™ Gene Expression Cells-to-$C_T$™ Kit (ThermoFisher) according to the manufacturers protocol. The QuantStudio 6 Flex (Applied Biosciences) was used to analyze mRNA levels of CYP1A1 using GAPDH as the endogenous control. TaqMan™ probe sets for both genes were acquired from ThermoFisher. Samples were run in triplicate and data was analyzed using the QuantStudio software and reported as linear (Table 1) and log 2(ΔΔCT) values. Statistical analysis was performed using a two-tailed t-test comparing CYP1A1 levels in the presence of each individual compound to the vehicle negative control.

Activation of AHR has been with associated with immune modulation and active compounds (+, ++, +++) may be beneficial in treating a variety of inflammatory and autoimmune diseases including ulcerative colitis, multiple sclerosis, rheumatoid arthritis.

TABLE 5

| | Conc. (µM) | Average CYP1A1 mRNA levels |
|---|---|---|
| vehicle control | N/A | − |
| acetate | 1000.0 | − |
| acetate | 3000.0 | − |
| L-arabinose | 1000.0 | − |
| EGCG | 0.1 | − |
| EGCG | 1.0 | − |
| quercetin | 0.1 | − |
| quercetin | 1.0 | + |
| butanediol | 500.0 | − |
| beta-hydroxybutyric acid | 2000.0 | − |
| butyrate | 1000.0 | − |
| butyrate | 3000.0 | − |
| propionate | 1000.0 | − |
| propionate | 3000.0 | − |
| Indole-3-acetic acid | 500.0 | − |
| Indole-3-acetic acid | 1000.0 | − |
| Indole-3-butyric acid | 500.0 | − |
| Indole-3-butyric acid | 1000.0 | − |
| Indole-3-propionic acid | 500.0 | − |
| Indole-3-propionic acid | 1000.0 | − |
| indole | 1000.0 | + |
| Indole-3-aldehyde | 1000.0 | + |
| indole-3-carbinol | 1000.0 | + |
| Indole-3-acetic acid | 500.0 | +++ |
| Indole-3-acetic acid | 1000.0 | ++ |
| Indole-3-carboxylic acid | 1000.0 | − |
| Indole-3-acrylic acid | 10.0 | +++ |
| Indole-3-acrylic acid | 100.0 | +++ |
| Indole-3-acrylic acid | 1000.0 | +++ |
| Indole-3-pyruvic acid | 10.0 | +++ |
| Indole-3-pyruvic acid | 100.0 | +++ |
| Indole-3-pyruvic acid | 1000.0 | +++ |
| ITE 1pM | 1.0 | +++ |
| Urolithin B | 10.0 | ++ |
| Urolithin B | 100.0 | +++ |
| Urolithin C | 10.0 | ++ |
| Urolithin C | 100.0 | ++ |
| 4-hydroxy-3-methylbenzoic acid | 10.0 | +++ |
| 4-hydroxy-3-methylbenzoic acid | 100.0 | +++ |
| Benzoic acid | 10.0 | + |
| Benzoic acid | 100.0 | + |
| Hydrocinnamic acid | 10.0 | + |
| Hydrocinnamic acid | 100.0 | + |
| L-tryptophan | 10.0 | ++ |
| L-tryptophan | 100.0 | +++ |
| D-tryptophan | 10.0 | ++ |
| D-tryptophan | 100.0 | +++ |
| L-homoserine | 5.0 | + |
| L-homoserine | 50.0 | + |
| L-arginine | 5.0 | + |
| L-arginine | 50.0 | + |
| Myricetin | 10.0 | + |
| Myricetin | 100.0 | ++ |
| Indole-3-lactic acid | 10.0 | + |
| Indole-3-lactic acid | 100.0 | +++ |
| 4-hydroxyphenylpyruvic acid | 10.0 | ++ |
| 4-hydroxyphenylpyruvic acid | 100.0 | +++ |
| Pterostilbene | 10.0 | ++ |
| Pterostilbene | 100.0 | ++ |
| Astaxanthine | 10.0 | + |
| Astaxanthine | 100.0 | + |
| 3,4-dihydroxyphenylacetic acid | 10.0 | + |
| 3,4-dihydroxyphenylacetic acid | 100.0 | ++++ |
| δ-tocopherol | 10.0 | + |
| δ-tocopherol | 100.0 | +++ |
| 1-methylindole-3-alanine | 10.0 | + |
| 1-methylindole-3-alanine | 100.0 | +++ |
| Piceatannol | 10.0 | + |
| Piceatannol | 100.0 | +++ |
| Kynurenine | 10.0 | + |
| Kynurenine | 100.0 | ++ |

In Table 5, vehicle = baseline; − = <2-fold Vehicle; + = >2-fold Vehicle; ++ = >5-fold Vehicle; +++ = >10-fold Vehicle; ++++ = >40-fold Vehicle Example 9: Human Caco-2 Barrier Integrity Assay Caco-2 colonocytes were maintained at 3TC and 5% $CO_2$ in Dulbecco's Modified Eagle Medium (DMEM) and supplemented with 10% FBS, 1% NEAA, and 1% penicillin-streptomycin. At 70-80% confluency, cells were trypsinized and seeded in 0.4 $cm^2$ transwell collagen I coated membranes with supplemented DMEM in both apical and basolateral compartments. Cells were seeded at a density of 200,000 cells per well and maintained for 10 days to form a polarized barrier with a TransEpithelial Electrial Resistance (TEER) reading above 1000Ω. On the first day of the assay, initial TEER readings were taken and cytokines were added to the basolateral media (50 ng/mL TNFα, 25 ng/mL IFNγ and 10 ng/mL IL-1β) to reduce barrier integrity while compounds diluted in (dimethyl-sulfoxide) DMSO were added to the apical media in triplicate. After 48 hours, TEER readings were taken again and viability was measured by CellTiter 96® $AQ_{ueous}$ One Solution Cell Proliferation Assay (Promega). The percent change in TEER over the 48 hours was determined and normalized to the 0.1% DMSO control (Table 6). None of the compounds reduced proliferation and therefore did not alter cell viability.

TABLE 6

| | % Change in TEER from DMSO |
|---|---|
| No treatment | ++ (170%) |
| DMSO + cytokines | − (100%) |
| Acetate 1 mM + cytokines | − |
| Acetate 3 mM + cytokines | − |
| Arabinose 0.5 mM + cytokines | − |
| Arabinose 1 mM + cytokines | − |
| EGCG 100 nM + cytokines | − |
| EGCG 1 µM + cytokines | − |
| Quercetin 100 nM + cytokines | − |
| Quercetin 1 µM + cytokines | + |
| Butanediol 100µM + cytokines | − |
| Butanediol 0.5 mM + cytokines | − |
| BHB 200 µM + cytokines | + |
| BHB 2 mM + cytokines | − |
| Butyrate 1 mM + cytokines | − |
| Butyrate 3 mM + cytokines | − |
| Butyrate 5 mM + cytokines | ++ |
| Propionate 1 mM + cytokines | + |
| Propionate 3 mM + cytokines | ++ |

Statistical changes in TEER were determined by way ANOVA and compared to DMSO.
<125%: −
125% > <150%: +
150% > <200%: ++
200% >: +++

Barrier function and integrity is an important feature of a variety of diseases and can be a hallmark of a damaged GI tract. Inflammation can drive a reduction of barrier function. By improving TEER less translocation of bacteria and bacterial products occur, thus dampening the immune response and damage to the GI tract and systemic immune system. This is important for the following disease areas: leaky gut, IBD/autoimmune, metabolic disorders, NASH, multiple sclerosis.

Example 10: Human Regulatory T cell differentiation assay

Peripheral blood mononuclear cells (PBMCs) from whole blood donated by health volunteers were separated by Ficoll-Paque gradient centrifugation and naïve CD4$^+$ T cells were subsequently isolated using magnet beads (EasySep™ Human Naïve CD4$^+$ T Cell Isolation Kit, Cambridge, Mass.). For regulatory T cell (Treg) differentiation assay, naïve CD4$^+$ T cells were cultured (1-10×10$^4$ cells) in CTS OpTmizer medium for 6 days and stimulated with 5 ng/ml TGF-β, 100 U/ml IL-2, and ImmunoCult™ Human CC3/CD28/CD2 T Cell Activator; Stemcell #10990) with/without our Compounds. Cell viability was determined using a viability dye (eBioscience Fixable Viability Dye eFluor 780: ThermoFisher 65-0865-14) at 1:500 dilution. The cells were gated for Treg, defined as Live, CD11c$^-$, CD14$^-$, CD19$^-$, CD8$^-$, CD4$^+$, CD3$^+$, CD25$^+$, FOXP3$^+$. Percent (%) Tregs were calculated as percentage of CD4$^+$, CD25$^+$, FOXP3$^+$ cells over total CD4$^+$ T cells. Statistical analysis was performed with GraphPad Prism Software Using One-Way ANOVA.

TABLE 7

| Treatment | Treg induction % DMSO | Cell viability % DMSO |
| --- | --- | --- |
| Acetic acid 1 mM | + | = |
| Acetic acid 3 mM | ++ | = |
| L-Arabinose 0.5 mM | = | = |
| L-Arabinose 1 mM | = | = |
| EGCG 100 nM | = | = |
| EGCG 1 uM | = | = |
| Quercetin 100 nM | = | = |
| Quercetin 1 uM | = | = |
| (R)-1,3-Butanediol 100 uM | = | = |
| (R)-1,3-Butanediol 0.5 mM | = | = |
| Sodium BHB 2 mM | + | = |
| Sodium BHB 20 mM | = | − |
| Butyric Acid 3 mM | − | − |
| Propionic acid 3 mM | ++ | = |
| Rosiglitazone 10 uM | = | = |
| Rosiglitazone 100 uM | = | − |
| Obeticholic acid 100 uM | + | = |
| DMSO | = (100.0) | = (100%) |

<90%: −
90% > <110%: =
110% > <130%: +
130% >: ++

Compounds that increased the differentiation of naïve CD4$^+$ T cells into Tregs are indicated as (+) or (++). Compounds that decreased the differentiation of naïve CD4$^+$ T cells into Tregs are indicated as (−). Tregs play an important role in keeping the balance of the immune system, and compounds that increase Tregs (+, ++) may be useful in the treatment of autoimmune and inflammatory diseases, whereas compounds that reduce Tregs (−) may enhance the efficacy of immunotherapy in cancer patients.

These data demonstrate that acylated active agents (e.g., those including) can modulate autoimmunity markers (e.g., increase Treg cell counts).

Example 11: Ulcerative Colitis Animal PK Studies

Detection of D5-Butyrate in Feces after Dosing with Compound 189

Three female CD-1 mice, single housed in separate metabolism cages, were fasted for 2-4 hours before administration via oral gavage of a 10 mg/mL suspension of compound 189 in 1% methyl cellulose at a dose volume of 10 mL/kg. Feces were collected at the following intervals (0-4 hrs, 4-6 hrs, 6-8 hrs, 8-12 hrs and 12-24 hrs). Samples were frozen and stored at −80° C. until analysis. Quantification of butyrate on the samples was done via a modification of J. Han et al. Analytica Chimica Acta 854 (2015) 86-94.

Detection of Mesalamine and Compound 44 in Feces after Dosing with Compound 44

Five female Swiss Webster mice were placed in metabolic cages and were administered via oral gavage of a 10 mg/mL suspension of compound 44 in 1% methyl cellulose at a dose volume of 10 mL/kg. Feces were collected at the following intervals (0-4 hrs, 4-8 hrs, 8-24 hrs). Samples were frozen and stored at −70° C. until analysis. Quantification of mesalamine and compound 44 were done via bioanalysis using LC-MS/MS.

Detection of Compound 44 in Whole Blood after Dosing with Compound 44

Nine female Swiss Webster mice were placed individually housed cages and were administered via oral gavage of a 10 mg/mL suspension of compound 44 in 1% methyl cellulose at a dose volume of 10 mL/kg. Whole blood (125 uL) was collected submandibular and transferred to chilled K$_2$EDTA tubes pre-filled with 125 uL of acetonitrile and frozen at −70° C. until analysis. Mice (1-3) were sampled at 5 min, 1 hr, and 8 hr. Mice (4-6) were sampled at 15 min, 2 hours and 24 hours. Mice (7-9) were sampled at 30 min and 4 hrs. Quantification of compound 44 was done via bioanalysis using LC-MS/MS.

The results of the studies are shown in Table 8 below.

TABLE 8

| Compound | Medium | Concentration, uM |
| --- | --- | --- |
| Mesalamine[1] | Feces | 224.18 |
| Compound 44[1] | Feces | 10.72 |
| Compound 44[1] | Blood | 0.68 |
| d5-Butyrate[2] | Feces | 397.25 |

[1]Detected after dosing with Compound 44
[2]Detected after dosing with Compound 189

Example 12: In Vivo Rheumatoid Arthritis Model

A study was conducted to determine the efficacy of test articles dosed by the oral (PO) route for inhibition of the inflammation (paw swelling), cartilage destruction, and bone resorption that occurs in semi-established type II collagen arthritis in female Lewis rats. Rats (10 per group) were injected intradermally (ID) with porcine type II collagen to induce arthritis; one group of rats (4 per group) served as vehicle-treated naïve controls. The animals were dosed PO, twice daily (BID) on study days 6 through 20 (animals #1-5 in each group, animals #1-2 in naïve group) or 21 (animals #6-10 in each group, animals #3-4 in naïve group) with vehicle (methylcellulose, viscosity: 1500 cP), Quercetin (230 mg/kg), Butyric acid (420 mg/kg), Compound 5 (100 mg/kg or 500 mg/kg), or Compound 45 (500 mg/kg). Positive controls were treated PO, BID with the reference compound Tofacitinib citrate (10 mg/kg). The rats were euthanized for necropsy on study day 21 (animals #1-5 in each group, animals #1-2 in naïve group) or 22 (animals #6-10 in each group, animals #3-4 in naïve group). Efficacy evaluation was based on animal body weights (Table 9), daily ankle caliper measurements (FIG. 4), ankle diameter expressed as area under the curve (AUC) (Table 10), terminal hind paw weights (Table 11), histopathologic evaluation of hind paws (Ankle Inflammation score: Table 12, Ankle Pannus score: Table 13, Ankle Cartilage Damage score: Table 14, Ankle Bone Resorption score: Table 15, Ankle Periosteal Bone score: Table 16, Ankle Periosteal Bone Width: Table 17) and knees (Knee Inflammation score: Table 18, Knee Pannus score: Table 19, Knee Cartilage Damage score: Table 20, Knee Bone Resorption score: Table 21), and relative spleen to body weight ratio (Table 22). Terminal serum was analyzed by enzyme-linked immunosorbent assay (ELISA) for anti-type II collagen antibodies (IgG) (Table 23). Treatment with compound 5 showed significant beneficial effects on spleen weights relative to body weight, ankle diameter AUC, ankle pannus score, ankle bone resorption score, and ankle periosteal bone score. All animals survived to study termination. Statistics were conducted using ordinary one-way ANOVA with Dunnett's multiple comparison correction in GraphPad Prism.

Figure 4:
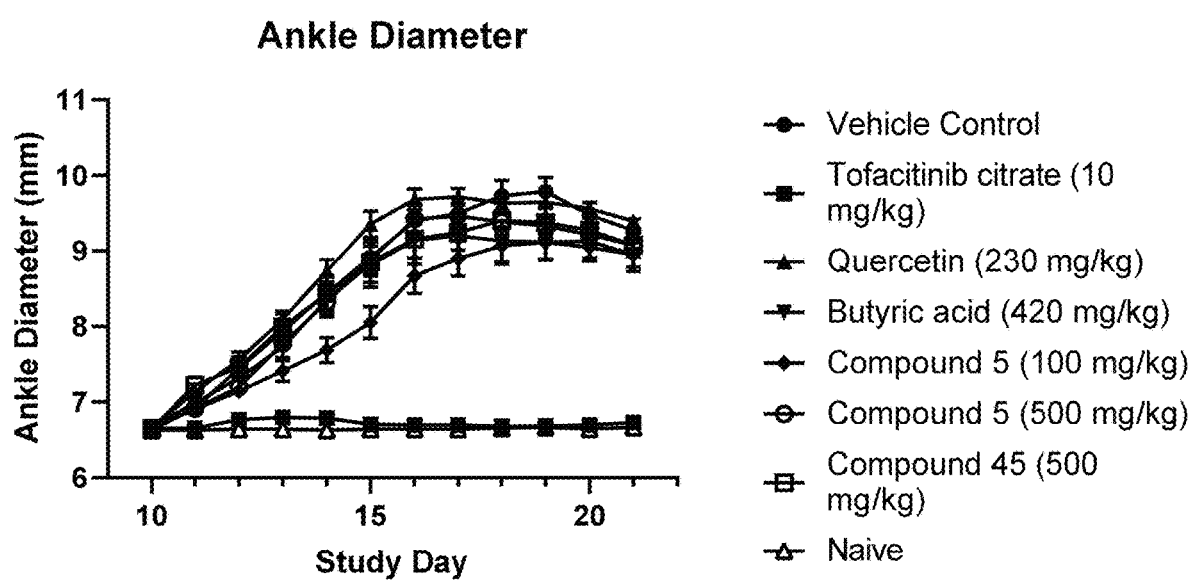
FIG. 4 is a graph showing oral exposure of mesalamine and d5-butyrate in the colon of mice administered compound 44.

The results of the study are summarized in Tables 9-23 below and FIG. 4.

TABLE 9

Change in body weight, day −1 to 21

| Treatment | Mean body weight change, day −1 to 21 (%) | p-value, (if significant) compared to vehicle control |
| --- | --- | --- |
| Vehicle Control | −12.5 | |
| Tofacitinib citrate (10 mg/kg) | 20.2 | p < 0.0001 |
| Quercetin (230 mg/kg) | −13.9 | |
| Butyric acid (420 mg/kg) | −2.3 | p < 0.05 |
| Compound 5 (100 mg/kg) | −7.1 | |
| Compound 5 (500 mg/kg) | −10.1 | |
| Compound 45 (500 mg/kg) | −6.3 | |
| Naïve Vehicle | 17.3 | p < 0.0001 |

TABLE 10

Ankle Diameter AUC

| Treatment | Mean Ankle Diameter AUC (mm*day) | p-value (if significant), compared to vehicle control |
| --- | --- | --- |
| Vehicle Control | 95.29 | |
| Tofacitinib citrate (10 mg/kg) | 73.82 | p < 0.0001 |
| Quercetin (230 mg/kg) | 96.85 | |
| Butyric acid (420 mg/kg) | 92.46 | |
| Compound 5 (100 mg/kg) | 89.38 | p < 0.05 |
| Compound 5 (500 mg/kg) | 93.57 | |
| Compound 45 (500 mg/kg) | 94.20 | |
| Naïve Vehicle | 73.09 | p < 0.0001 |

TABLE 11

Terminal hind paw weights

| Treatment | Mean Terminal hind paw weights (g) | p-value (if significant), compared to vehicle control |
| --- | --- | --- |
| Vehicle Control | 2.4776 | |
| Tofacitinib citrate (10 mg/kg) | 1.4321 | p < 0.0001 |
| Quercetin (230 mg/kg) | 2.5210 | |
| Butyric acid (420 mg/kg) | 2.4759 | |
| Compound 5 (100 mg/kg) | 2.3990 | |
| Compound 5 (500 mg/kg) | 2.3994 | |
| Compound 45 (500 mg/kg) | 2.3988 | |
| Naïve Vehicle | 1.3854 | p < 0.0001 |

TABLE 12

Ankle inflammation score, 0-5 (0 = normal, 5 = severe)

| Treatment | Mean Ankle inflammation score (0-5) | p-value (if significant), compared to vehicle control |
| --- | --- | --- |
| Vehicle Control | 2.4776 | |
| Tofacitinib citrate (10 mg/kg) | 1.4321 | p < 0.0001 |
| Quercetin (230 mg/kg) | 2.5210 | |
| Butyric acid (420 mg/kg) | 2.4759 | |
| Compound 5 (100 mg/kg) | 2.3990 | |
| Compound 5 (500 mg/kg) | 2.3994 | |
| Compound 45 (500 mg/kg) | 2.3988 | |
| Naïve Vehicle | 1.3854 | p < 0.0001 |

TABLE 13

Ankle Pannus score, 0-5 (0 = normal, 5 = severe)

| Treatment | Mean Ankle Pannus score (0-5) | p-value (if significant), compared to vehicle control |
| --- | --- | --- |
| Vehicle Control | 3.45 | |
| Tofacitinib citrate (10 mg/kg) | 0.00 | p < 0.0001 |
| Quercetin (230 mg/kg) | 3.55 | |
| Butyric acid (420 mg/kg) | 2.95 | |
| Compound 5 (100 mg/kg) | 2.53 | p < 0.05 |
| Compound 5 (500 mg/kg) | 3.33 | |
| Compound 45 (500 mg/kg) | 3.48 | |
| Naïve Vehicle | 0.00 | p < 0.0001 |

TABLE 14

Ankle Cartilage Damage score, 0-5 (0 = normal, 5 = severe)

| Treatment | Mean Ankle Cartilage Damage score (0-5) | p-value (if significant), compared to vehicle control |
| --- | --- | --- |
| Vehicle Control | 4.43 | |
| Tofacitinib citrate (10 mg/kg) | 0.00 | p < 0.0001 |
| Quercetin (230 mg/kg) | 4.70 | |
| Butyric acid (420 mg/kg) | 3.80 | |
| Compound 5 (100 mg/kg) | 3.55 | |
| Compound 5 (500 mg/kg) | 4.45 | |
| Compound 45 (500 mg/kg) | 4.20 | |
| Naïve Vehicle | 0.00 | p < 0.0001 |

TABLE 15

Ankle Bone Resorption score, 0-5 (0 = normal, 5 = severe)

| Treatment | Mean Ankle Bone Resorption score (0-5) | p-value (if significant), compared to vehicle control |
|---|---|---|
| Vehicle Control | 3.45 | |
| Tofacitinib citrate (10 mg/kg) | 0.00 | $p < 0.0001$ |
| Quercetin (230 mg/kg) | 3.55 | |
| Butyric acid (420 mg/kg) | 2.95 | |
| Compound 5 (100 mg/kg) | 2.53 | $p < 0.05$ |
| Compound 5 (500 mg/kg) | 3.33 | |
| Compound 45 (500 mg/kg) | 3.48 | |
| Naïve Vehicle | 0.00 | $p < 0.0001$ |

TABLE 16

Ankle Periosteal Bone score, 0-5 (0 = normal, 5 = severe)

| Treatment | Mean Ankle Periosteal Bone score (0-5) | p-value (if significant), compared to vehicle control |
|---|---|---|
| Vehicle Control | 3.85 | |
| Tofacitinib citrate (10 mg/kg) | 0.00 | $p < 0.0001$ |
| Quercetin (230 mg/kg) | 3.95 | |
| Butyric acid (420 mg/kg) | 3.08 | |
| Compound 5 (100 mg/kg) | 2.68 | $p < 0.05$ |
| Compound 5 (500 mg/kg) | 3.70 | |
| Compound 45 (500 mg/kg) | 3.38 | |
| Naïve Vehicle | 0.00 | $p < 0.0001$ |

TABLE 17

Ankle Periosteal Bone width (um)

| Treatment | Mean Ankle Periosteal Bone width (um) | p-value (if significant), compared to vehicle control |
|---|---|---|
| Vehicle Control | 727.65 | |
| Tofacitinib citrate (10 mg/kg) | 0.00 | $p < 0.0001$ |
| Quercetin (230 mg/kg) | 727.65 | |
| Butyric acid (420 mg/kg) | 573.30 | |
| Compound 5 (100 mg/kg) | 510.30 | |
| Compound 5 (500 mg/kg) | 699.30 | |
| Compound 45 (500 mg/kg) | 630.00 | |
| Naïve Vehicle | 0.00 | $p < 0.0001$ |

TABLE 18

Knee Inflammation score, 0-5 (0 = normal, 5 = severe)

| Treatment | Mean Knee Inflammation score (0-5) | p-value (if significant), compared to vehicle control |
|---|---|---|
| Vehicle Control | 5.35 | |
| Tofacitinib citrate (10 mg/kg) | 0.10 | $p < 0.0001$ |
| Quercetin (230 mg/kg) | 5.48 | |
| Butyric acid (420 mg/kg) | 4.83 | |
| Compound 5 (100 mg/kg) | 5.23 | |
| Compound 5 (500 mg/kg) | 5.65 | |
| Compound 45 (500 mg/kg) | 5.25 | |
| Naïve Vehicle | 0.00 | $p < 0.0001$ |

TABLE 19

Knee Pannus score, 0-5 (0 = normal, 5 = severe)

| Treatment | Mean Knee Pannus score (0-5) | p-value (if significant), compared to vehicle control |
|---|---|---|
| Vehicle Control | 2.60 | |
| Tofacitinib citrate (10 mg/kg) | 0.00 | $p < 0.0001$ |
| Quercetin (230 mg/kg) | 3.18 | |
| Butyric acid (420 mg/kg) | 2.43 | |
| Compound 5 (100 mg/kg) | 2.08 | |
| Compound 5 (500 mg/kg) | 2.65 | |
| Compound 45 (500 mg/kg) | 2.48 | |
| Naïve Vehicle | 0.00 | $p < 0.0001$ |

TABLE 20

Knee Cartilage Damage score, 0-5 (0 = normal, 5 = severe)

| Treatment | Mean Knee Cartilage Damage score (0-5) | p-value (if significant), compared to vehicle control |
|---|---|---|
| Vehicle Control | 3.55 | |
| Tofacitinib citrate (10 mg/kg) | 0.00 | $p < 0.0001$ |
| Quercetin (230 mg/kg) | 3.98 | |
| Butyric acid (420 mg/kg) | 3.28 | |
| Compound 5 (100 mg/kg) | 2.93 | |
| Compound 5 (500 mg/kg) | 4.00 | |
| Compound 45 (500 mg/kg) | 3.63 | |
| Naïve Vehicle | 0.00 | $p < 0.0001$ |

TABLE 21

Knee Bone Resorption score, 0-5 (0 = normal, 5 = severe)

| Treatment | Mean Knee Bone Resorption score (0-5) | p-value (if significant), compared to vehicle control |
|---|---|---|
| Vehicle Control | 2.60 | |
| Tofacitinib citrate (10 mg/kg) | 0.00 | $p < 0.0001$ |
| Quercetin (230 mg/kg) | 3.15 | |
| Butyric acid (420 mg/kg) | 2.43 | |
| Compound 5 (100 mg/kg) | 2.08 | |
| Compound 5 (500 mg/kg) | 2.65 | |
| Compound 45 (500 mg/kg) | 2.40 | |
| Naïve Vehicle | 0.00 | $p < 0.0001$ |

TABLE 22

Relative Spleen to Body Weight

| Treatment | Relative Spleen to Body Weight (Mean) | p-value (if significant), compared to vehicle control |
|---|---|---|
| Vehicle Control | 0.2779 | |
| Tofacitinib citrate (10 mg/kg) | 0.1796 | $p < 0.0001$ |
| Quercetin (230 mg/kg) | 0.2539 | |
| Butyric acid (420 mg/kg) | 0.2416 | $p < 0.01$ |
| Compound 5 (100 mg/kg) | 0.2453 | $p < 0.05$ |
| Compound 5 (500 mg/kg) | 0.2534 | |
| Compound 45 (500 mg/kg) | 0.2534 | |
| Naïve Vehicle | 0.2345 | $p < 0.05$ |

TABLE 23

Serum IgG ELISA

| Treatment | Serum IgG (ug/mL) | p-value (if significant), compared to vehicle control |
|---|---|---|
| Vehicle Control | 6569.33 | |
| Tofacitinib citrate (10 mg/kg) | 2524.70 | $p < 0.0001$ |
| Quercetin (230 mg/kg) | 7014.93 | |
| Butyric acid (420 mg/kg) | 5824.57 | |
| Compound 5 (100 mg/kg) | 5937.67 | |
| Compound 5 (500 mg/kg) | 5350.41 | |
| Compound 45 (500 mg/kg) | 5431.64 | |
| Naïve Vehicle | 1.19 | $p < 0.05$ |

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A compound of the following structure:

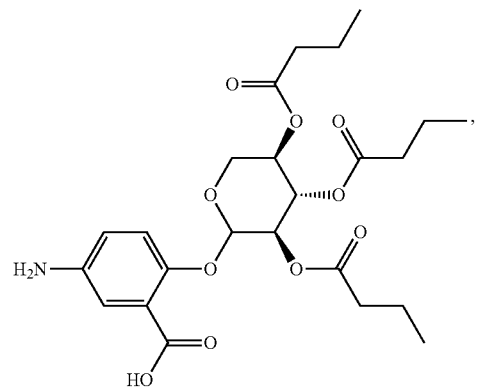 [SMILES: CCCC(=O)O[C@H]1[C@H](OC(=O)CCC)COC(Oc2ccc(N)cc2C(=O)O)[C@@H]1OC(=O)CCC]

or a pharmaceutically acceptable salt thereof.

2. A composition comprising an excipient and the compound of claim 1 or a pharmaceutically acceptable salt thereof.

* * * * *

UNITED STATES PATENT AND TRADEMARK OFFICE
CERTIFICATE OF CORRECTION

PATENT NO. : 11,058,698 B2
APPLICATION NO. : 16/803284
DATED : July 13, 2021
INVENTOR(S) : Steven John Taylor et al.

It is certified that error appears in the above-identified patent and that said Letters Patent is hereby corrected as shown below:

In the Specification

Column 2, Line 61, replace "protein 10 (MIP-1p)" with --protein 1β (MIP-1β)--;
    Line 63, replace "T1 cell" with --$T_h1$ cell--.

Column 6, Line 42, replace "$R^3$" with --$R^{3C}$--.

Column 12, Line 42, replace "-L-$L^2$" with -- -$L^1$-$L^2$--.

Column 16, Line 40, replace "(CO)—$R^{58}$" with --(CO)—$R^{5B}$--.

Column 18, Line 19, replace "aryene" with --arylene--.

Column 19, Line 1, replace "and alky" with --and alkyl--.

Column 20, Line 4, replace "T1 cell" with --$T_h1$ cell--;
    Line 6, replace "1p (MIP-1)" with --1β (MIP-1β)--;
    Line 23, replace "(8-iso-$PGF_{2\alpha}$)" with --(8-iso-PGF2α)--.

Column 27, Line 46, replace "p-hydroxybutyric acid" with --β-hydroxybutyric acid--;
    Lines 46-47, replace "p-hydroxybutyric acid" with --β-hydroxybutyric acid--;
    Line 51, replace "p-hydroxybutyric acid" with --β-hydroxybutyric acid--;
    Line 63, replace "C-s alkyl" with --$C_{1-6}$ alkyl--.

Column 33, Line 65, replace "p-hydroxybutyrate acyl" with --β-hydroxybutyrate acyl--.

Column 41, Line 16, replace "each R'" with --each $R^1$--.

Column 43, Line 20, replace "T1 cell" with --$T_h1$ cell--;
    Line 22, replace "(MIP-1p)" with --(MIP-1β)--;

Signed and Sealed this
Eighth Day of October, 2024

Katherine Kelly Vidal
*Director of the United States Patent and Trademark Office*

CERTIFICATE OF CORRECTION (continued)
U.S. Pat. No. 11,058,698 B2

Line 26, replace "F$_2$a" with --F$_{2\alpha}$--;
Line 33, replace "T1 cell" with --T$_h$1 cell--.

Column 44, Line 12, replace "PGF$_{2\alpha}$" with --PGF2α--;
Line 30, replace "protein 10 (MIP-10)" with --protein 1β (MIP-1β)--;
Line 37, replace "T1 cell" with --T$_h$1 cell--.

Column 53, Line 60, replace "benzyoxycarbonyl" with --benzyloxycarbonyl--.

Column 62, Line 59, replace "THE" with --THF--.

Column 67, Line 5, replace "1M HC" with --1 M HCl--.

Column 69, Line 10, replace "THE" with --THF--;
Line 29, replace "M+H$^4$" with --M+H$^+$--.

Column 73, Line 46, replace "THE" with --THF--.

Column 77, Line 1, replace "ACN]0.2" with --ACN]. 2--;
Line 41, replace "THE" with --THF--.

Column 78, Line 26, replace "THE" with --THF--.

Column 79, Line 65, replace "Sum; mobile" with --5um; mobile--.

Column 81, Line 32, replace "THE" with --THF--;
Line 43, replace "THE" with --THF--.

Column 89, Line 66, replace "C$_{21}$H$_{34}$" with --C$_{25}$H$_{34}$--.

Column 90, Line 40, replace "CDCl$_3$) 8.75" with --CDCl$_3$) δ 8.75--;
Line 62, replace "1H" with --$^1$H--.

Column 92, Line 55, replace "M+NH$_4$" with --M+NH$_4^+$--.

Column 93, Line 42, replace "1 H" with --$^1$H--.

Column 94, Line 22, replace "SiO2" with --SiO$_2$--.

Column 95, Line 8, replace "THE" with --THF--.

Column 99, Line 12, replace "δ6.35" with --δ 6.35--;
Line 26, replace "THE" with --THF--.

Column 102, Line 8, replace "5.27" with --δ 5.27--;
Line 31, replace "5.27" with --δ 5.27--.

Column 103, Line 1, replace " 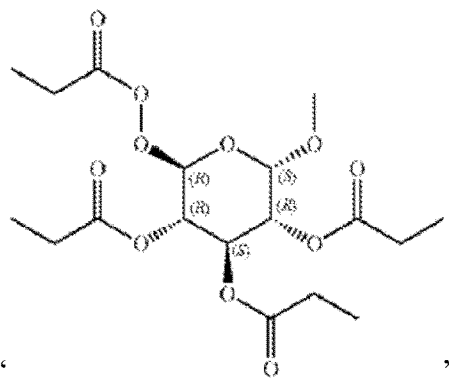 " with
-- 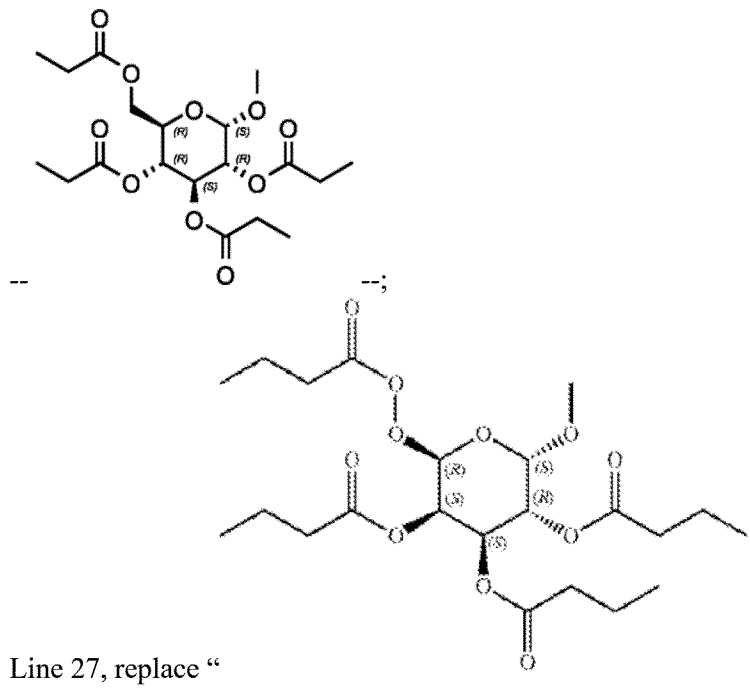 --;
Line 27, replace " 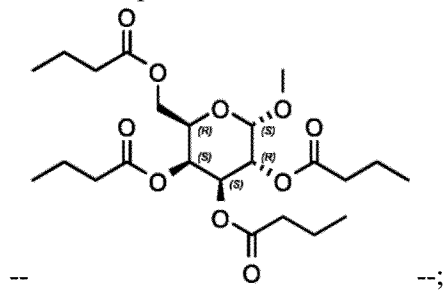 " with Line 55, replace " 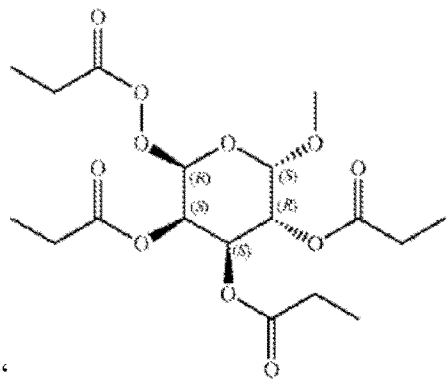 " with

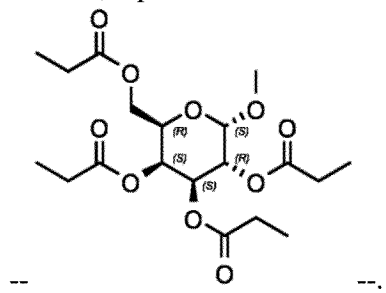

-- --.

Column 129, Line 1, replace "2R,3R,4,5R" with --2R,3R,4S,5R--.

Column 131, Line 24, replace "oxan-2-yl(2E)" with --oxan-2-yl (2E)--.

Column 139, Line 60, replace "THE" with --THF--.

Column 140, Line 4, replace "(M+Na$^4$)" with --(M+Na$^+$)--.

Column 143, Line 25, replace "acetyloxy" with --acetyl]oxy--.

Column 148, Line 36, replace "THE" with --THF--.

Column 152, Line 4, replace "THE" with --THF--.

Column 154, Line 7, replace "(M+NH$_4$)" with --(M+NH$_4^+$)--;
    Line 26, replace "(2,3,4,5R,6)" with --(2S,38,4S,5R,6S)--.

Column 155, Line 63, replace "THE" with --THF--.

Column 159, Line 54, replace "8 eg)" with --8 *eq*)--.

Column 165, Line 6, replace "THE" with --THF--.

Column 167, Line 6, replace "THE" with --THF--;
    Line 39, replace "THE" with --THF--.

Column 168, Line 37, replace "THE" with --THF--.

Column 170, Line 7, replace "a/anomers" with --α/β anomers--.

Column 171, Line 7, replace "THE" with --THF--.

Column 172, Line 42, replace "2R,3R,4,5R" with --2R,3R,4S,5R--.

Column 174, Line 27, replace "THE" with --THF--;
　　　Lines 34-35, replace "desired p isomer" with --desired β isomer--;
　　　Line 35, replace "and a isomer" with --and α isomer--;
　　　Line 47, replace "THE" with --THF--.

Column 180, Line 35, replace " 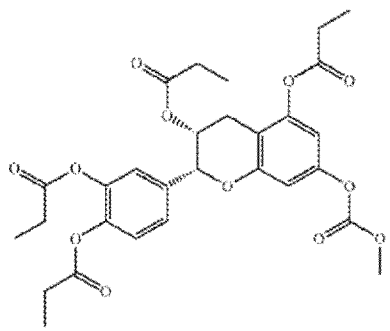 " with -- 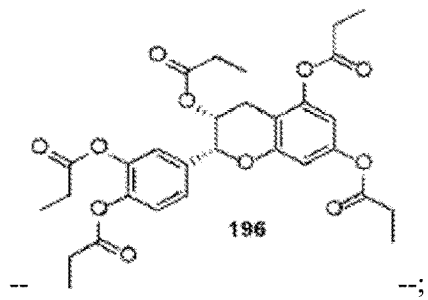 --;
　　　Line 52, replace "THE" with --THF--.

Column 185, Line 6, replace "(M+Na)+" with --(M+Na)$^+$--.

Column 194, Line 25, replace " 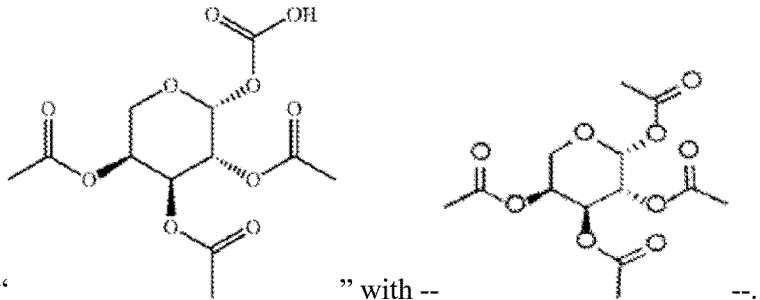 " with -- --.

Column 200, Line 16, replace "IL10 levels" with --IL1β levels--.

Column 201, Line 20, replace "Histopaque-1077" with --Histopaque®-1077--;
　　　Line 22, replace "Histopaque-1077" with --Histopaque®-1077--.

Column 202, Line 62, replace "log 2(ΔΔCT)" with --$\log 2(\Delta\Delta C_T)$--.

Column 203, Line 37, replace "ITE 1pM" with --ITE 1μM--.